United States Patent
Huh et al.

(10) Patent No.: US 12,016,243 B2
(45) Date of Patent: *Jun. 18, 2024

(54) CONDENSED CYCLIC COMPOUND AND ORGANIC LIGHT EMITTING DEVICE COMPRISING SAME

(71) Applicant: LG CHEM, LTD., Seoul (KR)

(72) Inventors: Jungoh Huh, Daejeon (KR); Sung Kil Hong, Daejeon (KR); Sangbin Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 661 days.

This patent is subject to a terminal disclaimer.

(21) Appl. No.: 17/271,762

(22) PCT Filed: Oct. 2, 2019

(86) PCT No.: PCT/KR2019/012896
§ 371 (c)(1),
(2) Date: Feb. 26, 2021

(87) PCT Pub. No.: WO2020/122384
PCT Pub. Date: Jun. 18, 2020

(65) Prior Publication Data
US 2021/0336155 A1 Oct. 28, 2021

(30) Foreign Application Priority Data

Dec. 14, 2018 (KR) .................. 10-2018-0161787

(51) Int. Cl.
*H10K 50/11* (2023.01)
*C07D 405/04* (2006.01)
(Continued)

(52) U.S. Cl.
CPC ....... *H10K 85/6574* (2023.02); *C07D 405/04* (2013.01); *C07D 405/10* (2013.01); *C07D 405/14* (2013.01); *C07D 409/04* (2013.01); *C09K 11/06* (2013.01); *H10K 85/615* (2023.02); *H10K 85/626* (2023.02);
(Continued)

(58) Field of Classification Search
None
See application file for complete search history.

(56) References Cited

U.S. PATENT DOCUMENTS

2010/0066239 A1* 3/2010 Spindler .............. H10K 50/125
313/506
2015/0171336 A1* 6/2015 Park ..................... C07D 403/04
257/40
(Continued)

FOREIGN PATENT DOCUMENTS

CN 106536485 3/2017
CN 108997201 12/2018
(Continued)

OTHER PUBLICATIONS

Machine translation of WO-2018038401, translation generated May 2023, 35 pages. (Year: 2023).*
(Continued)

*Primary Examiner* — Robert S Loewe
(74) *Attorney, Agent, or Firm* — Bryan Cave Leighton Paisner LLP

(57) ABSTRACT

Provided is a compound of Chemical Formula 1:

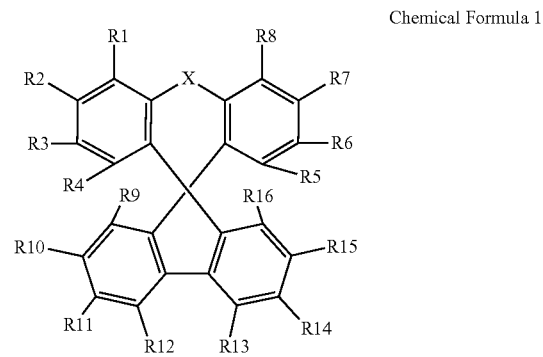

Chemical Formula 1 wherein:
X is O or S;
one or more of R9 to R16 are linked to * of the following Chemical Formula 2; and
R1 to R8, and the rest of R9 to R16 not linked to Chemical Formula 2, are the same as or different from each other, and each independently is hydrogen, deuterium, a cyano group, a nitro group, a carbonyl group, or a substituted or unsubstituted: silyl group, boron group, alkyl group, alkoxy group, aryloxy group, cycloalkyl group, aryl group or heterocyclic group, or bond to adjacent groups to form a substituted or unsubstituted benzene ring;

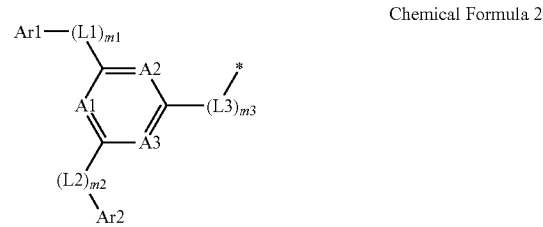

Chemical Formula 2 and an organic light emitting device including the same.

12 Claims, 7 Drawing Sheets

(51) Int. Cl.
*C07D 405/10* (2006.01)
*C07D 405/14* (2006.01)
*C07D 409/04* (2006.01)
*C09K 11/06* (2006.01)
*H10K 85/60* (2023.01)
*H10K 50/13* (2023.01)
*H10K 50/15* (2023.01)
*H10K 50/16* (2023.01)
*H10K 50/17* (2023.01)
*H10K 50/18* (2023.01)

(52) U.S. Cl.
CPC ....... *H10K 85/654* (2023.02); *H10K 85/6576* (2023.02); *C09K 2211/1018* (2013.01); *H10K 50/131* (2023.02); *H10K 50/15* (2023.02); *H10K 50/16* (2023.02); *H10K 50/17* (2023.02); *H10K 50/171* (2023.02); *H10K 50/18* (2023.02)

(56) References Cited

U.S. PATENT DOCUMENTS

| | | | |
|---|---|---|---|
| 2016/0079545 A1 | 3/2016 | Fukuzaki | |
| 2016/0118599 A1* | 4/2016 | Jeong | H10K 85/6572 546/276.7 |
| 2017/0222157 A1* | 8/2017 | Jatsch | C07D 405/14 |
| 2018/0331297 A1 | 11/2018 | Suh et al. | |
| 2019/0214571 A1* | 7/2019 | Huh | C07D 405/10 |
| 2019/0292169 A1* | 9/2019 | Park | H10K 85/654 |
| 2019/0296243 A1* | 9/2019 | Suh | H10K 85/615 |
| 2020/0048230 A1 | 2/2020 | Heo et al. | |
| 2020/0136055 A1 | 4/2020 | Heo et al. | |
| 2020/0190070 A1 | 6/2020 | Cho et al. | |
| 2020/0227646 A1* | 7/2020 | Jung | H10K 85/6574 |
| 2020/0317646 A1* | 10/2020 | He | H10K 85/615 |
| 2021/0013422 A1 | 1/2021 | Heo et al. | |
| 2021/0114998 A1 | 4/2021 | Heo et al. | |

FOREIGN PATENT DOCUMENTS

| | | |
|---|---|---|
| CN | 109748909 A | 5/2019 |
| KR | 10-2012-0032572 | 4/2012 |
| KR | 10-1593368 | 2/2016 |
| KR | 10-2017-0071399 | 6/2017 |
| KR | 10-2018-0022190 | 3/2018 |
| KR | 10-2018-0111558 | 10/2018 |
| KR | 10-2018-0124735 | 11/2018 |
| KR | 10-2019-0061314 | 6/2019 |
| WO | 2018-038401 | 3/2018 |
| WO | 2018-164510 | 9/2018 |
| WO | 2019-004790 | 1/2019 |
| WO | 2019-004791 | 1/2019 |
| WO | 2019-013542 | 1/2019 |
| WO | 2019-027263 | 2/2019 |
| WO | 2019-172699 | 9/2019 |

OTHER PUBLICATIONS

Machine translation of CN-108997201, translation generated May 2023, 9 pages. (Year: 2023).*
Datasheet for Ir(ppy)3, datasheet retrieved from the web Jan. 2024, 9 pages. (Year: 2024).*
Machine translation of CN-109748909, translation generated Jan. 2024, 13 pages. (Year: 2024).*

* cited by examiner

【FIG. 1】

| 8 |
|---|
| 7 |
| 6 |
| 5 |
| 4 |
| 3 |
| 2 |
| 1 |

【FIG. 2】

| 8 |
|---|
| 7 |
| 5 |
| 9 |
| 4 |
| 3 |
| 2 |
| 1 |

[FIG. 3]

| 8 |
|---|
| 7 |
| 18 |
| 17 |
| 16 |
| 15 |
| 14 |
| 13 |
| 12 |
| 11 |
| 3 |
| 2 |
| 1 |

【FIG. 4】

| 8 |
|---|
| 22 |
| 21 |
| 20 |
| 16 |
| 15 |
| 19 |
| 18 |
| 17 |
| 16 |
| 15 |
| 14 |
| 13 |
| 12 |
| 11 |
| 3 |
| 2 |
| 1 |

[FIG. 5]

| |
|---|
| 129 |
| 8 |
| 128 |
| 127 |
| 126 |
| 125 |
| 124 |
| 123 |
| 122 |
| 121 |
| 120 |
| 119 |
| 118 |
| 117 |
| 116 |
| 115 |
| 114 |
| 113 |
| 112 |
| 111 |
| 3 |
| 2 |
| 1 |

[FIG. 6]

| |
|---|
| 129 |
| 8 |
| 128 |
| 127 |
| 126 |
| 125 |
| 124 |
| 123 |
| 122 |
| 121 |
| 120 |
| 118 |
| 117 |
| 116 |
| 115 |
| 114 |
| 113 |
| 112 |
| 111 |
| 3 |
| 2 |
| 1 |

【FIG. 7】

| 129 |
|---|
| 8 |
| 218 |
| 217 |
| 216 |
| 215 |
| 214 |
| 213 |
| 212 |
| 211 |
| 210 |
| 209 |
| 208 |
| 207 |
| 206 |
| 205 |
| 204 |
| 203 |
| 202 |
| 201 |
| 2 |
| 1 |

【FIG. 8】

| 129 |
|---|
| 8 |
| 306 |
| 305 |
| 304 |

| 303-1 | 303-2 | 303-3 |
|---|---|---|
| 302-1 | 302-2 | 302-3 |

| 301 |
|---|
| 2 |
| 1 |

CONDENSED CYCLIC COMPOUND AND ORGANIC LIGHT EMITTING DEVICE COMPRISING SAME

CROSS-REFERENCE TO RELATED APPLICATIONS

This application is a National Stage Application of International Application No. PCT/KR2019/012896 filed on Oct. 2, 2019, which claims priority to and the benefits of Korean Patent Application No. 10-2018-0161787, filed with the Korean Intellectual Property Office on Dec. 14, 2018, the entire contents of which are incorporated herein by reference.

TECHNICAL FIELD

The present specification relates to a compound, and an organic light emitting device including the same.

BACKGROUND

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film can be formed in a single layer or a multilayer as necessary.

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, can be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

PRIOR ART DOCUMENTS—PATENT DOCUMENTS (Patent Document 1) Korean Patent Application Laid-Open Publication No. 10-2012-0032572

BRIEF DESCRIPTION

Technical Problem

The present specification describes a compound, and an organic light emitting device including the same.

Technical Solution

One embodiment of the present specification provides a compound of Chemical Formula 1:

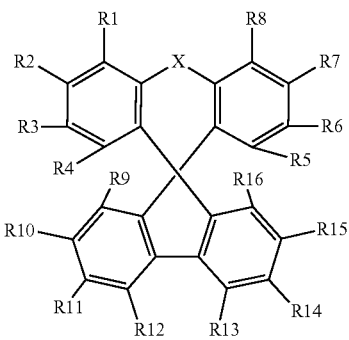

Chemical Formula 1 wherein in Chemical Formula 1:

X is O or S;

one or more of R9 to R16 are linked to * of the following Chemical Formula 2; and R1 to R8, and the rest of R9 to R16 not linked to Chemical Formula 2, are the same as or different from each other, and each independently is hydrogen, deuterium, a cyano group, a nitro group, a carbonyl group, a substituted or unsubstituted silyl group, a substituted or unsubstituted boron group, a substituted or unsubstituted alkyl group, a substituted or unsubstituted alkoxy group, a substituted or unsubstituted aryloxy group, a substituted or unsubstituted cycloalkyl group, a substituted or unsubstituted aryl group, or a substituted or unsubstituted heterocyclic group, or bond to adjacent groups to form a substituted or unsubstituted benzene ring;

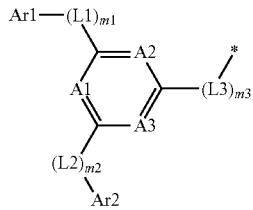

Chemical Formula 2 wherein in Chemical Formula 2:

A1 to A3 are the same as or different from each other and each is independently N or CR, and one or more of A1 to A3 are N;

L1 and L2 are the same as or different from each other, and each independently is a direct bond, a substituted or unsubstituted cycloalkylene group, or a substituted or unsubstituted arylene group;

L3 is a direct bond, a substituted or unsubstituted cycloalkylene group, or a substituted or unsubstituted arylene group;

one or more of Ar1 and Ar2 are a substituted or unsubstituted dicyclic or higher condensed aryl group, and the rest are the same as or different from each other, and each independently is a substituted or unsubstituted aryl group or a substituted or unsubstituted heterocyclic group;

Rs are the same as or different from each other, and each independently is hydrogen, deuterium, a cyano group, a nitro group, a carbonyl group, a substituted or unsubstituted silyl group, a substituted or unsubstituted boron group, a substituted or unsubstituted alkyl group, a substituted or unsubstituted alkoxy group, a substituted or unsubstituted aryloxy group, a substituted or unsubstituted cycloalkyl group, a substituted or unsubstituted aryl group, or a substituted or unsubstituted heterocyclic group; and m1 to m3 are each an integer of 0 to 3, and when m1 to m3 are each 2 or greater, two or more substituents in the parentheses are the same as or different from each other.

Another embodiment of the present specification provides an organic light emitting device including a first electrode; a second electrode; and one or more organic material layers provided between the first electrode and the second electrode, wherein one or more layers of the organic material layers include the compound described above.

Advantageous Effects

According to one embodiment of the present specification, a compound of Chemical Formula 1 can be used as a material of an organic material layer of an organic light emitting device.

When manufacturing an organic light emitting device including the compound of Chemical Formula 1 according to one embodiment of the present specification, an organic light emitting device having low driving voltage, high efficiency and long lifetime can be obtained.

DESCRIPTION OF THE DRAWINGS

FIGS. 1 to 8 illustrate examples of an organic light emitting device.

REFERENCE NUMERALS

1: Substrate/2: Anode/3: Hole Injection Layer/4: Hole Transfer Layer/5: Light Emitting Layer/6: Hole Blocking Layer/7: Layer Carrying Out Electron Transfer And Electron Injection At The Same Time/8: Cathode/9: Electron Blocking Layer/11: First Hole Transfer Layer/12: First Electron Blocking Layer/13: First Light Emitting Layer/14: First Electron Transfer Layer/15: N-type Charge Generating Layer/16: P-type Charge Generating Layer/17: Second Hole Transfer Layer/18: Second Light Emitting Layer/19: Second Electron Transfer Layer/20: Third Hole Transfer Layer/21: Third Light Emitting Layer/22: Third Electron Transfer Layer/111, 202: Hole Transfer Layer1/112, 208: Hole Transfer Layer2/113, 204, 303-3: Blue Fluorescent Light Emitting Layer1/114, 205, 304: Electron Transfer Layer1/115, 206: N-type Charge Generating Layer1/116: P-Type Charge Generating Layer1/117, 214: Hole Transfer Layer3/118, 303-1: Red Phosphorescent Light Emitting Layer/119: Yellow Green Phosphorescent Light Emitting Layer/120, 303-2: Green Phosphorescent Light Emitting Layer/121, 211: Electron Transfer Layer2/122, 212: N-type Charge Generating Layer2/123, 201, 207, 213, 301: P-Doping Hole Transfer Layer/124: Hole Transfer Layer4/125: Hole Transfer Layer5/126, 210: Blue Fluorescent Light Emitting Layer2/ 127, 217: Electron Transfer Layer3/128, 218, 306: Electron Injection Layer/129: Capping Layer/203: Hole Transfer Layer1-1/209: Hole Transfer Layer2-1/215: Hole Transfer Layer3-1/216: Blue Fluorescent Light Emitting Layer3/302-1: Red Hole Transfer Layer/302-2: Green Hole Transfer Layer/302-3: Blue Hole Transfer Layer/305: Electron Transfer Layer1-1

DETAILED DESCRIPTION

Hereinafter, the present specification will be described in more detail.

One embodiment of the present specification provides a compound of the following Chemical Formula 1. In the compound of the following Chemical Formula 1, a fluorene part of a spirofluorenexanthene derivative bonds to an N-containing monocyclic ring, and a dicyclic or higher condensed aryl group bonds thereto.

When a fluorene part of the spirofluorenexanthene derivative bonds to an N-containing monocyclic ring instead of a xanthene part in the compound of the following Chemical Formula 1, the LUMO is delocalized to the N-containing monocyclic ring by electron donor and non-conjugation effects of the heteroatom (O or S), and the compound having an N-containing monocyclic ring linked to the xanthene part has an excessively high LUMO energy value compared to the compound having an N-containing monocyclic ring bonding to the fluorene part instead of the xanthene part. Accordingly, when including the compound having an N-containing monocyclic ring linked to the xanthene part in an organic light emitting device, electrons are not favorably injected from a cathode due to the high LUMO energy value, and a voltage greatly increases and efficiency decreases when driving the device.

In addition, by the compound of the following Chemical Formula 1 including a dicyclic or higher condensed aryl group (one or more of Ar1 and Ar2) as an essential component, a compound having a large difference between a singlet energy (S1) value and a triplet energy (T1) value (ΔEST) can be obtained, and when using the compound having a large difference between a singlet energy (S1) value and a triplet energy (T1) value (ΔEST) in a device, a lifetime improving effect can be obtained. Specifically, having a large difference between a singlet energy (S1) value and a triplet energy (T1) value means having a large overlap between molecular orbitals (HOMO and LUMO) in the molecule. As the degree of overlap between molecular orbitals (HOMO and LUMO) increases, bond strength between atoms becomes rigid in the molecule by being free from structural steric hindrance, and as a result, a lifetime improving effect can be obtained when used in a device:

Chemical Formula 1

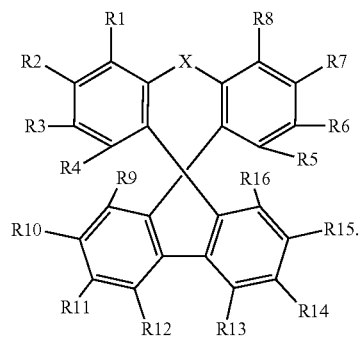

In Chemical Formula 1:

X is O or S;

one or more of R9 to R16 are linked to * of the following Chemical Formula 2; and R1 to R*, and the rest of R9 to R16 not linked to Chemical Formula 2, are the same as or different from each other, and each independently is hydrogen, deuterium, a cyano group, a nitro group, a carbonyl group, a substituted or unsubstituted silyl group, a substituted or unsubstituted boron group, a substituted or unsubstituted alkyl group, a substituted or unsubstituted alkoxy group, a substituted or unsubstituted aryloxy group, a substituted or unsubstituted cycloalkyl group, a substituted or unsubstituted aryl group, or a substituted or unsubstituted heterocyclic group, or bond to adjacent groups to form a substituted or unsubstituted benzene ring;

Chemical Formula 2

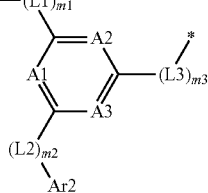

wherein in Chemical Formula 2:
A1 to A3 are the same as or different from each other and each independently is N or CR, and one or more of A1 to A3 are N;
L1 and L2 are the same as or different from each other, and each independently is a direct bond, a substituted or unsubstituted cycloalkylene group, or a substituted or unsubstituted arylene group;
L3 is a direct bond, a substituted or unsubstituted cycloalkylene group, or a substituted or unsubstituted arylene group;
one or more of Ar1 and Ar2 are a substituted or unsubstituted dicyclic or higher condensed aryl group, and the rest are the same as or different from each other, and each independently is a substituted or unsubstituted aryl group or a substituted or unsubstituted heterocyclic group;
Rs are the same as or different from each other, and each independently is hydrogen, deuterium, a cyano group, a nitro group, a carbonyl group, a substituted or unsubstituted silyl group, a substituted or unsubstituted boron group, a substituted or unsubstituted alkyl group, a substituted or unsubstituted alkoxy group, a substituted or unsubstituted aryloxy group, a substituted or unsubstituted cycloalkyl group, a substituted or unsubstituted aryl group, or a substituted or unsubstituted heterocyclic group, and
m1 to m3 are each an integer of 0 to 3, and when m1 to m3 are each 2 or greater, two or more substituents in the parentheses are the same as or different from each other.

In the present specification, a description of a certain part "including" certain constituents means capable of further including other constituents, and does not exclude other constituents unless particularly stated on the contrary.

In the present specification, a description of one member being placed "on" another member includes not only a case of the one member being in contact with the another member but a case of still another member being present between the two members.

In the present specification, a "substituent in a parenthesis" means a substituent described within the symbols '( )'. Specifically, in '(W)', a substituent in a parenthesis means 'W', and "two or more substituents in the parentheses are the same as or different from each other" means that, when two Ws are present, the types of the two Ws are the same as or different from each other.

Examples of substituents in the present specification will be described below, however, the substituents are not limited thereto.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents can be the same as or different from each other.

In the present specification, the term "substituted or unsubstituted" means being substituted with one, two or more substituents selected from the group consisting of deuterium (-D), a halogen group, a cyano group, a nitro group, a carbonyl group, a hydroxyl group, a silyl group, a boron group, an alkoxy group, an alkyl group, an aryloxy group, a cycloalkyl group, an aryl group, and a heterocyclic group, or being substituted with a substituent linking two or more substituents of the substituents illustrated above, or having no substituents. For example, a "substituent linking two or more substituents" can include a biphenyl group. In other words, a biphenyl group can be an aryl group, or can be interpreted as a substituent linking two phenyl groups.

Examples of the substituents will be described below, however, the substituents are not limited thereto.

In the present specification, examples of the halogen group can include fluorine (—F), chlorine (—Cl), bromine (—Br) or iodine (—I).

In the present specification, the silyl group can be a chemical formula of —SiYaYbYc, and Ya, Yb and Yc can each be hydrogen, a substituted or unsubstituted alkyl group, a substituted or unsubstituted cycloalkyl group, or a substituted or unsubstituted aryl group.

The silyl group can be an alkylsilyl group, an arylsilyl group, an arylalkylsilyl group or the like. The alkylsilyl group means that one or more of Ya, Yb and Yc are a substituted or unsubstituted alkyl group and the rest are hydrogen, the arylsilyl group means that one or more of Ya, Yb and Yc are a substituted or unsubstituted aryl group and the rest are hydrogen, and the arylalkylsilyl group means that one or more of Ya, Yb and Yc are a substituted or unsubstituted alkyl group, one or more of the rest are a substituted or unsubstituted aryl group, and the rest is hydrogen. Specific examples of the silyl group can include a trimethylsilyl group, a triethylsilyl group, a tert-butyldimethylsilyl group, an ethyldimethylsilyl group, a propyldimethylsilyl group, a triphenylsilyl group, a diphenylsilyl group, a phenylsilyl group, a dimethylphenylsilyl group, a methyldiphenylsilyl group and the like, but are not limited thereto.

In the present specification, the carbonyl group can be —C(=O)Yf, and Yf can be a substituent such as an alkyl group having 1 to 40 carbon atoms or an aryl group having 6 to 60 carbon atoms, but is not limited thereto.

In the present specification, the boron group can be a chemical formula of —BYdYe, and Yd and Ye can each be hydrogen, a substituted or unsubstituted alkyl group, a substituted or unsubstituted cycloalkyl group, or a substituted or unsubstituted aryl group. Specific examples of the boron group can include a dimethylboron group, a diethylboron group, a tert-butyldimethylboron group, a diphenylboron group, a phenylboron group and the like, but are not limited thereto.

In the present specification, the alkyl group can be linear or branched. The number of carbon atoms of the alkyl group is not particularly limited, but is preferably from 1 to 60. According to one embodiment, the number of carbon atoms of the alkyl group is from 1 to 30. According to another embodiment, the number of carbon atoms of the alkyl group is from 1 to 20. According to another embodiment, the number of carbon atoms of the alkyl group is from 1 to 10.

Specific examples of the alkyl group can include a methyl group, an ethyl group, a propyl group, a butyl group, a pentyl group, a hexyl group, a heptyl group, an octyl group, a nonyl group and the like, and the alkyl group can be linear or branched. According to one embodiment, the propyl group includes an n-propyl group and an isopropyl group, and the butyl group includes an n-butyl group, an isobutyl group and a tert-butyl group.

In the present specification, the alkoxy group can be linear or branched. The number of carbon atoms of the alkoxy group is not particularly limited, but is preferably from 1 to 20. Specific examples thereof can include methoxy, ethoxy, n-propoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy and the like, but are not limited thereto.

In the present specification, the cycloalkyl group is not particularly limited, but preferably has 3 to 60 carbon atoms, and according to one embodiment, the number of carbon atoms of the cycloalkyl group is from 3 to 30. According to another embodiment, the number of carbon atoms of the cycloalkyl group is from 3 to 20. According to another embodiment, the number of carbon atoms of the cycloalkyl group is from 3 to 6. Specific examples thereof can include a cyclopropyl group, a cyclobutyl group, a cyclopentyl group, a cyclohexyl group, a cycloheptyl group, a cyclooctyl group and the like, but are not limited thereto.

In the present specification, the aryl group is not particularly limited, but preferably has 6 to 60 carbon atoms, and can be a monocyclic aryl group or a polycyclic aryl group. According to one embodiment, the number of carbon atoms of the aryl group is from 6 to 39. According to one embodiment, the number of carbon atoms of the aryl group is from 6 to 30. When the aryl group is a monocyclic aryl group, examples thereof can include a phenyl group, a biphenyl group, a terphenyl group, a quaterphenyl group and the like, but are not limited thereto. Examples of the polycyclic aryl group can include a naphthyl group, an anthracene group, a phenalene group

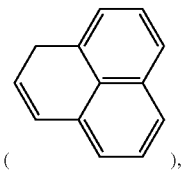
( ), a phenanthrene group, a pyrene group, a perylenyl group, a triphenyl group, a chrysene group, a fluorene group, a triphenylene group, a fluoranthene group and the like, but are not limited thereto.

In the present specification, the fluorene group can be substituted, and two substituents can bond to each other to form a spiro structure.

When the fluorene group is substituted, a spirofluorene group such as spirocyclopentanefluorene and spirobifluorene, or a substituted fluorene group such as a 9,9-dimethylfluorene group and a 9,9-diphenylfluorene group can be included. However, the structure is not limited thereto.

In the present specification, the heterocyclic group is a cyclic group including one or more of N, O, S and Si as a heteroatom, and although not particularly limited thereto, the number of carbon atoms is preferably from 2 to 60. According to one embodiment, the number of carbon atoms of the heterocyclic group is from 2 to 30. Examples of the heterocyclic group can include a pyridine group, a pyrrole group, a pyrimidine group, a quinoline group, a pyridazine group, a triazine group, a furan group, a thiophene group, an imidazole group, a pyrazole group, a dibenzofuran group, a dibenzothiophene group, a carbazole group, a benzocarbazole group, a benzonaphthofuran group, a benzonaphthothiophene group, an indenocarbazole group, an indolocarbazole group, a spirofluorenexanthene group

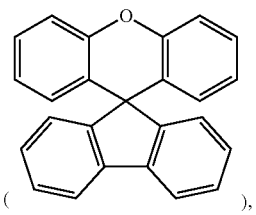
( ), a spirofluorenethioxanthene group

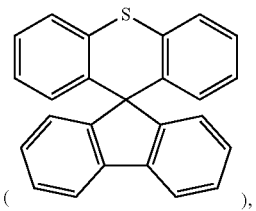 [SMILES: c1ccc2c(c1)Sc1ccccc1C21c2ccccc2-c2ccccc21]
( ), a 9,9-dimethylsilole group

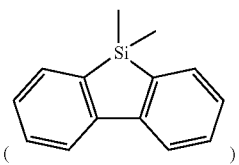
( )

and the like, but are not limited thereto.

In the present specification, the descriptions on the heterocyclic group provided above can be applied to the heteroaryl group except for being aromatic.

In the present specification, the descriptions on the cycloalkyl group provided above can be applied to the cycloalkylene group except for being divalent.

In the present specification, the descriptions on the aryl group provided above can be applied to the arylene group except for being divalent.

In the present specification, the descriptions on the heteroaryl group provided above can be applied to the heteroarylene group except for being divalent.

In the present specification, the dicyclic or higher condensed aryl group means a substituent formed by condensing two or more aromatic hydrocarbon rings, and examples thereof can include a naphthyl group, a phenanthrene group, a phenalene group, a triphenylene group, a fluoranthene group and the like, but are not limited thereto.

In the present specification, in the substituted or unsubstituted ring formed by bonding to adjacent groups, the "ring" means a hydrocarbon ring or a heteroring.

The hydrocarbon ring can be aromatic, aliphatic, or a condensed ring of aromatic and aliphatic, and can be selected from among the examples of the cycloalkyl group or the aryl group except for those that are not monovalent.

In the present specification, the descriptions on the aryl group provided above can be applied to the aromatic hydrocarbon ring except for those that are not monovalent.

The descriptions on the heterocyclic group provided above can be applied to the heteroring except for those that are not monovalent.

According to one embodiment of the present specification, X is O or S.

In one embodiment of the present specification, A1 to A3 are the same as or different from each other and each independently is N or CR, and one or more of A1 to A3 are N.

According to another embodiment, two or more of A1 to A3 are N, and the rest is CR.

In another embodiment, two or three of A1 to A3 are N, and the rest is CR.

According to one embodiment of the present specification, R is hydrogen, deuterium, a cyano group, a substituted or unsubstituted alkyl group having 1 to 20 carbon atoms, a substituted or unsubstituted alkoxy group having 1 to 20 carbon atoms, a substituted or unsubstituted aryloxy group having 6 to 30 carbon atoms, a substituted or unsubstituted cycloalkyl group having 3 to 30 carbon atoms, a substituted or unsubstituted aryl group having 6 to 30 carbon atoms, or a substituted or unsubstituted heterocyclic group having 2 to 30 carbon atoms.

According to another embodiment, R is hydrogen or deuterium.

In one embodiment of the present specification, one or more of R9 to R16 are linked to * of Chemical Formula 2; and R1 to R8, and the rest of R9 to R16 not linked to Chemical Formula 2, are the same as or different from each other, and each independently is hydrogen, deuterium, a cyano group, a nitro group, a carbonyl group, a substituted or unsubstituted trialkylsilyl group having 1 to 20 carbon atoms, a substituted or unsubstituted diarylboron group having 6 to 30 carbon atoms, a substituted or unsubstituted alkyl group having 1 to 20 carbon atoms, a substituted or unsubstituted alkoxy group having 1 to 20 carbon atoms, a substituted or unsubstituted aryloxy group having 6 to 30 carbon atoms, a substituted or unsubstituted cycloalkyl group having 3 to 30 carbon atoms, a substituted or unsubstituted aryl group having 6 to 30 carbon atoms, or a substituted or unsubstituted heterocyclic group having 2 to 30 carbon atoms and including one or more of O, S and N as a heteroatom, or bond to adjacent groups to form a substituted or unsubstituted benzene ring.

In another embodiment, one or more of R9 to R16 are linked to * of Chemical Formula 2; and R1 to R8, and the rest of R9 to R16 not linked to Chemical Formula 2, are the same as or different from each other, and each independently is hydrogen, deuterium, a cyano group, a carbonyl group, a trialkylsilyl group having 1 to 20 carbon atoms, an alkyl group having 1 to 20 carbon atoms unsubstituted or substituted with a halogen group, an aryloxy group having 6 to 30 carbon atoms, a cycloalkyl group having 3 to 30 carbon atoms, an aryl group having 6 to 30 carbon atoms unsubstituted or substituted with one or more of a cyano group, a diarylboron group having 6 to 30 carbon atoms, an alkyl group having 1 to 20 carbon atoms, an alkoxy group having 1 to 20 carbon atoms unsubstituted or substituted with a halogen group, and a heteroaryl group having 2 to 30 carbon atoms, or an heterocyclic group having 2 to 30 carbon atoms and including one or more of O, S and N as a heteroatom unsubstituted or substituted with an alkyl group having 1 to 20 carbon atoms, or bond to adjacent groups to form a substituted or unsubstituted benzene ring.

According to another embodiment, one or more of R9 to R16 are linked to * of Chemical Formula 2; and R1 to R8, and the rest of R9 to R16 not linked to Chemical Formula 2, are the same as or different from each other, and each independently is hydrogen, deuterium, a cyano group, a carbonyl group, a trimethylsilyl group, a methyl group that is unsubstituted or substituted with a halogen group, a propyl group, a butyl group, a phenoxy group, a cyclohexyl group, a phenyl group that is unsubstituted or substituted with a cyano group, a diphenylboron group, a methyl group, trifluoromethoxy group or a pyridine group, a biphenyl group, a naphthyl group, a dibenzofuran group, a carbazole group, a benzofuran group, or a methylbenzimidazole group, or bond to adjacent groups to form a benzene ring.

According to one embodiment of the present specification, in Chemical Formula 1, when adjacent two groups of R1 to R8, or two adjacent groups of R9 to R16 not linked to Chemical Formula 2, bond to each other to form a benzene ring, structures as follows can be obtained, however, the structure is not limited thereto:

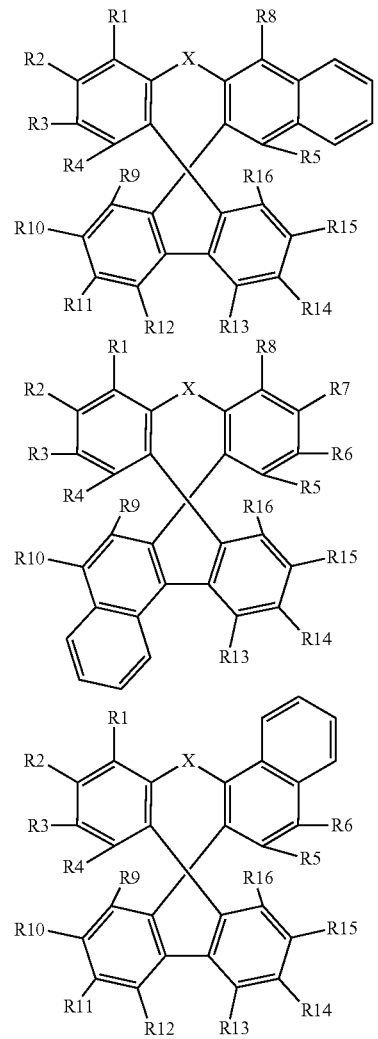

-continued

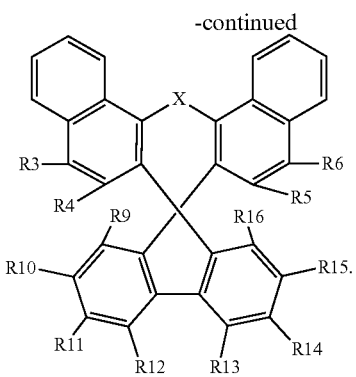

According to one embodiment of the present specification, one or more of R9 to R16 are linked to * of the following Chemical Formula 2.

According to one embodiment of the present specification, one or more of R9, R11, R14 or R16 are linked to * of the following Chemical Formula 2.

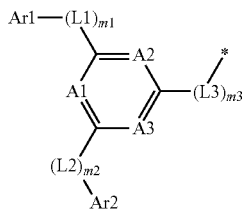

Chemical Formula 2

In Chemical Formula 2:
A1 to A3 are the same as or different from each other and each independently is N or CR, and one or more of A1 to A3 are N;
L1 and L2 are the same as or different from each other, and each independently is a direct bond, a substituted or unsubstituted cycloalkylene group, or a substituted or unsubstituted arylene group;
L3 is a direct bond, a substituted or unsubstituted cycloalkylene group, or a substituted or unsubstituted arylene group;
one or more of Ar1 and Ar2 are a substituted or unsubstituted dicyclic or higher condensed aryl group, and the rest are the same as or different from each other, and each independently is a substituted or unsubstituted aryl group or a substituted or unsubstituted heterocyclic group;
Rs are the same as or different from each other, and each independently is hydrogen, deuterium, a cyano group, a nitro group, a carbonyl group, a substituted or unsubstituted silyl group, a substituted or unsubstituted boron group, a substituted or unsubstituted alkyl group, a substituted or unsubstituted alkoxy group, a substituted or unsubstituted aryloxy group, a substituted or unsubstituted cycloalkyl group, a substituted or unsubstituted aryl group, or a substituted or unsubstituted heterocyclic group; and
m1 to m3 are each an integer of 0 to 3, and when m1 to m3 are each 2 or greater, two or more substituents in the parentheses are the same as or different from each other.

According to one embodiment of the present specification, L1 and L2 are the same as or different from each other, and each independently is a direct bond, a substituted or unsubstituted cycloalkylene group having 3 to 30 carbon atoms, or a substituted or unsubstituted arylene group having 6 to 60 carbon atoms.

According to another embodiment, L1 and L2 are the same as or different from each other, and each independently is a direct bond, a substituted or unsubstituted cycloalkylene group having 3 to 30 carbon atoms, or a substituted or unsubstituted arylene group having 6 to 30 carbon atoms.

In another embodiment, L1 and L2 are the same as or different from each other, and each independently is a direct bond, a substituted or unsubstituted cyclohexylene group, a substituted or unsubstituted phenylene group, a substituted or unsubstituted biphenylene group, a substituted or unsubstituted fluorenylene group, or a substituted or unsubstituted naphthylene group.

In another embodiment, L1 and L2 are the same as or different from each other, and each independently is a direct bond; a cyclohexylene group; a phenylene group that is unsubstituted or substituted with an alkyl group having 1 to 20 carbon atoms; a biphenylene group that is unsubstituted or substituted with an alkyl group having 1 to 20 carbon atoms; a fluorenylene group that is unsubstituted or substituted with an alkyl group having 1 to 20 carbon atoms; or a naphthylene group that is unsubstituted or substituted with an alkyl group having 1 to 20 carbon atoms.

According to another embodiment, L1 and L2 are the same as or different from each other, and each independently is a direct bond; a cyclohexylene group; a phenylene group that is unsubstituted or substituted with a methyl group; a biphenylene group that is unsubstituted or substituted with a methyl group; a fluorenylene group that is unsubstituted or substituted with a methyl group; or a naphthylene group that is unsubstituted or substituted with a methyl group.

In one embodiment of the present specification, L3 is a direct bond, a substituted or unsubstituted cycloalkylene group having 3 to 60 carbon atoms, or a substituted or unsubstituted arylene group having 6 to 60 carbon atoms.

According to another embodiment, L3 is a direct bond, a substituted or unsubstituted cycloalkylene group having 3 to 30 carbon atoms, or a substituted or unsubstituted arylene group having 6 to 30 carbon atoms.

In another embodiment, L3 is a direct bond, a substituted or unsubstituted cyclohexylene group, a substituted or unsubstituted phenylene group, a substituted or unsubstituted biphenylene group, a substituted or unsubstituted fluorenylene group, or a substituted or unsubstituted naphthylene group.

According to another embodiment, L3 is a direct bond; a phenylene group that is unsubstituted or substituted with an alkyl group having 1 to 20 carbon atoms; a biphenylene group that is unsubstituted or substituted with an alkyl group having 1 to 20 carbon atoms; a fluorenylene group that is unsubstituted or substituted with an alkyl group having 1 to 20 carbon atoms; or a naphthylene group that is unsubstituted or substituted with an alkyl group having 1 to 20 carbon atoms.

According to another embodiment, L3 is a direct bond; a cyclohexylene group; a phenylene group that is unsubstituted or substituted with a methyl group; a biphenylene group that is unsubstituted or substituted with a methyl group; a fluorenylene group that is unsubstituted or substituted with a methyl group; or a naphthylene group that is unsubstituted or substituted with a methyl group.

In Chemical Formula 1, the N-containing monocyclic ring and the spirofluorenexanthene are linked through L3, a linker, and when L3 is a divalent heterocyclic group, the heteroring excessively increases or decreases the LUMO value of the N-containing monocyclic ring since the heteroring has electron donor and acceptor ability excessively weighed chemically on one side resulting in significant changes in the electron injection ability or electron transfer ability to a light emitting layer when used in a device, and as a result, driving voltage, efficiency and lifetime properties of the device decline by breaking the balance between holes and electrons in the device.

In addition, when Ar1 and Ar2 are a monocyclic aryl group and L3 is a dicyclic or higher condensed aryl group in Chemical Formula 1 of the present application, steric hindrance (high degree of distortion) of the spirofluorenexanthene and the N-containing monocyclic ring are structurally induced resulting in weak bond strength between atoms in the molecule unlike a case of one or more of Ar1 and Ar2 including a dicyclic or higher condensed aryl group, and in addition thereto, the degree of overlap between molecular orbitals (HOMO and LUMO) in the molecule becomes small. This leads to results of poor device properties not only in terms of driving voltage and efficiency of a device, but, in particular, in terms of a lifetime.

According to one embodiment of the present specification, one or more of Ar1 and Ar2 are any one of the following structures, and the rest are the same as or different from each other, and each independently is a substituted or unsubstituted aryl group or a substituted or unsubstituted heterocyclic group:

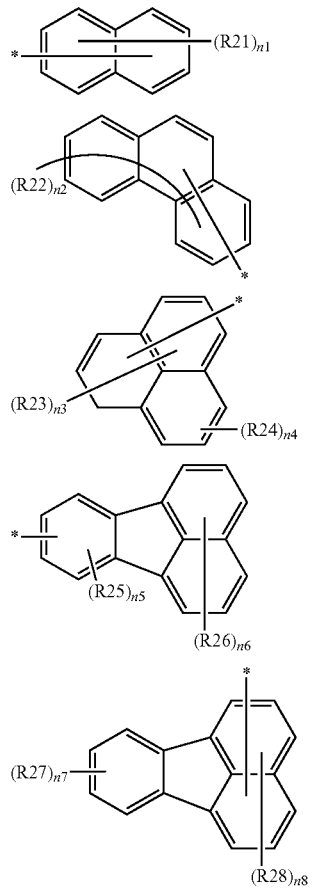

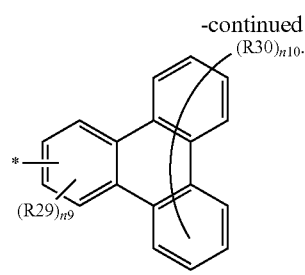

In the structures:

R21 to R30 are the same as or different from each other, and each independently is hydrogen, deuterium, a cyano group, a nitro group, a carbonyl group, a substituted or unsubstituted silyl group, a substituted or unsubstituted boron group, a substituted or unsubstituted alkyl group, a substituted or unsubstituted alkoxy group, a substituted or unsubstituted aryloxy group, a substituted or unsubstituted cycloalkyl group, a substituted or unsubstituted aryl group, or a substituted or unsubstituted heterocyclic group;

n1 is an integer of 0 to 7, n2 is an integer of 0 to 9, n3 and n6 are each an integer of 0 to 6, n4, n5 and n9 are each an integer of 0 to 3, n7 is an integer of 0 to 4, n8 is an integer of 0 to 5, n10 is an integer of 0 to 8, and when n1 to n10 are each 2 or greater, two or more substituents in the parentheses are the same as or different from each other, and

* means a linked site.

According to one embodiment of the present specification, one or more of Ar1 and Ar2 are a substituted or unsubstituted dicyclic or higher condensed aryl group, and the rest are a substituted or unsubstituted heterocyclic group.

According to one embodiment of the present specification, Ar1 and Ar2 are the same as or different from each other, and each independently is a substituted or unsubstituted dicyclic or higher condensed aryl group.

According to one embodiment of the present specification, one or more of Ar1 and Ar2 are a substituted or unsubstituted dicyclic or higher condensed aryl group having 12 to 60 carbon atoms, and the rest are the same as or different from each other, and each independently is a substituted or unsubstituted aryl group having 6 to 60 carbon atoms, or a substituted or unsubstituted heterocyclic group having 2 to 60 carbon atoms and including one or more of O, S, Si and N as a heteroatom.

According to one embodiment of the present specification, one or more of Ar1 and Ar2 are a substituted or unsubstituted dicyclic or higher condensed aryl group having 12 to 60 carbon atoms, and the rest are a substituted or unsubstituted heterocyclic group having 2 to 60 carbon atoms and including one or more of O, S, Si and N as a heteroatom.

According to one embodiment of the present specification, Ar1 and Ar2 are the same as or different from each other, and each independently is a substituted or unsubstituted dicyclic or higher condensed aryl group having 12 to 60 carbon atoms.

According to another embodiment, one or more of Ar1 and Ar2 are a substituted or unsubstituted dicyclic or higher condensed aryl group having 12 to 60 carbon atoms, and the rest are the same as or different from each other, and each independently is a substituted or unsubstituted aryl group having 6 to 30 carbon atoms, or a substituted or unsubstituted heterocyclic group having 2 to 30 carbon atoms and including one or more of O, S, Si and N as a heteroatom.

According to another embodiment, one or more of Ar1 and Ar2 are a substituted or unsubstituted dicyclic or higher condensed aryl group having 12 to 60 carbon atoms, and the rest are a substituted or unsubstituted heterocyclic group having 2 to 30 carbon atoms and including one or more of O, S, Si and N as a heteroatom.

According to another embodiment, one or more of Ar1 and Ar2 are a substituted or unsubstituted dicyclic or higher condensed aryl group having 12 to 60 carbon atoms, and the rest are the same as or different from each other, and each independently is an aryl group having 6 to 30 carbon atoms unsubstituted or substituted with one or more substituents selected from the group consisting of an alkyl group having 1 to 20 carbon atoms and a heteroaryl group having 2 to 30 carbon atoms, or an heterocyclic group having 2 to 30 carbon atoms and including one or more of O, S, N or Si as a heteroatom unsubstituted or substituted with one or more substituents selected from the group consisting of an alkyl group having 1 to 20 carbon atoms and a heteroaryl group having 2 to 30 carbon atoms. The heteroaryl group includes O, S, N or Si as a heteroatom.

According to another embodiment, one or more of Ar1 and Ar2 are a substituted or unsubstituted dicyclic or higher condensed aryl group having 12 to 60 carbon atoms, and the rest are a heterocyclic group having 2 to 30 carbon atoms and including one or more of O, S, N or Si as a heteroatom unsubstituted or substituted with one or more substituents selected from the group consisting of an alkyl group having 1 to 20 carbon atoms and a heteroaryl group having 2 to 30 carbon atoms. The heteroaryl group includes O, S, N or Si as a heteroatom.

In another embodiment, one or more of Ar1 and Ar2 are a substituted or unsubstituted naphthyl group, a substituted or unsubstituted phenanthrene group, a substituted or unsubstituted phenalene group, a substituted or unsubstituted triphenylene group, or a substituted or unsubstituted fluoranthene group, and the rest are the same as or different from each other, and each independently is a substituted or unsubstituted phenyl group, a substituted or unsubstituted biphenyl group, a substituted or unsubstituted terphenyl group, a substituted or unsubstituted silole group, a substituted or unsubstituted spirofluorenexanthene group

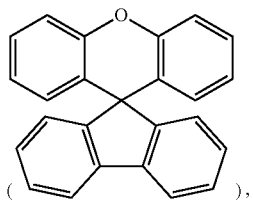

a substituted or unsubstituted spirofluorenethioxanthene group

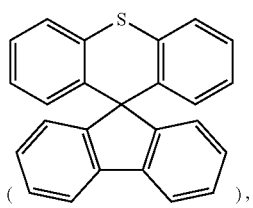

a substituted or unsubstituted dibenzofuran group, or a substituted or unsubstituted pyridine group.

In another embodiment, one or more of Ar1 and Ar2 are a substituted or unsubstituted naphthyl group, a substituted or unsubstituted phenanthrene group, a substituted or unsubstituted phenalene group, a substituted or unsubstituted triphenylene group, or a substituted or unsubstituted fluoranthene group, and the rest are a substituted or unsubstituted silole group, a substituted or unsubstituted spirofluorenexanthene group

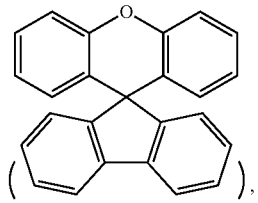

a substituted or unsubstituted spirofluorenethioxanthene group

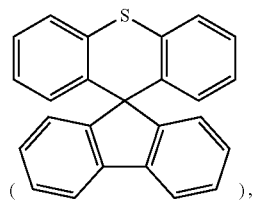

a substituted or unsubstituted dibenzofuran group, or a substituted or unsubstituted pyridine group.

In another embodiment, Ar1 and Ar2 are the same as or different from each other, and each independently is a substituted or unsubstituted naphthyl group, a substituted or unsubstituted phenanthrene group, a substituted or unsubstituted phenalene group, a substituted or unsubstituted triphenylene group, or a substituted or unsubstituted fluoranthene group.

According to another embodiment, one or more of Ar1 and Ar2 are a naphthyl group that is unsubstituted or substituted with one or more substituents selected from the group consisting of an alkyl group having 1 to 20 carbon atoms, an aryl group having 6 to 30 carbon atoms and a heterocyclic group having 2 to 30 carbon atoms; a phenanthrene group that is unsubstituted or substituted with one or more substituents selected from the group consisting of an alkyl group having 1 to 20 carbon atoms, an aryl group having 6 to 30 carbon atoms and a heterocyclic group having 2 to 30 carbon atoms; a phenalene group that is unsubstituted or substituted with one or more substituents selected from the group consisting of an alkyl group having 1 to 20 carbon atoms, an aryl group having 6 to 30 carbon atoms and a heterocyclic group having 2 to 30 carbon atoms; a triphenylene group that is unsubstituted or substituted with one or more substituents selected from the group consisting of an alkyl group having 1 to 20 carbon atoms, an aryl group having 6 to 30 carbon atoms and a heterocyclic group having 2 to 30 carbon atoms; or a fluoranthene group that is unsubstituted or substituted with one or more substituents selected from the group consisting of an alkyl group having 1 to 20 carbon atoms, an aryl group having 6 to 30 carbon atoms and a heterocyclic group having 2 to 30 carbon atoms, and the rest are the same as or different from each other, and each independently is a phenyl group that is unsubstituted or substituted with one or more substituents selected from the group consisting of an alkyl group having 1 to 20 carbon atoms and a heteroaryl group having 2 to 30 carbon atoms; a biphenyl group that is unsubstituted or substituted with one or more substituents selected from the group consisting of an alkyl group having 1 to 20 carbon atoms and a heteroaryl group having 2 to 30 carbon atoms; a terphenyl group that is unsubstituted or substituted with one or more substituents selected from the group consisting of an alkyl group having 1 to 20 carbon atoms and a heteroaryl group having 2 to 30 carbon atoms; a silole group that is unsubstituted or substituted with one or more substituents selected from the group consisting of an alkyl group having 1 to 20 carbon atoms and a heteroaryl group having 2 to 30 carbon atoms; a spirofluorenexanthene group

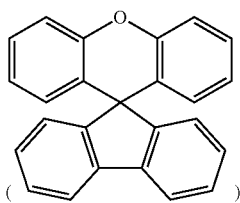 [SMILES: c1ccc2c(c1)Oc1ccccc1C21c2ccccc2-c2ccccc21]

unsubstituted or substituted with one or more substituents selected from the group consisting of an alkyl group having 1 to 20 carbon atoms and a heteroaryl group having 2 to 30 carbon atoms; a spirofluorenethioxanthene group

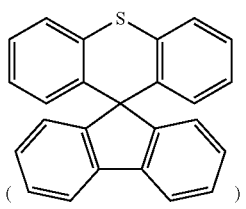 [SMILES: c1ccc2c(c1)Sc1ccccc1C21c2ccccc2-c2ccccc21]

unsubstituted or substituted with one or more substituents selected from the group consisting of an alkyl group having 1 to 20 carbon atoms and a heteroaryl group having 2 to 30 carbon atoms; a dibenzofuran group that is unsubstituted or substituted with one or more substituents selected from the group consisting of an alkyl group having 1 to 20 carbon atoms and a heteroaryl group having 2 to 30 carbon atoms; or a pyridine group that is unsubstituted or substituted with one or more substituents selected from the group consisting of an alkyl group having 1 to 20 carbon atoms and a heteroaryl group having 2 to 30 carbon atoms.

According to another embodiment, one or more of Ar1 and Ar2 are a naphthyl group that is unsubstituted or substituted with one or more substituents selected from the group consisting of an alkyl group having 1 to 20 carbon atoms, an aryl group having 6 to 30 carbon atoms and a heterocyclic group having 2 to 30 carbon atoms; a phenanthrene group that is unsubstituted or substituted with one or more substituents selected from the group consisting of an alkyl group having 1 to 20 carbon atoms, an aryl group having 6 to 30 carbon atoms and a heterocyclic group having 2 to 30 carbon atoms; a phenalene group that is unsubstituted or substituted with one or more substituents selected from the group consisting of an alkyl group having 1 to 20 carbon atoms, an aryl group having 6 to 30 carbon atoms and a heterocyclic group having 2 to 30 carbon atoms; a triphenylene group that is unsubstituted or substituted with one or more substituents selected from the group consisting of an alkyl group having 1 to 20 carbon atoms, an aryl group having 6 to 30 carbon atoms and a heterocyclic group having 2 to 30 carbon atoms; or a fluoranthene group that is unsubstituted or substituted with one or more substituents selected from the group consisting of an alkyl group having 1 to 20 carbon atoms, an aryl group having 6 to 30 carbon atoms and a heterocyclic group having 2 to 30 carbon atoms, and the rest are an silole group that is unsubstituted or substituted with one or more substituents selected from the group consisting of an alkyl group having 1 to 20 carbon atoms and a heteroaryl group having 2 to 30 carbon atoms; a spirofluorenexanthene group

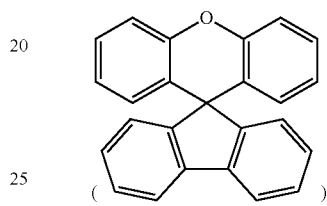

unsubstituted or substituted with one or more substituents selected from the group consisting of an alkyl group having 1 to 20 carbon atoms and a heteroaryl group having 2 to 30 carbon atoms; a spirofluorenethioxanthene group

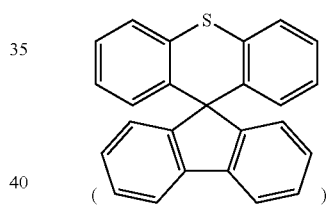

unsubstituted or substituted with one or more substituents selected from the group consisting of an alkyl group having 1 to 20 carbon atoms and a heteroaryl group having 2 to 30 carbon atoms; a dibenzofuran group that is unsubstituted or substituted with one or more substituents selected from the group consisting of an alkyl group having 1 to 20 carbon atoms and a heteroaryl group having 2 to 30 carbon atoms; or a pyridine group that is unsubstituted or substituted with one or more substituents selected from the group consisting of an alkyl group having 1 to 20 carbon atoms and a heteroaryl group having 2 to 30 carbon atoms.

According to another embodiment, Ar1 and Ar2 are the same as or different from each other, and each independently is a naphthyl group that is unsubstituted or substituted with one or more substituents selected from the group consisting of an alkyl group having 1 to 20 carbon atoms, an aryl group having 6 to 30 carbon atoms and a heterocyclic group having 2 to 30 carbon atoms; a phenanthrene group that is unsubstituted or substituted with one or more substituents selected from the group consisting of an alkyl group having 1 to 20 carbon atoms, an aryl group having 6 to 30 carbon atoms and a heterocyclic group having 2 to 30 carbon atoms; a phenalene group that is unsubstituted or substituted with one or more substituents selected from the group consisting of an alkyl group having 1 to 20 carbon atoms, an aryl group having 6 to 30 carbon atoms and a heterocyclic group having 2 to 30 carbon atoms; a triphenylene group that is unsubstituted or substituted with one or more substituents selected from the group consisting of an alkyl group having 1 to 20 carbon atoms, an aryl group having 6 to 30 carbon atoms and a heterocyclic group having 2 to 30 carbon atoms; or a fluoranthene group that is unsubstituted or substituted with one or more substituents selected from the group consisting of an alkyl group having 1 to 20 carbon atoms, an aryl group having 6 to 30 carbon atoms and a heterocyclic group having 2 to 30 carbon atoms.

According to another embodiment, one or more of Ar1 and Ar2 are a naphthyl group that is unsubstituted or substituted with one or more substituents selected from the group consisting of methyl, phenyl, naphthyl and pyridine; a phenanthrene group that is unsubstituted or substituted with one or more substituents selected from the group consisting of methyl, phenyl, naphthyl and pyridine; a phenalene group that is unsubstituted or substituted with one or more substituents selected from the group consisting of methyl, phenyl, naphthyl and pyridine; a triphenylene group that is unsubstituted or substituted with one or more substituents selected from the group consisting of methyl, phenyl, naphthyl and pyridine; or a fluoranthene group that is unsubstituted or substituted with one or more substituents selected from the group consisting of methyl, phenyl, naphthyl and pyridine, and the rest are the same as or different from each other, and each independently is a phenyl group that is unsubstituted or substituted with a dibenzofuran group or a pyridine group; a biphenyl group; a terphenyl group that is unsubstituted or substituted with a methyl group or a phenyl group; a 9,9-dimethylsilole group; a spirofluorenexanthene group

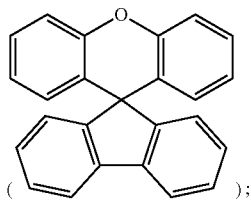 [SMILES: c1ccc2c(c1)Oc1ccccc1C21c2ccccc2-c2ccccc21]

a spirofluorenethioxanthene group

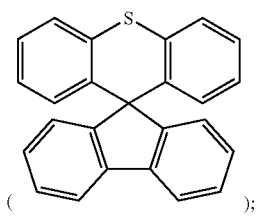 [SMILES: c1ccc2c(c1)Sc1ccccc1C21c2ccccc2-c2ccccc21]

a dibenzofuran group; or a pyridine group.

According to another embodiment, one or more of Ar1 and Ar2 are a naphthyl group that is unsubstituted or substituted with one or more substituents selected from the group consisting of methyl, phenyl, naphthyl and pyridine; a phenanthrene group that is unsubstituted or substituted with one or more substituents selected from the group consisting of methyl, phenyl, naphthyl and pyridine; a phenalene group that is unsubstituted or substituted with one or more substituents selected from the group consisting of methyl, phenyl, naphthyl and pyridine; a triphenylene group that is unsubstituted or substituted with one or more substituents selected from the group consisting of methyl, phenyl, naphthyl and pyridine; or a fluoranthene group that is unsubstituted or substituted with one or more substituents selected from the group consisting of methyl, phenyl, naphthyl and pyridine, and the rest are a 9,9-dimethylsilole group; a spirofluorenexanthene group

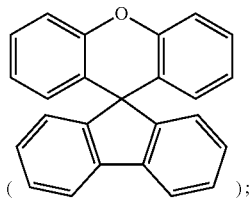

a spirofluorenethioxanthene group

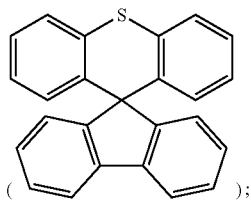 [SMILES: c1ccc2c(c1)Sc1ccccc1C21c2ccccc2-c2ccccc21]

a dibenzofuran group; or a pyridine group.

According to another embodiment, Ar1 and Ar2 are the same as or different from each other, and each independently is a naphthyl group that is unsubstituted or substituted with one or more substituents selected from the group consisting of methyl, phenyl, naphthyl and pyridine; a phenanthrene group that is unsubstituted or substituted with one or more substituents selected from the group consisting of methyl, phenyl, naphthyl and pyridine; a phenalene group that is unsubstituted or substituted with one or more substituents selected from the group consisting of methyl, phenyl, naphthyl and pyridine; a triphenylene group that is unsubstituted or substituted with one or more substituents selected from the group consisting of methyl, phenyl, naphthyl and pyridine; or a fluoranthene group that is unsubstituted or substituted with one or more substituents selected from the group consisting of methyl, phenyl, naphthyl and pyridine.

According to one embodiment of the present specification, one or more of Ar1 and Ar2 are a substituted or unsubstituted dicyclic or higher condensed aryl group. When including an N-type heteroring (ex. cyclic compound including N atom) instead of the dicyclic or higher condensed aryl group, electron affinity becomes too high as well as LUMO of the N-containing monocyclic ring becomes too low, and when the compound is included in a layer (ex. electron transfer layer) between a light emitting layer and a cathode of an organic light emitting device according to one embodiment of the present specification, an electron transfer ability to the light emitting layer or a hole blocking layer is reduced increasing a barrier to the light emitting layer, and as a result, an increase in the driving voltage, a decrease in the efficiency and a decrease in the lifetime occurs in the device. In addition, the compound in which a P-type heteroring or monocyclic aryl group bonds instead of the dicyclic or higher condensed aryl group causes a decrease in the device lifetime due to a relatively small difference ($\Delta EST$) between a singlet energy (S1) value and a triplet energy (T1) value.

According to one embodiment of the present specification, Chemical Formula 1 is any one of the following Chemical Formulae 3 to 8:
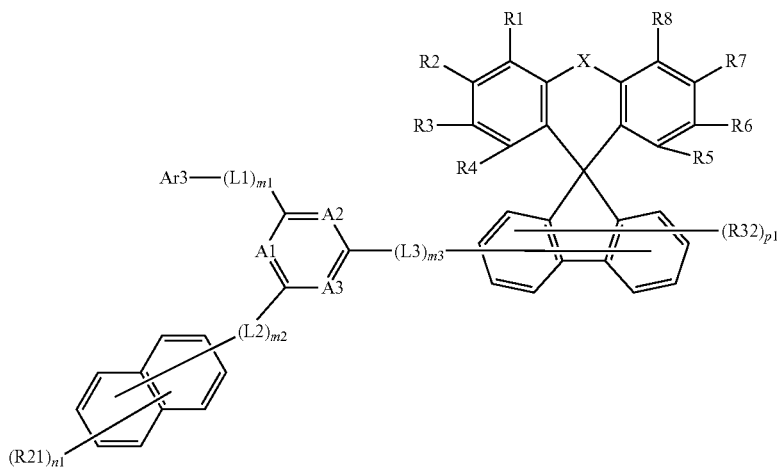
Chemical Formula 3
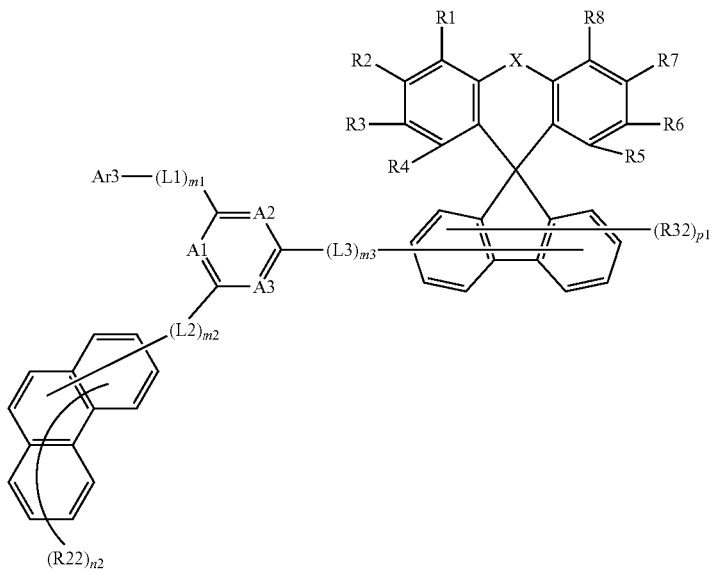
Chemical Formula 4
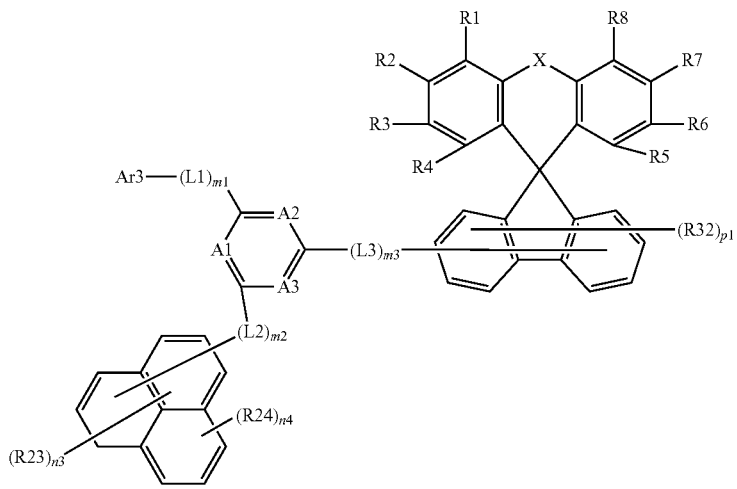
Chemical Formula 5

Chemical Formula 6
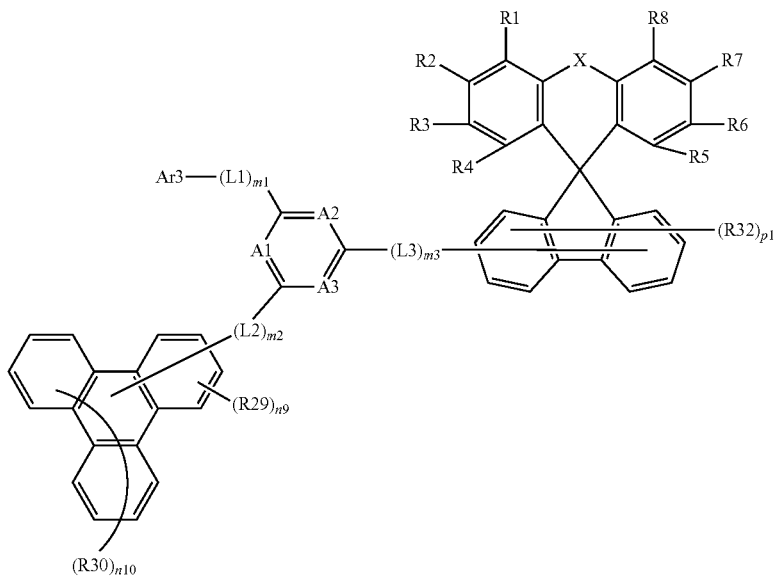
Chemical Formula 7
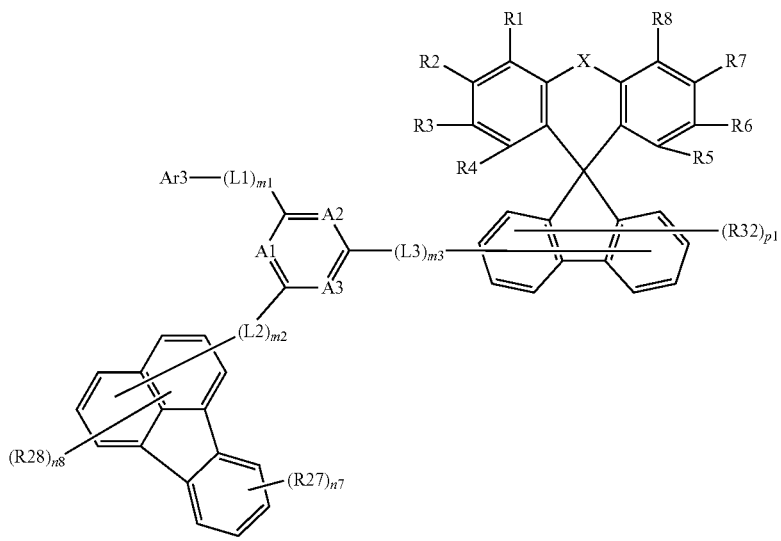
Chemical Formula 8
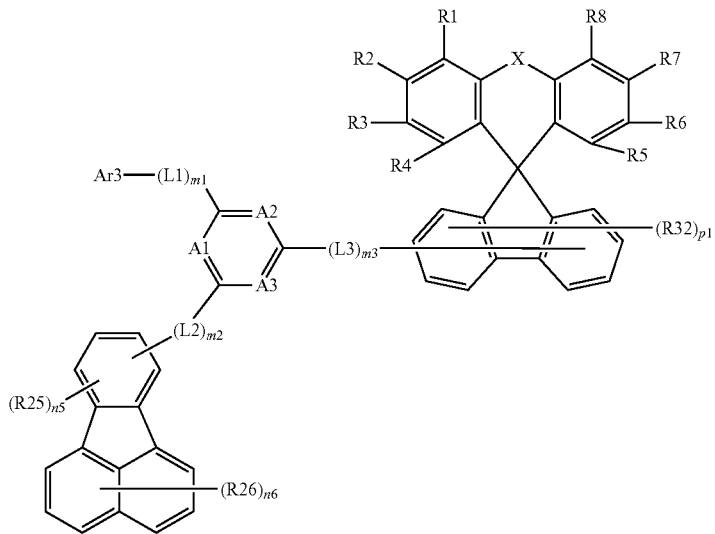

wherein in Chemical Formulae 3 to 8:
X, R1 to R8, A1 to A3, L1 to L3 and m1 to m3 have the same definitions as in Chemical Formula 1;
Ar3 is a substituted or unsubstituted dicyclic or higher condensed aryl group, a substituted or unsubstituted monocyclic aryl group, or a substituted or unsubstituted heterocyclic group;
R21 to R30 are the same as or different from each other, and each independently is hydrogen, deuterium, a cyano group, a nitro group, a carbonyl group, a substituted or unsubstituted silyl group, a substituted or unsubstituted boron group, a substituted or unsubstituted alkyl group, a substituted or unsubstituted alkoxy group, a substituted or unsubstituted aryloxy group, a substituted or unsubstituted cycloalkyl group, a substituted or unsubstituted aryl group, or a substituted or unsubstituted heterocyclic group;
R32 is hydrogen, deuterium, a cyano group, a nitro group, a carbonyl group, a substituted or unsubstituted silyl group, a substituted or unsubstituted boron group, a substituted or unsubstituted alkyl group, a substituted or unsubstituted alkoxy group, a substituted or unsubstituted aryloxy group, a substituted or unsubstituted cycloalkyl group, a substituted or unsubstituted aryl group, or a substituted or unsubstituted heterocyclic group, or bonds to adjacent groups to form a substituted or unsubstituted benzene ring;
n1 is an integer of 0 to 7, n2 is an integer of 0 to 9, n3 and n6 are each an integer of 0 to 6, n4, n5 and n9 are each an integer of 0 to 3, n7 is an integer of 0 to 4, n8 is an integer of 0 to 5, n10 is an integer of 0 to 8, and when n1 to n10 are each 2 or greater, two or more substituents in the parentheses are the same as or different from each other; and
p1 is an integer of 0 to 7, and when p1 is 2 or greater, two or more R32s are the same as or different from each other.

According to one embodiment of the present specification, Ar3 is a substituted or unsubstituted dicyclic or higher condensed aryl group, a substituted or unsubstituted monocyclic aryl group, or a substituted or unsubstituted heterocyclic group.

According to one embodiment of the present specification, Ar3 is a substituted or unsubstituted dicyclic or higher condensed aryl group having 12 to 60 carbon atoms, a substituted or unsubstituted monocyclic aryl group having 6 to 60 carbon atoms, or a substituted or unsubstituted heterocyclic group having 2 to 60 carbon atoms and including one or more of O, S, Si and N as a heteroatom.

According to another embodiment, Ar3 is a substituted or unsubstituted dicyclic or higher condensed aryl group having 12 to 60 carbon atoms, a substituted or unsubstituted monocyclic aryl group having 6 to 30 carbon atoms, or a substituted or unsubstituted heterocyclic group having 2 to 30 carbon atoms and including one or more of O, S, Si and N as a heteroatom.

According to another embodiment, Ar3 is a substituted or unsubstituted dicyclic or higher condensed aryl group having 12 to 60 carbon atoms; a monocyclic aryl group having 6 to 30 carbon atoms that are unsubstituted or substituted with one or more substituents selected from the group consisting of an alkyl group having 1 to 20 carbon atoms and a heteroaryl group having 2 to 30 carbon atoms; or a heterocyclic group having 2 to 30 carbon atoms and including one or more of O, S, N or Si as a heteroatom and the heterocyclic group is unsubstituted or substituted with one or more substituents selected from the group consisting of an alkyl group having 1 to 20 carbon atoms and a heteroaryl group having 2 to 30 carbon atoms. The heteroaryl group includes O, S, N or Si as a heteroatom.

In another embodiment, Ar3 is a substituted or unsubstituted naphthyl group, a substituted or unsubstituted phenanthrene group, a substituted or unsubstituted phenalene group, a substituted or unsubstituted triphenylene group, a substituted or unsubstituted fluoranthene group, a substituted or unsubstituted phenyl group, a substituted or unsubstituted biphenyl group, a substituted or unsubstituted terphenyl group; a substituted or unsubstituted silole group, a substituted or unsubstituted spirofluorenexanthene group

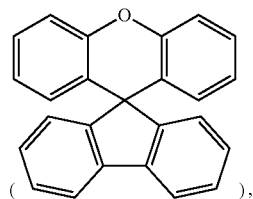

a substituted or unsubstituted spirofluorenethioxanthene group

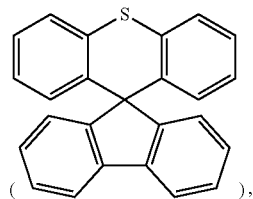

a substituted or unsubstituted dibenzofuran group, or a substituted or unsubstituted pyridine group.

According to another embodiment, Ar3 is a naphthyl group that is unsubstituted or substituted with one or more substituents selected from the group consisting of an alkyl group having 1 to 20 carbon atoms, an aryl group having 6 to 30 carbon atoms and a heterocyclic group having 2 to 30 carbon atoms; a phenanthrene group that is unsubstituted or substituted with one or more substituents selected from the group consisting of an alkyl group having 1 to 20 carbon atoms, an aryl group having 6 to 30 carbon atoms and a heterocyclic group having 2 to 30 carbon atoms; a phenalene group that is unsubstituted or substituted with one or more substituents selected from the group consisting of an alkyl group having 1 to 20 carbon atoms, an aryl group having 6 to 30 carbon atoms and a heterocyclic group having 2 to 30 carbon atoms; a triphenylene group that is unsubstituted or substituted with one or more substituents selected from the group consisting of an alkyl group having 1 to 20 carbon atoms, an aryl group having 6 to 30 carbon atoms and a heterocyclic group having 2 to 30 carbon atoms; a fluoranthene group that is unsubstituted or substituted with one or more substituents selected from the group consisting of an alkyl group having 1 to 20 carbon atoms, an aryl group having 6 to 30 carbon atoms and a heterocyclic group having 2 to 30 carbon atoms; a phenyl group that is unsubstituted or substituted with one or more substituents selected from the group consisting of an alkyl group having 1 to 20 carbon atoms and a heteroaryl group having 2 to 30 carbon atoms; a biphenyl group that is unsubstituted or substituted with one or more substituents selected from the group consisting of an alkyl group having 1 to 20 carbon atoms and a heteroaryl group having 2 to 30 carbon atoms; a terphenyl group that is unsubstituted or substituted with one or more substituents selected from the group consisting of an alkyl group having 1 to 20 carbon atoms and a heteroaryl group having 2 to 30 carbon atoms; a silole group that is unsubstituted or substituted with one or more substituents selected from the group consisting of an alkyl group having 1 to 20 carbon atoms and a heteroaryl group having 2 to 30 carbon atoms; a spirofluorenexanthene group

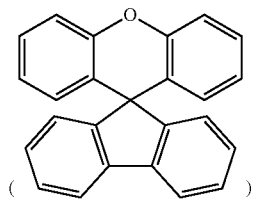 [SMILES: c1ccc2c(c1)Oc1ccccc1C21c2ccccc2-c2ccccc21]

that is unsubstituted or substituted with one or more substituents selected from the group consisting of an alkyl group having 1 to 20 carbon atoms and a heteroaryl group having 2 to 30 carbon atoms; a spirofluorenethioxanthene group

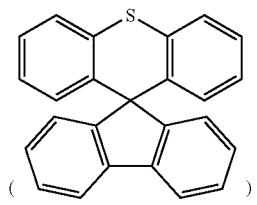 [SMILES: c1ccc2c(c1)Sc1ccccc1C21c2ccccc2-c2ccccc21]

that is unsubstituted or substituted with one or more substituents selected from the group consisting of an alkyl group having 1 to 20 carbon atoms and a heteroaryl group having 2 to 30 carbon atoms; a dibenzofuran group that is unsubstituted or substituted with one or more substituents selected from the group consisting of an alkyl group having 1 to 20 carbon atoms and a heteroaryl group having 2 to 30 carbon atoms; or a pyridine group that is unsubstituted or substituted with one or more substituents selected from the group consisting of an alkyl group having 1 to 20 carbon atoms and a heteroaryl group having 2 to 30 carbon atoms.

According to another embodiment, Ar3 is a naphthyl group that is unsubstituted or substituted with one or more substituents selected from the group consisting of methyl, phenyl, naphthyl and pyridine; a phenanthrene group that is unsubstituted or substituted with one or more substituents selected from the group consisting of methyl, phenyl, naphthyl and pyridine; a phenalene group that is unsubstituted or substituted with one or more substituents selected from the group consisting of methyl, phenyl, naphthyl and pyridine; a triphenylene group that is unsubstituted or substituted with one or more substituents selected from the group consisting of methyl, phenyl, naphthyl and pyridine; a fluoranthene group that is unsubstituted or substituted with one or more substituents selected from the group consisting of methyl, phenyl, naphthyl and pyridine; a phenyl group that is unsubstituted or substituted with a dibenzofuran group or a pyridine group; a biphenyl group; a terphenyl group that is unsubstituted or substituted with a methyl group or a phenyl group; a 9,9-dimethylsilole group; a spirofluorenexanthene group

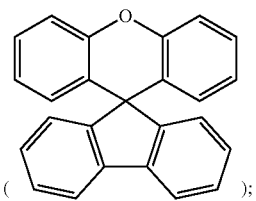

a spirofluorenethioxanthene group

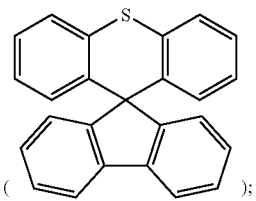

a dibenzofuran group; or a pyridine group.

According to one embodiment of the present specification, R21 to R30 are the same as or different from each other, and each independently is hydrogen, deuterium, a substituted or unsubstituted alkyl group having 1 to 20 carbon atoms, a substituted or unsubstituted aryl group having 6 to 30 carbon atoms, or a substituted or unsubstituted heterocyclic group having 2 to 60 carbon atoms and including O, S, N or Si as a heteroatom.

In another embodiment, R21 to R30 are the same as or different from each other, and each independently is hydrogen, deuterium; a substituted or unsubstituted methyl group, a substituted or unsubstituted phenyl group, a substituted or unsubstituted biphenyl group, a substituted or unsubstituted naphthyl group, or a substituted or unsubstituted pyridine group.

According to another embodiment, R21 to R30 are the same as or different from each other, and each independently is hydrogen, deuterium, a methyl group, a phenyl group, a biphenyl group, a naphthyl group, or a pyridine group.

According to another embodiment, n1 to n10 are each 0 or 1.

According to one embodiment of the present specification, R32 has the same definition as the rest of R9 to R16 that are not linked to Chemical Formula 2 as described above.

According to one embodiment of the present specification, in Chemical Formula 3, Ar3 is a substituted or unsubstituted dicyclic or higher condensed aryl group or a substituted or unsubstituted heterocyclic group.

According to one embodiment of the present specification, in Chemical Formula 3, Ar3 is a substituted or unsubstituted dicyclic or higher condensed aryl group having 12 to 60 carbon atoms, or a substituted or unsubstituted heterocyclic group having 2 to 60 carbon atoms and including one or more of O, S, Si and N as a heteroatom.

According to one embodiment of the present specification, in Chemical Formula 3, Ar3 is a substituted or unsubstituted dicyclic or higher condensed aryl group having 12 to 60 carbon atoms, or a substituted or unsubstituted heterocyclic group having 2 to 30 carbon atoms and including one or more of O, S, Si and N as a heteroatom.

According to one embodiment of the present specification, in Chemical Formula 3, Ar3 is a substituted or unsubstituted dicyclic or higher condensed aryl group having 12 to 60 carbon atoms, or a heterocyclic group having 2 to 30 carbon atoms and including one or more of O, S, N or Si as a heteroatom and the heterocyclic group is unsubstituted or substituted with one or more substituents selected from the group consisting of an alkyl group having 1 to 20 carbon atoms and a heteroaryl group having 2 to 30 carbon atoms. The heteroaryl group includes O, S, N or Si as a heteroatom.

According to one embodiment of the present specification, in Chemical Formula 3, Ar3 is a substituted or unsubstituted naphthyl group, a substituted or unsubstituted phenanthrene group; a substituted or unsubstituted phenalene group, a substituted or unsubstituted triphenylene group, a substituted or unsubstituted fluoranthene group, a substituted or unsubstituted silole group, a substituted or unsubstituted spirofluorenexanthene group

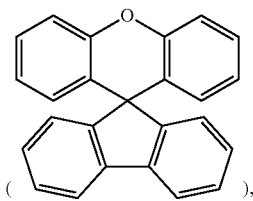 [SMILES: c1ccc2c(c1)Oc1ccccc1C21c2ccccc2-c2ccccc21]

a substituted or unsubstituted spirofluorenethioxanthene group

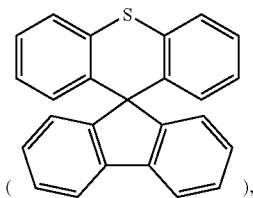 [SMILES: c1ccc2c(c1)Sc1ccccc1C21c2ccccc2-c2ccccc21]

a substituted or unsubstituted dibenzofuran group, or a substituted or unsubstituted pyridine group.

According to one embodiment of the present specification, in Chemical Formula 3, Ar3 is a naphthyl group that is unsubstituted or substituted with one or more substituents selected from the group consisting of an alkyl group having 1 to 20 carbon atoms, an aryl group having 6 to 30 carbon atoms and a heterocyclic group having 2 to 30 carbon atoms; a phenanthrene group that is unsubstituted or substituted with one or more substituents selected from the group consisting of an alkyl group having 1 to 20 carbon atoms, an aryl group having 6 to 30 carbon atoms and a heterocyclic group having 2 to 30 carbon atoms; a phenalene group that is unsubstituted or substituted with one or more substituents selected from the group consisting of an alkyl group having 1 to 20 carbon atoms, an aryl group having 6 to 30 carbon atoms and a heterocyclic group having 2 to 30 carbon atoms; a triphenylene group that is unsubstituted or substituted with one or more substituents selected from the group consisting of an alkyl group having 1 to 20 carbon atoms, an aryl group having 6 to 30 carbon atoms and a heterocyclic group having 2 to 30 carbon atoms; a fluoranthene group that is unsubstituted or substituted with one or more substituents selected from the group consisting of an alkyl group having 1 to 20 carbon atoms, an aryl group having 6 to 30 carbon atoms and a heterocyclic group having 2 to 30 carbon atoms; a silole group that is unsubstituted or substituted with one or more substituents selected from the group consisting of an alkyl group having 1 to 20 carbon atoms and a heteroaryl group having 2 to 30 carbon atoms; a spirofluorenexanthene group

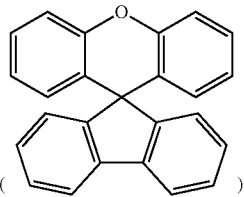 [SMILES: c1ccc2c(c1)Oc1ccccc1C21c2ccccc2-c2ccccc21]

that is unsubstituted or substituted with one or more substituents selected from the group consisting of an alkyl group having 1 to 20 carbon atoms and a heteroaryl group having 2 to 30 carbon atoms; a spirofluorenethioxanthene group

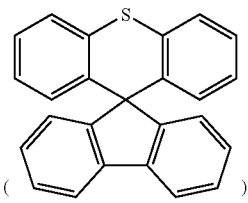 [SMILES: c1ccc2c(c1)Sc1ccccc1C21c2ccccc2-c2ccccc21]

that is unsubstituted or substituted with one or more substituents selected from the group consisting of an alkyl group having 1 to 20 carbon atoms and a heteroaryl group having 2 to 30 carbon atoms; a dibenzofuran group that is unsubstituted or substituted with one or more substituents selected from the group consisting of an alkyl group having 1 to 20 carbon atoms and a heteroaryl group having 2 to 30 carbon atoms; or a pyridine group that is unsubstituted or substituted with one or more substituents selected from the group consisting of an alkyl group having 1 to 20 carbon atoms and a heteroaryl group having 2 to 30 carbon atoms.

According to one embodiment of the present specification, in Chemical Formula 3, Ar3 is a naphthyl group that is unsubstituted or substituted with one or more substituents selected from the group consisting of methyl, phenyl, naphthyl and pyridine; a phenanthrene group that is unsubstituted or substituted with one or more substituents selected from the group consisting of methyl, phenyl, naphthyl and pyridine; a phenalene group that is unsubstituted or substituted with one or more substituents selected from the group consisting of methyl, phenyl, naphthyl and pyridine; a triphenylene group that is unsubstituted or substituted with one or more substituents selected from the group consisting of methyl, phenyl, naphthyl and pyridine; a fluoranthene group that is unsubstituted or substituted with one or more substituents selected from the group consisting of methyl, phenyl, naphthyl and pyridine; a 9,9-dimethylsilole group; a spirofluorenexanthene group

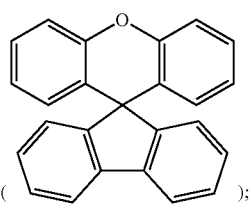 [SMILES: c1ccc2c(c1)Oc1ccccc1C21c2ccccc2-c2ccccc21]

( );

a spirofluorenethioxanthene group

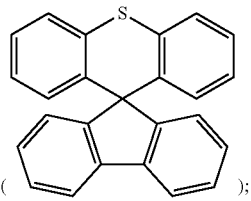 [SMILES: c1ccc2c(c1)Sc1ccccc1C21c2ccccc2-c2ccccc21]

( );

a dibenzofuran group; or a pyridine group.

According to one embodiment of the present specification, Chemical Formula 3 is the following Chemical Formula 3-1:

Chemical Formula 3-1

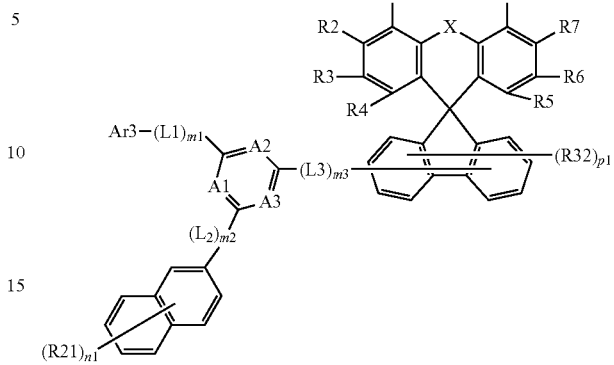

wherein in Chemical Formula 3-1, the substituents have the same definitions as in Chemical Formula 3.

According to one embodiment of the present specification, a compound of Chemical Formula 1 is any one of the following compounds:

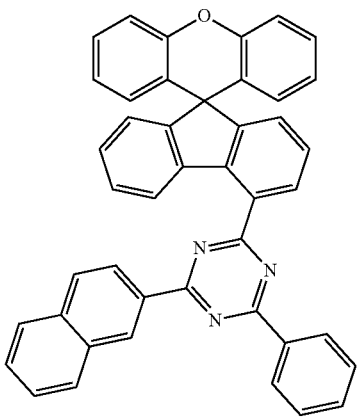 [SMILES: c1ccc(-c2nc(-c3ccc4ccccc4c3)nc(-c3cccc4c3-c3ccccc3C43c4ccccc4Oc4ccccc43)n2)cc1]

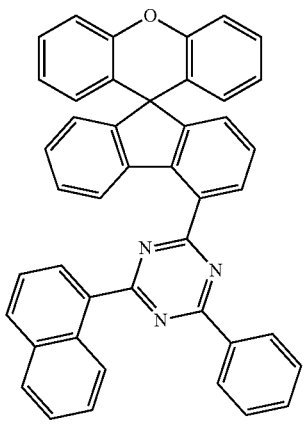 [SMILES: c1ccc(-c2nc(-c3cccc4c3-c3ccccc3C43c4ccccc4Oc4ccccc43)nc(-c3cccc4ccccc34)n2)cc1]

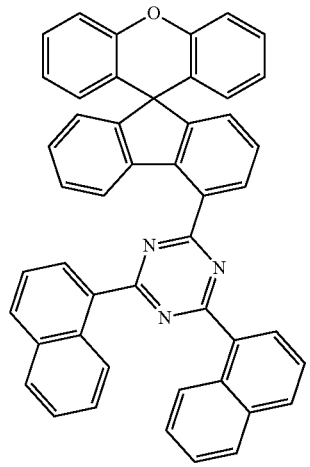 [SMILES: c1ccc2c(c1)Oc1ccccc1C21c2ccccc2-c2c(-c3nc(-c4cccc5ccccc45)nc(-c4cccc5ccccc45)n3)cccc21]

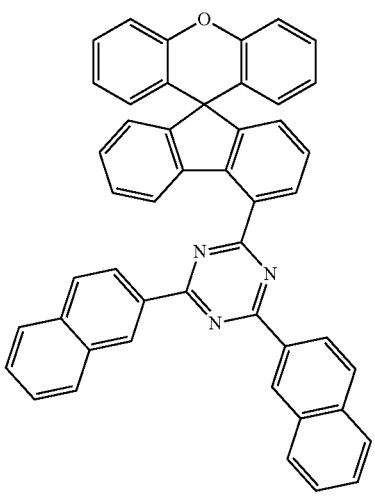 [SMILES: c1ccc2c(c1)Oc1ccccc1C21c2ccccc2-c2c(-c3nc(-c4ccc5ccccc5c4)nc(-c4ccc5ccccc5c4)n3)cccc21]

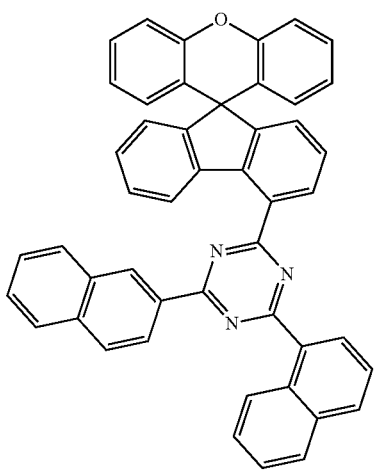

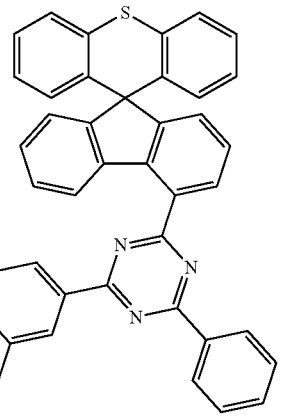

33
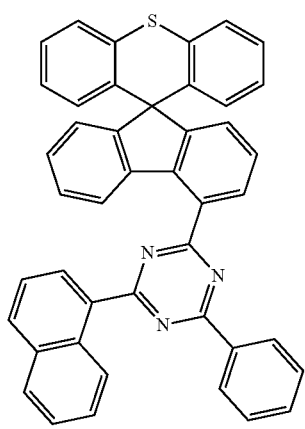
-continued
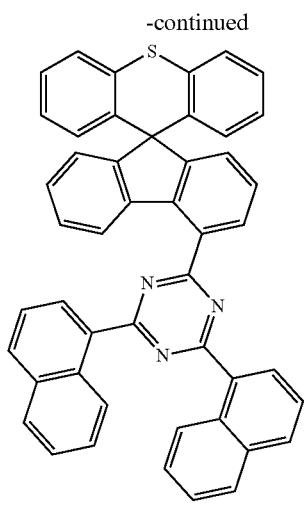
34
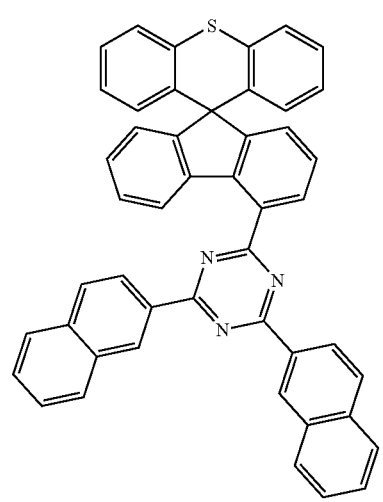
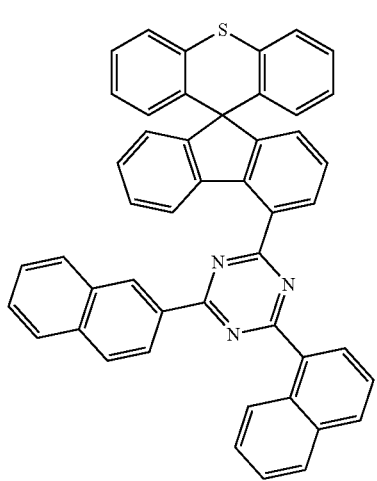
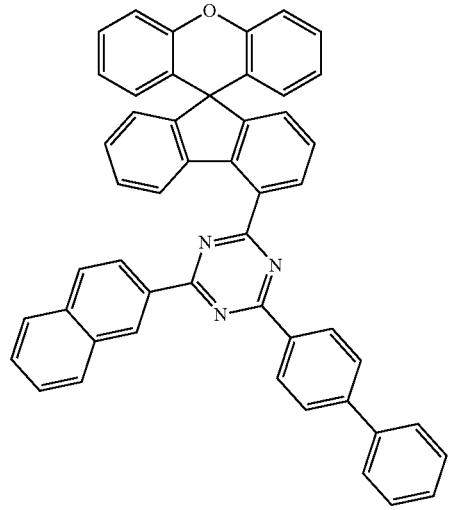

35
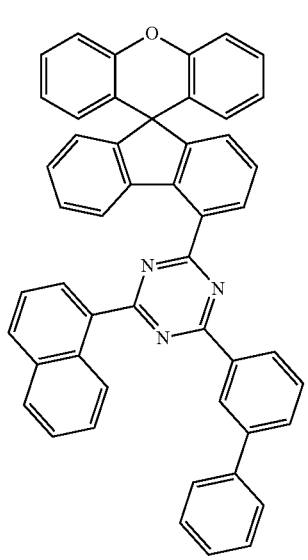 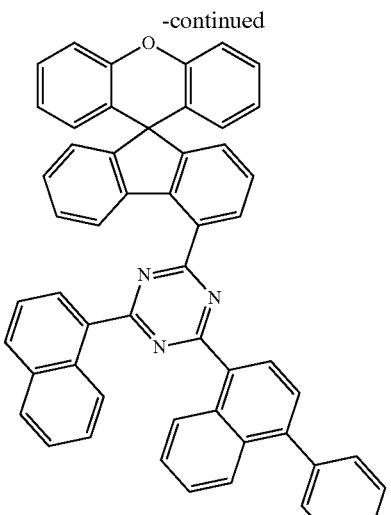
-continued
36
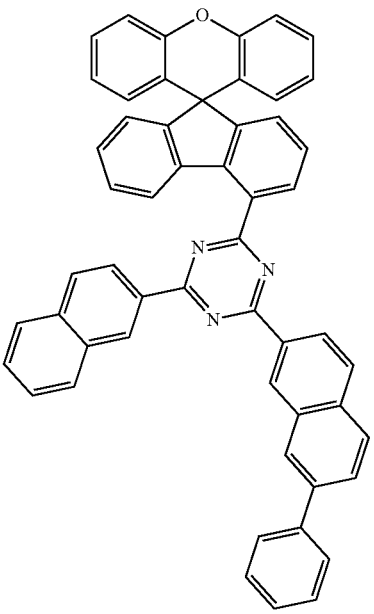
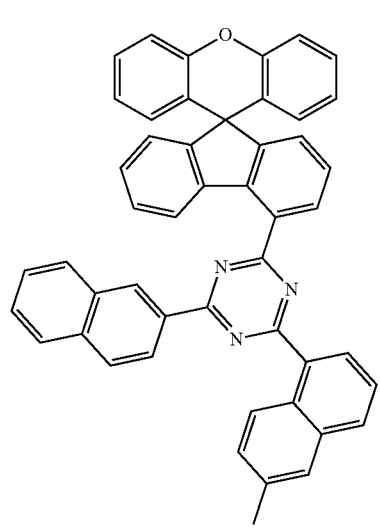 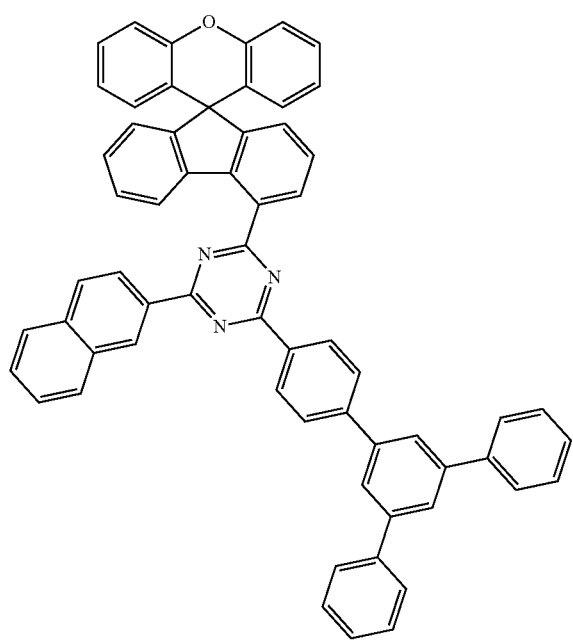

-continued
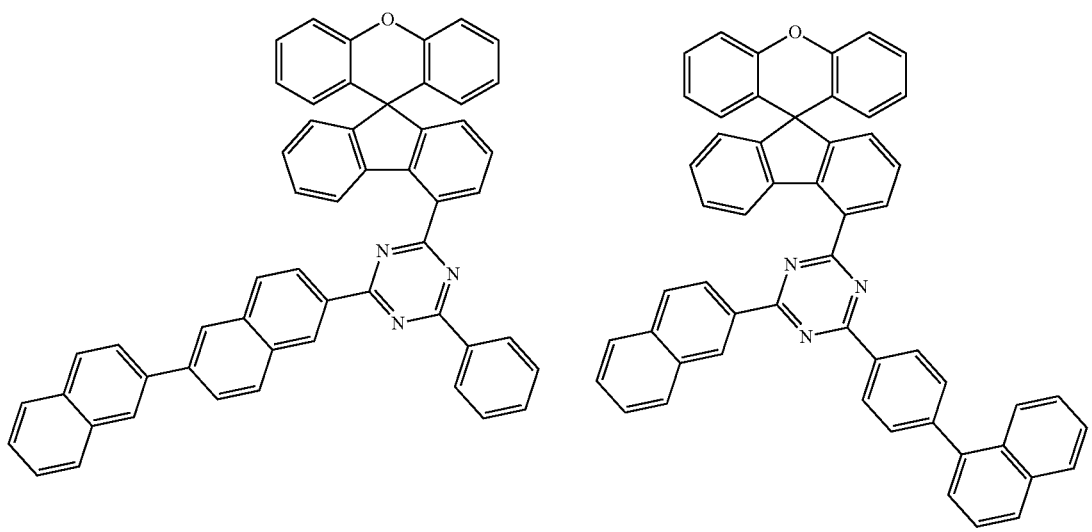
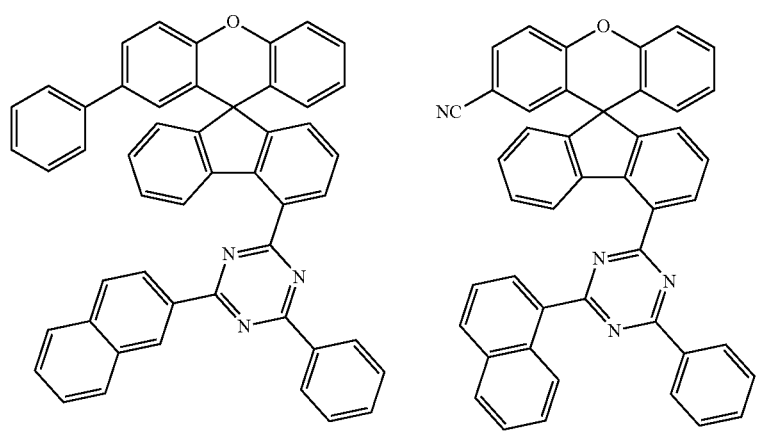
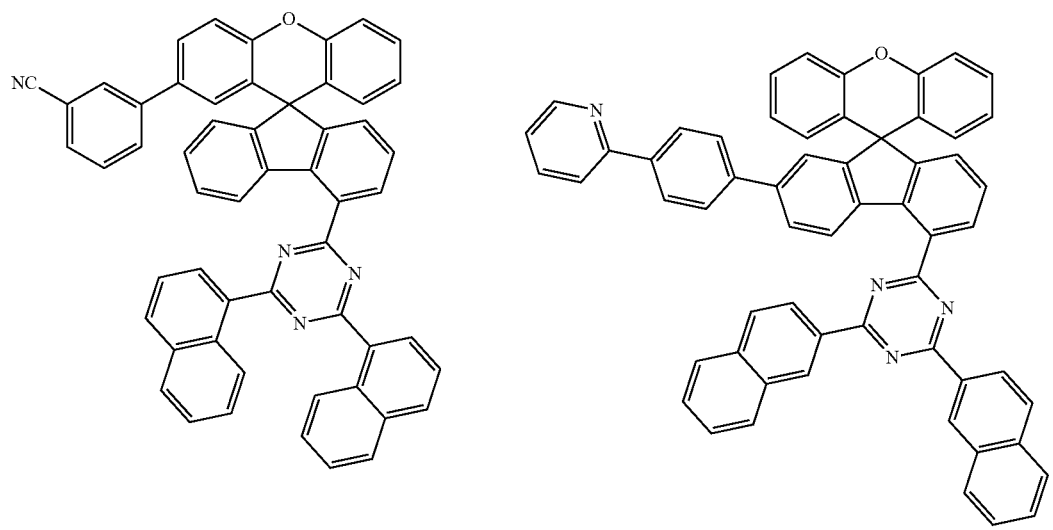

-continued
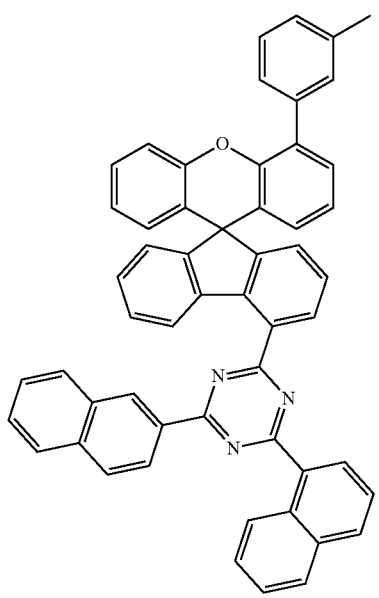
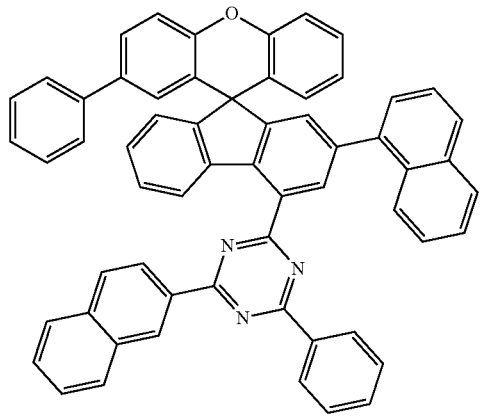
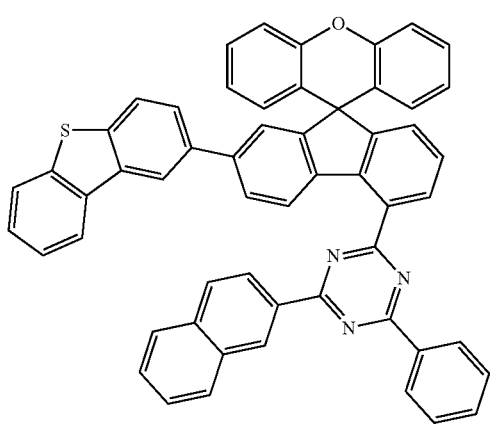
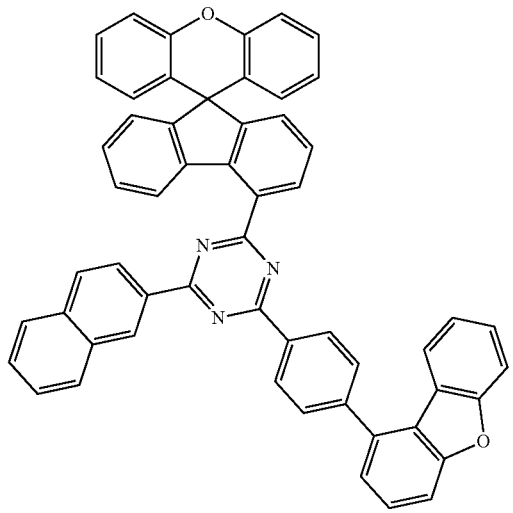
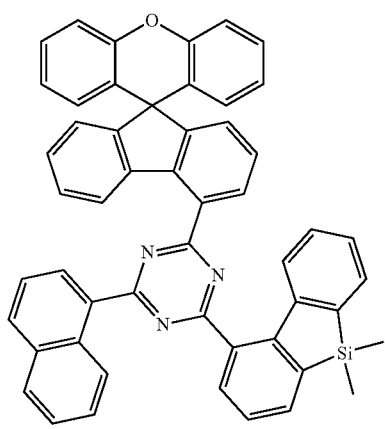
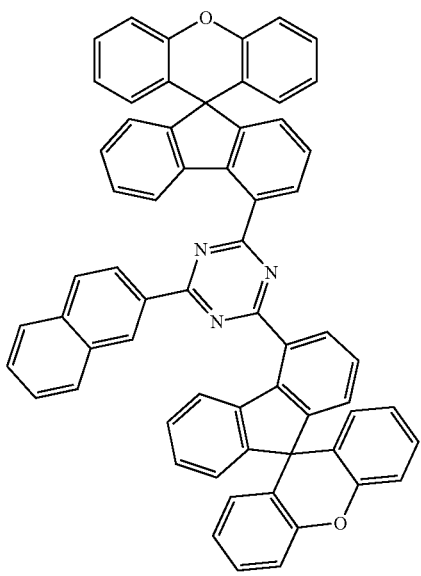

-continued
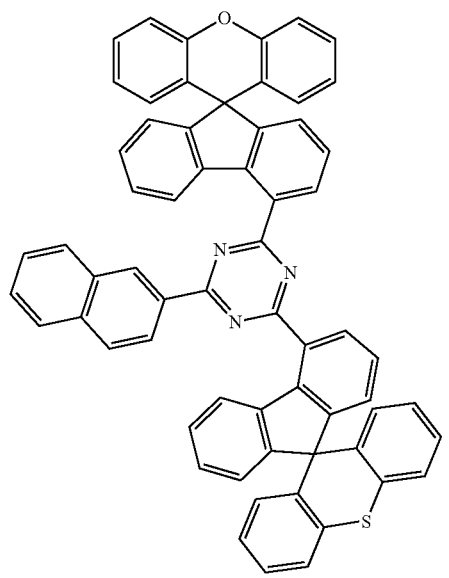
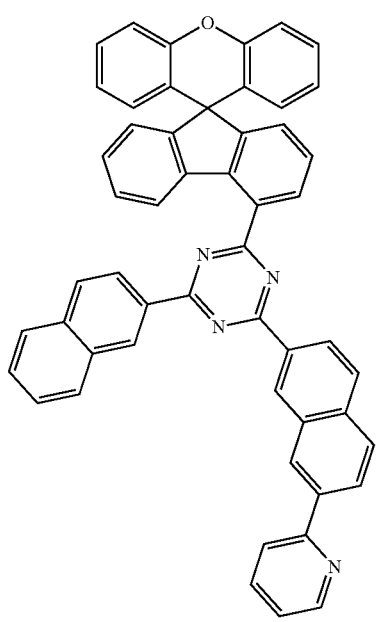
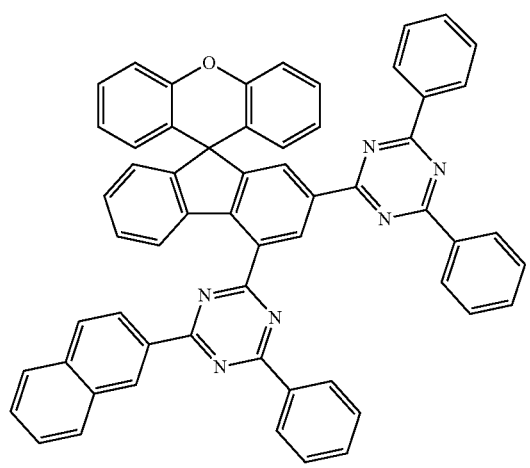
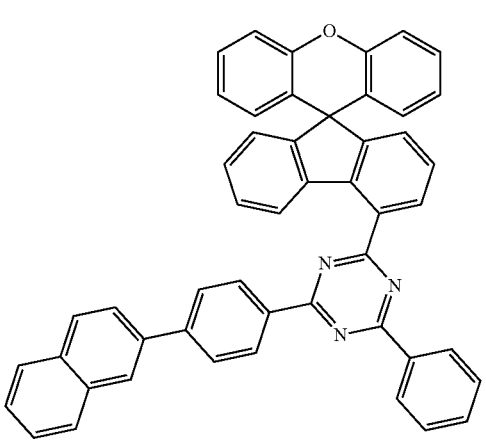
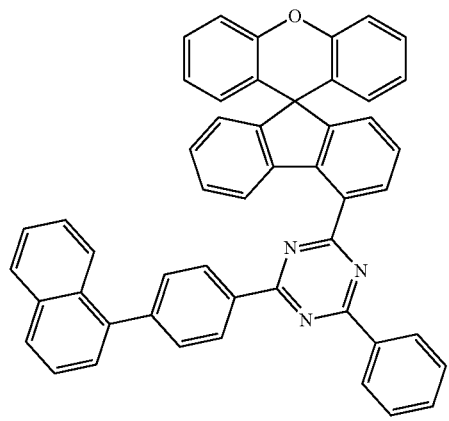
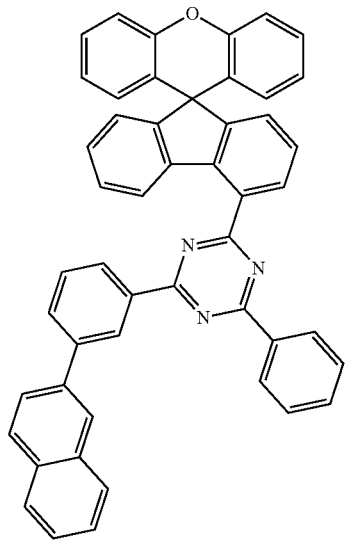

43 44
-continued
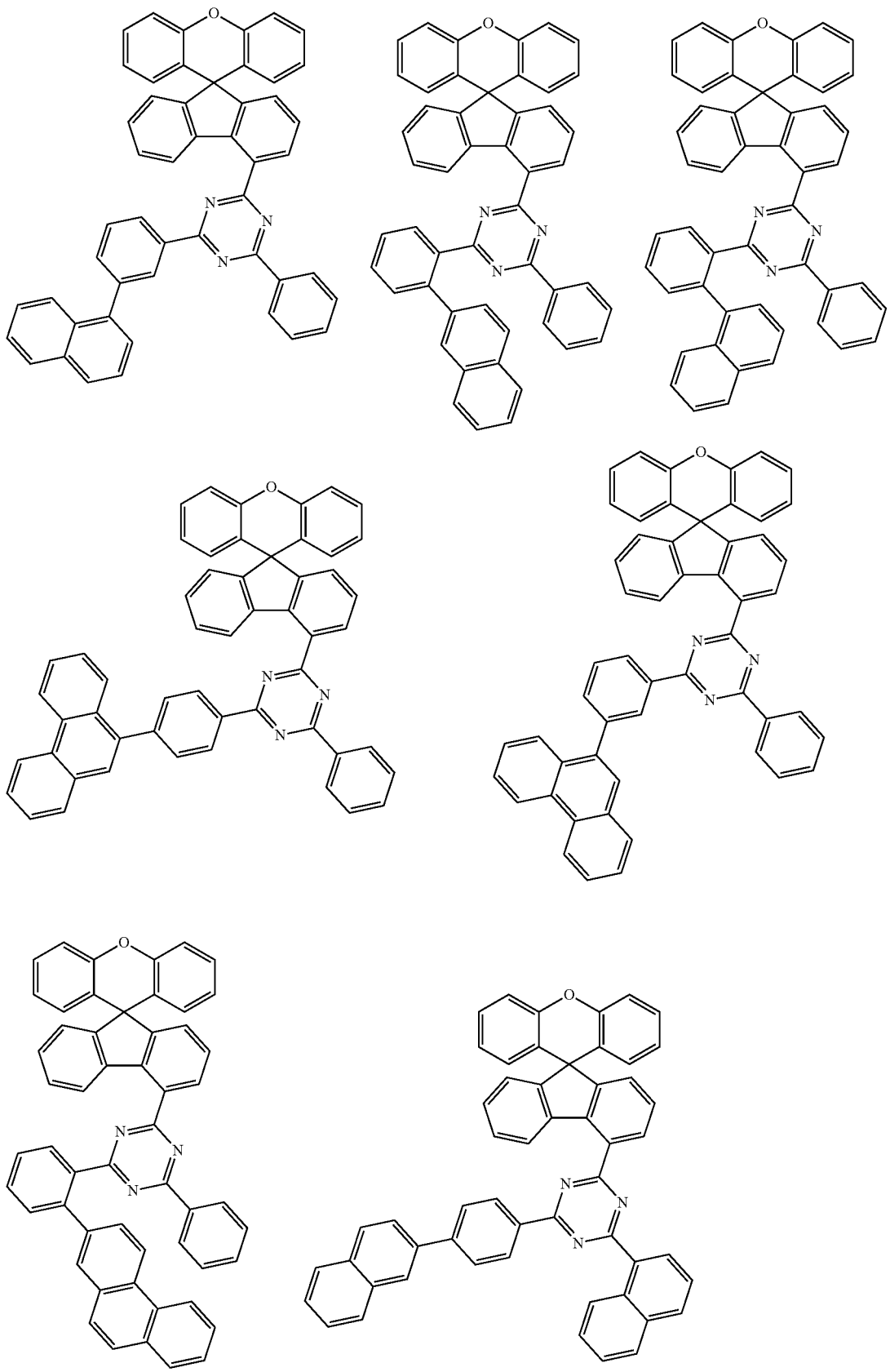

-continued
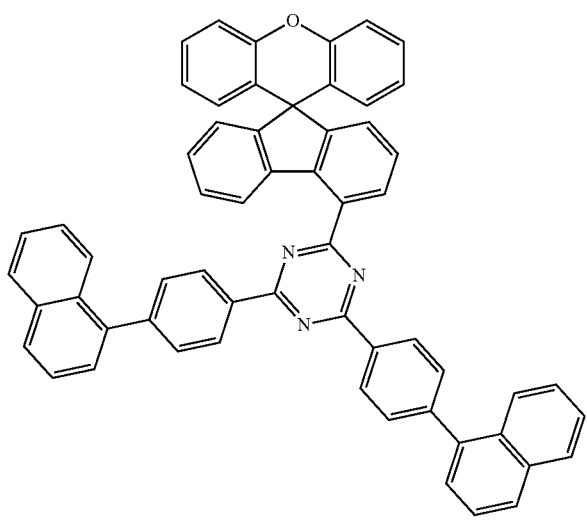
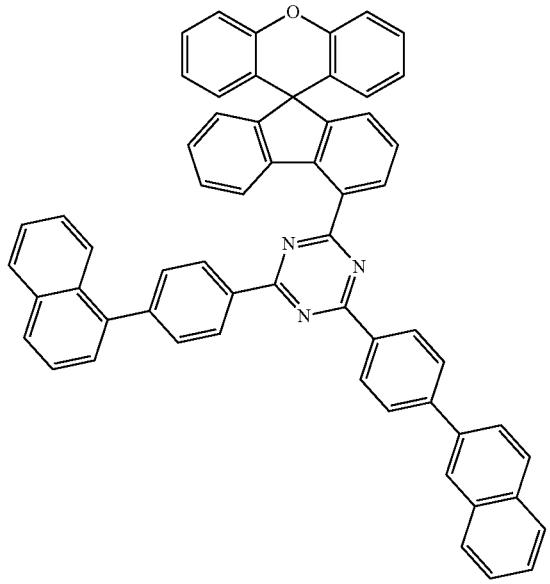
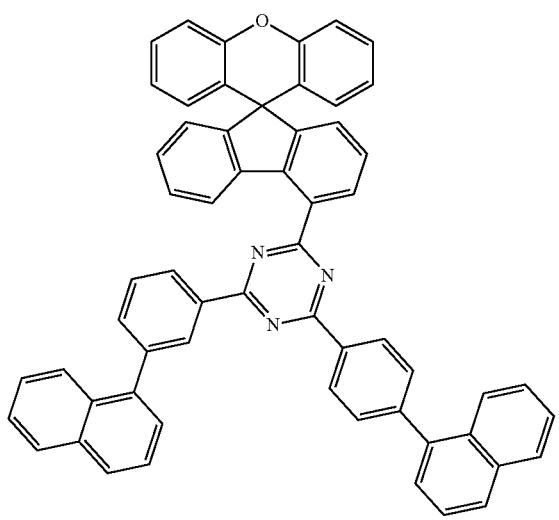
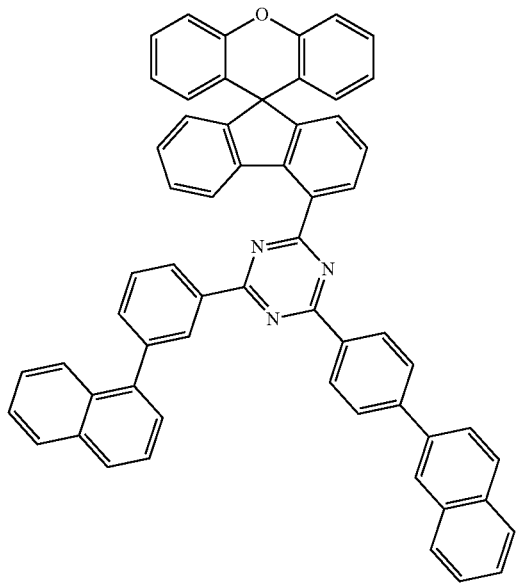
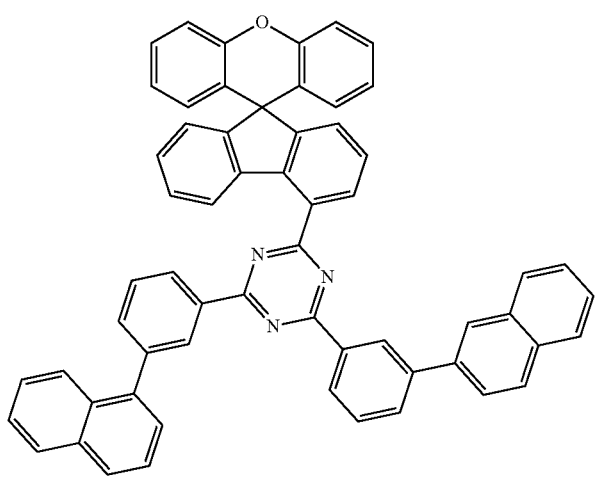

-continued
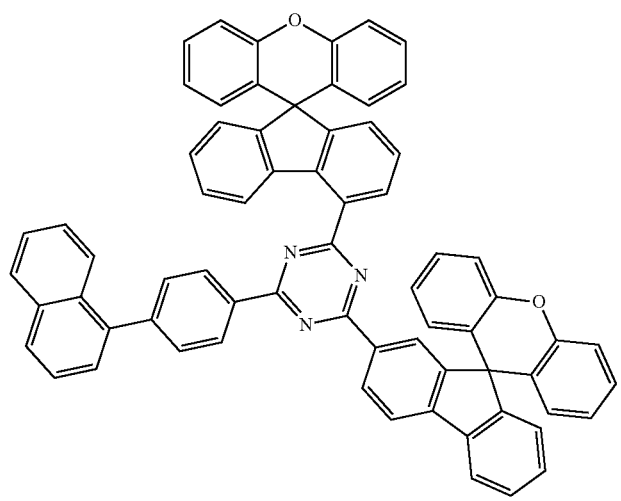
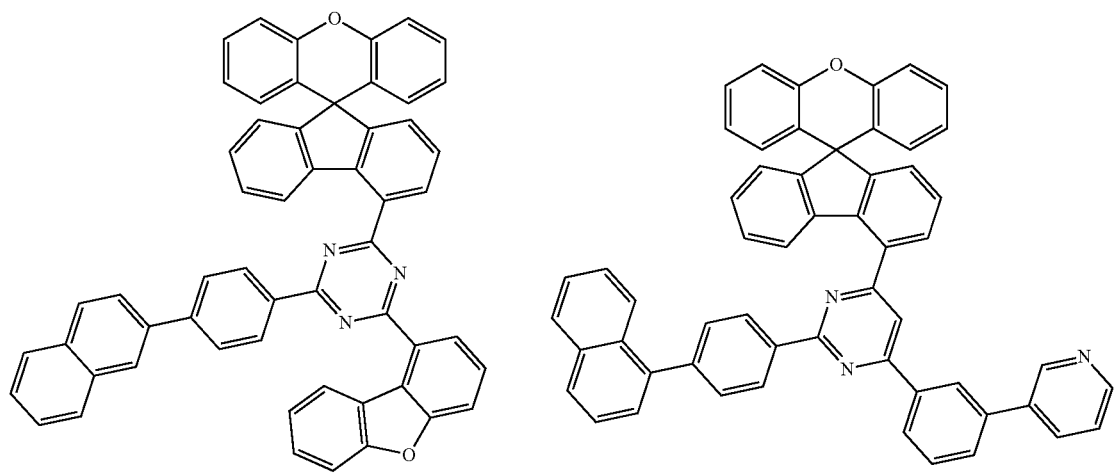
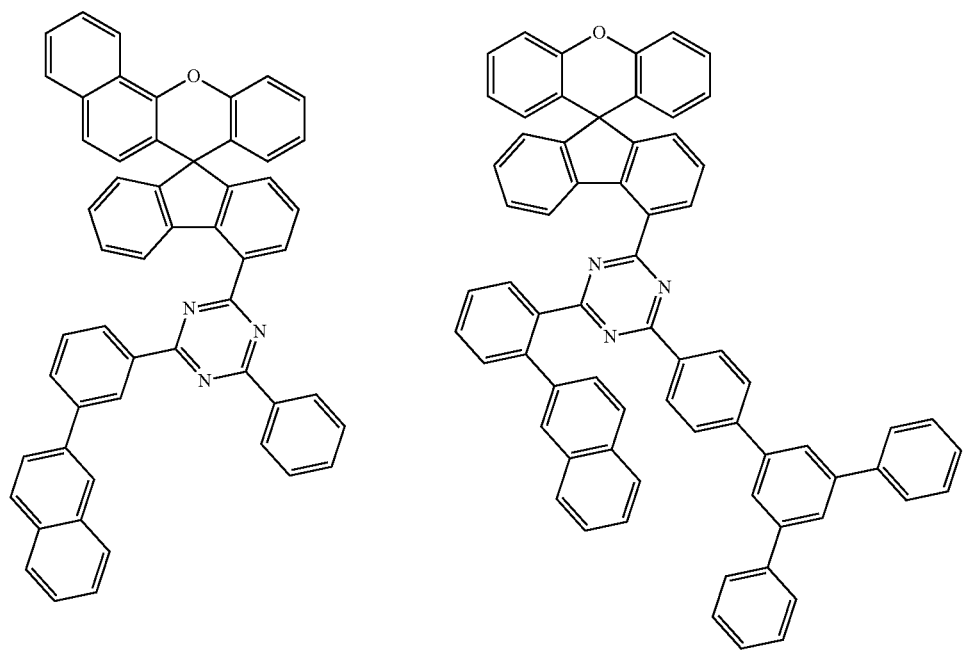

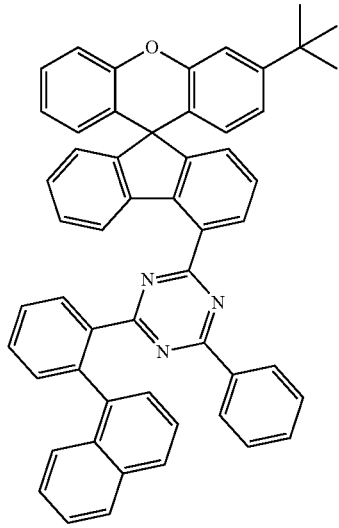
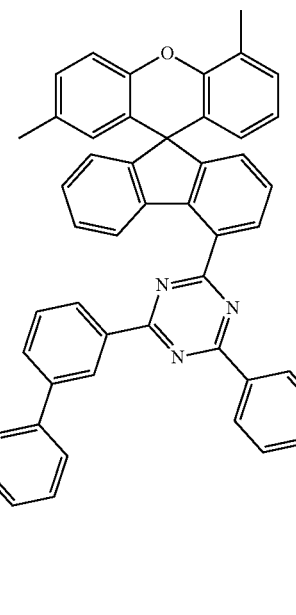
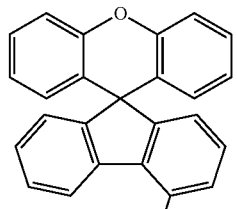
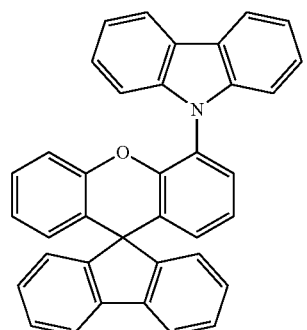
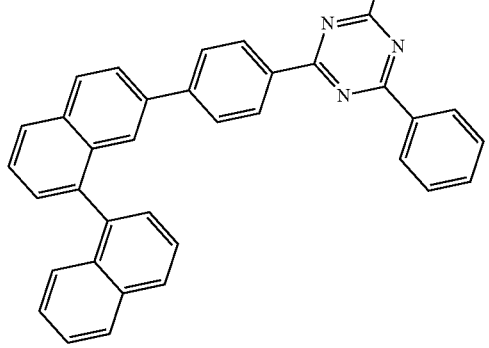
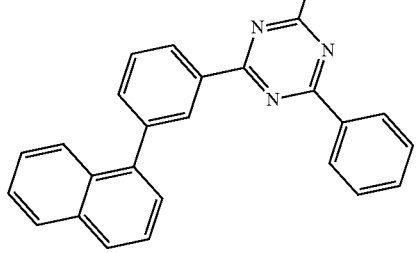
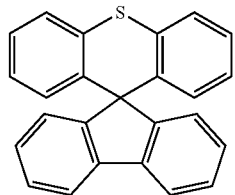
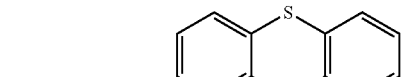
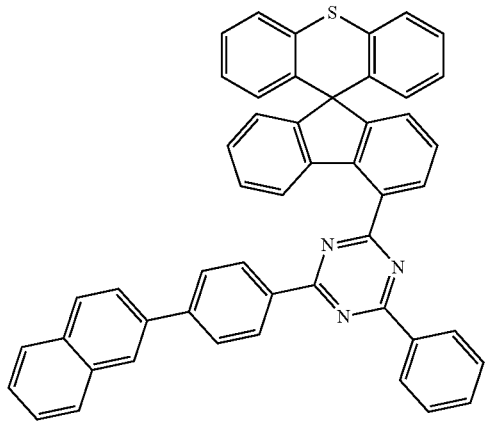
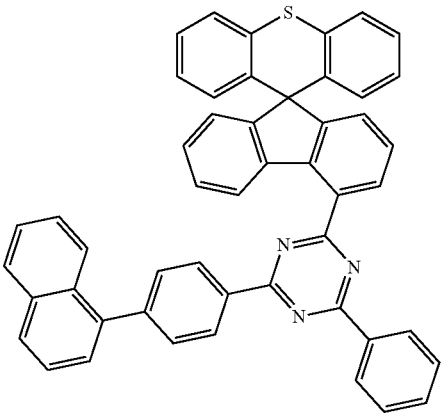

51 52
-continued
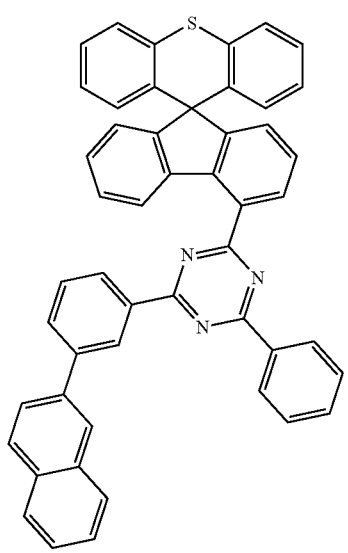
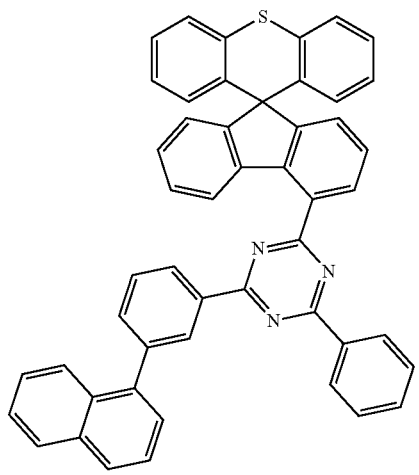
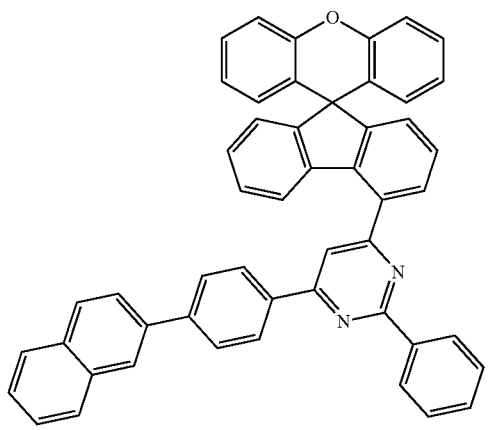
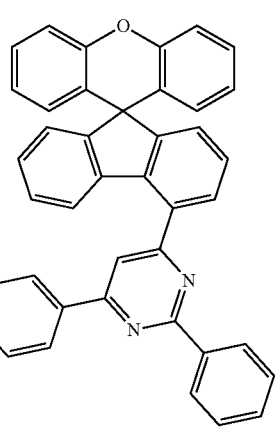
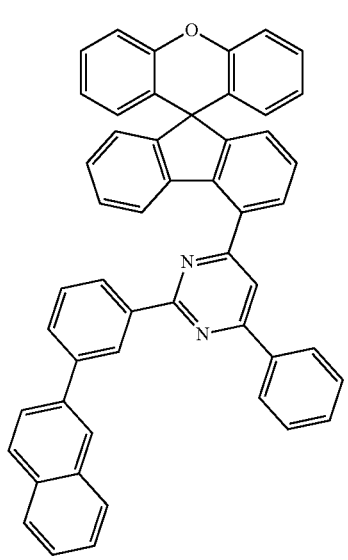
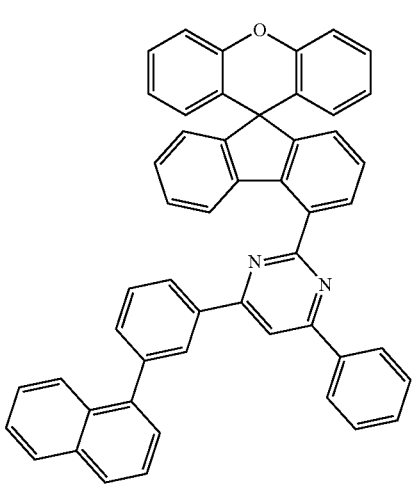
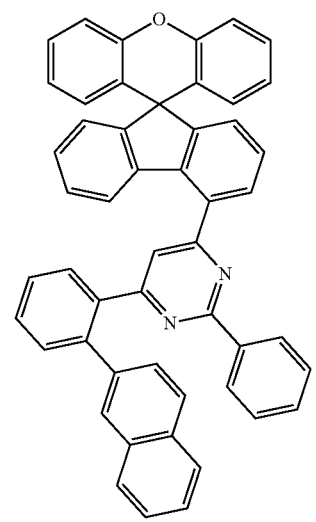

-continued
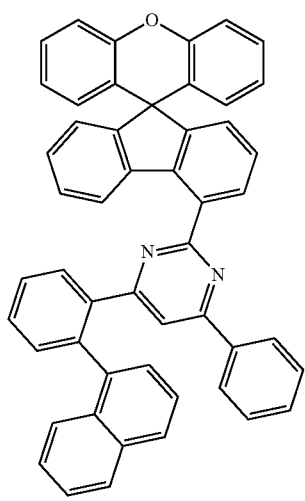
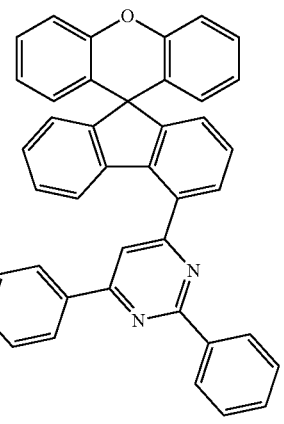
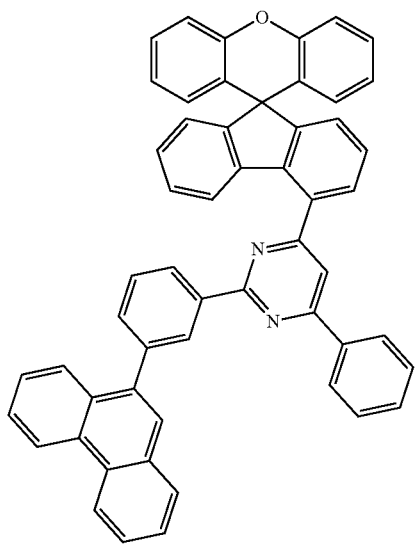
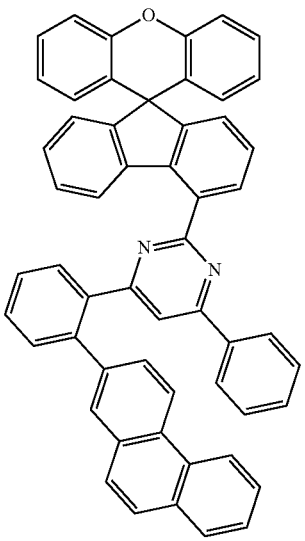
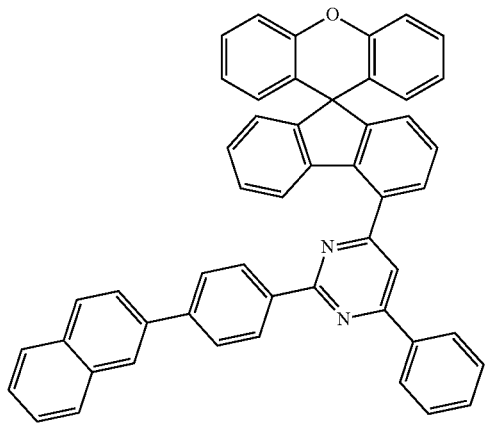
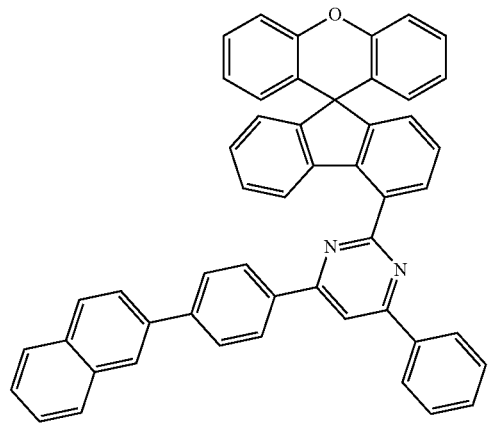

-continued
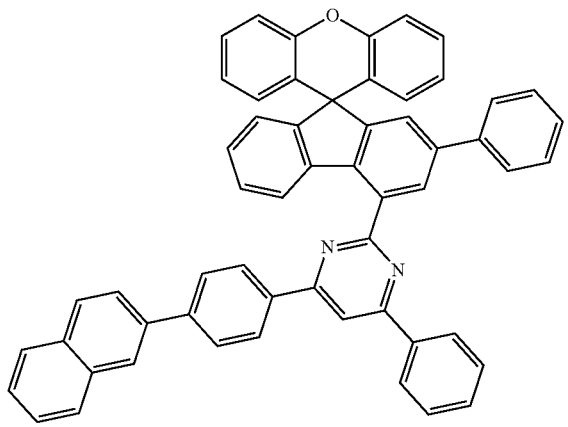
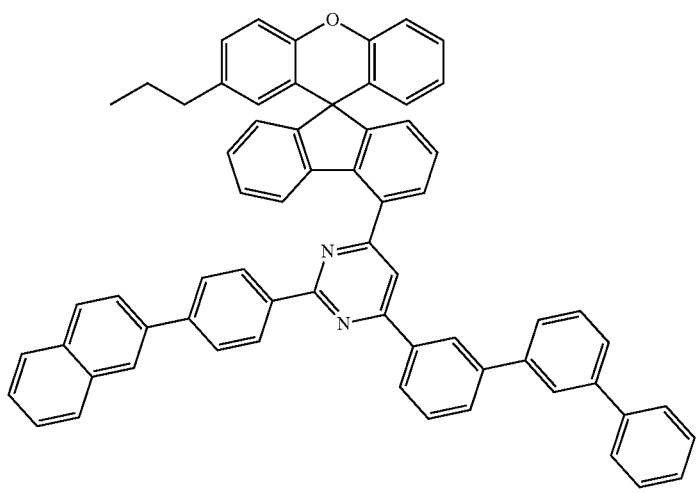
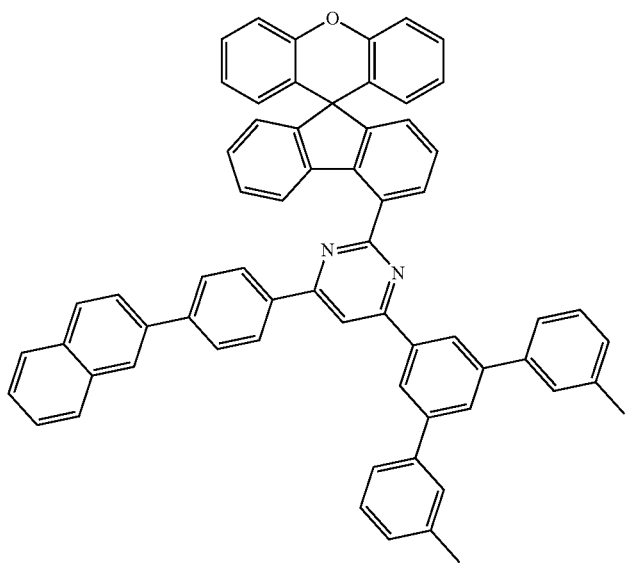

-continued
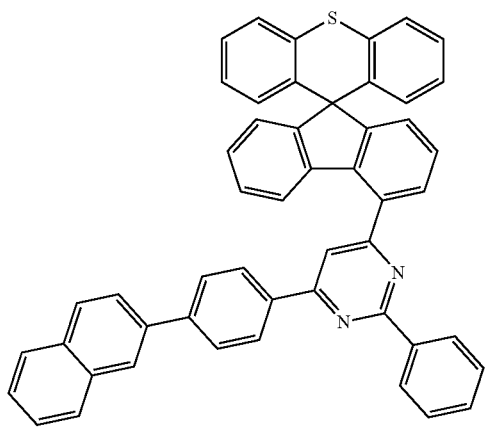
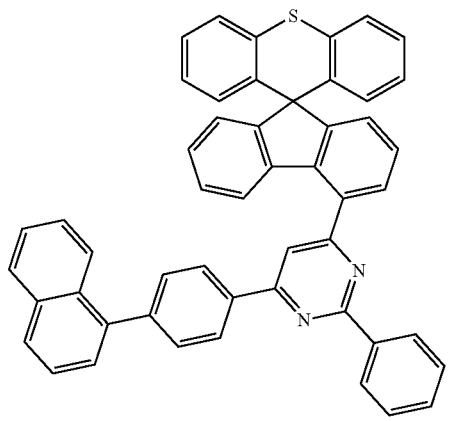
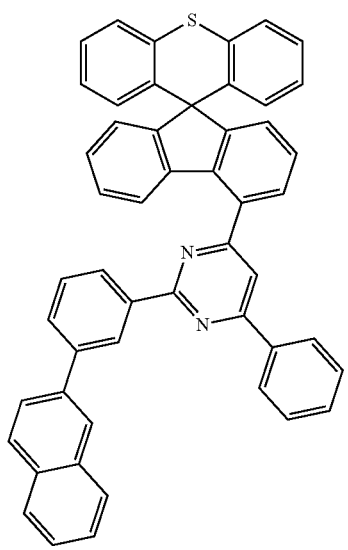
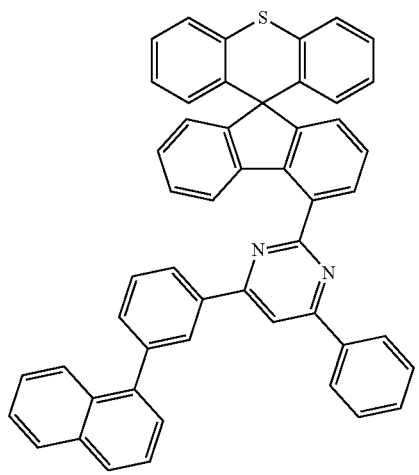
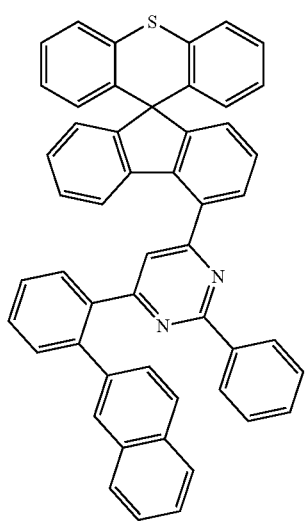
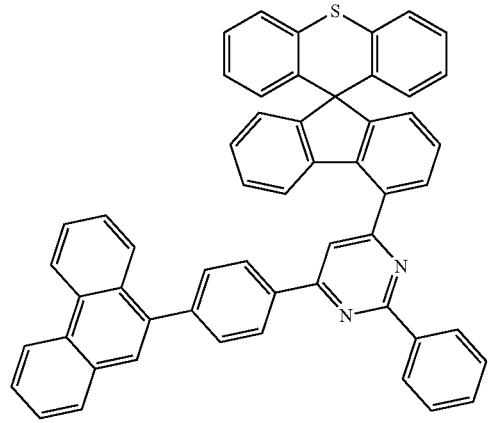

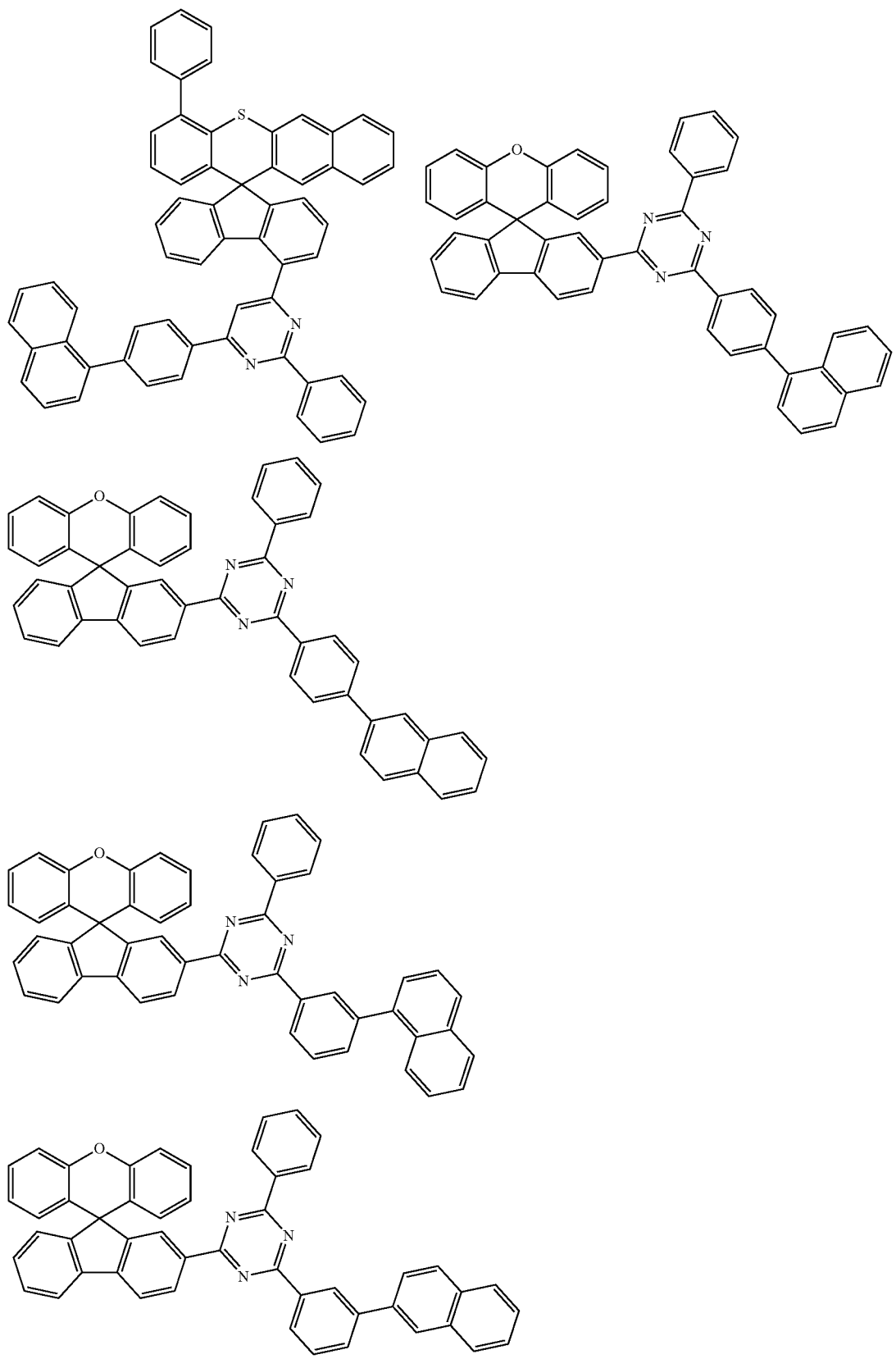

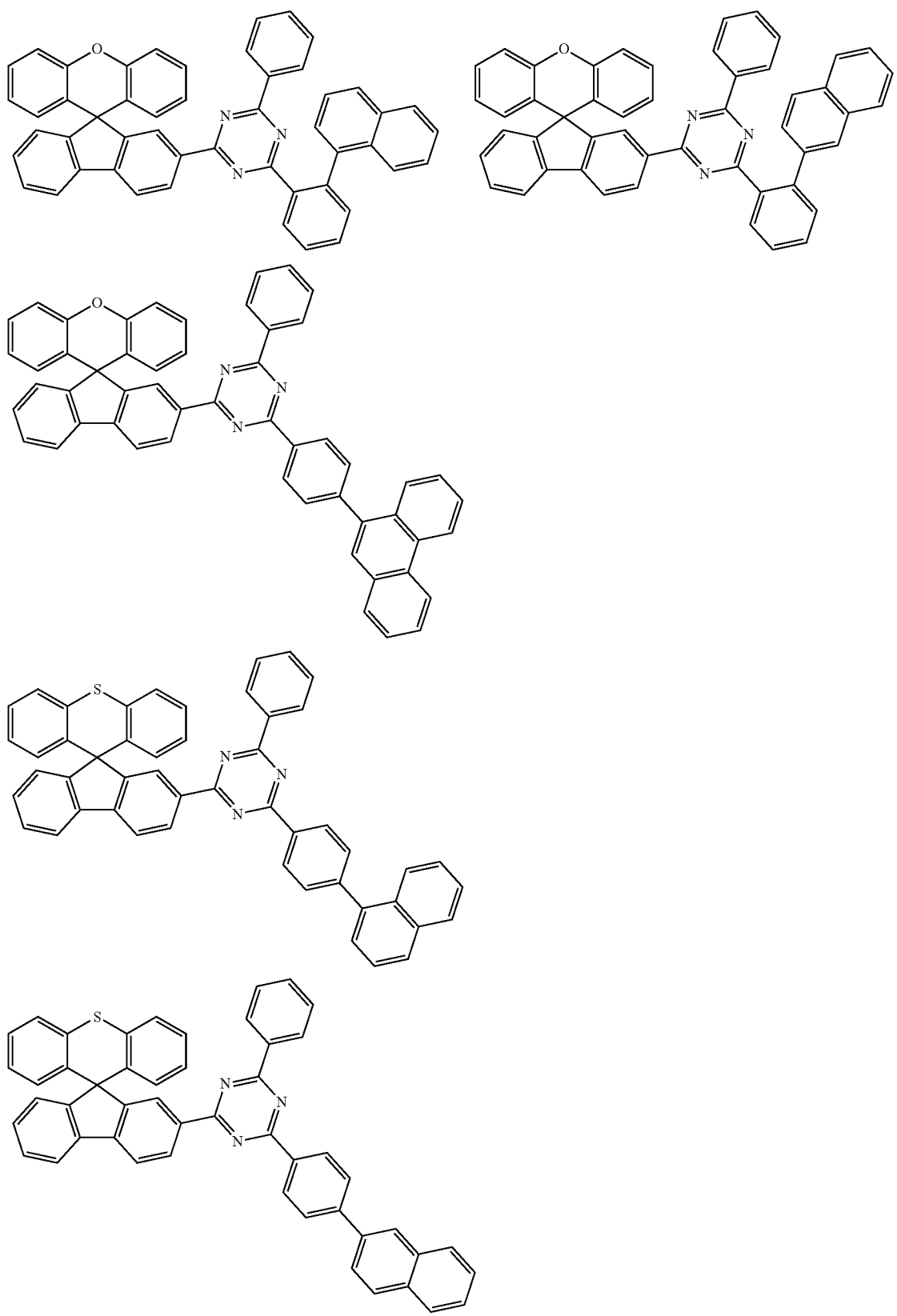

-continued
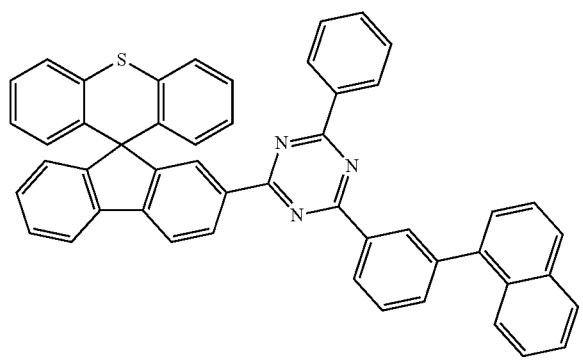
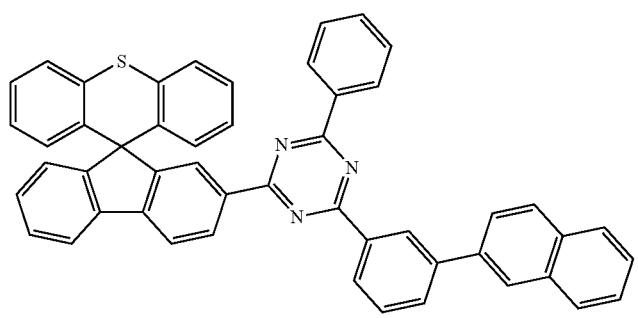
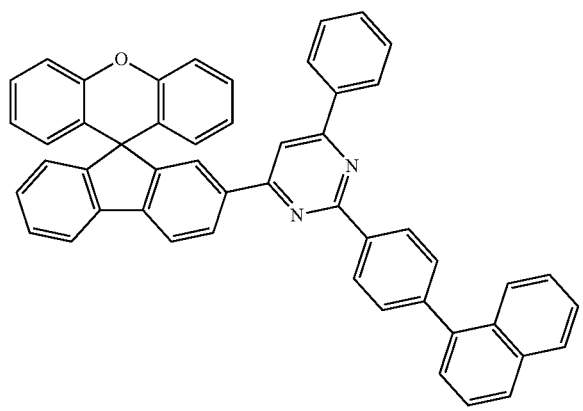
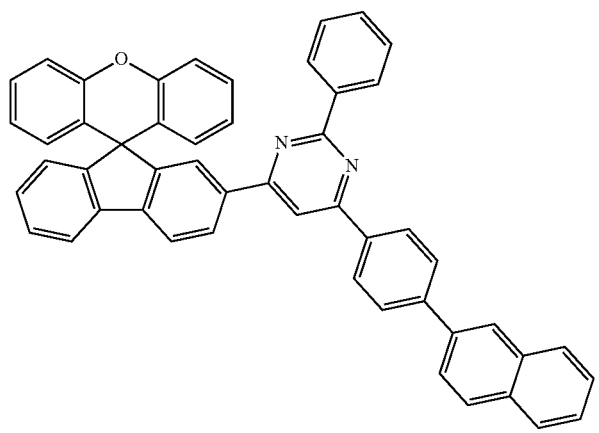

-continued
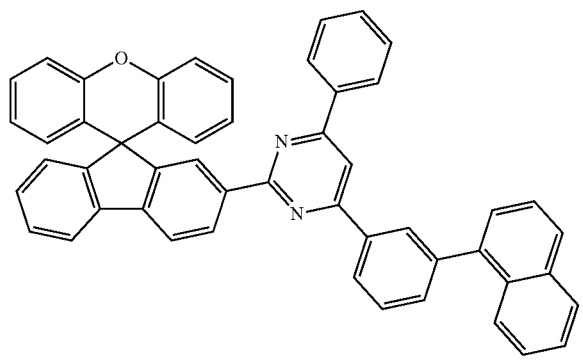
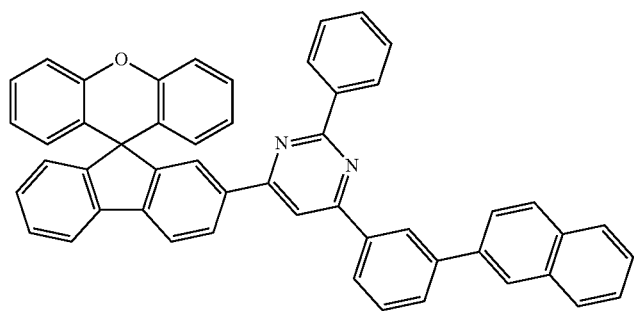
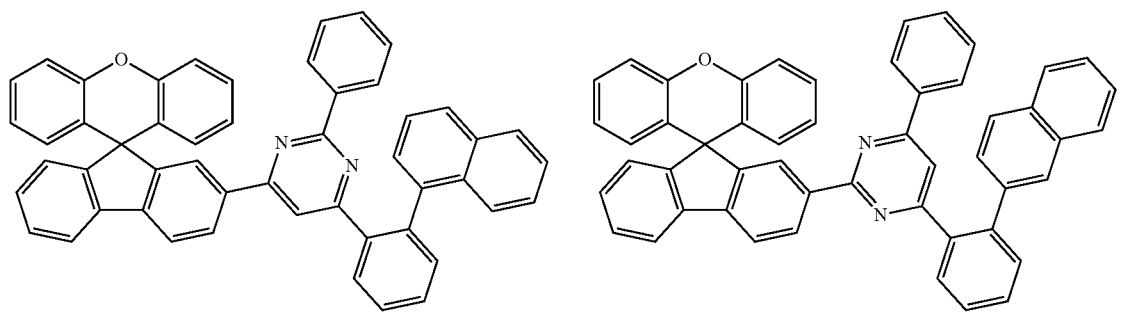
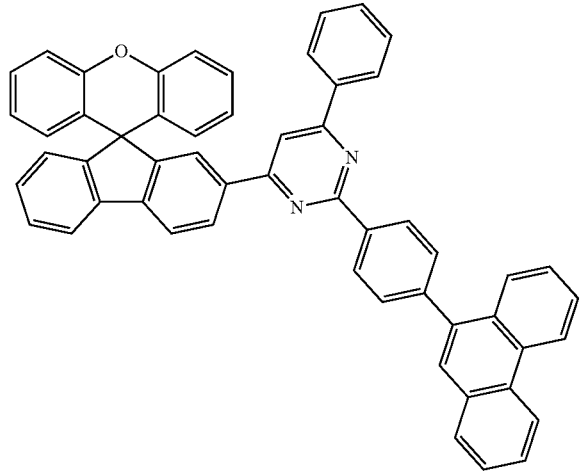

-continued
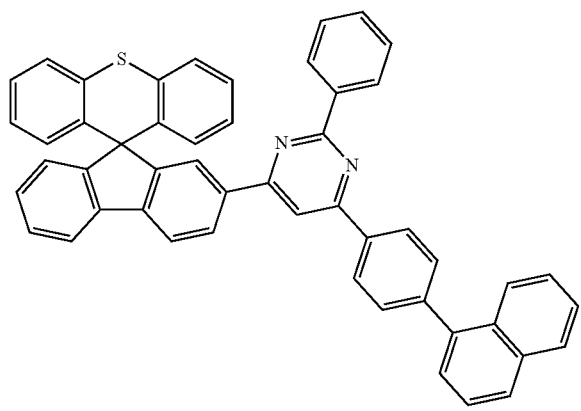
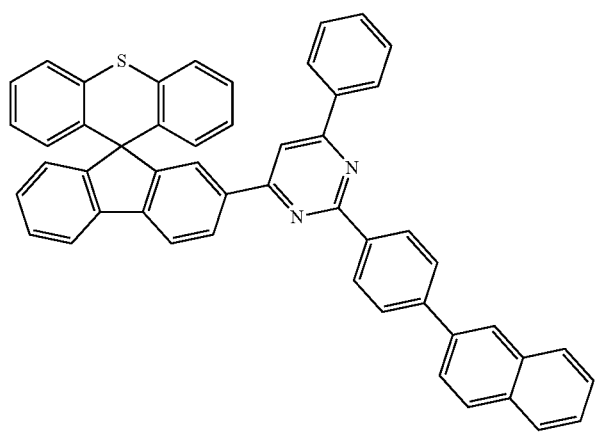
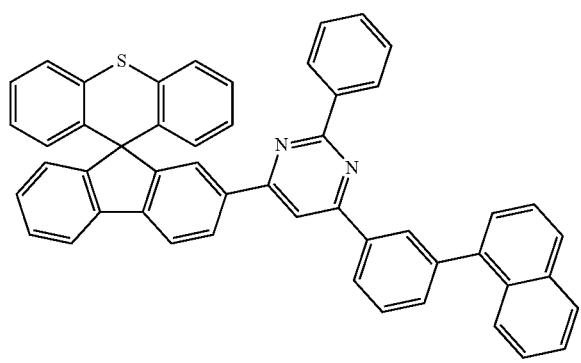
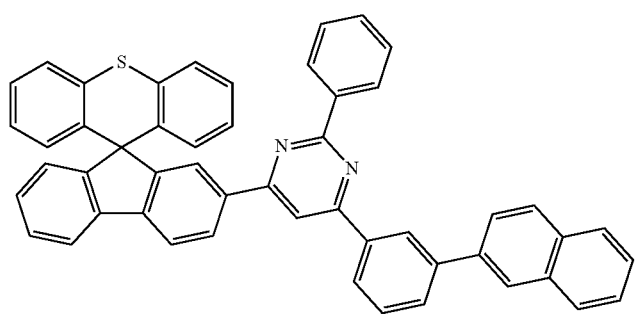

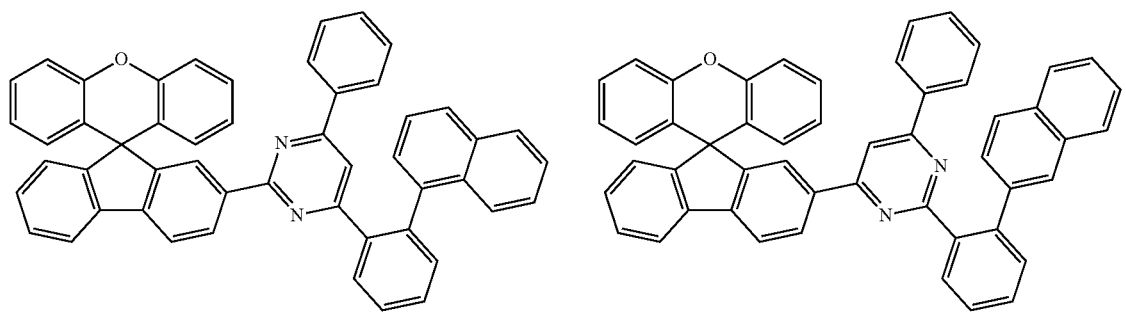
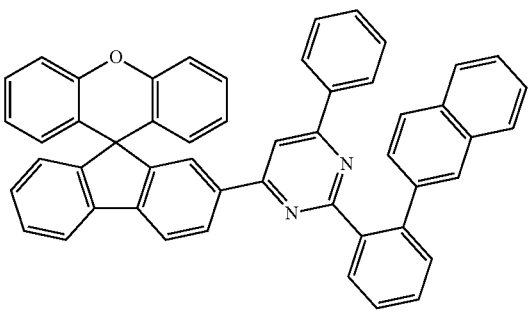
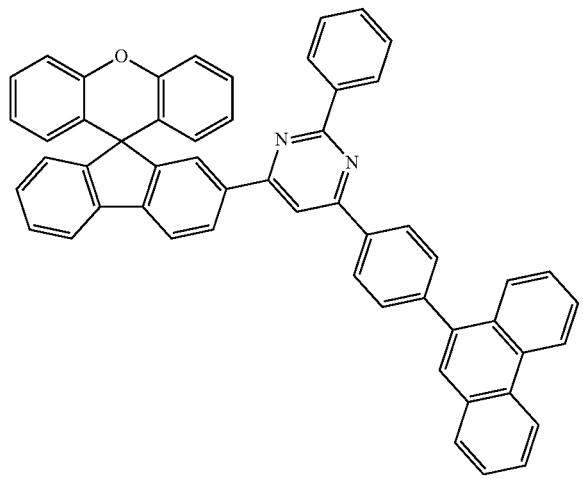
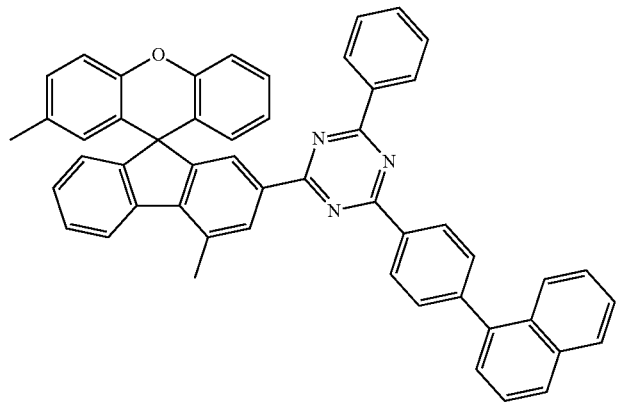
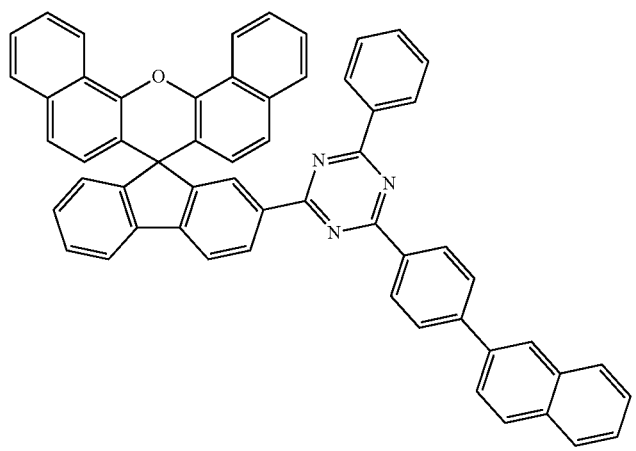

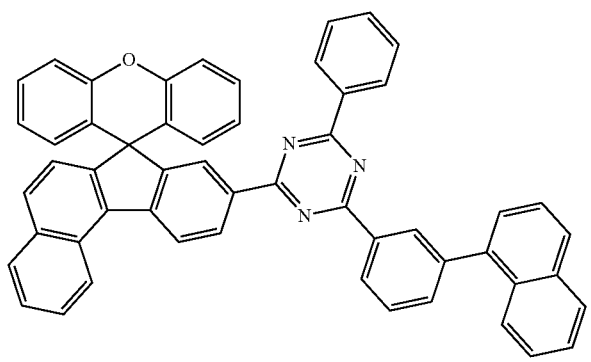
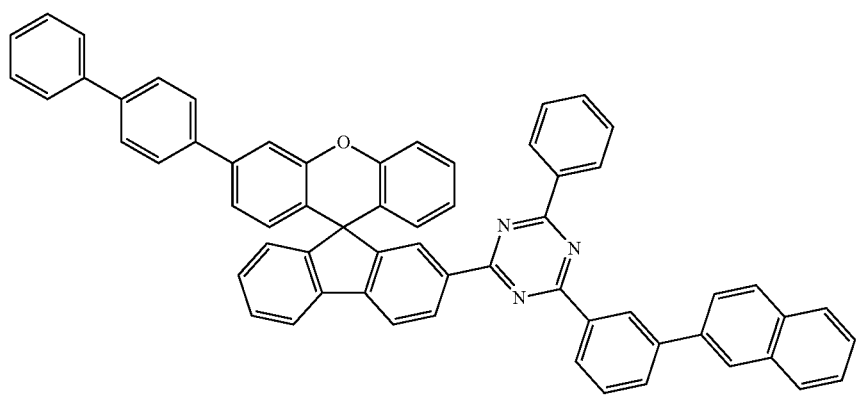
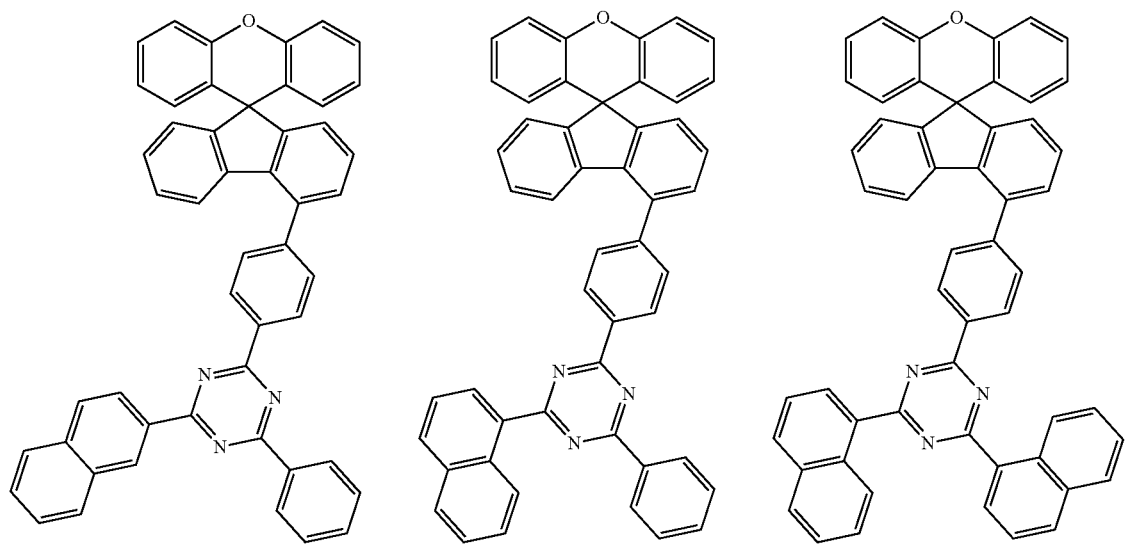

-continued
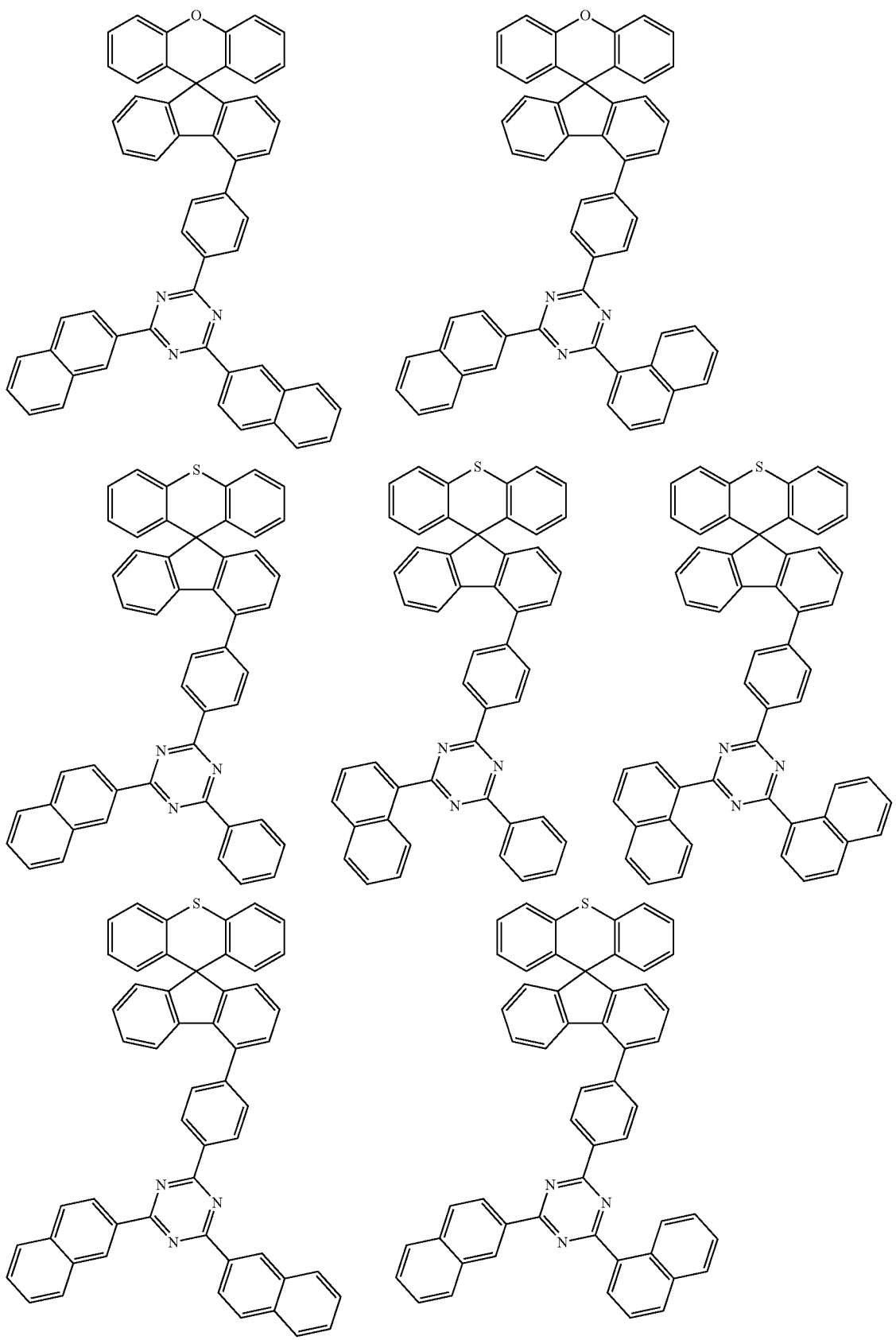

75
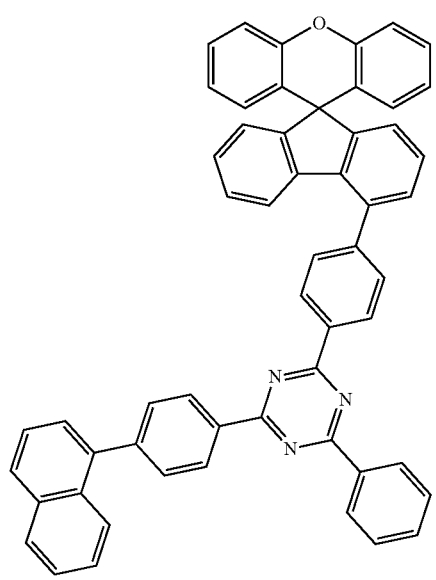
76
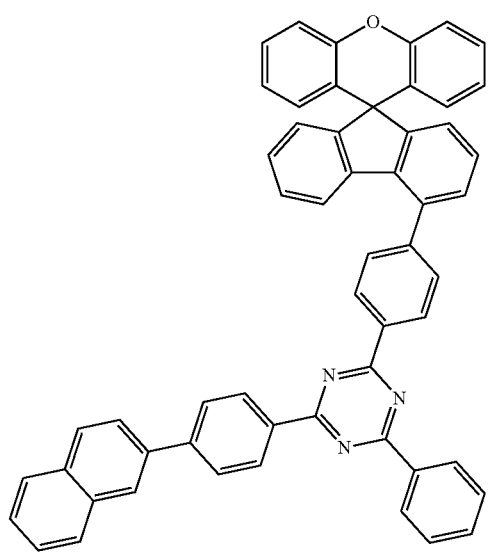
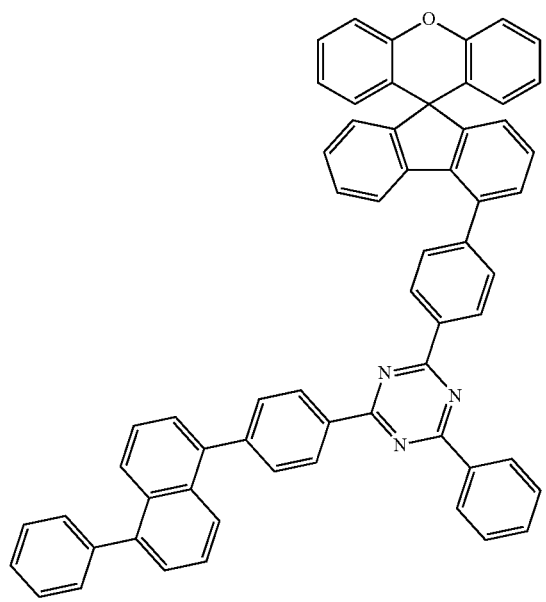
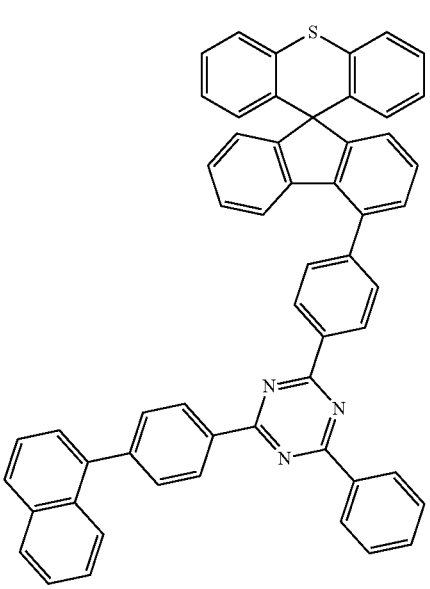

77 78
-continued
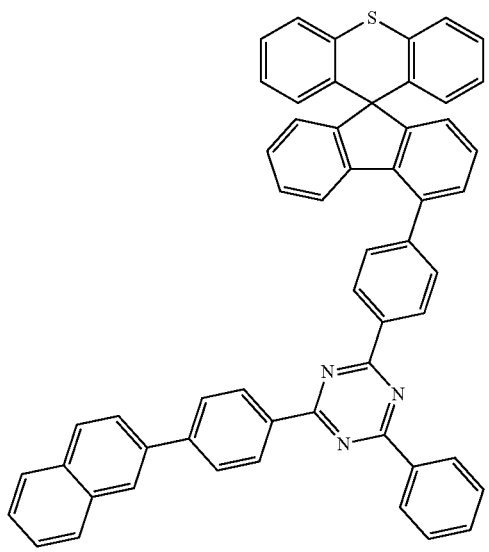
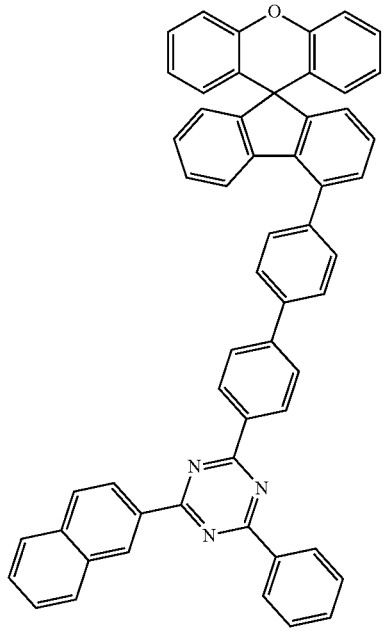
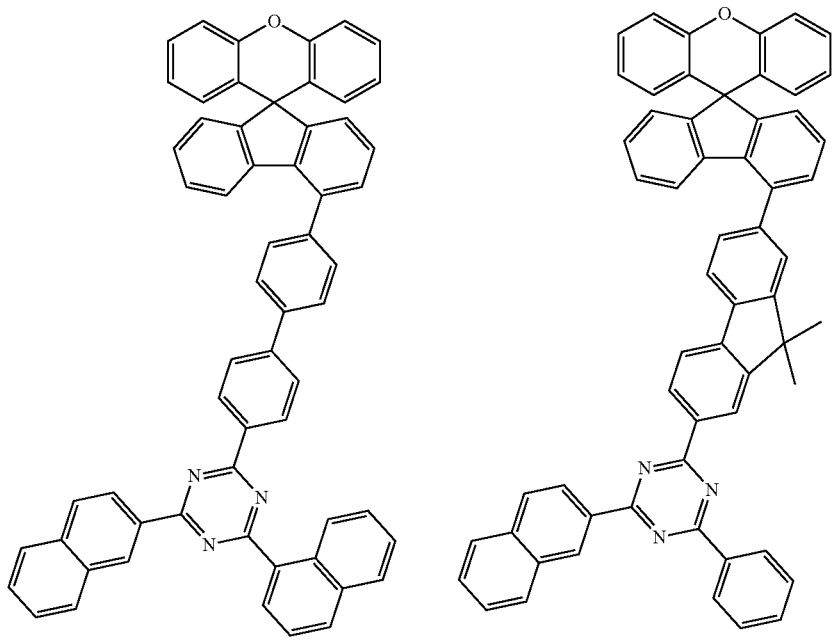

-continued
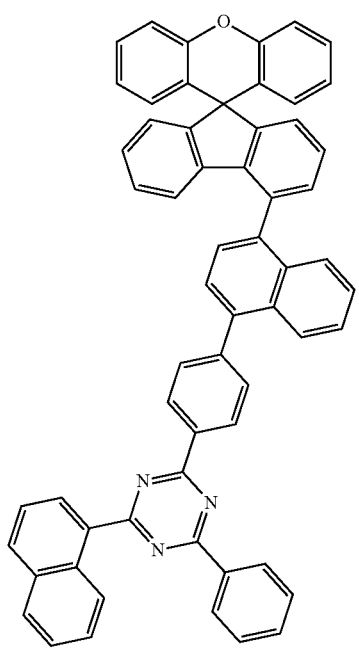
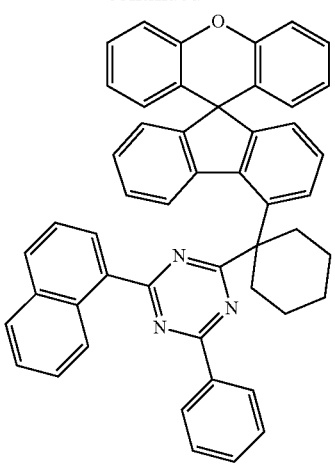
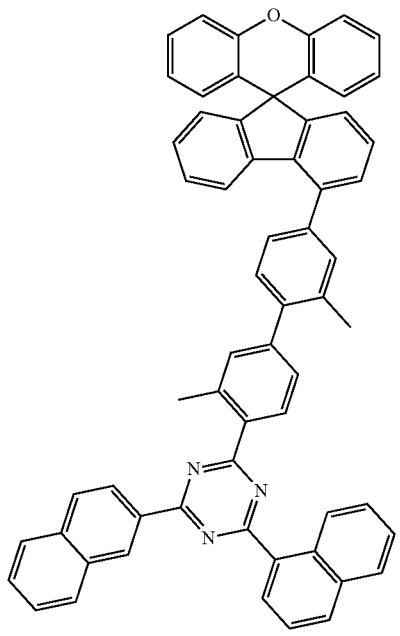
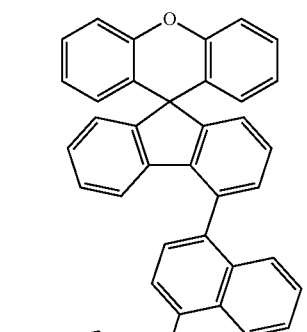
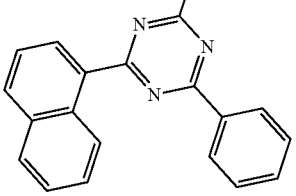
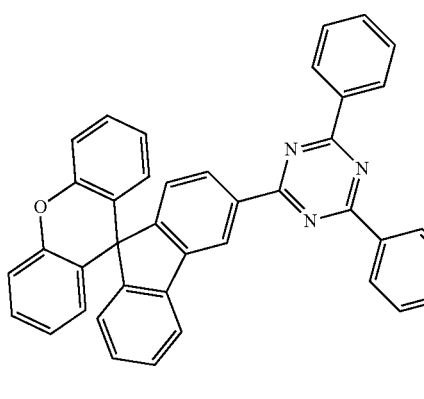

-continued
81
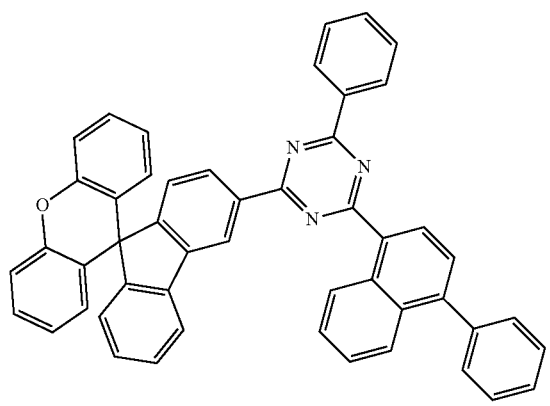
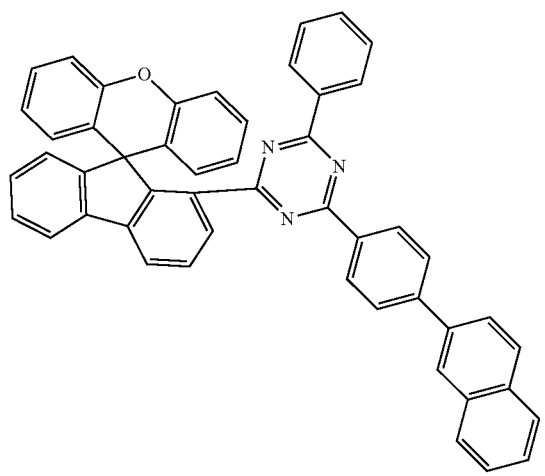
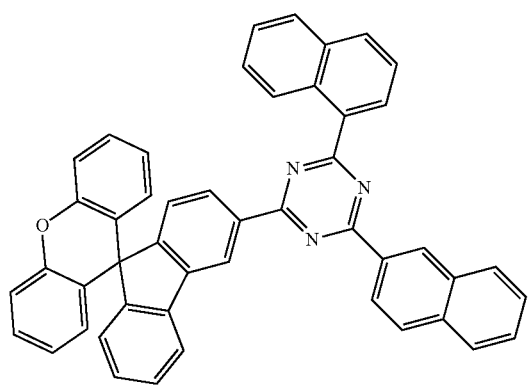
82
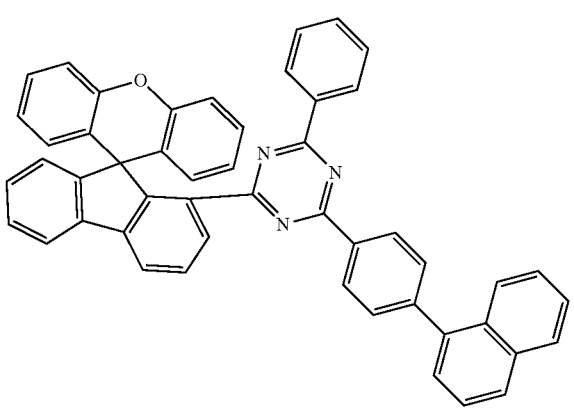
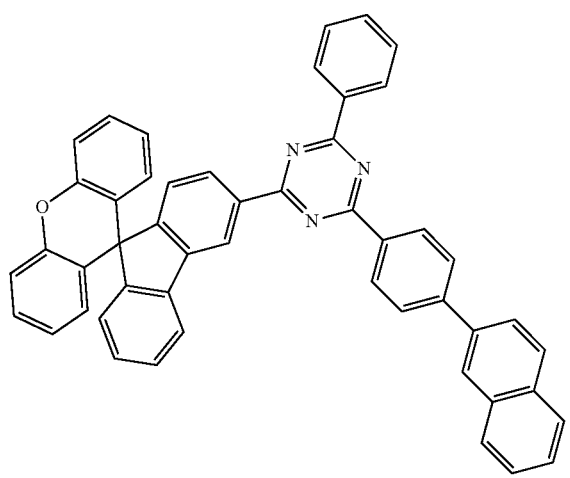
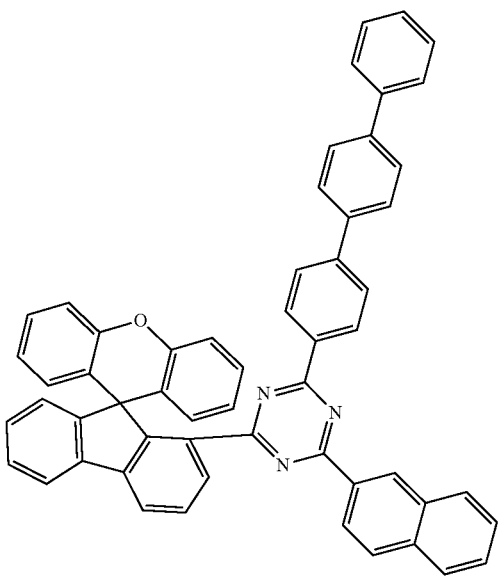

-continued
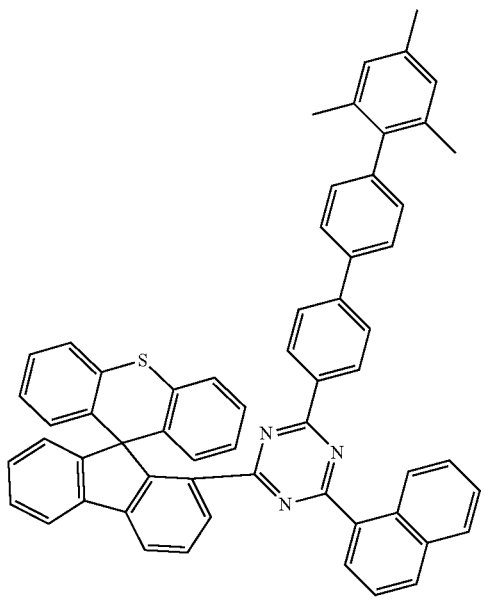
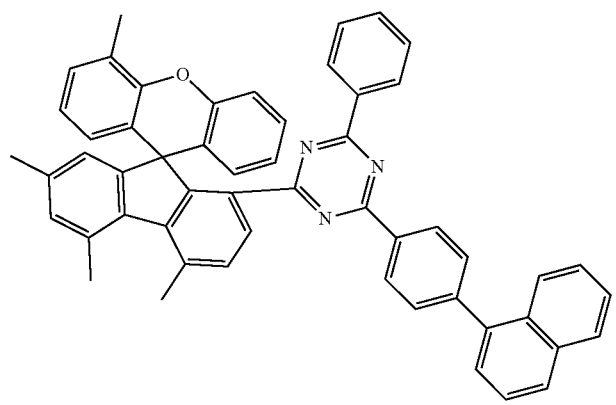
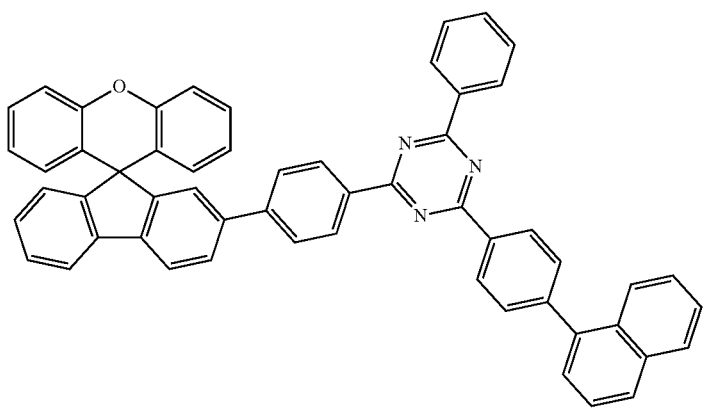
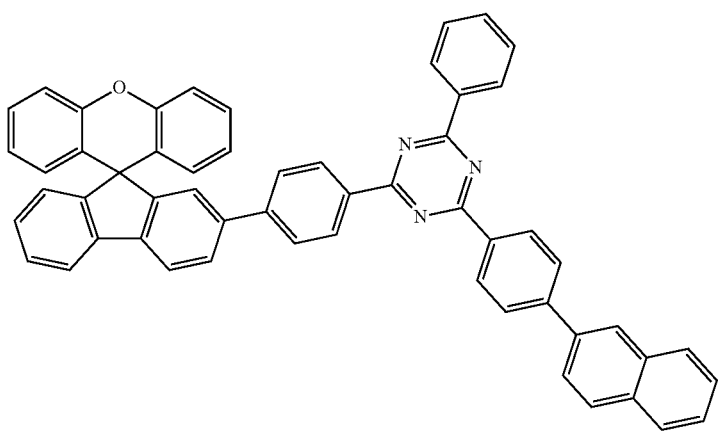

-continued
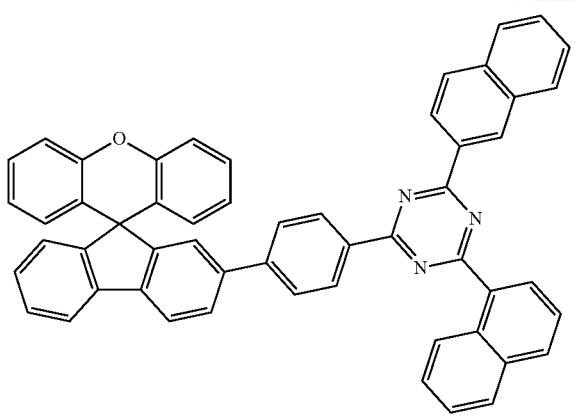
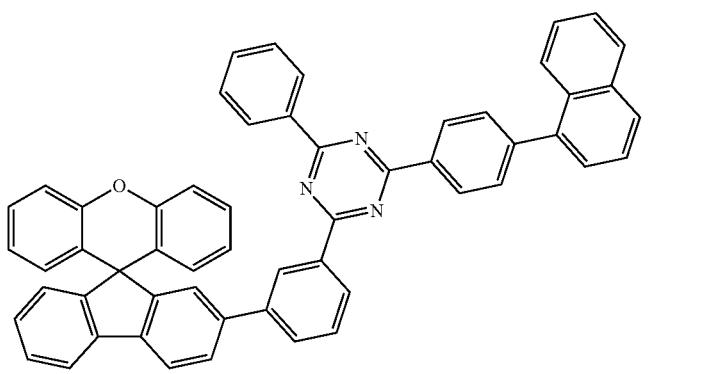
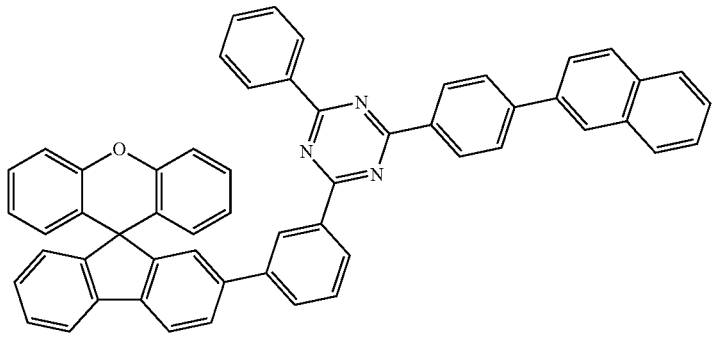
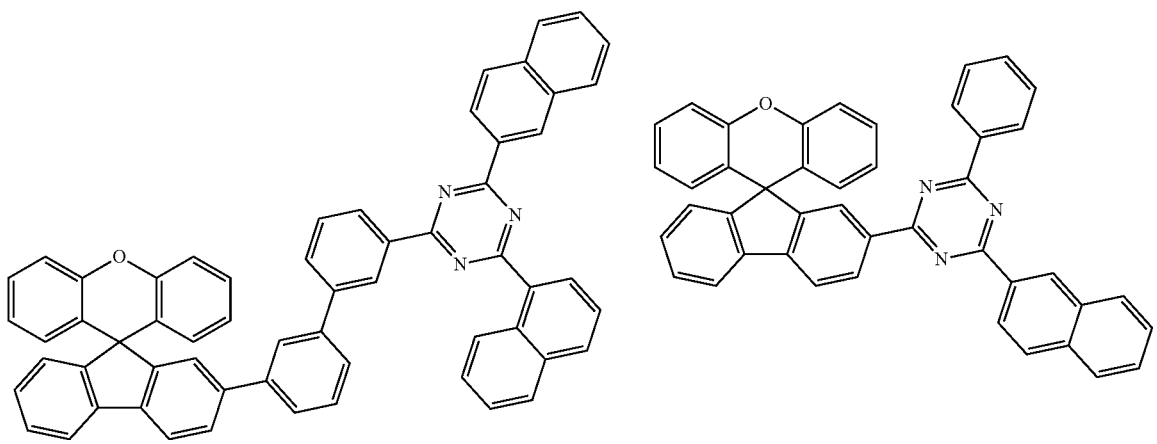

-continued
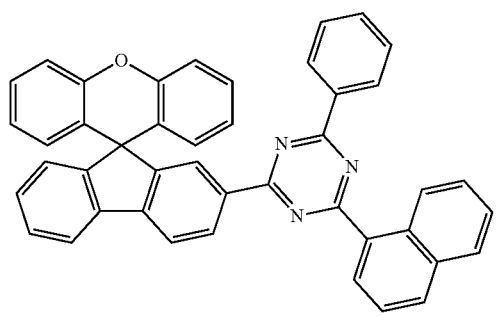
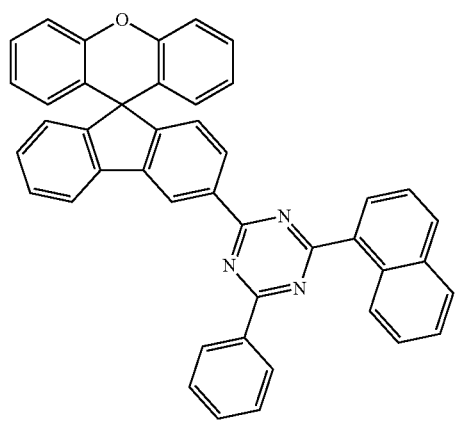
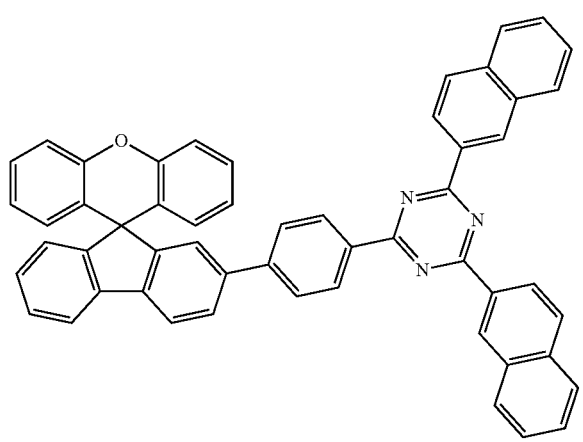
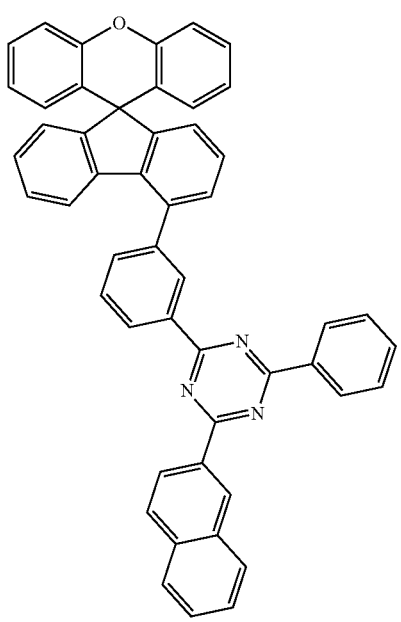
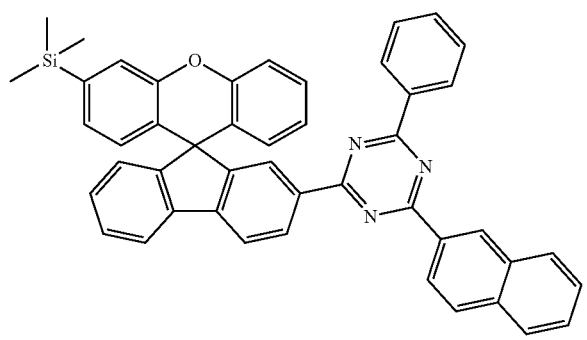

-continued
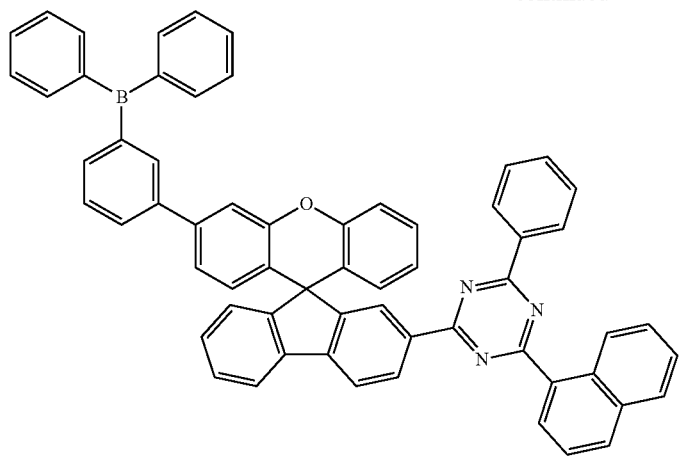
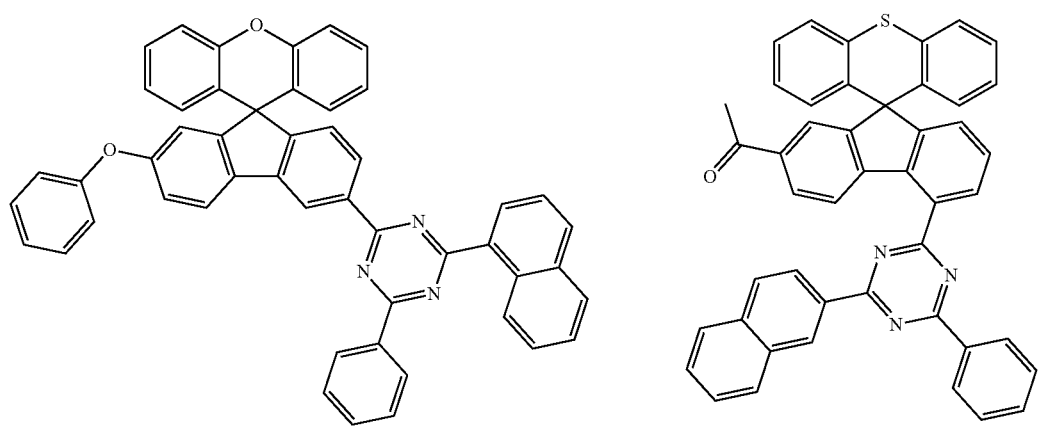
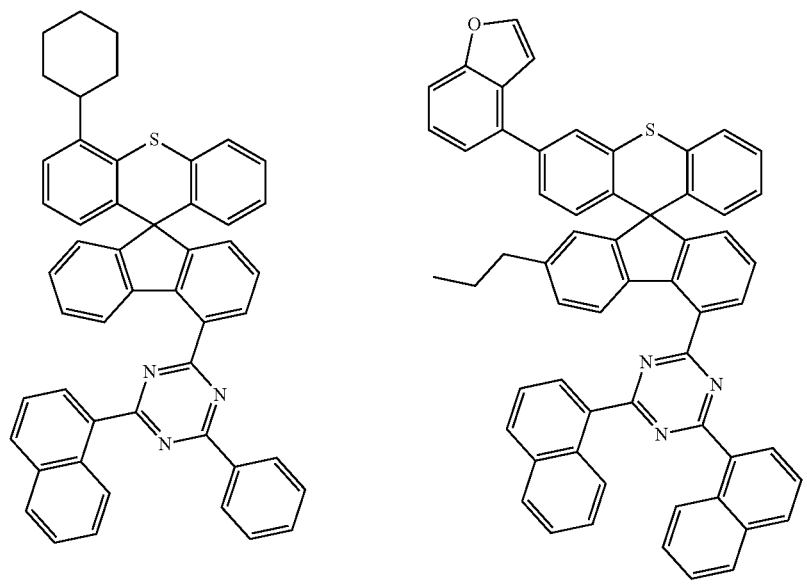

-continued
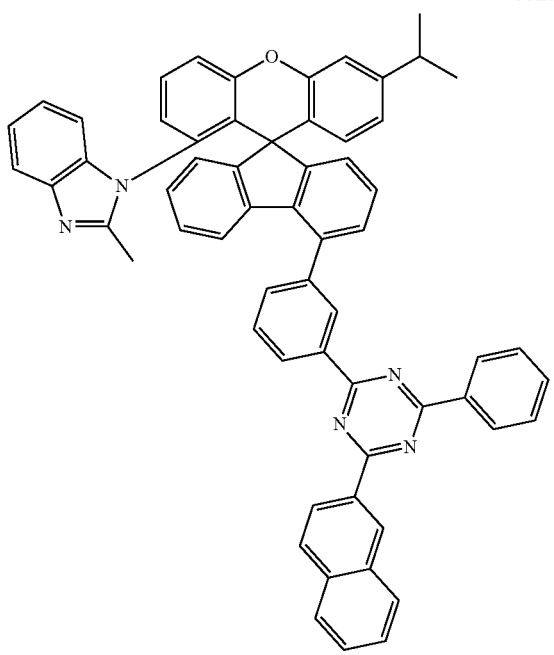
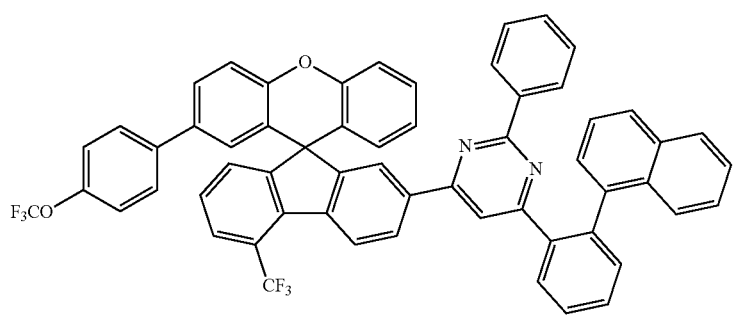
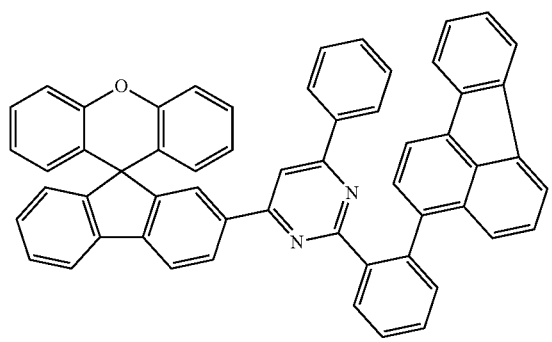

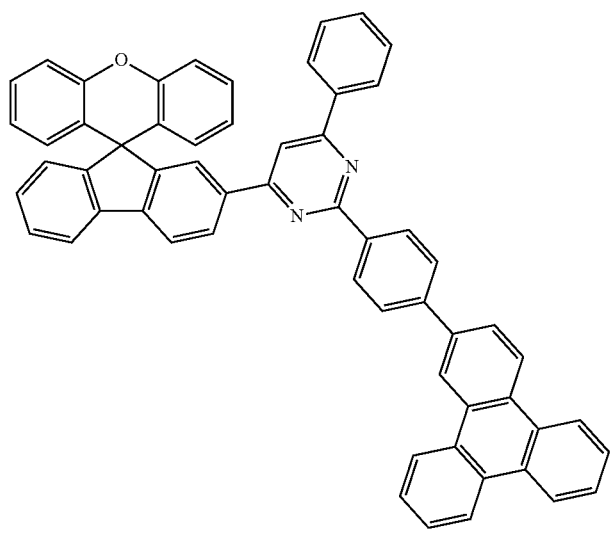
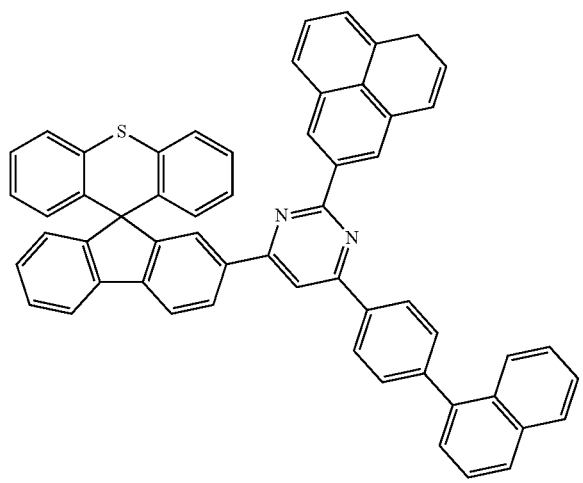
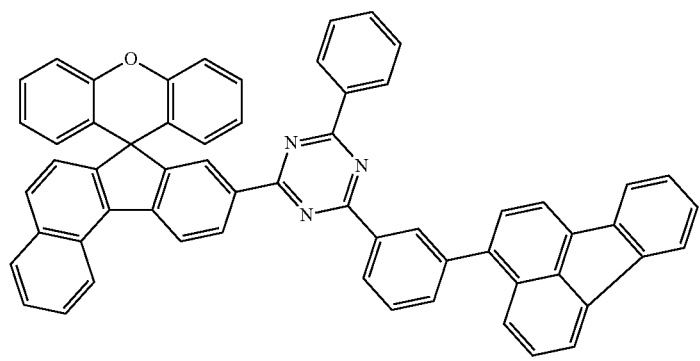

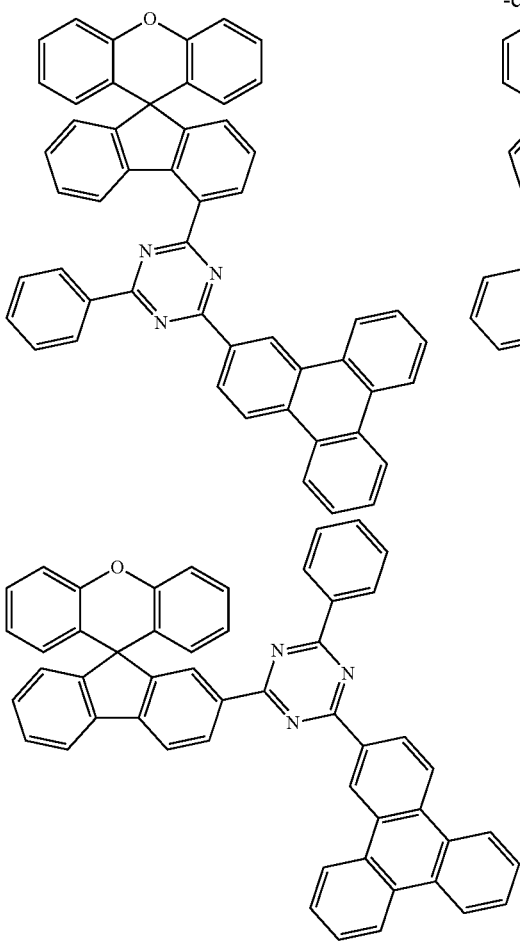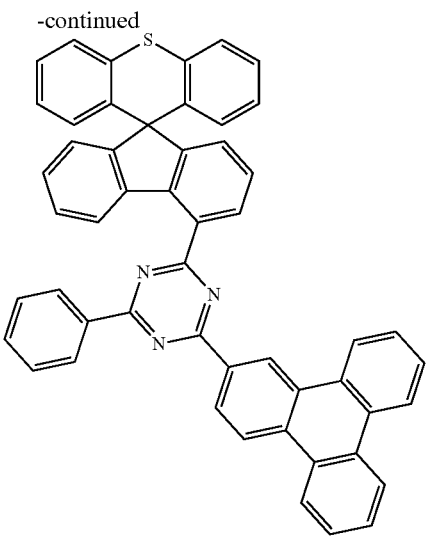

According to one embodiment of the present specification, the compound of Chemical Formula 1 satisfies the following Equation 1:

$$\Delta EST^C_{EI} > \Delta EST_{EI} \qquad <\text{Equation 1}>$$

In Equation 1,
$\Delta EST^C_{EI}$ is a difference between a singlet energy (S1) value and a triplet energy (T1) value of the compound of Chemical Formula 1, and
$\Delta EST_{EI}$ is a difference between a singlet energy (S1) value and a triplet energy (T1) value of the compound in which Ar1 and Ar2 do not include a dicyclic or higher condensed aryl group in the compound of Chemical Formula 1.

Equation 1 means that a difference between S1 and T1 energy values of the compound of Chemical Formula 1 of the present application having a dicyclic or higher condensed aryl group (one or more of Ar1 and Ar2) as an essential component is larger than a difference between S1 and T1 values of the compound having the same core structure as the compound of the present disclosure but not including a dicyclic or higher condensed aryl group in Ar1 and Ar2 of the present application. By the compound of Chemical Formula 1 including a dicyclic or higher condensed aryl group (one or more of Ar1 and Ar2) in the compound, a difference between S1 and T1 energy values is large, and as a result, a device having excellent lifetime properties can be obtained when used in the device.

According to one embodiment of the present specification, the compound of Chemical Formula 1 satisfies the following Equation 3. When the compound of Chemical Formula 1 satisfies the following Equation 3, a device having highly superior lifetime properties can be obtained when used in the device.

$$\Delta EST^C_{EI} - \Delta EST_{EI} > 0.05 \text{ eV} \qquad <\text{Equation 3}>$$

In Equation 3,
$\Delta EST^C_{EI}$ is a difference between a singlet energy (S1) value and a triplet energy (T1) value of the compound of Chemical Formula 1, and
$\Delta EST_{EI}$ is a difference between a singlet energy (S1) value and a triplet energy (T1) value of the compound in which Ar1 and Ar2 do not include a dicyclic or higher condensed aryl group in the compound of Chemical Formula 1.

Equation 3 can be 0.05 eV<$\Delta EST^C_{EI} - \Delta EST_{EI}$<1.00 eV.

According to one embodiment of the present specification, the compound of Chemical Formula 1 satisfies the following Equation 2.

$$0.30 \text{ eV} < \Delta EST^C_{EI} < 1.5 \text{ eV} \qquad <\text{Equation 2}>$$

In Equation 2,
$\Delta EST^C_{EI}$ is a difference between a singlet energy (S1) value and a triplet energy (T1) value of the compound of Chemical Formula 1.

In the calculation of the singlet energy (S1) and the triplet energy (T1) in the present specification, molecular structure optimization and calculation of each energy can be obtained by density functional theory (DFT) with B3PW91 function and 6-31G* basis function using Gaussian, a quantum chemistry calculation program made by Gaussian, Inc.

In the present specification, compounds having various energy band gaps can be synthesized by introducing various substituents to the core structure of the compound of Chemical Formula 1. In addition, HOMO and LUMO energy levels of the compound can also be adjusted in the present specification by introducing various substituents to the core structure having a structure as above.

In addition, an organic light emitting device according to the present specification includes a first electrode; a second electrode provided opposite to the first electrode; and one or more organic material layers provided between the first electrode and the second electrode, wherein one or more layers of the organic material layers include the compound described above.

The organic material layer includes a first stack including one or more light emitting layers; and a second stack including one or more light emitting layers, and includes one or more charge generating layers between the first stack and the second stack.

In addition, the organic material layer includes a first stack including one or more light emitting layers; a second stack including one or more light emitting layers; and a third stack including one or more light emitting layers, and one or more charge generating layers in between each of the first stack and the second stack; and the second stack and the third stack.

The one or more charge generating layers can be an N-type charge generating layer and a P-type charge generating layer, and the N-type charge generating layer and the P-type charge generating layer can be provided adjacent to each other.

The N-type charge generating layer can include both a benzimidazophenanthrinine-based derivative and a metal such as Li.

The P-type charge generating layer can include both an arylamine-based derivative and a compound including a cyano group.

The first stack, the second stack and the third stack each include one or more light emitting layers, and can further include one or more layers of a hole injection layer, a hole transfer layer, an electron blocking layer, an electron injection layer, an electron transfer layer, a hole blocking layer, a layer carrying out hole transfer and hole injection at the same time, and a layer carrying out electron transfer and electron injection at the same time.

The organic light emitting device of the present specification can be manufactured using common organic light emitting device manufacturing methods and materials except that one or more organic material layers are formed using the compound of Chemical Formula 1 described above.

When manufacturing the organic light emitting device in which an organic material layer including the compound of Chemical Formula 1 is formed, a solution coating method can be used when forming the organic material layer as well as a vacuum deposition method. Herein, the solution coating method means spin coating, dip coating, inkjet printing, screen printing, a spray method, roll coating and the like, but is not limited thereto.

The organic material layer of the organic light emitting device of the present specification can be formed in a single layer structure, but can be formed in a multilayer structure in which two or more organic material layers are laminated.

For example, the organic light emitting device of the present disclosure can have a structure including, as the organic material layer, one or more of a hole transfer layer, a hole injection layer, an electron blocking layer, a layer carrying out hole transfer and hole injection at the same time, an electron transfer layer, an electron injection layer, a hole blocking layer, and a layer carrying out electron transfer and electron injection at the same time. However, the structure of the organic light emitting device of the present specification is not limited thereto, and can include a smaller or a larger number of organic material layers.

According to one embodiment of the present specification, the organic material layer includes a light emitting layer, the light emitting layer includes a host and a dopant, and the dopant has a maximum light emission wavelength of 400 nm to 520 nm.

According to another embodiment, the dopant of the light emitting layer is a blue fluorescent dopant.

According to one embodiment of the present specification, the organic material layer includes two or more light emitting layers, and at least one of the two or more light emitting layers includes a blue fluorescent dopant.

According to another embodiment, at least two of the two or more light emitting layers have a different maximum light emission wavelength.

In another embodiment, at least one of the two or more light emitting layers includes a phosphorescent dopant, and at least one of the rest includes a fluorescent dopant.

When the organic light emitting device includes two or more light emitting layers, each of the light emitting layers can be vertically laminated as illustrated in FIGS. 5 to 7, or each of the light emitting layers can be horizontally laminated as illustrated in FIG. 8.

In the organic light emitting device of the present specification, the organic material layer includes a hole transfer layer, a hole injection layer, or a layer carrying out hole transfer and hole injection at the same time, and the hole transfer layer, the hole injection layer, or the layer carrying out hole transfer and hole injection at the same time can include the compound of Chemical Formula 1 described above.

In another organic light emitting device of the present specification, the organic material layer includes an electron transfer layer, an electron injection layer, or a layer carrying out electron transfer and electron injection at the same time, and the electron transfer layer, the electron injection layer, or the layer carrying out electron transfer and electron injection at the same time can include the compound of Chemical Formula 1 described above.

According to another embodiment, the compound of Chemical Formula 1 is included in an electron transfer layer, an electron injection layer, or a layer carrying out electron transfer and electron injection at the same time, and a blue fluorescent dopant can be included in a light emitting layer.

In another organic light emitting device of the present specification, the organic material layer includes a light emitting layer, and the light emitting layer can include the compound of Chemical Formula 1 described above.

According to another embodiment, the organic material layer includes a light emitting layer, and the light emitting layer can include the compound of Chemical Formula 1 as a host of the light emitting layer.

According to another embodiment, the organic material layer includes a light emitting layer, and the light emitting layer can include the compound of Chemical Formula 1 as a dopant.

In one embodiment of the present specification, the organic material layer includes a light emitting layer, and the light emitting layer includes a host and a dopant. Herein, the dopant can be included in 1 parts by weight to 20 parts by weight and preferably in 1 parts by weight to 10 parts by weight based on 100 parts by weight of the host.

In one embodiment of the present specification, the first electrode is an anode, and the second electrode is a cathode.

According to another embodiment, the first electrode is a cathode, and the second electrode is an anode.

Figure 3:
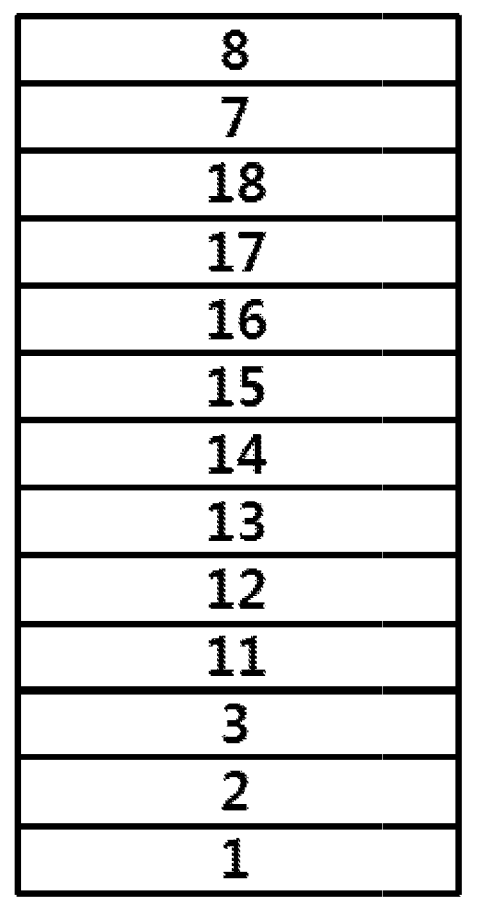

The organic light emitting device of the present specification can have structures as illustrated in FIGS. 1 to 8, however, the structure is not limited thereto.

FIG. 1 illustrates a structure of the organic light emitting device in which an anode (2), a hole injection layer (3), a hole transfer layer (4), a light emitting layer (5), a hole blocking layer (6), a layer carrying out electron transfer and electron injection at the same time (7) and a cathode (8) are consecutively laminated on a substrate (1). In such a structure, the compound of Chemical Formula 1 can be included in the layer carrying out electron transfer and electron injection at the same time (7).

FIG. 2 illustrates a structure of the organic light emitting device in which an anode (2), a hole injection layer (3), a hole transfer layer (4), an electron blocking layer (9), a light emitting layer (5), a layer carrying out electron transfer and electron injection at the same time (7) and a cathode (8) are consecutively laminated on a substrate (1). In such a structure, the compound of Chemical Formula 1 can be included in the layer carrying out electron transfer and electron injection at the same time (7).

FIG. 3 illustrates a structure of the organic light emitting device in which an anode (2), a hole injection layer (3), a first hole transfer layer (11), a first electron blocking layer (12), a first light emitting layer (13), a first electron transfer layer (14), an N-type charge generating layer (15), a P-type charge generating layer (16), a second hole transfer layer (17), a second light emitting layer (18), a layer carrying out electron transfer and electron injection at the same time (7) and a cathode (8) are consecutively laminated on a substrate (1). In such a structure, the compound of Chemical Formula 1 can be included in the layer carrying out electron transfer and electron injection at the same time (7).

FIG. 4 illustrates a structure of the organic light emitting device in which an anode (2), a hole injection layer (3), a first hole transfer layer (11), a first electron blocking layer (12), a first light emitting layer (13), a first electron transfer layer (14), an N-type charge generating layer (15), a P-type charge generating layer (16), a second hole transfer layer (17), a second light emitting layer (18), a second electron transfer layer (19), an N-type charge generating layer (15), a P-type charge generating layer (16), a third hole transfer layer (20), a third light emitting layer (21), a third electron transfer layer (22) and a cathode (8) are consecutively laminated on a substrate (1). In such a structure, the compound of Chemical Formula 1 can be included in the first electron transfer layer (14) and the third electron transfer layer (22).

FIG. 5 illustrates a structure of the organic light emitting device in which an anode (2), a hole injection layer (3), a hole transfer layer1 (111), a hole transfer layer2 (112), a blue fluorescent light emitting layer1 (113), an electron transfer layer1 (114), an N-type charge generating layer1 (115), a P-type charge generating layer1 (116), a hole transfer layer3 (117), a red phosphorescent light emitting layer (118), a yellow green phosphorescent light emitting layer (119), a green phosphorescent light emitting layer (120), an electron transfer layer2 (121), an N-type charge generating layer2 (122), a p-doping hole transfer layer (123), a hole transfer layer4 (124), a hole transfer layer5 (125), a blue fluorescent light emitting layer2 (126), an electron transfer layer3 (127), an electron injection layer (128), a cathode (8) and a capping layer (129) are consecutively laminated on a substrate (1). In such a structure, the compound of Chemical Formula 1 can be included one or more of the electron transfer layer3 (127), the electron transfer layer2 (121) and the electron transfer layer1 (114).

FIG. 6 illustrates a structure of the organic light emitting device in which an anode (2), a hole injection layer (3), a hole transfer layer1 (111), a hole transfer layer2 (112), a blue fluorescent light emitting layer1 (113), an electron transfer layer1 (114), an N-type charge generating layer1 (115), a P-type charge generating layer1 (116), a hole transfer layer3 (117), a red phosphorescent light emitting layer (118), a green phosphorescent light emitting layer (120), an electron transfer layer2 (121), an N-type charge generating layer2 (122), a p-doping hole transfer layer (123), a hole transfer layer4 (124), a hole transfer layer5 (125), a blue fluorescent light emitting layer2 (126), an electron transfer layer3 (127), an electron injection layer (128), a cathode (8) and a capping layer (129) are consecutively laminated on a substrate (1). In such a structure, the compound of Chemical Formula 1 can be included in one or more of the electron transfer layer3 (127), the electron transfer layer2 (121) and the electron transfer layer1 (114).

FIG. 7 illustrates a structure of the organic light emitting device in which an anode (2), a p-doping hole transfer layer (201), a hole transfer layer1 (202), a hole transfer layer1-1 (203), a blue fluorescent light emitting layer1 (204), an electron transfer layer1 (205), an N-type charge generating layer1 (206), a p-doping hole transfer layer (207), a hole transfer layer2 (208), a hole transfer layer2-1 (209), a blue fluorescent light emitting layer2 (210), an electron transfer layer2 (211), an N-type charge generating layer2 (212), a p-doping hole transfer layer (213), a hole transfer layer3 (214), a hole transfer layer3-1 (215), a blue fluorescent light emitting layer3 (216), an electron transfer layer3 (217), an electron injection layer (218), a cathode (8) and a capping layer (129) are consecutively laminated on a substrate (1). In such a structure, the compound of Chemical Formula 1 can be included in one or more of the electron transfer layer3 (217), the electron transfer layer2 (211) and the electron transfer layer1 (205).

FIG. 8 illustrates a structure of the organic light emitting device in which an anode (2), a p-doping hole transfer layer (301), a hole transfer layer (302-1, 302-2, 302-3), a light emitting layer (303-1, 303-2, 303-3), an electron transfer layer1 (304), an electron transfer layer1-1 (305), an electron injection layer (306), a cathode (8) and a capping layer (129) are consecutively laminated on a substrate (1). In such a structure, the compound of Chemical Formula 1 can be included in one or more of the electron transfer layer1 (304) and the electron transfer layer1-1 (305).

For example, the organic light emitting device according to the present specification can be manufactured by forming an anode on a substrate by depositing a metal, a metal oxide having conductivity, or an alloy thereof using a physical vapor deposition (PVD) method such as sputtering or e-beam evaporation, forming an organic material layer including a hole injection layer, a hole transfer layer, a light emitting layer, an electron blocking layer, an electron transfer layer, an electron injection layer and the like thereon, and then depositing a material capable of being used as a cathode thereon. In addition to such a method, the organic light emitting device can also be manufactured by consecutively depositing a cathode material, an organic material layer and an anode material on a substrate.

The organic material layer can have a multilayer structure including a hole injection layer, a hole transfer layer, a layer carrying out hole injection and hole transfer at the same time, an electron blocking layer, a light emitting layer, an electron transfer layer, an electron injection layer, a layer carrying out electron injection and electron transfer at the same time and the like, but is not limited thereto, and can have a single layer structure. In addition, the organic material layer can be formed to a smaller number of layers using a solvent process instead of a deposition method with various polymer materials. The solution process can be a method such as spin coating, dip coating, doctor blading, screen printing, inkjet printing or a heat transfer method.

The anode is an electrode injecting holes, and as the anode material, materials having large work function are normally preferred so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as $ZnO:Al$ or $SnO_2:Sb$; conductive polymers such as poly(3-methylthiophene), poly[3,4-(ethylene-1,2-dioxy)thiophene] (PEDOT), polypyrrole and polyaniline, but are not limited thereto.

The cathode is an electrode injecting electrons, and as the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as $LiF/Al$ or $LiO_2/Al$, and the like, but are not limited thereto.

The hole injection layer is a layer performing a role of facilitating hole injection from an anode to a light emitting layer. The hole injection material is a material capable of favorably receiving holes from an anode at a low voltage, and the highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer can perform a role of facilitating hole transfer. As the hole transfer material, materials capable of receiving holes from an anode or a hole injection layer, moving the holes to a light emitting layer, and having high mobility for the holes are suitable. Specific examples thereof include arylamine-based organic materials, conductive polymers, block copolymers having conjugated parts and non-conjugated parts together, and the like, but are not limited thereto.

An electron blocking layer can be provided between the hole transfer layer and a light emitting layer. As the electron blocking layer, materials known in the art can be used.

The light emitting layer can emit red, green or blue light, and can be formed with a phosphorescent material or a fluorescent material. The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes ($Alq_3$); carbazole-based compounds; dimerized styryl compounds; BAlq; 10-hydroxybenzo quinoline-metal compounds; benzoxazole-, benzothiazole- and benzimidazole-based compounds; poly(p-phenylenevinylene) (PPV)-based polymers; spiro compounds; polyfluorene, rubrene, and the like, but are not limited thereto.

A host material of the light emitting layer includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes carbazole derivatives, dibenzofuran derivatives, ladder-type furan compounds, pyrimidine derivatives and the like, however, the material is not limited thereto.

When the light emitting layer emits red light, a phosphorescent material such as bis(1-phenylisoquinoline)acetylacetonate iridium (PIQIr(acac)), bis(1-phenylquinoline)acetylacetonate iridium (PQIr(acac)), tris(1-phenylquinoline) iridium (PQIr) or octaethylporphyrin platinum (PtOEP), or a fluorescent material such as tris(8-hydroxyquinolino)aluminum ($Alq_3$) can be used as a light emitting dopant, however, the light emitting dopant is not limited thereto. When the light emitting layer emits green light, a phosphorescent material such as fac-tris(2-phenylpyridine)iridium ($Ir(ppy)_3$), or a fluorescent material such as tris(8-hydroxyquinolino)aluminum ($Alq_3$), an anthracene-based compound, a pyrene-based compound or a boron-based compound can be used as a light emitting dopant, however, the light emitting dopant is not limited thereto. When the light emitting layer emits blue light, a phosphorescent material such as $(4,6-F2ppy)_2Irpic$, or a fluorescent material such as spiro-DPVBi, spiro-6P, distyrylbenzene (DSB), distyrylarylene (DSA), a PFO-based polymer, a PPV-based polymer, an anthracene-based compound, a pyrene-based compound or a boron-based compound can be used as a light emitting dopant, however, the light emitting dopant is not limited thereto.

The electron transfer layer can perform a role of facilitating electron transfer. As the electron transfer material, materials capable of favorably receiving electrons from a cathode, moving the electrons to a light emitting layer, and having high mobility for the electrons are suitable. Specific examples thereof include Al complexes of 8-hydroxyquinoline; complexes including $Alq_3$; organic radical compounds; hydroxyflavon-metal complexes; and the like, but are not limited thereto.

The electron injection layer can perform a role of facilitating electron injection. The electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

As the layer carrying out electron transfer and electron injection at the same time, the compound of the present disclosure, or materials known in the art can be used, and when including the compound of the present disclosure, compounds such as lithium quinolate (LiQ) can be further included.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato) (2-naphtholato)gallium and the like, but is not limited thereto.

The hole blocking layer is a layer blocking holes from reaching a cathode and can be generally formed under the same condition as the hole injection layer. Specifically, oxadiazole derivatives, triazole derivatives, phenanthroline derivatives, BCP, aluminum complexes and the like are included, however, the hole blocking layer is not limited thereto.

The organic light emitting device according to the present specification can be a top-emission type, a bottom-emission type or a dual-emission type depending on the materials used.

EXAMPLES

Hereinafter, the present specification will be described in detail with reference to examples in order to specifically describe the present specification. However, the examples according to the present specification can be modified to various other forms, and the scope of the present application is not to be construed as being limited to the examples described below. Examples of the present specification are provided in order to more fully describe the present specification to those having average knowledge in the art.

Synthesis Example 1

Preparation of Compound 1

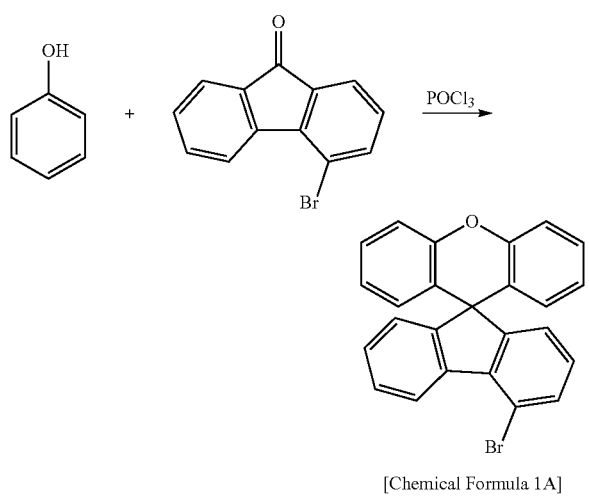

[Chemical Formula 1A]

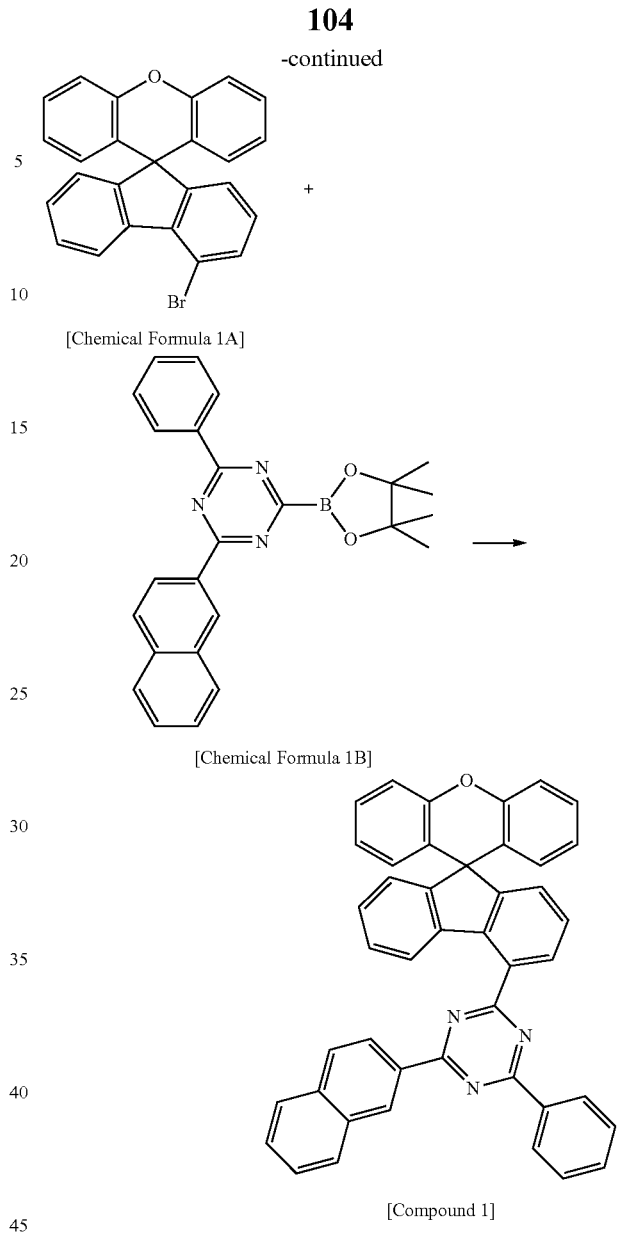

[Chemical Formula 1A]

[Chemical Formula 1B]

[Compound 1]

(1) Preparation of Chemical Formula 1A

A mixture of 4-bromo-9H-fluoren-9-one (10 g, 38.6 mmol), phenol (7.25 g, 77.2 mmol) and excess phosphoryl chloride ($POCl_3$) was refluxed at 120° C. After cooling the result to room temperature, excess ethanol was introduced thereto, and the result was filtered. Filtered solids were dissolved in pyridine, and the result was heated, cooled to room temperature, and then filtered. The result was recrystallized with chloroform and ethyl acetate to obtain Chemical Formula 1A (14 g, yield 87%).

MS: $[M+H]^+$=411

(2) Preparation of Compound 1

After dissolving Chemical Formula 1A (10 g, 24.3 mmol), Chemical Formula 1B-triazine boronic acid (9.82 g, 24 mmol) and potassium carbonate ($K_2CO_3$) (10 g, 72.9 mmol) in tetrahydrofuran (THF) (300 mL) and $H_2O$ (100 ml), the result was heated to 90° C. Tetrakis(triphenylphosphine)palladium ($Pd(PPh_3)_4$) (0.56 g, 0.48 mmol) was added thereto, and the result was refluxed for 4 hours. After cooling the result to room temperature, the water layer was removed.

To the organic layer, magnesium sulfate (MgSO$_4$) was introduced, and the result was filtered. The result was concentrated and then purified by column chromatography to obtain Compound 1 (10 g, yield 67%).

MS: [M+H]$^+$=613

Synthesis Example 2

Preparation of Compound 2

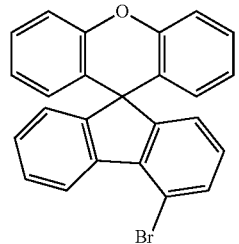

[Chemical Formula 1A]

+

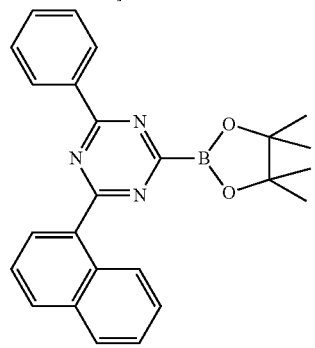

[Chemical Formula 2B]

→

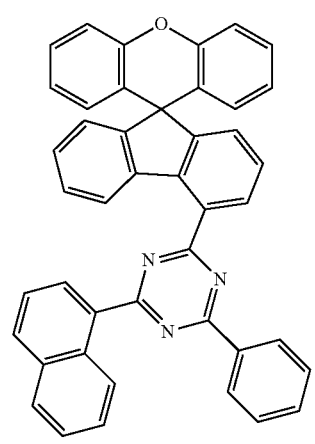

[Compound 2]

Compound 2 (11 g, yield 74%) was obtained in the same manner as in the preparation of Compound 1 of Synthesis Example 1, except that Chemical Formula 2B was used instead of Chemical Formula 1B.

MS: [M+H]$^+$=613

Synthesis Example 3

Preparation of Compound 3

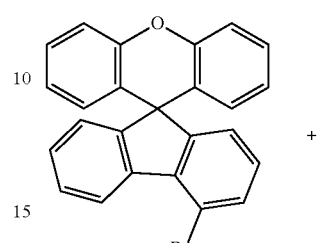

[Chemical Formula 1A]

+

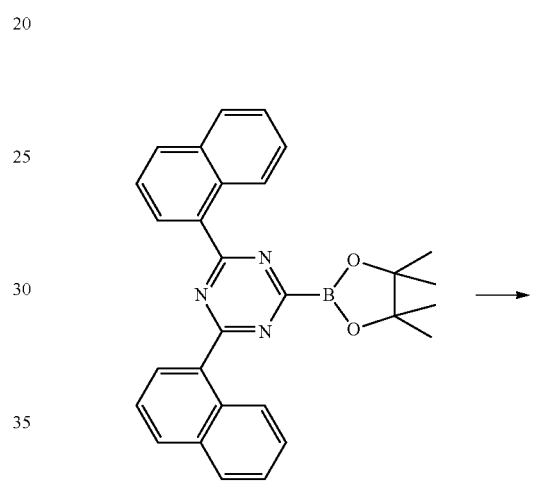

[Chemical Formula 3B]

→

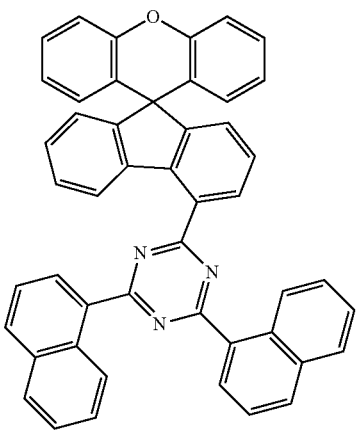

[Compound 3]

Compound 3 (13 g, yield 81%) was obtained in the same manner as in the preparation of Compound 1 of Synthesis Example 1, except that Chemical Formula 3B was used instead of Chemical Formula 1B.

MS: [M+H]$^+$=663

Synthesis Example 4

Preparation of Compound 4

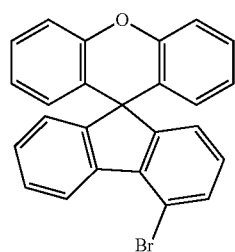

[Chemical Formula 1A]

+

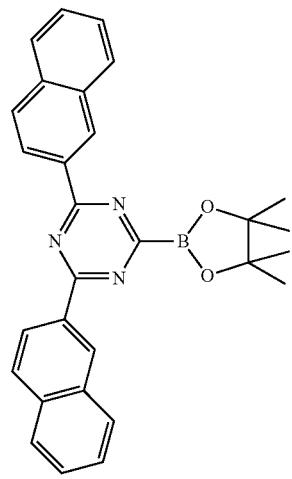

[Chemical Formula 4B]

→

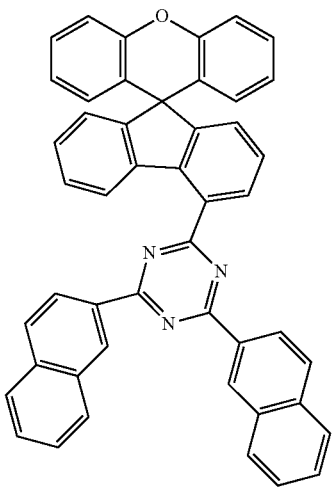

[Compound 4]

Compound 4 (12.5 g, yield 78%) was obtained in the same manner as in the preparation of Compound 1 of Synthesis Example 1, except that Chemical Formula 4B was used instead of Chemical Formula 1B.

MS: $[M+H]^+$=663

Synthesis Example 5

Preparation of Compound 5

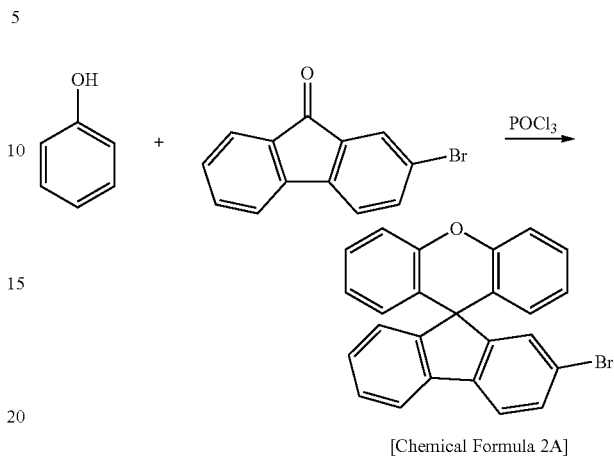

[Chemical Formula 2A]

+

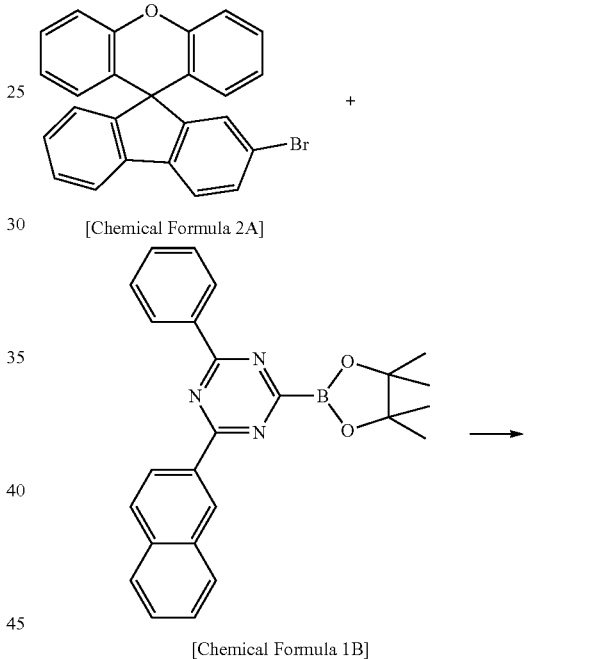

[Chemical Formula 1B]

→

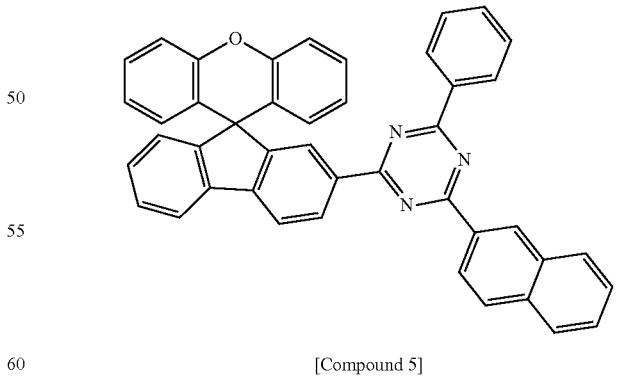

[Compound 5]

Compound 5 (9 g, yield 60%) was obtained in the same manner as in the preparation of Compound 1 of Synthesis Example 1, except that Chemical Formula 2A was used instead of Chemical Formula 1A.

MS: $[M+H]^+$=613

Synthesis Example 6

Preparation of Compound 6

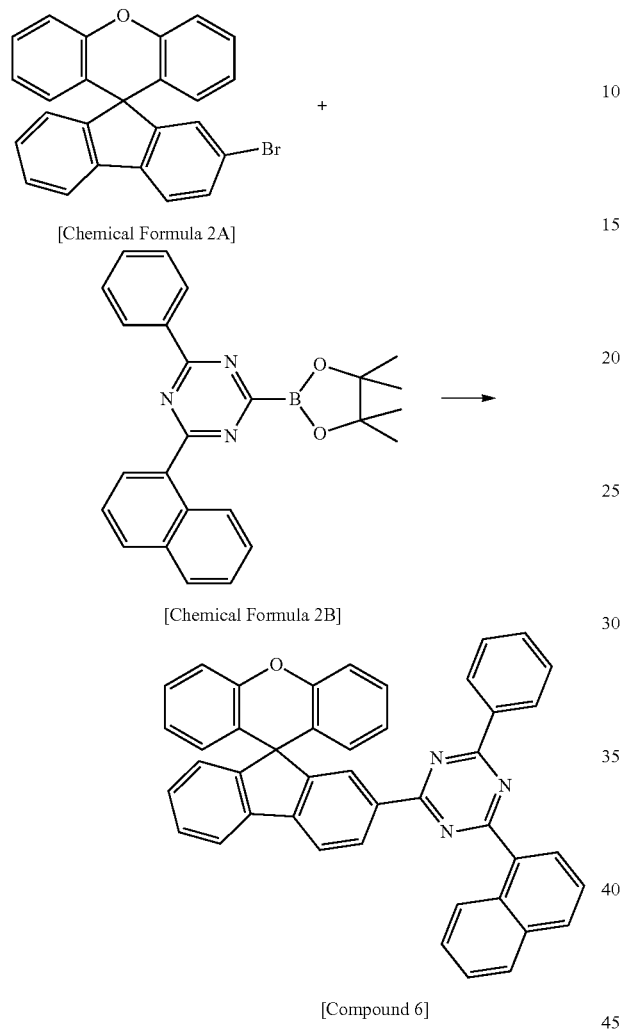

Compound 6 (12 g, yield 81%) was obtained in the same manner as in the preparation of Compound 1 of Synthesis Example 1, except that Chemical Formula 2B was used instead of Chemical Formula 1B.

MS: $[M+H]^+=613$

Synthesis Example 7

Preparation of Compound 7

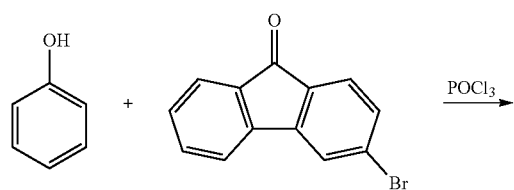

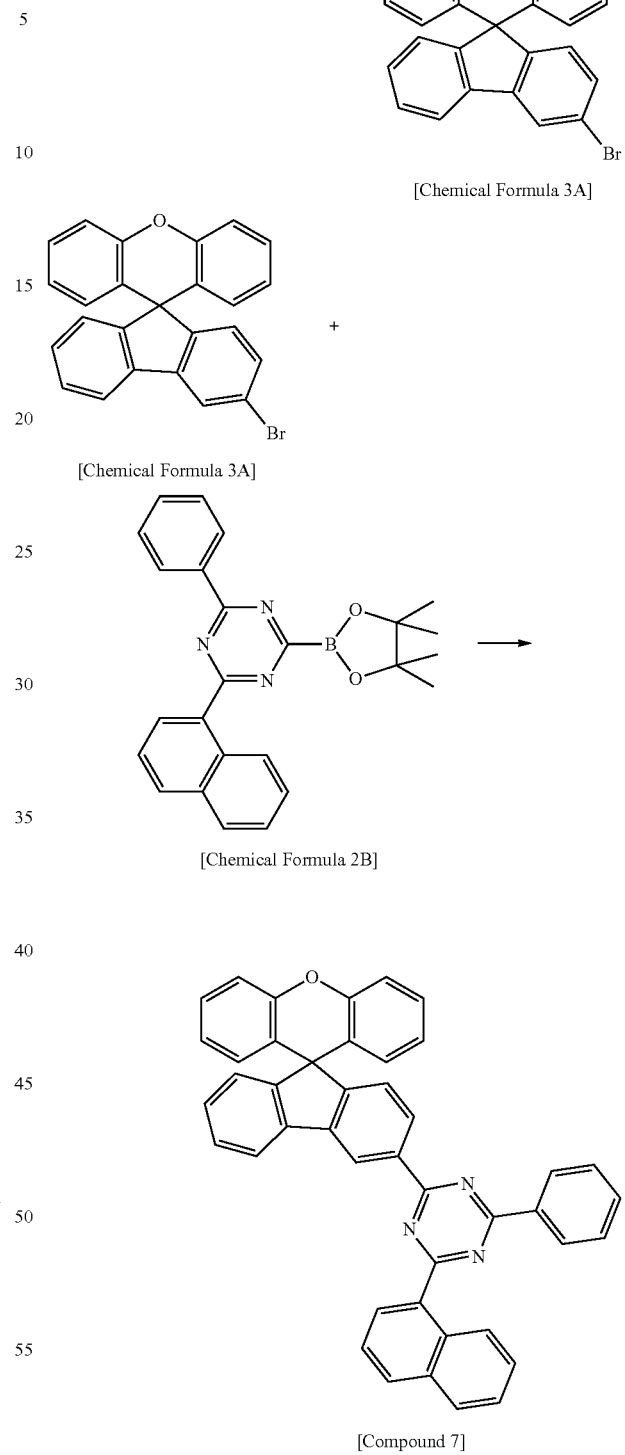

Compound 7 (11 g, yield 74%) was obtained in the same manner as in the preparation of Compound 1 of Synthesis Example 1, except that Chemical Formula 3A was used instead of Chemical Formula 1A, and Chemical Formula 2B was used instead of Chemical Formula 1B.

MS: $[M+H]^+=613$

Synthesis Example 8

Preparation of Compound 8

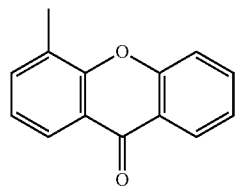

[Chemical Formula 4A-1]

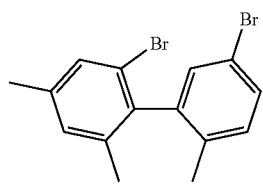

[Chemical Formula 4A-2]

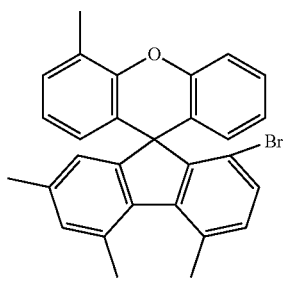

[Chemical Formula 4A]

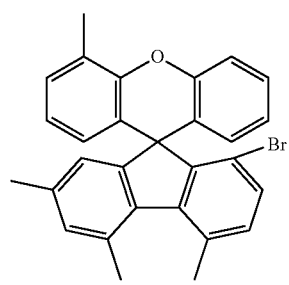

[Chemical Formula 4A]

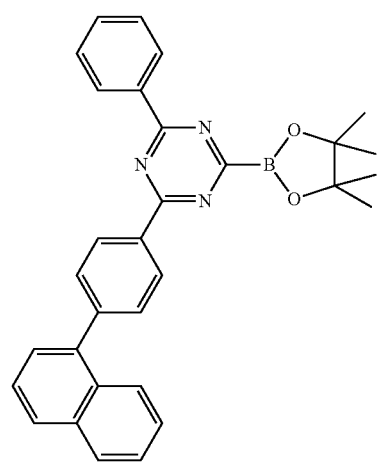

[Chemical Formula 5B]

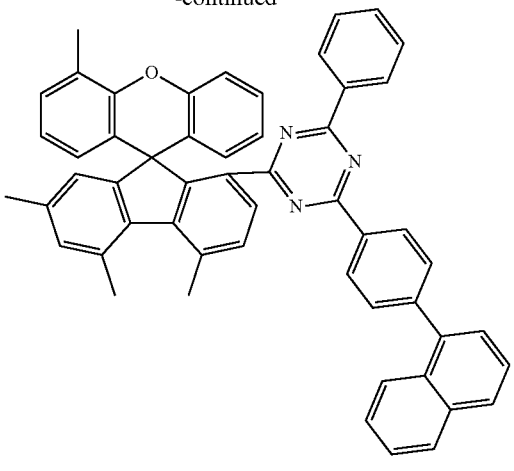

[Compound 8]

(1) Preparation of Chemical Formula 4A

After dissolving Chemical Formula 4A-2 (13.6 g, 38.6 mmol) in tetrahydrofuran and cooling the result to −78° C. under nitrogen, n-BuLi (1.05 eq.) was introduced thereto. After 30 minutes, Chemical Formula 4A-1 (8.1 g, 38.6 mmol) was introduced thereto, and the result was stirred at room temperature. A produced phenol intermediate was filtered, an excess aqueous $H_2SO_4$ solution was introduced thereto, and the result was refluxed. After cooling the result to room temperature, excess ethanol was introduced thereto, and the result was filtered. Filtered solids were recrystallized with chloroform and ethyl acetate to obtain Chemical Formula 4A (10 g, yield 56%).

MS: $[M+H]^+$=467

(2) Preparation of Compound 8

Compound 8 (15 g, yield 83%) was obtained in the same manner as in the preparation of Compound 1 of Synthesis Example 1, except that Chemical Formulae 4A and 5B were respectively used instead of Chemical Formulae 1A and 1B.

MS: $[M+H]^+$=745

Synthesis Example 9

Preparation of Compound 9

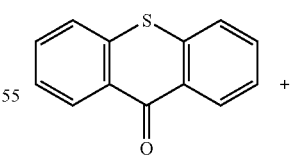

[Chemical Formula 5A-1]

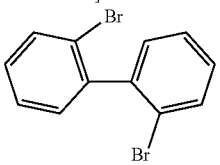

[Chemical Formula 5A-2]

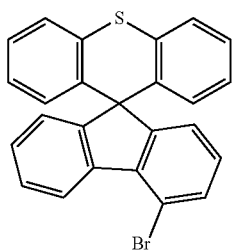

[Chemical Formula 5A]

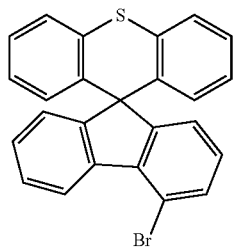

[Chemical Formula 5A]

+

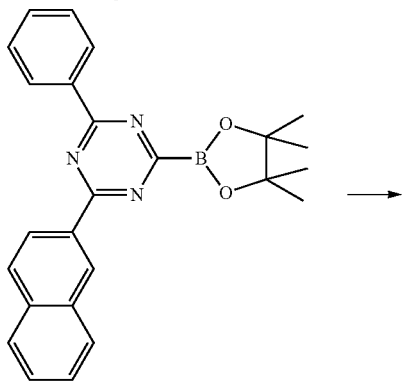

[Chemical Formula 1B]

→

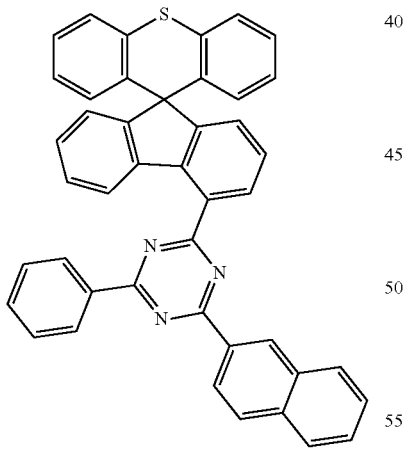

[Compound 9]

(1) Preparation of Chemical Formula 5A

Chemical Formula 5A (10 g, yield 61%) was obtained in the same manner as in the preparation of Compound 8 of Synthesis Example 8, except that Chemical Formulae 5A-1 and 5A-2 were respectively used instead of Chemical Formulae 4A-1 and 4A-2.

MS: [M+H]$^+$=427

(2) Preparation of Compound 9

Compound 9 (10 g, yield 65%) was obtained in the same manner as in the preparation of Compound 1 of Synthesis Example 1, except that Chemical Formula 5A was used instead of Chemical Formula 1A.

MS: [M+H]$^+$=629

Synthesis Example 10

Preparation of Compound 10

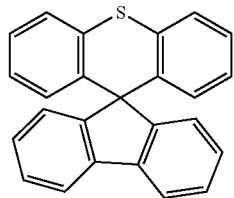

+

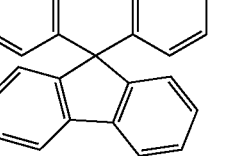

[Chemical Formula 5A]

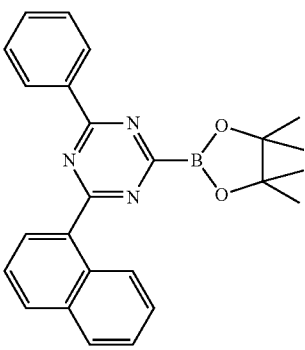

[Chemical Formula 2B]

→

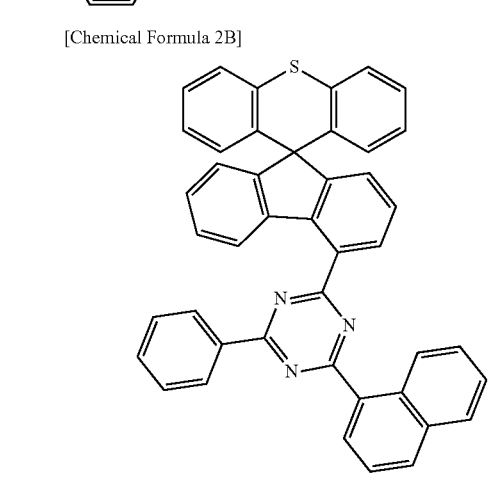

[Compound 10]

(1) Preparation of Compound 10

Compound 10 (10.5 g, yield 67%) was obtained in the same manner as in the preparation of Compound 9 of Synthesis Example 9, except that Chemical Formula 2B was used instead of Chemical Formula 1B.

MS: [M+H]$^+$=629

Synthesis Example 11

Preparation of Compound 11

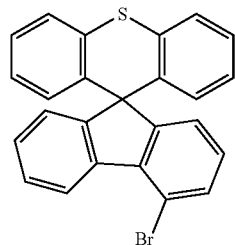

[Chemical Formula 5A]

+

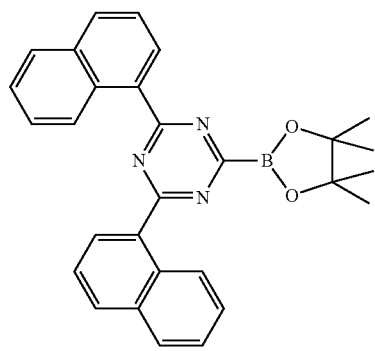

[Chemical Formula 4B]

→

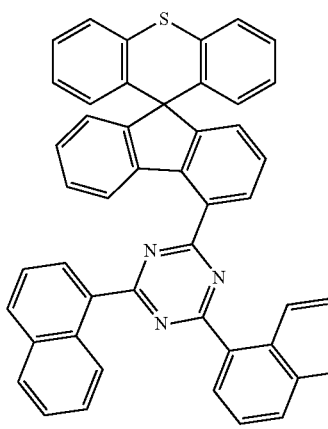

[Compound 11]

(1) Preparation of Compound 11

Compound 11 (12 g, yield 73%) was obtained in the same manner as in the preparation of Compound 9 of Synthesis Example 9, except that Chemical Formula 4B was used instead of Chemical Formula 1B.

MS: $[M+H]^+=679$

Synthesis Example 12

Preparation of Compound 12

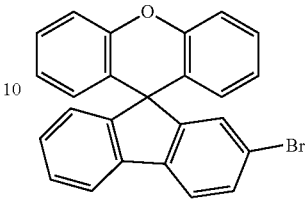

[Chemical Formula 2A]

+

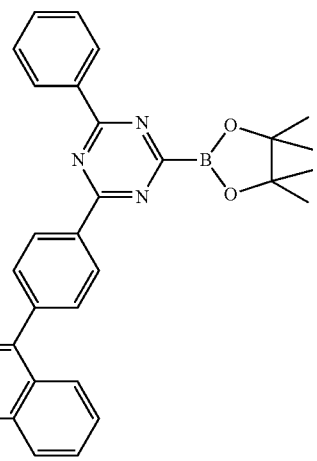

[Chemical Formula 5B]

→

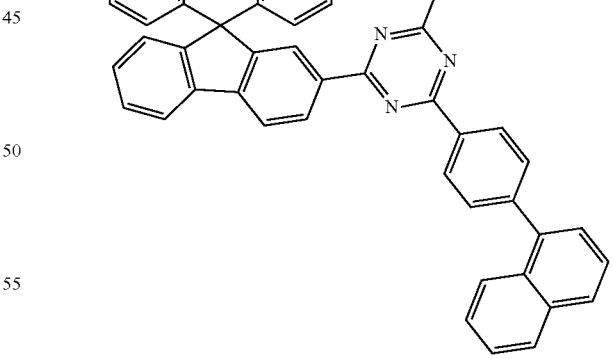

[Compound 12]

(1) Preparation of Compound 12

Compound 12 (12 g, yield 72%) was obtained in the same manner as in the preparation of Compound 5 of Synthesis Example 5, except that Chemical Formula 5B was used instead of Chemical Formula 1B.

MS: $[M+H]^+=689$

Synthesis Example 13

Preparation of Compound 13

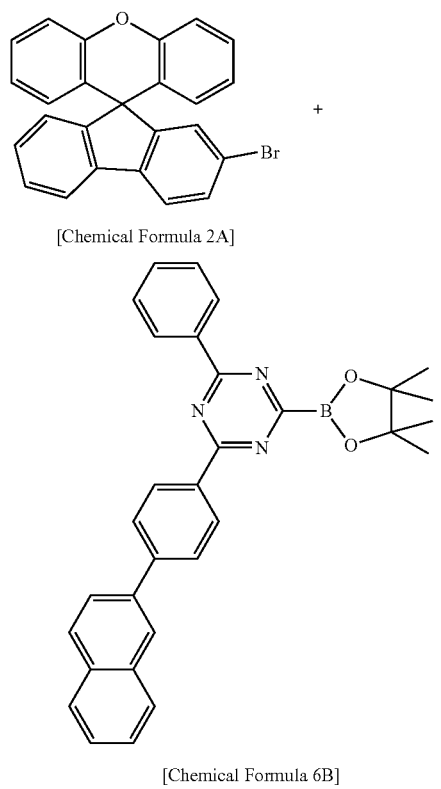

[Compound 13]

(1) Preparation of Compound 13

Compound 13 (13 g, yield 78%) was obtained in the same manner as in the preparation of Compound 5 of Synthesis Example 5, except that Chemical Formula 6B was used instead of Chemical Formula 1B.

MS: $[M+H]^+=689$

Synthesis Example 14

Preparation of Compound 14

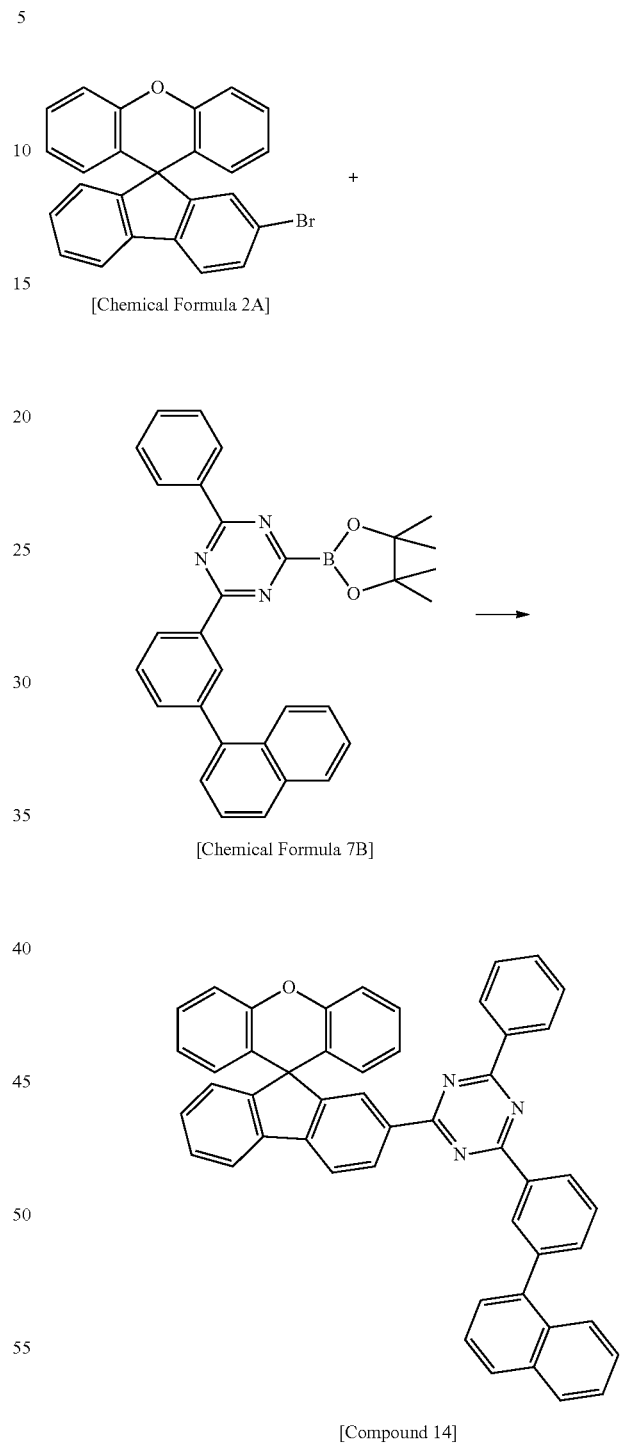

[Compound 14]

(1) Preparation of Compound 14

Compound 14 (11 g, yield 66%) was obtained in the same manner as in the preparation of Compound 5 of Synthesis Example 5, except that Chemical Formula 7B was used instead of Chemical Formula 1B.

MS: $[M+H]^+=689$

Synthesis Example 15

Preparation of Compound 15

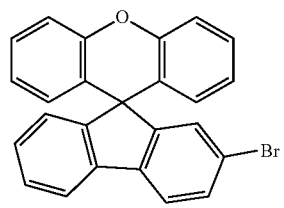

[Chemical Formula 2A]

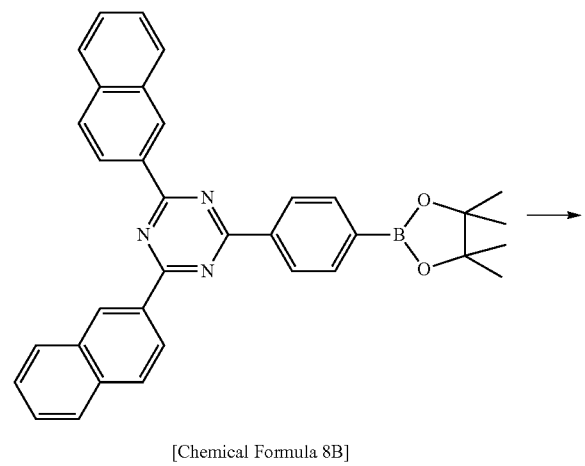

[Chemical Formula 8B]

[Compound 15]

(1) Preparation of Compound 15

Compound 15 (14 g, yield 78%) was obtained in the same manner as in the preparation of Compound 5 of Synthesis Example 5, except that Chemical Formula 8B was used instead of Chemical Formula 1B.

MS: [M+H]$^+$=739

Synthesis Example 16

Preparation of Compound 16

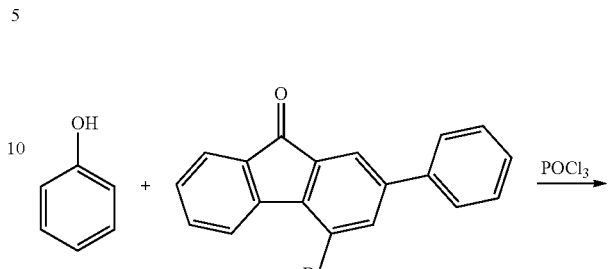

[Chemical Formula 6A]

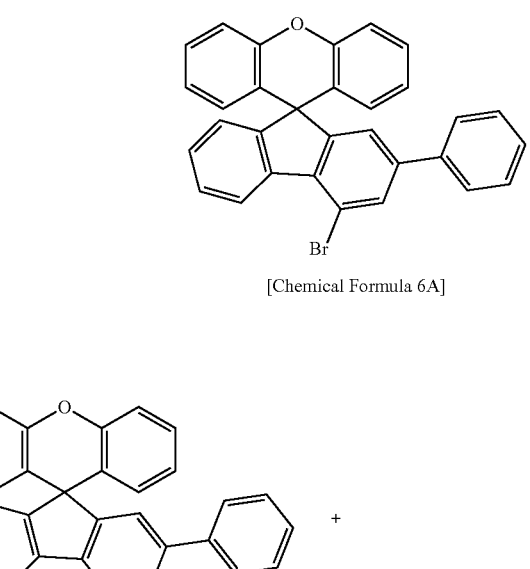

[Chemical Formula 6A]

[Chemical Formula 9B]

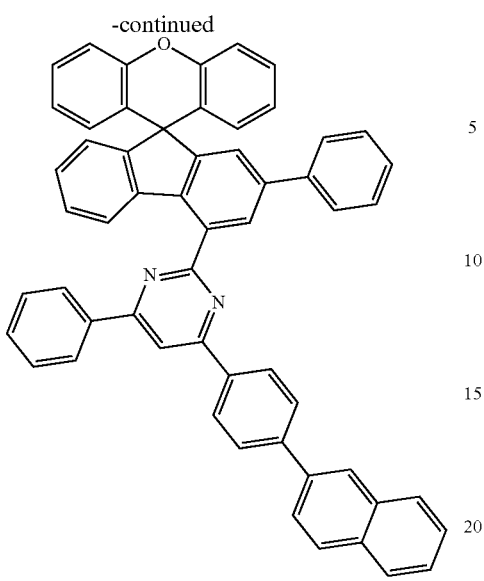

[Compound 16]

Compound 16 (15 g, yield 81%) was obtained in the same manner as in the preparation of Compound 1 of Synthesis Example 1, except that Chemical Formulae 6A and 9B were respectively used instead of Chemical Formulae 1A and 1B.

MS: [M+H]$^+$=764

Synthesis Example 17

Preparation of Compound 17

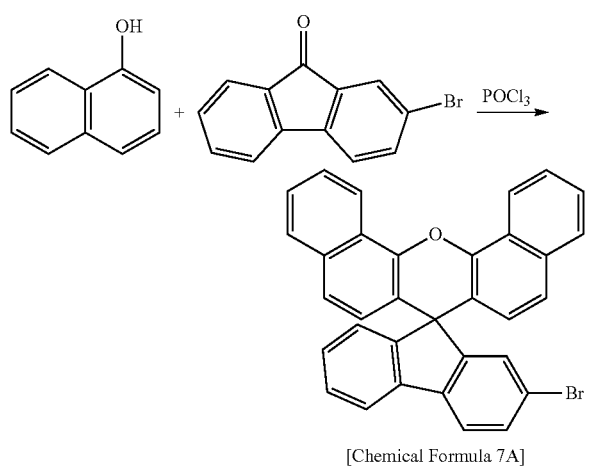

[Chemical Formula 7A]

+

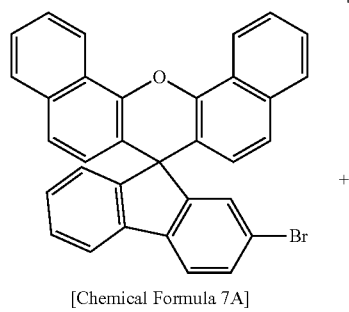

[Chemical Formula 7A]

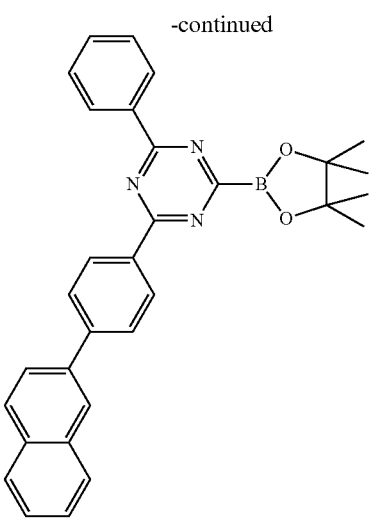

[Chemical Formula 6B]

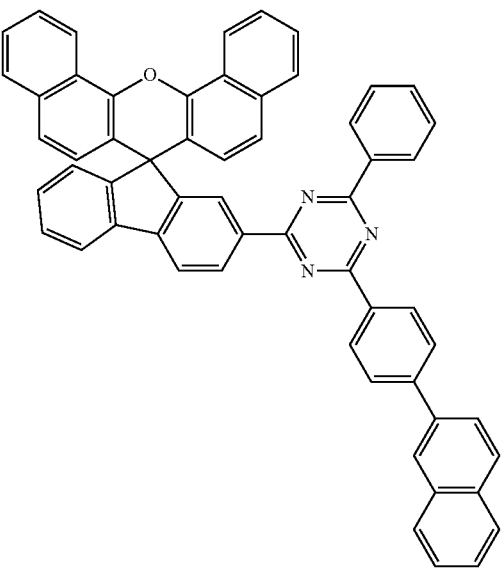

[Compound 17]

(1) Preparation of Chemical Formula 7A

Chemical Formula 7A (15 g, yield 76%) was obtained in the same manner as in the preparation of Chemical Formula 1A of Synthesis Example 1, except that naphthol was used instead of phenol.

MS: [M+H]$^+$=511

(2) Preparation of Compound 17

Compound 17 (13 g, yield 68%) was obtained in the same manner as in the preparation of Compound 13 of Synthesis Example 13, except that Chemical Formula 7A was used instead of Chemical Formula 2A.

MS: [M+H]$^+$=789

Synthesis Example 18

Preparation of Compound 18

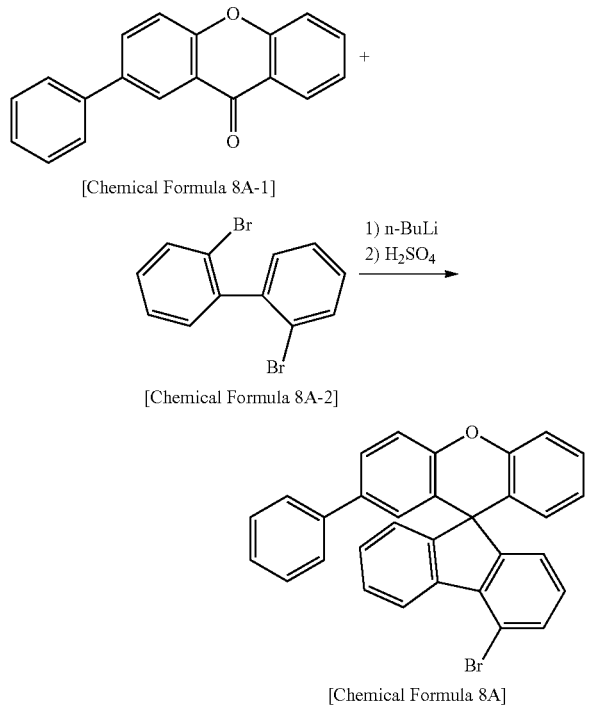

[Chemical Formula 8A-1]

[Chemical Formula 8A-2]

[Chemical Formula 8A]

[Chemical Formula 8A]

[Chemical Formula 1B]

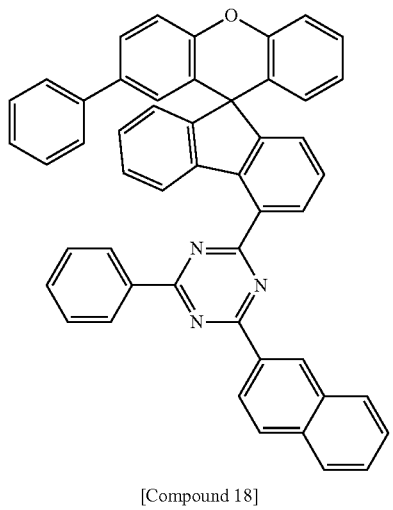

[Compound 18]

(1) Preparation of Chemical Formula 8A

Chemical Formula 8A (13 g, yield 69%) was obtained in the same manner as in the preparation of Chemical Formula 5A of Synthesis Example 9, except that Chemical Formula 8A-1 was used instead of Chemical Formula 5A-1.

MS: [M+H]$^+$=487

(2) Preparation of Compound 18

Compound 18 (12 g, yield 72%) was obtained in the same manner as in the preparation of Compound 9 of Synthesis Example 9, except that Chemical Formula 8A was used instead of Chemical Formula 5A.

MS: [M+H]$^+$=689

Synthesis Example 19

Preparation of Compound 19

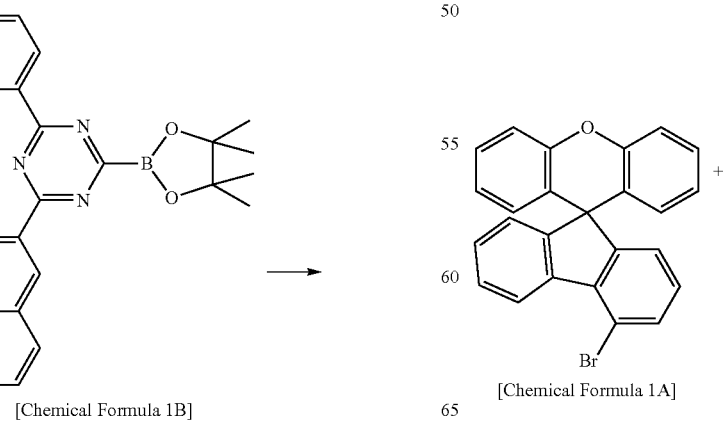

[Chemical Formula 1A]

-continued

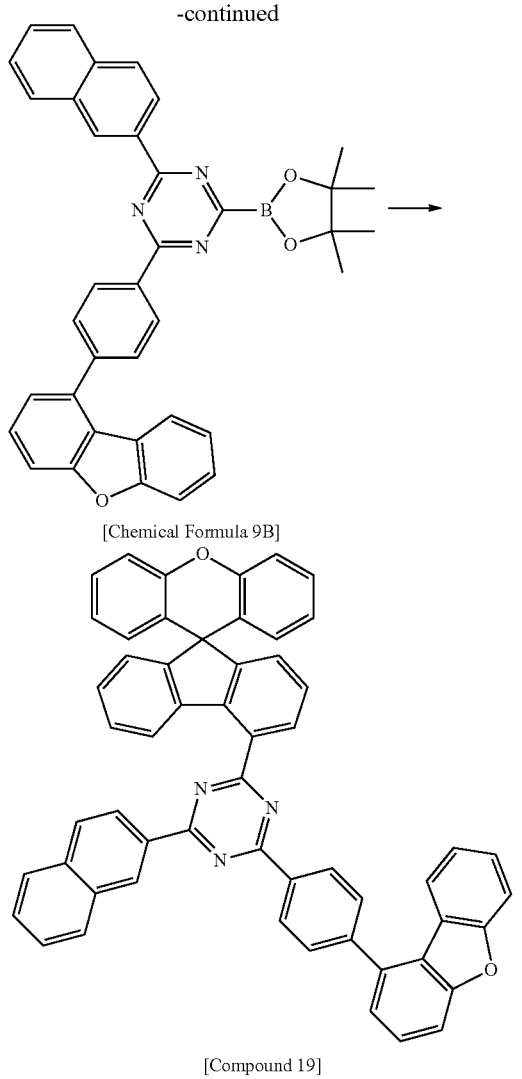

[Chemical Formula 9B]

[Compound 19]

Compound 19 (15 g, yield 79%) was obtained in the same manner as in the preparation of Compound 1 of Synthesis Example 1, except that Chemical Formula 9B was used instead of Chemical Formula 1B.

MS: [M+H]$^+$=779

Synthesis Example 20

Preparation of Compound 20

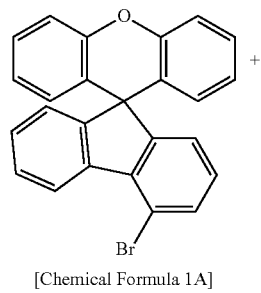

[Chemical Formula 1A]

-continued

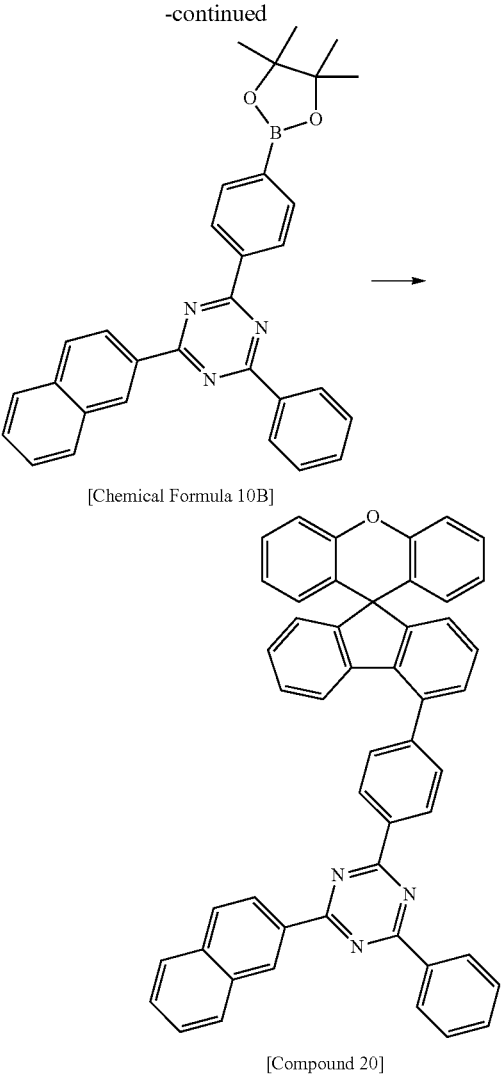

[Chemical Formula 10B]

[Compound 20]

Compound 20 (9 g, yield 54%) was obtained in the same manner as in the preparation of Compound 1 of Synthesis Example 1, except that Chemical Formula 10B was used instead of Chemical Formula 1B.

MS: [M+H]$^+$=689

Synthesis Example 21

Preparation of Compound 21

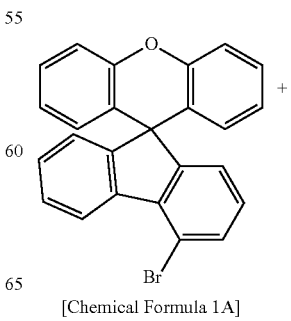

[Chemical Formula 1A]

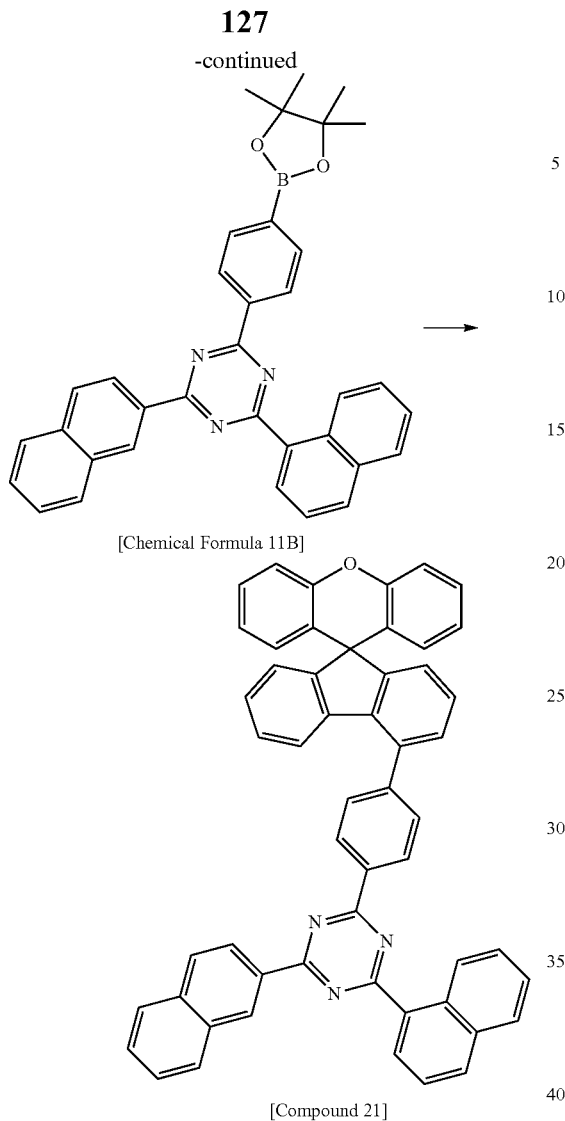

[Chemical Formula 11B]

[Compound 21]

Compound 21 (10 g, yield 56%) was obtained in the same manner as in the preparation of Compound 1 of Synthesis Example 1, except that Chemical Formula 11B was used instead of Chemical Formula 1B.

MS: [M+H]$^+$=739

Synthesis Example 22

Preparation of Compound 22

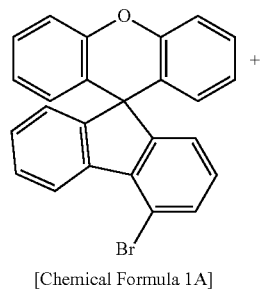

[Chemical Formula 1A]

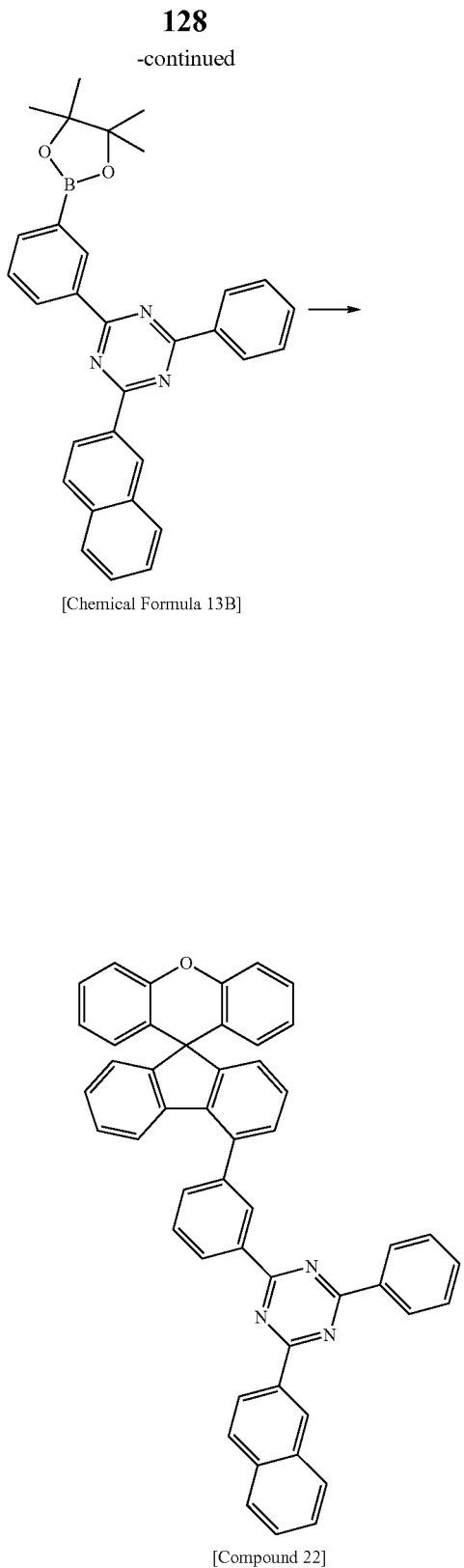

[Chemical Formula 13B]

[Compound 22]

Compound 22 (11 g, yield 66%) was obtained in the same manner as in the preparation of Compound 1 of Synthesis Example 1, except that Chemical Formula 13B was used instead of Chemical Formula 1B.

MS: [M+H]$^+$=689

Synthesis Example 23

Preparation of Compound 23

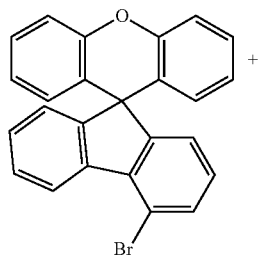

[Chemical Formula 1A]

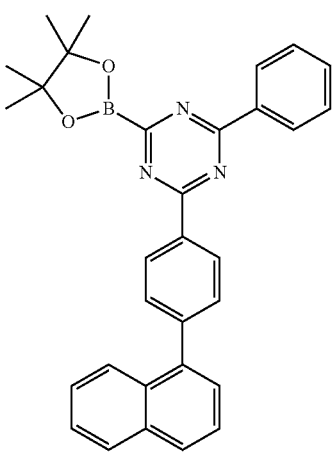

[Chemical Formula 5B]

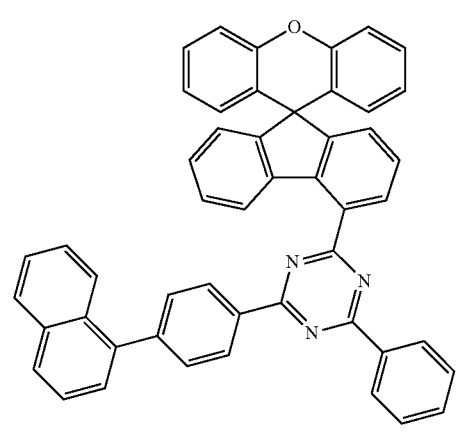

[Compound 23]

Compound 23 (14 g, yield 84%) was obtained in the same manner as in the preparation of Compound 1 of Synthesis Example 1, except that Chemical Formula 5B was used instead of Chemical Formula 1B.

MS: $[M+H]^+=689$

Synthesis Example 24

Preparation of Compound 24

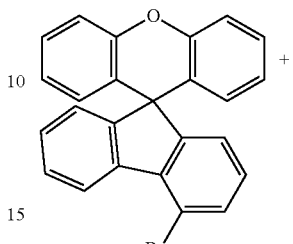

[Chemical Formula 1A]

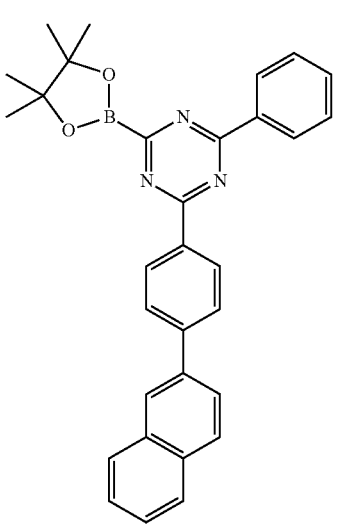

[Chemical Formula 6B]

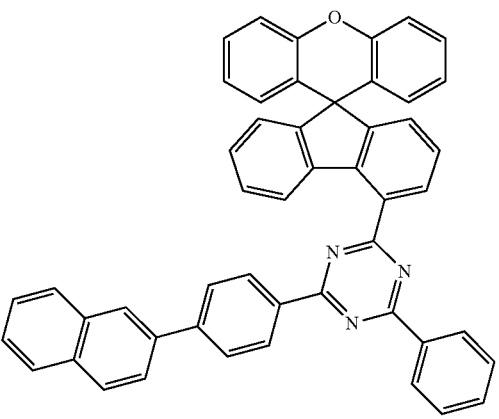

[Compound 24]

Compound 24 (12 g, yield 72%) was obtained in the same manner as in the preparation of Compound 1 of Synthesis Example 1, except that Chemical Formula 6B was used instead of Chemical Formula 1B.

MS: $[M+H]^+=689$

Synthesis Example 25

Preparation of Compound 25

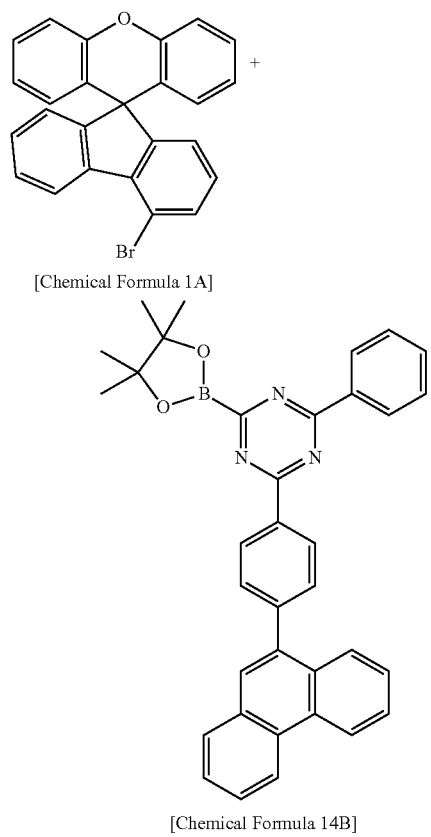

[Compound 25]

Compound 25 (13 g, yield 72%) was obtained in the same manner as in the preparation of Compound 1 of Synthesis Example 1, except that Chemical Formula 14B was used instead of Chemical Formula 1B.

MS: $[M+H]^+$=739

Synthesis Example 26

Preparation of Compound 26

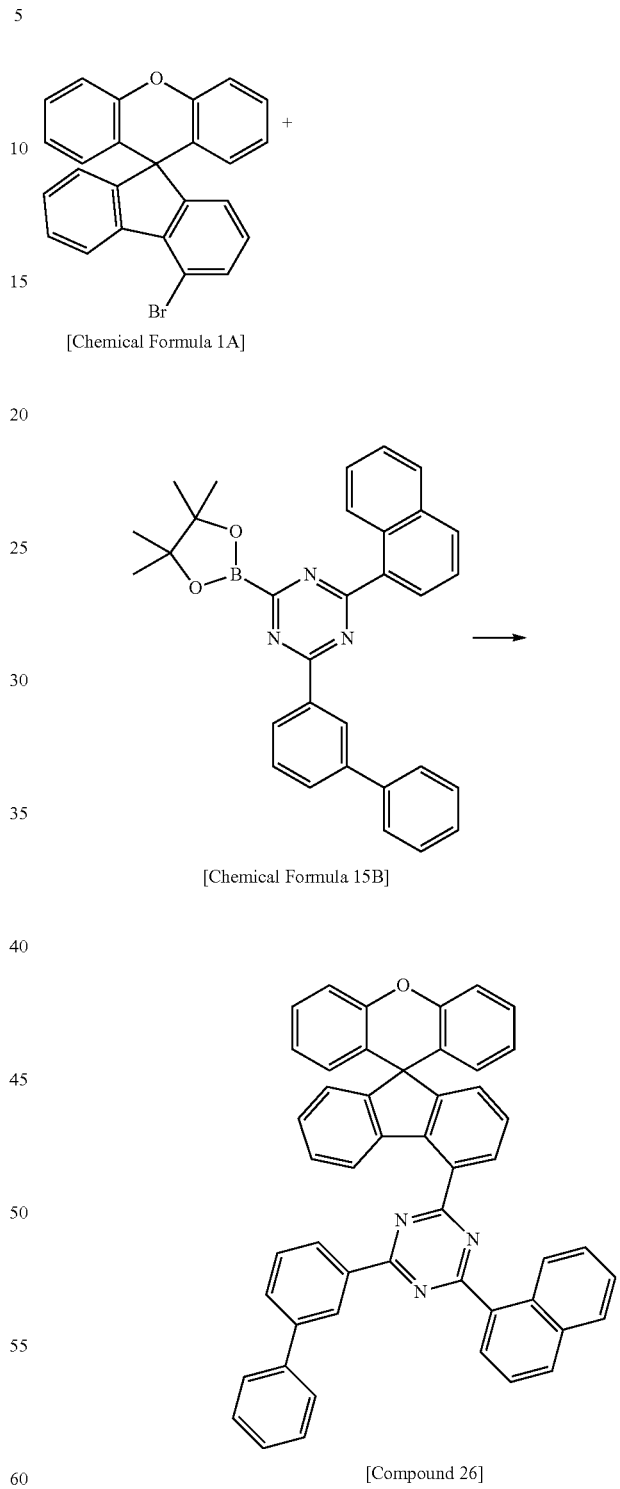

[Compound 26]

Compound 26 (8 g, yield 48%) was obtained in the same manner as in the preparation of Compound 1 of Synthesis Example 1, except that Chemical Formula 15B was used instead of Chemical Formula 1B.

MS: $[M+H]^+$=689

Synthesis Example 27

Preparation of Compound 27

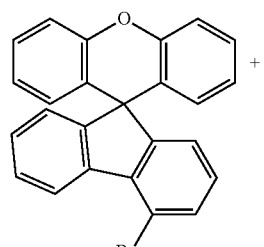

[Chemical Formula 1A]

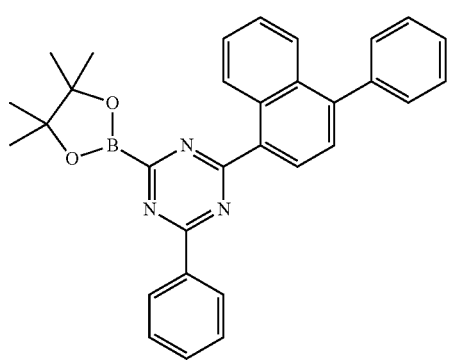

[Chemical Formula 16B]

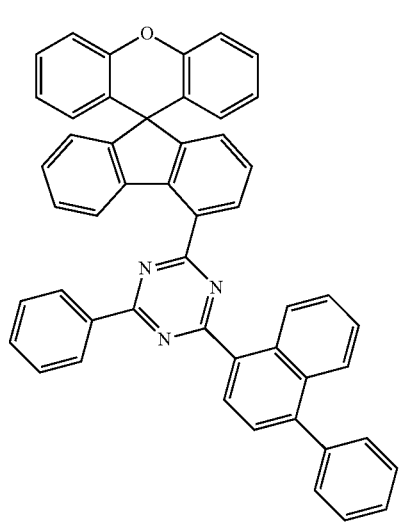

[Compound 27]

Compound 27 (11 g, yield 66%) was obtained in the same manner as in the preparation of Compound 1 of Synthesis Example 1, except that Chemical Formula 16B was used instead of Chemical Formula 1B.

MS: $[M+H]^+=689$

Synthesis Example 28

Preparation of Compound 28

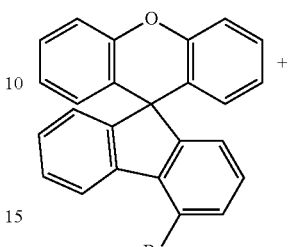

[Chemical Formula 1A]

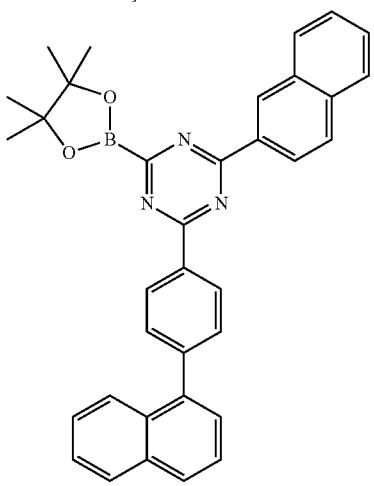

[Chemical Formula 17B]

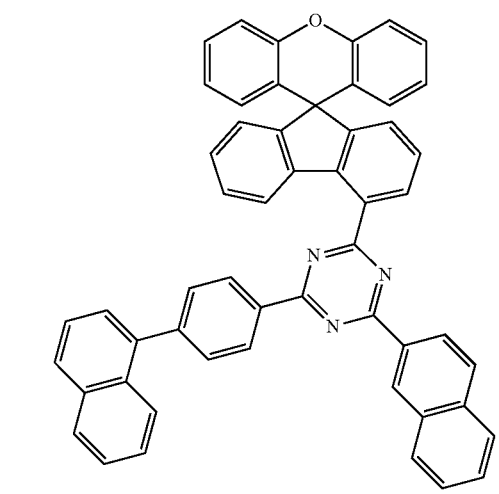

[Compound 28]

Compound 28 (15 g, yield 83%) was obtained in the same manner as in the preparation of Compound 1 of Synthesis Example 1, except that Chemical Formula 17B was used instead of Chemical Formula 1B.

MS: $[M+H]^+=739$

EXPERIMENTAL EXAMPLES

Experimental Example 1

Calculation of Difference Between S1 and T1 Energy Values (ΔEST)

A difference between S1 and T1 energy values of the compound corresponding to Chemical Formula 1, and a difference between S1 and T1 energy values of the compound having the same core structure as the compound of the present disclosure but not including a dicyclic or higher condensed aryl group were calculated, and shown in the following Table 1, and the difference between S1 and T1 energy values (ΔEST, eV) are shown below each of the compounds.

TABLE 1

| Measurement 1 |
| --- |

Compounds 1 to 4

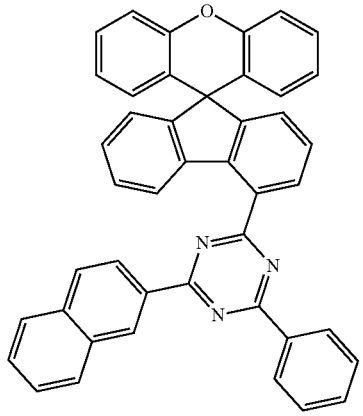

0.94 eV

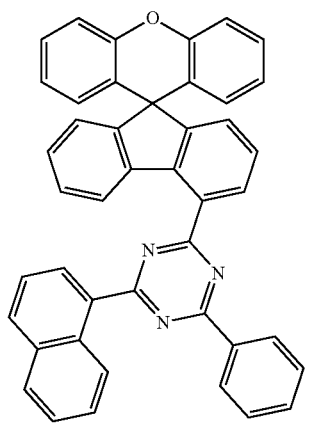

1.03 eV

TABLE 1-continued
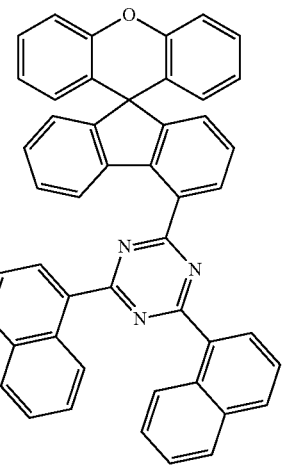
1.01 eV
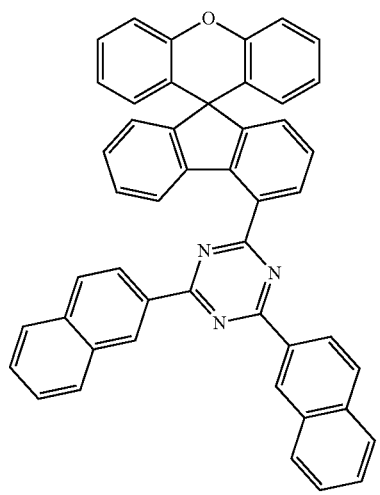
0.97 eV
Comparative Compound 1
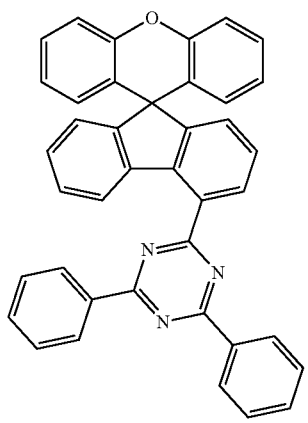 [SMILES: c1ccc(-c2nc(-c3ccccc3)nc(-c3cccc4c3-c3ccccc3C43c4ccccc4Oc4ccccc43)n2)cc1]
0.67 eV TABLE 1-continued
Measurement 2
Compounds 5 and 6
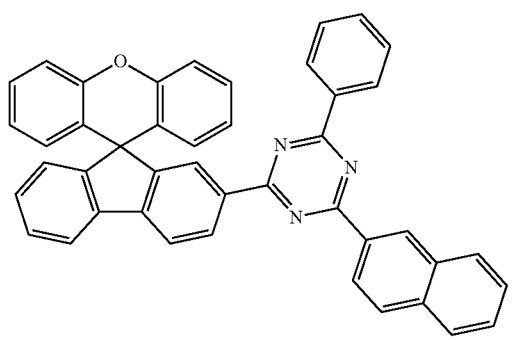 [SMILES: c1ccc(-c2nc(-c3ccc4c(c3)C3(c5ccccc5Oc5ccccc53)c3ccccc3-4)nc(-c3ccc4ccccc4c3)n2)cc1]
0.85 eV
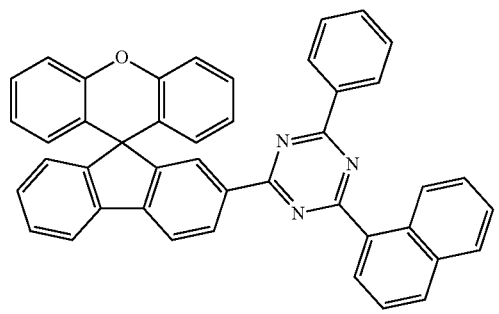 [SMILES: c1ccc(-c2nc(-c3ccc4c(c3)C3(c5ccccc5Oc5ccccc53)c3ccccc3-4)nc(-c3cccc4ccccc34)n2)cc1]
0.89 eV
Comparative Compound 2
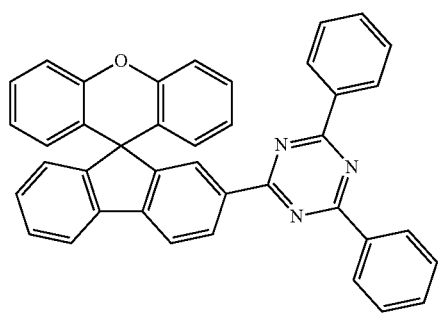 [SMILES: c1ccc(-c2nc(-c3ccccc3)nc(-c3ccc4c(c3)C3(c5ccccc5Oc5ccccc53)c3ccccc3-4)n2)cc1]
0.71 eV
Measurement 3
Compound 7
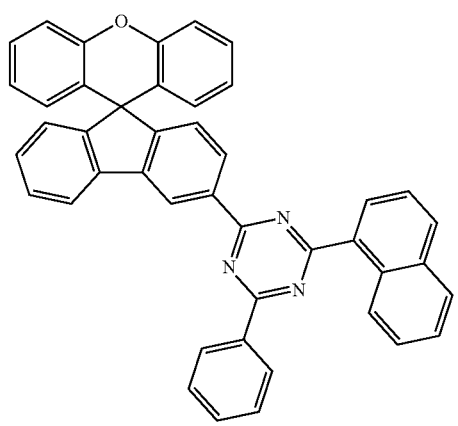 [SMILES: c1ccc(-c2nc(-c3ccc4c(c3)-c3ccccc3C43c4ccccc4Oc4ccccc43)nc(-c3cccc4ccccc34)n2)cc1]
0.86 eV

TABLE 1-continued
| | |
|---|---|
| Comparative Compound 3 | 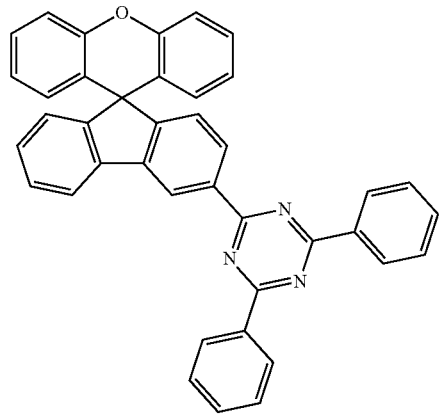 [SMILES: c1ccc(-c2nc(-c3ccccc3)nc(-c3ccc4c(c3)-c3ccccc3C43c4ccccc4Oc4ccccc43)n2)cc1] |
0.49 eV
Measurement 4
| | |
|---|---|
| Compound 8 | 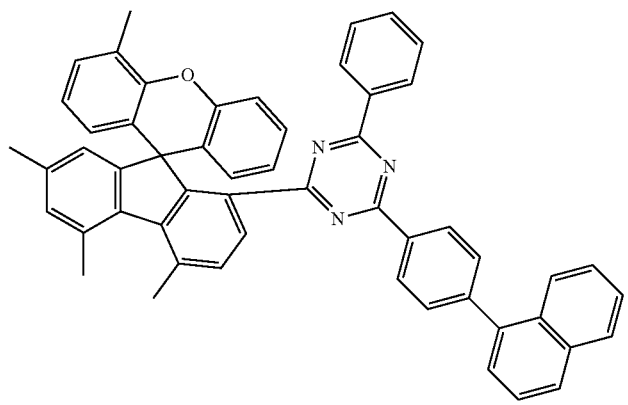 [SMILES: Cc1cc(C)c2c(c1)C1(c3ccccc3Oc3c(C)cccc31)c1c(-c3nc(-c4ccccc4)nc(-c4ccc(-c5cccc6ccccc56)cc4)n3)ccc(C)c1-2] |
0.60 eV
| | |
|---|---|
| Comparative Compound 4 | 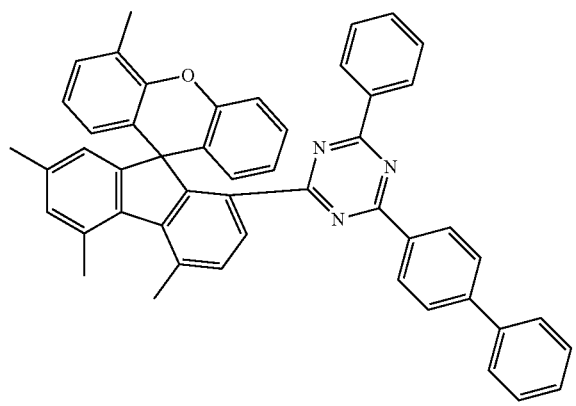 [SMILES: Cc1cc(C)c2c(c1)C1(c3ccccc3Oc3c(C)cccc31)c1c(-c3nc(-c4ccccc4)nc(-c4ccc(-c5ccccc5)cc4)n3)ccc(C)c1-2] |
0.38 eV

TABLE 1-continued
Measurement 5
Compounds 9 to 11
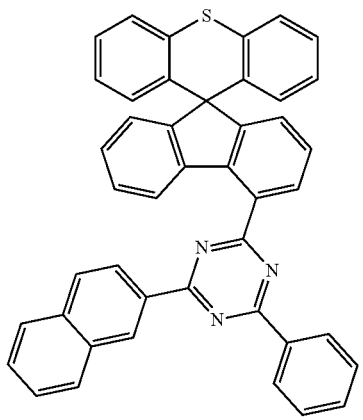
0.73 eV
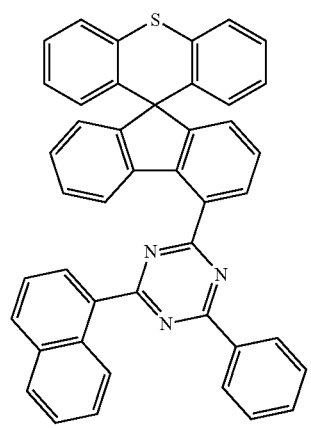
0.83 eV
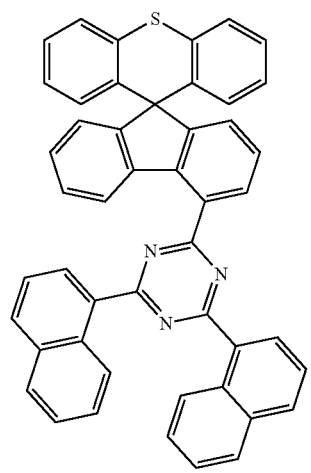
0.80 eV

TABLE 1-continued
| | |
|---|---|
| Comparative Compound 5 | 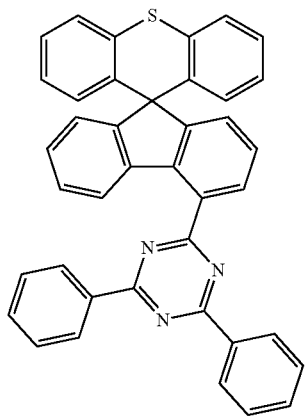 [SMILES: c1ccc(-c2nc(-c3ccccc3)nc(-c3cccc4c3-c3ccccc3C43c4ccccc4Sc4ccccc43)n2)cc1] |
| | 0.31 eV |
Measurement 6
| | |
|---|---|
| Compounds 12 to 14 | 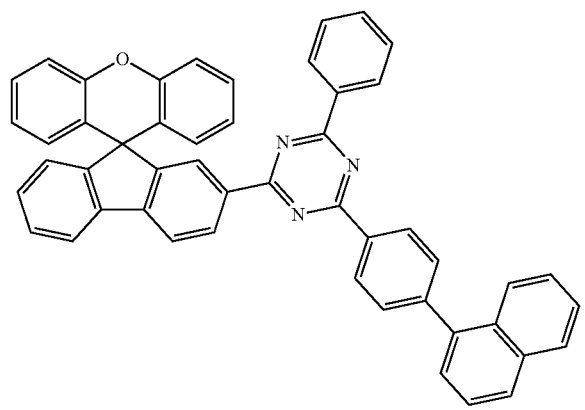 [SMILES: c1ccc(-c2nc(-c3ccc(-c4cccc5ccccc45)cc3)nc(-c3ccc4c(c3)C3(c5ccccc5Oc5ccccc53)c3ccccc3-4)n2)cc1] |
| | 0.78 eV |
| | 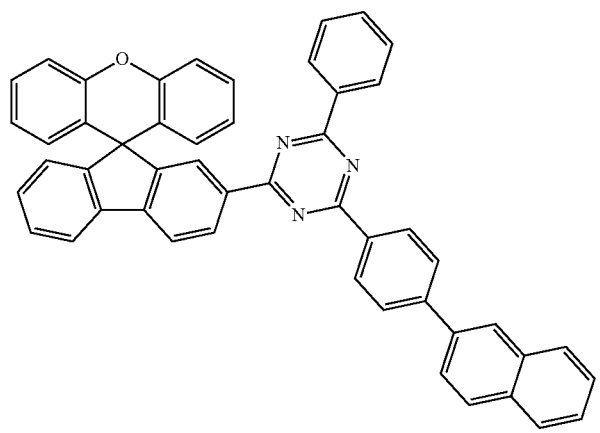 [SMILES: c1ccc(-c2nc(-c3ccc(-c4ccc5ccccc5c4)cc3)nc(-c3ccc4c(c3)C3(c5ccccc5Oc5ccccc53)c3ccccc3-4)n2)cc1] |
| | 0.85 eV |

TABLE 1-continued
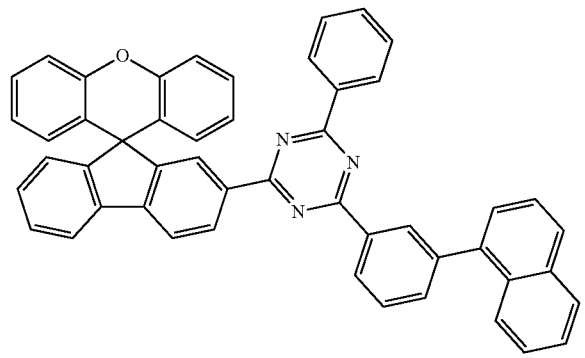 [SMILES: c1ccc(-c2nc(-c3cccc(-c4cccc5ccccc45)c3)nc(-c3ccc4c(c3)C3(c5ccccc5Oc5ccccc53)c3ccccc3-4)n2)cc1]
0.78 eV
Comparative Compound 6
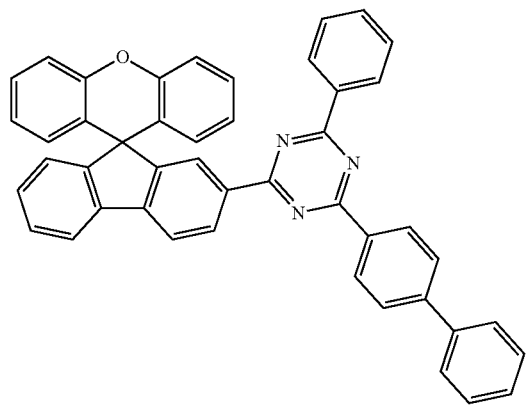 [SMILES: c1ccc(-c2ccc(-c3nc(-c4ccccc4)nc(-c4ccc5c(c4)C4(c6ccccc6Oc6ccccc64)c4ccccc4-5)n3)cc2)cc1]
0.71 eV
Measurement 7
Compound 15
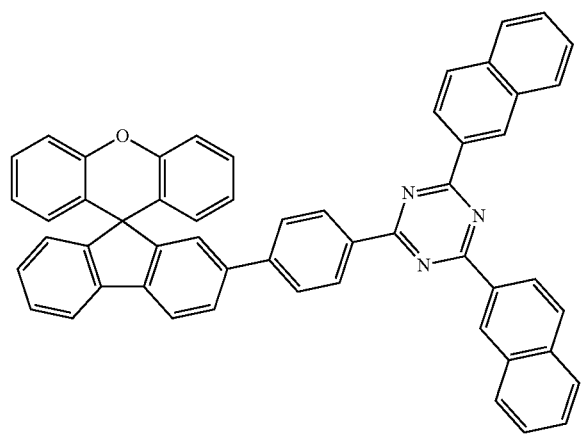 [SMILES: c1ccc2c(c1)Oc1ccccc1C21c2ccccc2-c2ccc(-c3ccc(-c4nc(-c5ccc6ccccc6c5)nc(-c5ccc6ccccc6c5)n4)cc3)cc21]
0.97 eV TABLE 1-continued
Comparative Compound 7
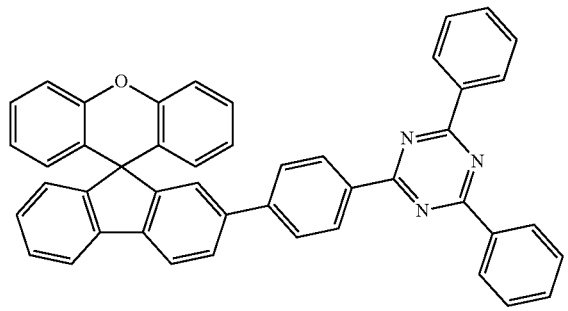 [SMILES: c1ccc(-c2nc(-c3ccccc3)nc(-c3ccc(-c4ccc5c(c4)C4(c6ccccc6Oc6ccccc64)c4ccccc4-5)cc3)n2)cc1]
0.85 eV
Measurement 8
Compound 16
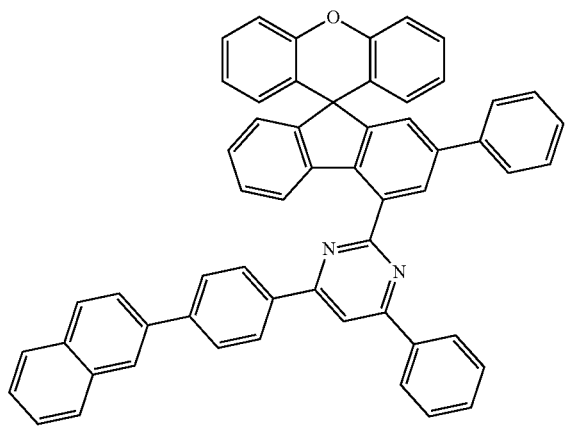 [SMILES: c1ccc(-c2cc(-c3nc(-c4ccccc4)cc(-c4ccc(-c5ccc6ccccc6c5)cc4)n3)c3c(c2)C2(c4ccccc4Oc4ccccc42)c2ccccc2-3)cc1]
0.65 eV
Comparative Compound 8
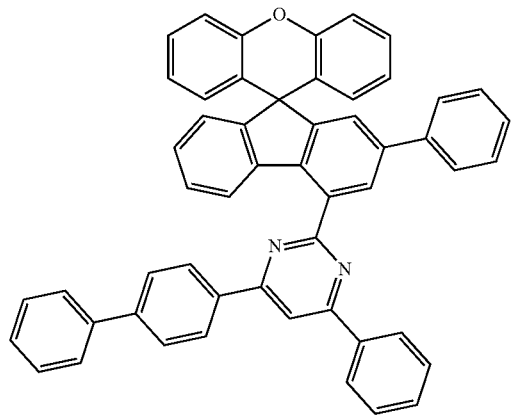 [SMILES: c1ccc(-c2ccc(-c3cc(-c4ccccc4)nc(-c4cc(-c5ccccc5)cc5c4-c4ccccc4C54c5ccccc5Oc5ccccc54)n3)cc2)cc1]
0.50 eV TABLE 1-continued
| Measurement 9 |
Compound 17
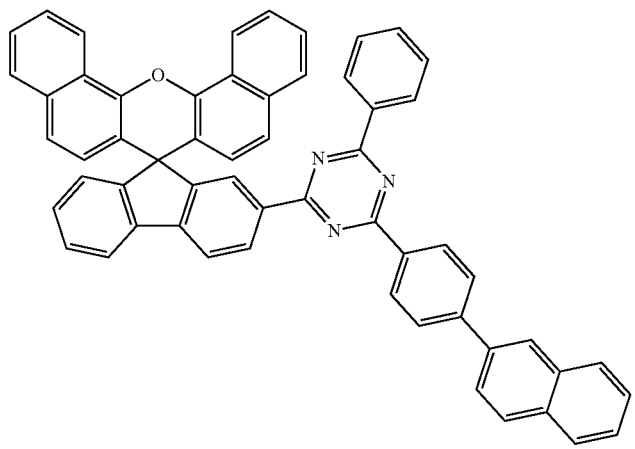 [SMILES: c1ccc(-c2nc(-c3ccc(-c4ccc5ccccc5c4)cc3)nc(-c3ccc4c(c3)C3(c5ccccc5-4)c4ccc5ccccc5c4Oc4c3ccc3ccccc43)n2)cc1]
0.50 eV
Comparative
Compound 9
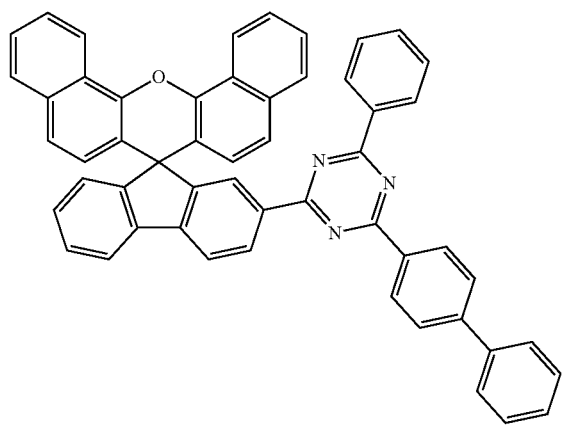 [SMILES: c1ccc(-c2ccc(-c3nc(-c4ccccc4)nc(-c4ccc5c(c4)C4(c6ccccc6-5)c5ccc6ccccc6c5Oc5c4ccc4ccccc54)n3)cc2)cc1]
0.41 eV
| Measurement 10 |
Compound 18
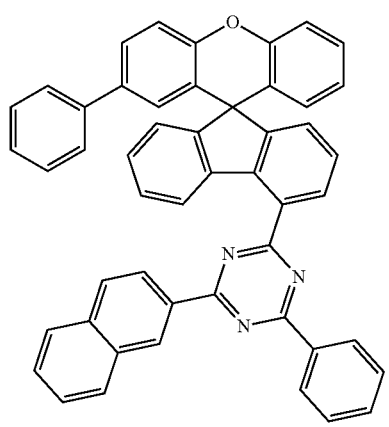 [SMILES: c1ccc(-c2ccc3c(c2)C2(c4ccccc4O3)c3ccccc3-c3c(-c4nc(-c5ccccc5)nc(-c5ccc6ccccc6c5)n4)cccc32)cc1]
0.84 eV

TABLE 1-continued
| Comparative Compound 10 | 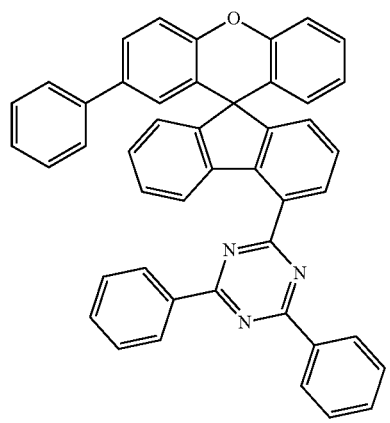 [SMILES: c1ccc(-c2ccc3c(c2)C2(c4ccccc4O3)c3ccccc3-c3c(-c4nc(-c5ccccc5)nc(-c5ccccc5)n4)cccc32)cc1] |
|---|---|
| | 0.49 eV |
Measurement 11
| Compound 19 | 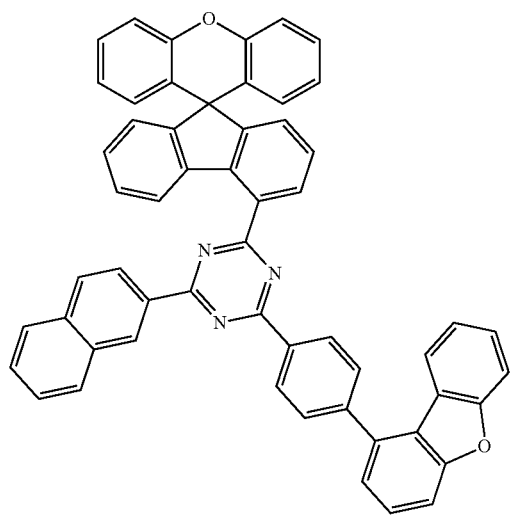 [SMILES: c1ccc2c(c1)Oc1ccccc1C21c2ccccc2-c2c(-c3nc(-c4ccc(-c5cccc6oc7ccccc7c56)cc4)nc(-c4ccc5ccccc5c4)n3)cccc21] |
|---|---|
| | 0.93 eV |
| Comparative Compound 11 | 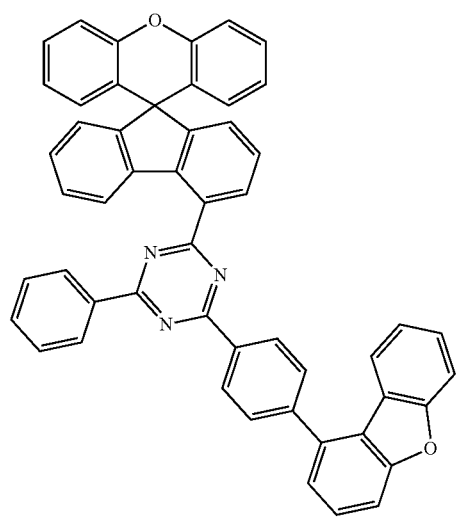 [SMILES: c1ccc(-c2nc(-c3ccc(-c4cccc5oc6ccccc6c45)cc3)nc(-c3cccc4c3-c3ccccc3C43c4ccccc4Oc4ccccc43)n2)cc1] |
|---|---|
| | 0.54 eV |

TABLE 1-continued
| Measurement 12 |
|---|
| Compounds 20 to 22 | 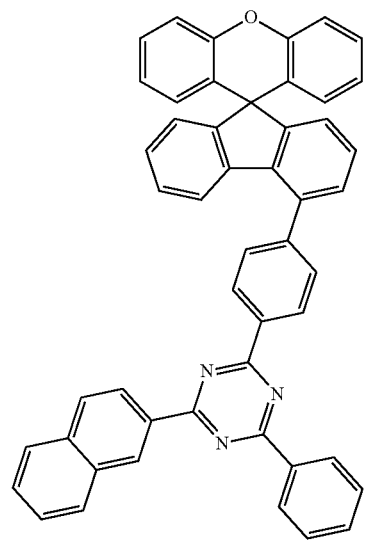 [SMILES: c1ccc(-c2nc(-c3ccc(-c4cccc5c4-c4ccccc4C54c5ccccc5Oc5ccccc54)cc3)nc(-c3ccc4ccccc4c3)n2)cc1] |
0.77 eV
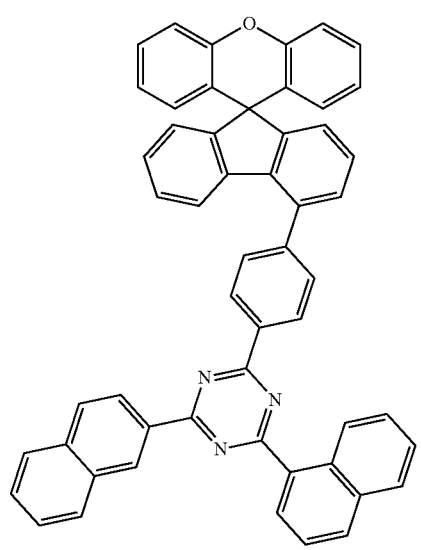 [SMILES: c1ccc2c(c1)Oc1ccccc1C21c2ccccc2-c2c(-c3ccc(-c4nc(-c5ccc6ccccc6c5)nc(-c5cccc6ccccc56)n4)cc3)cccc21]
0.67 eV TABLE 1-continued
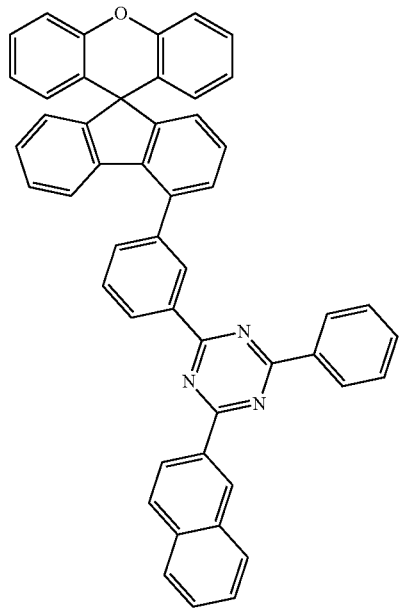 [SMILES: c1ccc(-c2nc(-c3cccc(-c4cccc5c4-c4ccccc4C54c5ccccc5Oc5ccccc54)c3)nc(-c3ccc4ccccc4c3)n2)cc1]
0.78 eV
Comparative Compound 12
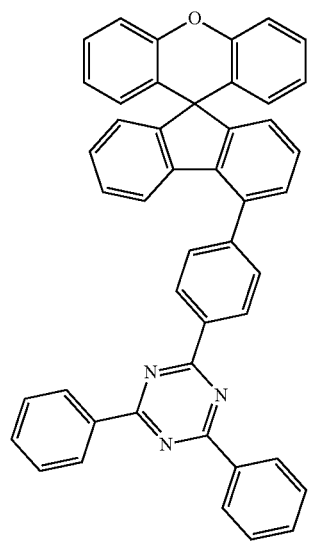 [SMILES: c1ccc(-c2nc(-c3ccccc3)nc(-c3ccc(-c4cccc5c4-c4ccccc4C54c5ccccc5Oc5ccccc54)cc3)n2)cc1]
0.65 eV TABLE 1-continued
Measurement 13
Compounds 23 to 28
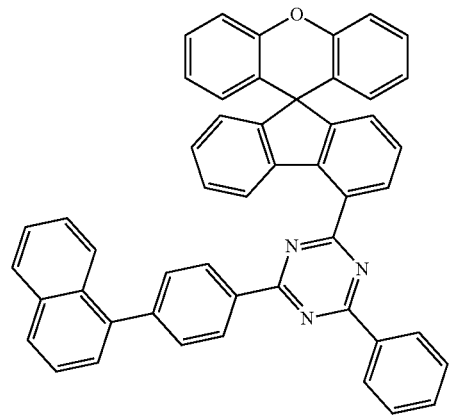 [SMILES: c1ccc(-c2nc(-c3ccc(-c4cccc5ccccc45)cc3)nc(-c3cccc4c3-c3ccccc3C43c4ccccc4Oc4ccccc43)n2)cc1]
0.82 eV
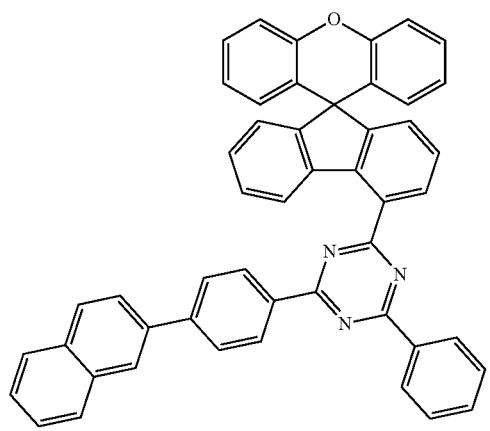 [SMILES: c1ccc(-c2nc(-c3ccc(-c4ccc5ccccc5c4)cc3)nc(-c3cccc4c3-c3ccccc3C43c4ccccc4Oc4ccccc43)n2)cc1]
0.90 eV
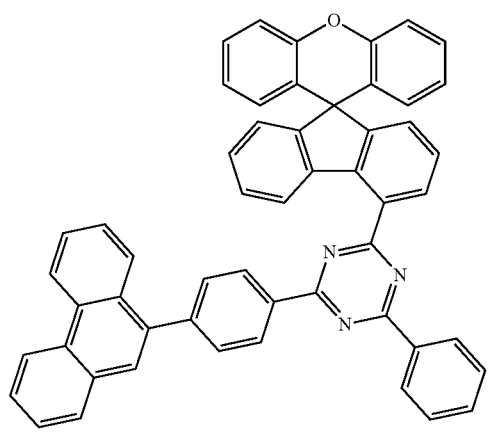 [SMILES: c1ccc(-c2nc(-c3ccc(-c4cc5ccccc5c5ccccc45)cc3)nc(-c3cccc4c3-c3ccccc3C43c4ccccc4Oc4ccccc43)n2)cc1]
0.81 eV TABLE 1-continued
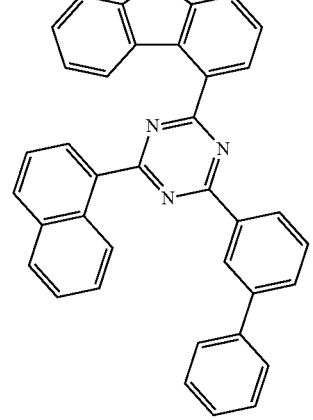
0.95 eV
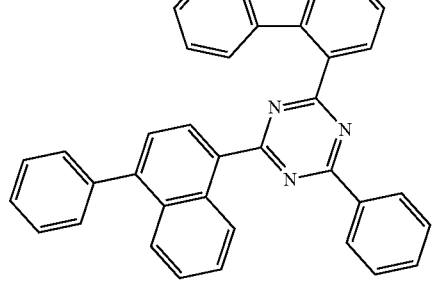
1.00 eV
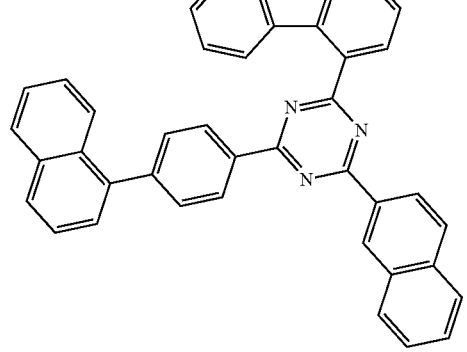
0.75 eV TABLE 1-continued

| Comparative Compound 13 | 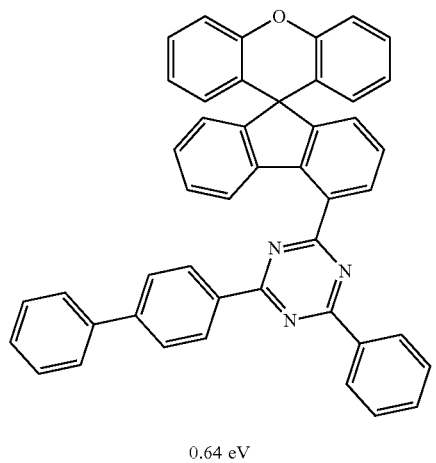 |
|---|---|
| | 0.64 eV |

From Table 1, it was identified that the compound (Compounds 1 to 28) including a dicyclic or higher condensed aryl group in one or more of Ar1 and Ar2 of Chemical Formula 1 of the present application had a larger difference between S1 and T1 energy values (ΔEST) compared to the compound (Comparative Compounds 1 to 13) not including a dicyclic or higher condensed aryl group.

Experimental Example 2

Manufacture of Device

Example 1-1

A glass substrate (corning 7059 glass) on which indium tin oxide (ITO) was coated as a thin film to a thickness of 1,000 Å was placed in distilled water containing a dissolved detergent and ultrasonically cleaned. A product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonically cleaned with solvents of isopropyl alcohol, acetone and methanol in this order, and then dried.

On the transparent ITO electrode prepared as above, a hole injection layer was formed by thermal vacuum depositing hexanitrile hexaazatriphenylene (HAT) to a thickness of 500 Å. HT1 (400 Å), a material transferring holes, was vacuum deposited thereon, and as a light emitting layer, host compound BH1 and dopant BD1 compound were vacuum deposited to a thickness of 300 Å. After depositing a hole blocking layer (electron control layer) on the light emitting layer to a thickness of 50 Å using the compound ET-A, Compound 1 synthesized in Synthesis Example 1 and lithium quinolate (LiQ) were vacuum deposited in a weight ratio of 1:1 to a thickness of 350 Å to form an electron injection and transfer layer. On the electron injection and transfer layer, a cathode was formed by depositing lithium fluoride (LiF) to a thickness of 12 Å and aluminum to a thickness of 2,000 Å in consecutive order. As a result, an organic light emitting device was manufactured.

In the above-mentioned process, the deposition rates of the organic materials were maintained at 0.4 Å/sec to 0.7 Å/sec, the deposition rates of the lithium fluoride and the aluminum of the cathode were maintained at 0.3 Å/sec and 2 Å/sec, respectively, and the degree of vacuum during the deposition was maintained at $2 \times 10^{-7}$ torr to $5 \times 10^{-6}$ torr to manufacture the organic light emitting device.

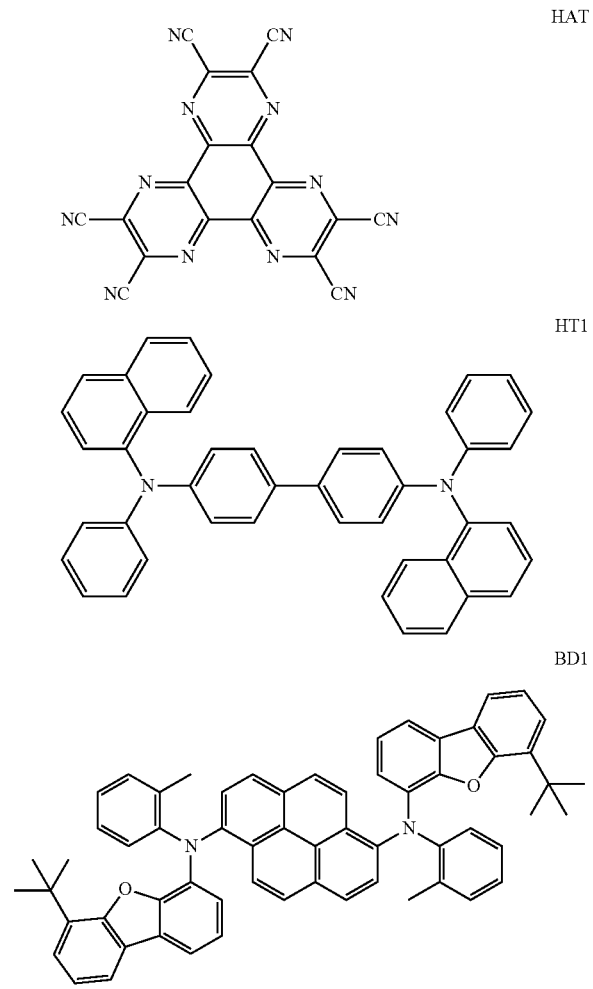

Liq
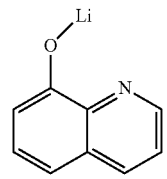
BH1
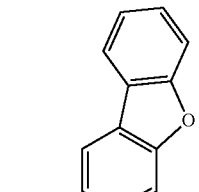
ET-A
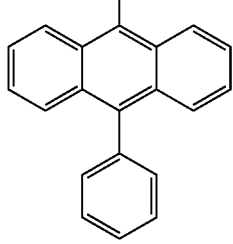
ET1
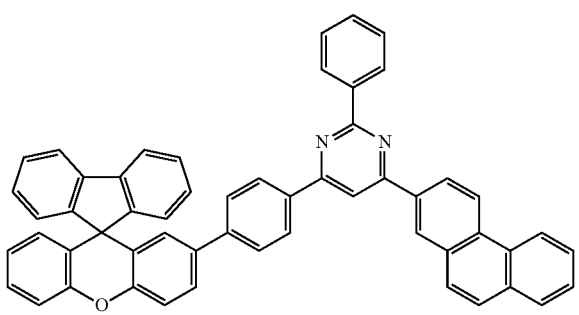
ET2
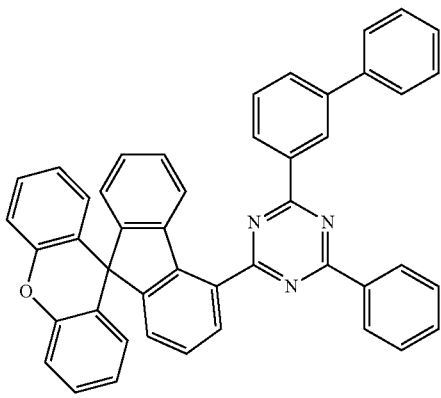
ET3
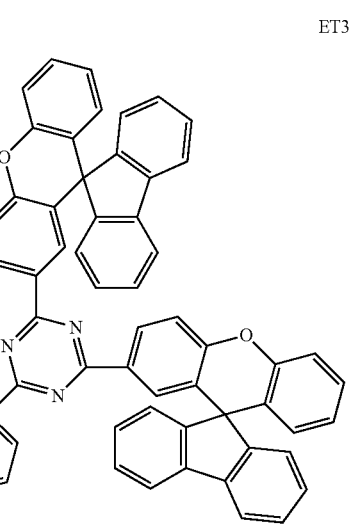
ET4
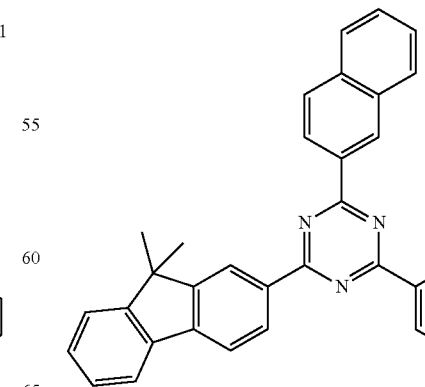

-continued
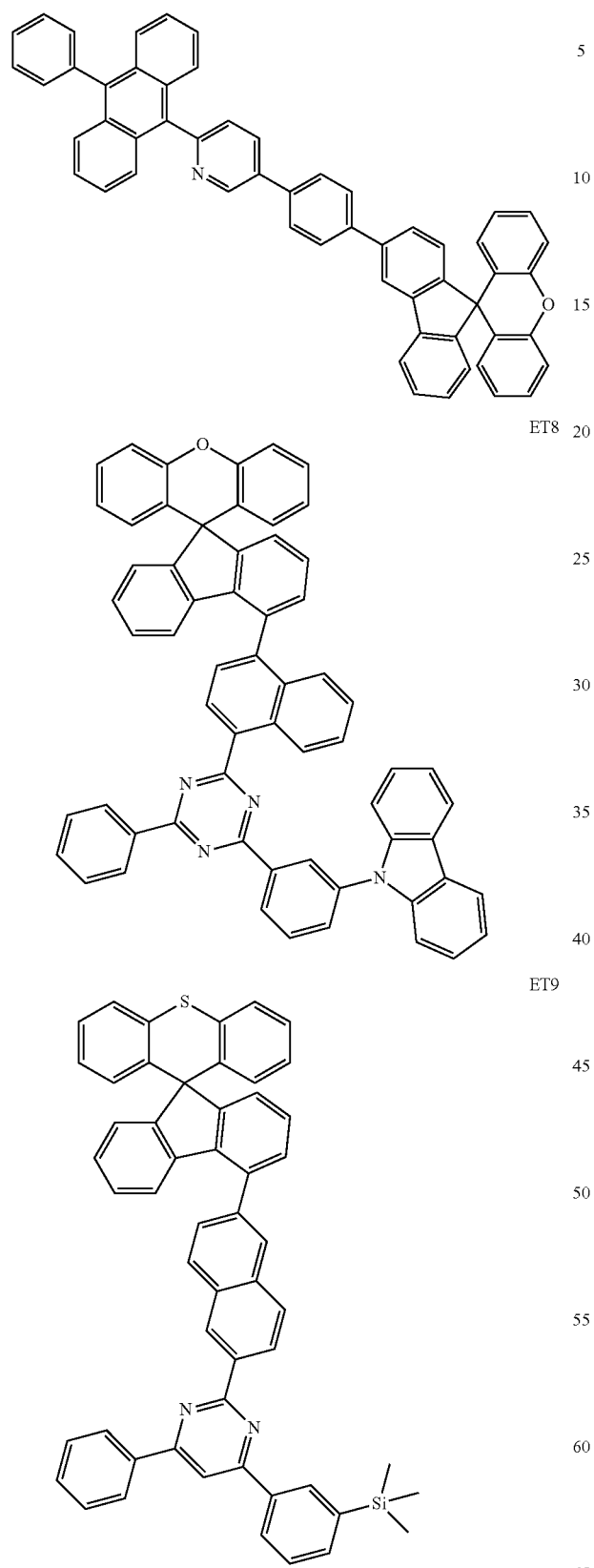
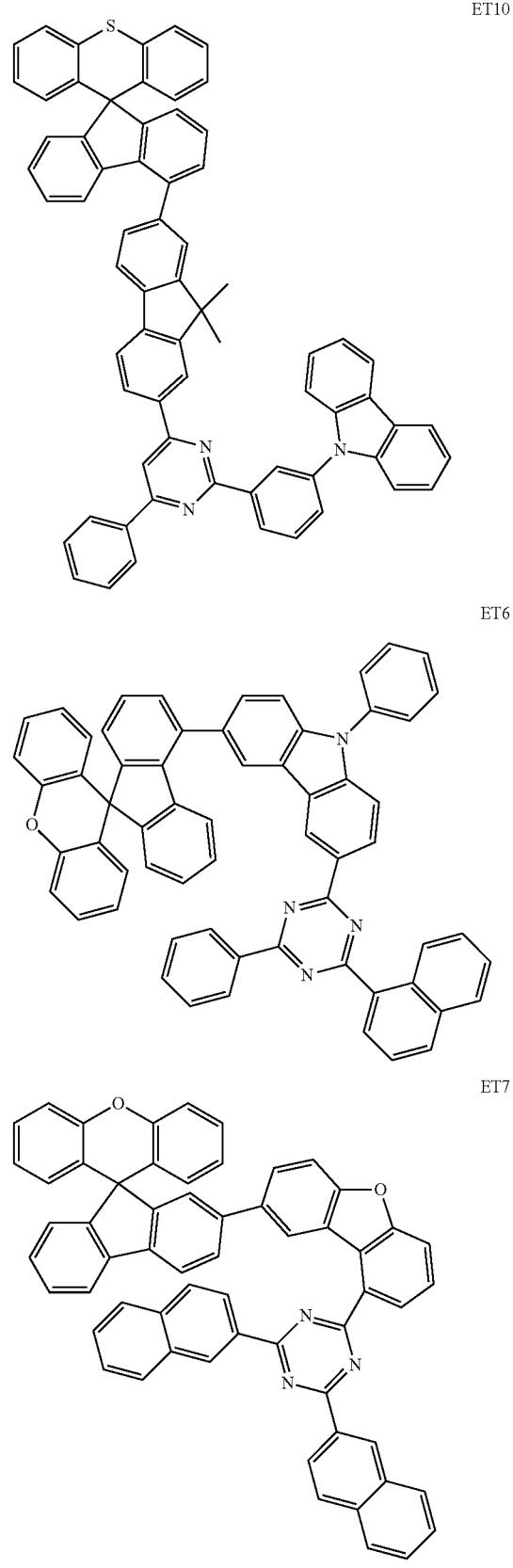

ET11

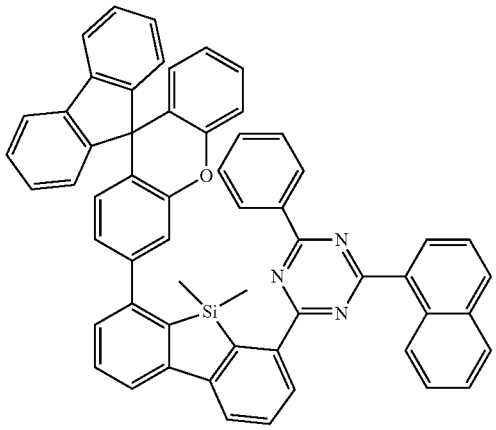

ET12

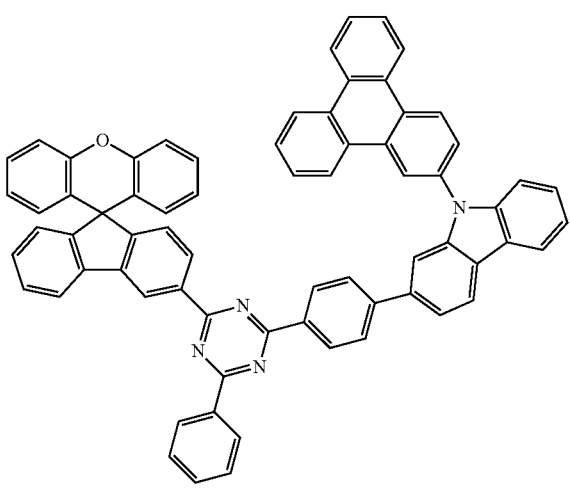

Additional Example and Comparative Example

Organic light emitting devices were manufactured in the same manner as in Example 1-1 except that compounds described in the following Table 2 were each used instead of using Compound 1 of the electron injection and transfer layer.

For each of the organic light emitting devices manufactured in the experimental examples, driving voltage and light emission efficiency were measured at current density of 10 mA/cm$^2$, and time taken for luminance decreasing to 98% compared to initial luminance (LT98) was measured at current density of 20 mA/cm$^2$. The results are shown in the following Table 2.

TABLE 2

| Experimental Example 10 mA/cm$^2$ | Compound | Voltage (V) | Current Efficiency (cd/A) | Color Coordinate (x, y) | Lifetime 98 at 20 mA/cm$^2$ |
|---|---|---|---|---|---|
| Example 1-1 | Compound 1 | 3.95 | 4.89 | (0.137, 0.126) | 64 |
| Example 1-2 | Compound 2 | 3.91 | 5.11 | (0.139, 0.123) | 71 |
| Example 1-3 | Compound 3 | 3.92 | 5.05 | (0.138, 0.127) | 68 |
| Example 1-4 | Compound 4 | 3.97 | 4.81 | (0.138, 0.129) | 65 |
| Comparative Example 1-1 | Comparative Compound 1 | 3.99 | 4.71 | (0.139, 0.124) | 28 |
| Example 1-5 | Compound 5 | 3.94 | 4.82 | (0.138, 0.125) | 60 |
| Example 1-6 | Compound 6 | 3.88 | 5.09 | (0.137, 0.125) | 61 |
| Comparative Example 1-2 | Comparative Compound 2 | 3.95 | 4.61 | (0.137, 0.124) | 32 |
| Example 1-7 | Compound 7 | 3.98 | 5.14 | (0.137, 0.126) | 59 |
| Comparative Example 1-3 | Comparative Compound 3 | 4.01 | 4.65 | (0.137, 0.124) | 15 |
| Example 1-8 | Compound 8 | 3.97 | 5.05 | (0.138, 0.124) | 45 |
| Comparative Example 1-4 | Comparative Compound 4 | 3.99 | 4.67 | (0.137, 0.126) | 11 |
| Example 1-9 | Compound 9 | 4.01 | 4.81 | (0.137, 0.126) | 65 |
| Example 1-10 | Compound 10 | 4.00 | 4.88 | (0.139, 0.123) | 63 |
| Example 1-11 | Compound 11 | 3.99 | 4.92 | (0.138, 0.126) | 62 |
| Comparative Example 1-5 | Comparative Compound 5 | 4.05 | 4.51 | (0.138, 0.126) | 13 |
| Example 1-12 | Compound 12 | 3.92 | 5.02 | (0.136, 0.126) | 61 |
| Example 1-13 | Compound 13 | 3.98 | 4.79 | (0.138, 0.125) | 60 |
| Example 1-14 | Compound 14 | 3.88 | 5.25 | (0.137, 0.125) | 52 |
| Comparative Example 1-6 | Comparative Compound 6 | 3.99 | 4.61 | (0.137, 0.124) | 35 |
| Example 1-15 | Compound 15 | 3.95 | 5.15 | (0.137, 0.126) | 65 |
| Comparative Example 1-7 | Comparative Compound 7 | 3.96 | 4.78 | (0.137, 0.125) | 42 |
| Example 1-16 | Compound 16 | 3.77 | 4.87 | (0.138, 0.127) | 49 |
| Comparative Example 1-8 | Comparative Compound 8 | 3.79 | 4.25 | (0.137, 0.125) | 28 |
| Example 1-17 | Compound 17 | 4.02 | 4.88 | (0.137, 0.125) | 48 |
| Comparative Example 1-9 | Comparative Compound 9 | 4.11 | 4.10 | (0.137, 0.124) | 31 |
| Example 1-18 | Compound 18 | 3.91 | 5.02 | (0.137, 0.124) | 59 |
| Comparative Example 1-10 | Comparative Compound 10 | 3.95 | 4.85 | (0.139, 0.124) | 24 |
| Example 1-19 | Compound 19 | 3.78 | 4.89 | (0.138, 0.127) | 58 |
| Comparative Example 1-11 | Comparative Compound 11 | 3.79 | 4.33 | (0.137, 0.126) | 29 |
| Example 1-20 | Compound 20 | 3.92 | 4.99 | (0.137, 0.126) | 52 |
| Example 1-21 | Compound 21 | 3.89 | 5.21 | (0.139, 0.123) | 50 |
| Example 1-22 | Compound 22 | 3.81 | 5.31 | (0.138, 0.124) | 55 |
| Comparative Example 1-12 | Comparative Compound 12 | 3.95 | 4.82 | (0.137, 0.124) | 27 |
| Example 1-23 | Compound 23 | 3.93 | 5.11 | (0.137, 0.124) | 61 |
| Example 1-24 | Compound 24 | 3.94 | 5.09 | (0.139, 0.124) | 63 |
| Example 1-25 | Compound 25 | 3.90 | 5.16 | (0.136, 0.126) | 60 |
| Example 1-26 | Compound 26 | 3.92 | 5.05 | (0.137, 0.124) | 65 |
| Example 1-27 | Compound 27 | 3.97 | 5.00 | (0.137, 0.126) | 69 |
| Example 1-28 | Compound 28 | 3.89 | 5.22 | (0.138, 0.124) | 53 |
| Comparative Example 1-13 | Comparative Compound 13 | 4.01 | 4.77 | (0.136, 0.125) | 30 |
| Comparative Example 1-14 | ET1 | 4.21 | 3.94 | (0.140, 0.129) | 21 |
| Comparative Example 1-15 | ET2 | 4.02 | 4.79 | (0.140, 0.128) | 25 |
| Comparative Example 1-16 | ET3 | 4.33 | 4.01 | (0.140, 0.129) | 30 |
| Comparative Example 1-17 | ET4 | 4.09 | 4.69 | (0.139, 0.126) | 18 |
| Comparative Example 1-18 | ET5 | 5.01 | 3.89 | (0.134, 0.122) | 7 |
| Comparative Example 1-19 | ET6 | 4.21 | 4.23 | (0.140, 0.129) | 29 |
| Comparative Example 1-20 | ET7 | 4.26 | 4.15 | (0.140, 0.128) | 33 |
| Comparative Example 1-21 | ET8 | 4.02 | 4.76 | (0.140, 0.129) | 19 |
| Comparative Example 1-22 | ET9 | 3.89 | 4.55 | (0.138, 0.125) | 21 |
| Comparative Example 1-23 | ET10 | 3.88 | 4.51 | (0.139, 0.127) | 18 |
| Comparative Example 1-24 | ET11 | 4.20 | 4.25 | (0.140, 0.128) | 24 |
| Comparative Example 1-25 | ET12 | 4.45 | 4.06 | (0.140, 0.129) | 31 |

Example 2-1

A glass substrate (corning 7059 glass) on which indium tin oxide (ITO) was coated as a thin film to a thickness of 1,000 Å was placed in distilled water containing a dissolved detergent and ultrasonically cleaned. A product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonically cleaned with solvents of isopropyl alcohol, acetone and methanol in this order, and then dried.

On the transparent ITO electrode prepared as above, a hole injection layer was formed by thermal vacuum depositing hexanitrile hexaazatriphenylene (HAT) to a thickness of 500 Å. HT2 (300 Å), a material transferring holes, was vacuum deposited thereon to form a hole transfer layer. Subsequently, an electron blocking layer was formed on the hole transfer layer by vacuum depositing the following Compound HT3 to a film thickness of 100 Å. As a light emitting layer, host compound BH2 and dopant compound BD2 were vacuum deposited to a thickness of 300 Å. On the light emitting layer, Compound 1 prepared in Synthesis Example 1 was vacuum deposited to a thickness of 200 Å, and a cathode was formed by depositing lithium fluoride (LiF) to a thickness of 12 Å and aluminum to a thickness of 2,000 Å in consecutive order. As a result, an organic light emitting device was manufactured.

In the above-mentioned process, the deposition rates of the organic materials were maintained at 0.4 Å/sec to 0.7 Å/sec, the deposition rates of the lithium fluoride and the aluminum of the cathode were maintained at 0.3 Å/sec and 2 Å/sec, respectively, and the degree of vacuum during the deposition was maintained at $2 \times 10^{-7}$ torr to $5 \times 10^{-6}$ torr to manufacture the organic light emitting device.

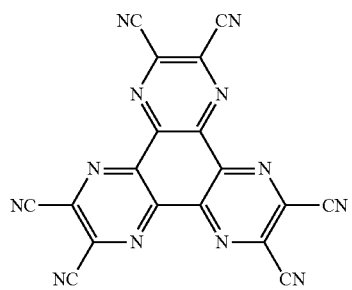
HAT

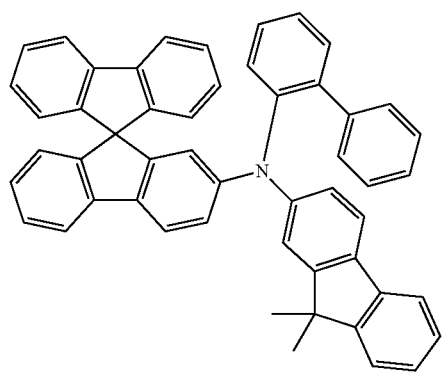
HT2

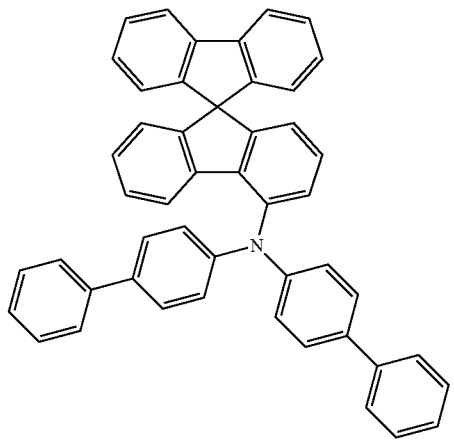
HT3

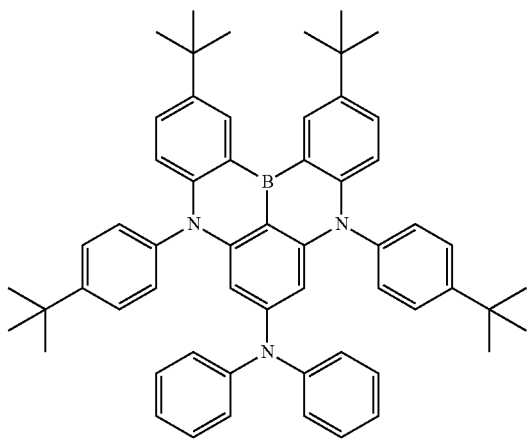
BD2

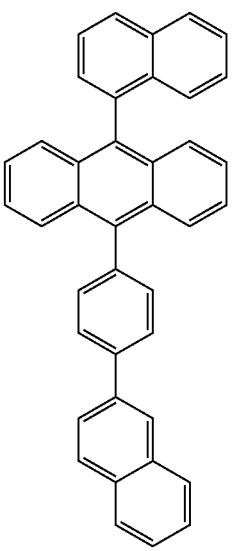
BH2

Additional Example and Comparative Example

Organic light emitting devices were manufactured in the same manner as in Example 2-1 except that compounds described in the following Table 3 were each used instead of using Compound 1 of the electron injection and transfer layer.

For each of the organic light emitting devices manufactured in the experimental examples, driving voltage and light emission efficiency were measured at current density of 10 mA/cm², and time taken for luminance decreasing to 98% compared to initial luminance (LT98) was measured at current density of 20 mA/cm². The results are shown in the following Table 3.

TABLE 3

| Experimental Example 10 mA/cm2 | Compound | Voltage (V) | Current Efficiency (cd/A) | Color Coordinate (x, y) | Lifetime 98 at 20 mA/cm² |
|---|---|---|---|---|---|
| Example 2-1 | Compound 1 | 3.73 | 4.77 | (0.142, 0.060) | 73 |
| Example 2-2 | Compound 2 | 3.81 | 4.55 | (0.142, 0.060) | 88 |
| Example 2-3 | Compound 3 | 3.75 | 4.71 | (0.141, 0.060) | 77 |
| Example 2-4 | Compound 4 | 3.74 | 4.81 | (0.142, 0.059) | 72 |
| Comparative Example 2-1 | Comparative Compound 1 | 3.92 | 4.03 | (0.143, 0.057) | 42 |
| Example 2-5 | Compound 5 | 3.89 | 4.75 | (0.142, 0.060) | 67 |
| Example 2-6 | Compound 6 | 3.85 | 4.82 | (0.142, 0.060) | 69 |
| Comparative Example 2-2 | Comparative Compound 2 | 3.95 | 4.22 | (0.142, 0.061) | 44 |
| Example 2-7 | Compound 7 | 3.88 | 4.79 | (0.141, 0.160) | 66 |
| Comparative Example 2-3 | Comparative Compound 3 | 4.00 | 4.24 | (0.139, 0.060) | 26 |
| Example 2-8 | Compound 8 | 3.62 | 5.01 | (0.140, 0.061) | 56 |
| Comparative Example 2-4 | Comparative Compound 4 | 3.81 | 4.30 | (0.140, 0.060) | 19 |
| Example 2-9 | Compound 9 | 3.95 | 4.41 | (0.140, 0.060) | 68 |
| Example 2-10 | Compound 10 | 3.92 | 4.44 | (0.140, 0.060) | 62 |
| Example 2-11 | Compound 11 | 3.89 | 4.51 | (0.140, 0.060) | 60 |
| Comparative Example 2-5 | Comparative Compound 5 | 4.10 | 4.22 | (0.140, 0.060) | 20 |
| Example 2-12 | Compound 12 | 3.70 | 4.87 | (0.140, 0.060) | 67 |
| Example 2-13 | Compound 13 | 3.67 | 4.71 | (0.141, 0.060) | 65 |
| Example 2-14 | Compound 14 | 3.69 | 4.98 | (0.140, 0.061) | 58 |
| Comparative Example 2-6 | Comparative Compound 6 | 4.01 | 4.23 | (0.140, 0.059) | 44 |
| Example 2-15 | Compound 15 | 3.76 | 4.78 | (0.140, 0.060) | 77 |
| Comparative Example 2-7 | Comparative Compound 7 | 3.96 | 4.10 | (0.140, 0.060) | 42 |
| Example 2-16 | Compound 16 | 3.70 | 4.84 | (0.140, 0.060) | 52 |
| Comparative Example 2-8 | Comparative Compound 8 | 3.81 | 4.15 | (0.141, 0.062) | 33 |
| Example 2-17 | Compound 17 | 4.03 | 4.63 | (0.140, 0.059) | 50 |
| Comparative Example 2-9 | Comparative Compound 9 | 4.22 | 4.00 | (0.140, 0.060) | 28 |
| Example 2-18 | Compound 18 | 3.79 | 4.71 | (0.140, 0.060) | 63 |
| Comparative Example 2-10 | Comparative Compound 10 | 3.91 | 4.26 | (0.139, 0.060) | 21 |
| Example 2-19 | Compound 19 | 3.81 | 4.64 | (0.140, 0.060) | 70 |
| Comparative Example 2-11 | Comparative Compound 11 | 4.13 | 3.99 | (0.140, 0.060) | 36 |
| Example 2-20 | Compound 20 | 3.87 | 4.91 | (0.140, 0.060) | 62 |
| Example 2-21 | Compound 21 | 3.84 | 5.03 | (0.140, 0.060) | 59 |
| Example 2-22 | Compound 22 | 3.76 | 5.11 | (0.140, 0.060) | 62 |
| Comparative Example 2-12 | Comparative Compound 12 | 3.92 | 4.41 | (0.140, 0.060) | 33 |
| Example 2-23 | Compound 23 | 3.77 | 4.99 | (0.140, 0.060) | 72 |
| Example 2-24 | Compound 24 | 3.73 | 4.84 | (0.140, 0.060) | 75 |
| Example 2-25 | Compound 25 | 3.79 | 5.01 | (0.140, 0.060) | 72 |
| Example 2-26 | Compound 26 | 3.85 | 4.87 | (0.140, 0.060) | 77 |
| Example 2-27 | Compound 27 | 3.89 | 4.79 | (0.140, 0.060) | 81 |
| Example 2-28 | Compound 28 | 3.81 | 5.12 | (0.139, 0.060) | 66 |
| Comparative Example 2-13 | Comparative Compound 13 | 4.00 | 4.55 | (0.140, 0.060) | 38 |
| Comparative Example 2-14 | ET1 | 4.00 | 4.01 | (0.140, 0.060) | 31 |
| Comparative Example 2-15 | ET2 | 3.98 | 4.38 | (0.140, 0.060) | 36 |
| Comparative Example 2-16 | ET3 | 4.11 | 4.32 | (0.140, 0.060) | 38 |
| Comparative Example 2-17 | ET4 | 3.99 | 4.29 | (0.141, 0.060) | 29 |
| Comparative Example 2-18 | ET5 | 4.87 | 3.95 | (0.139, 0.062) | 16 |
| Comparative Example 2-19 | ET6 | 4.05 | 4.37 | (0.140, 0.060) | 37 |
| Comparative Example 2-20 | ET7 | 4.07 | 4.31 | (0.139, 0.060) | 39 |
| Comparative Example 2-21 | ET8 | 4.00 | 4.41 | (0.140, 0.060) | 31 |
| Comparative Example 2-22 | ET9 | 3.99 | 4.35 | (0.141, 0.062) | 32 |
| Comparative Example 2-23 | ET10 | 3.97 | 4.35 | (0.140, 0.060) | 25 |
| Comparative Example 2-24 | ET11 | 4.04 | 4.39 | (0.141, 0.060) | 29 |
| Comparative Example 2-25 | ET12 | 4.31 | 4.15 | (0.141, 0.061) | 33 |

Example 3-1

A glass substrate (corning 7059 glass) on which indium tin oxide (ITO) was coated as a thin film to a thickness of 1,000 Å was placed in distilled water containing dissolved detergent and ultrasonically cleaned. A product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonically cleaned with solvents of isopropyl alcohol, acetone and methanol in this order, and then dried.

On the transparent ITO electrode prepared as above, a hole injection layer was formed by thermal vacuum depositing hexanitrile hexaazatriphenylene (HAT) to a thickness of 50 Å, and then NPB was vacuum deposited to a thickness of 100 Å to form a first hole transfer layer. Subsequently, the following Compound HT3 was vacuum deposited on the first hole transfer layer to a film thickness of 100 Å to form a first electron blocking layer. Subsequently, a first light emitting layer was formed on the first electron blocking layer by vacuum depositing the following compounds YGH-A, YGH-B and YGD in a weight ratio of 2:2:1 to a film thickness of 400 Å. Then, Compound ET-B was vacuum deposited on the first light emitting layer to a thickness of 250 Å to form a first electron transfer layer. Subsequently, an N-type charge generating layer was formed on the first electron transfer layer to a thickness of 100 Å by vacuum depositing the following Compound NCG and lithium (Li) in a weight ratio of 50:1.

Then, a P-type charge generating layer was formed by forming HT-A to a thickness of 100 Å and doping Compound PCG in a doping concentration of 30% by weight, and only HT-A was further vacuum deposited to a thickness of 800 Å to form a second hole transfer layer. Subsequently, as a second light emitting layer, the following compounds BH3 and BD3 were vacuum deposited in a weight ratio of 96:4 to a thickness of 250 Å.

On the light emitting layer, Compound 12 prepared in Synthesis Example 12 was vacuum deposited to a thickness of 300 Å, and lithium fluoride (LiF) and aluminum were consecutively deposited to a thickness of 10 Å and to a thickness of 800 Å, respectively, to form a cathode. As a result, an organic light emitting device was manufactured.

In the above-mentioned process, the deposition rates of the organic materials were maintained at 0.4 Å/sec to 0.7

Å/sec, the deposition rates of the lithium fluoride and the aluminum of the cathode were maintained at 0.3 Å/sec and 2 Å/sec, respectively, and the degree of vacuum during the deposition was maintained at $2\times10^{-7}$ torr to $5\times10^{-6}$ torr to manufacture the organic light emitting device.
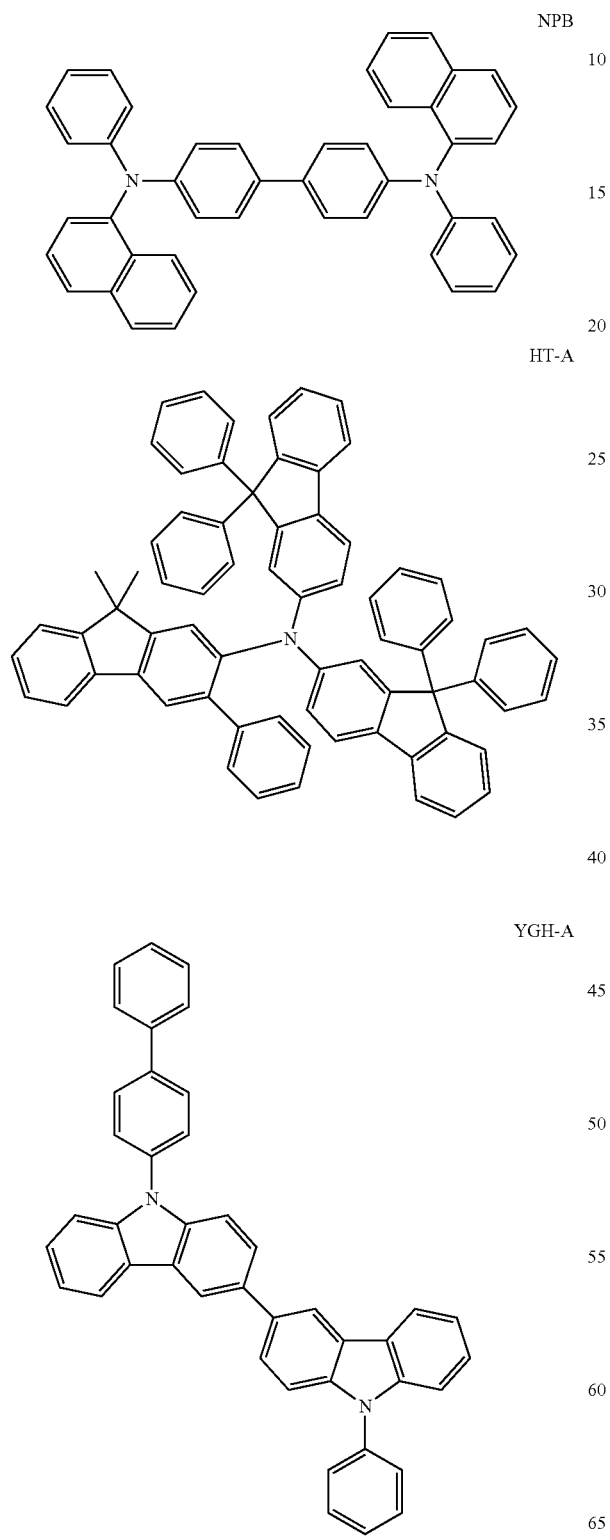
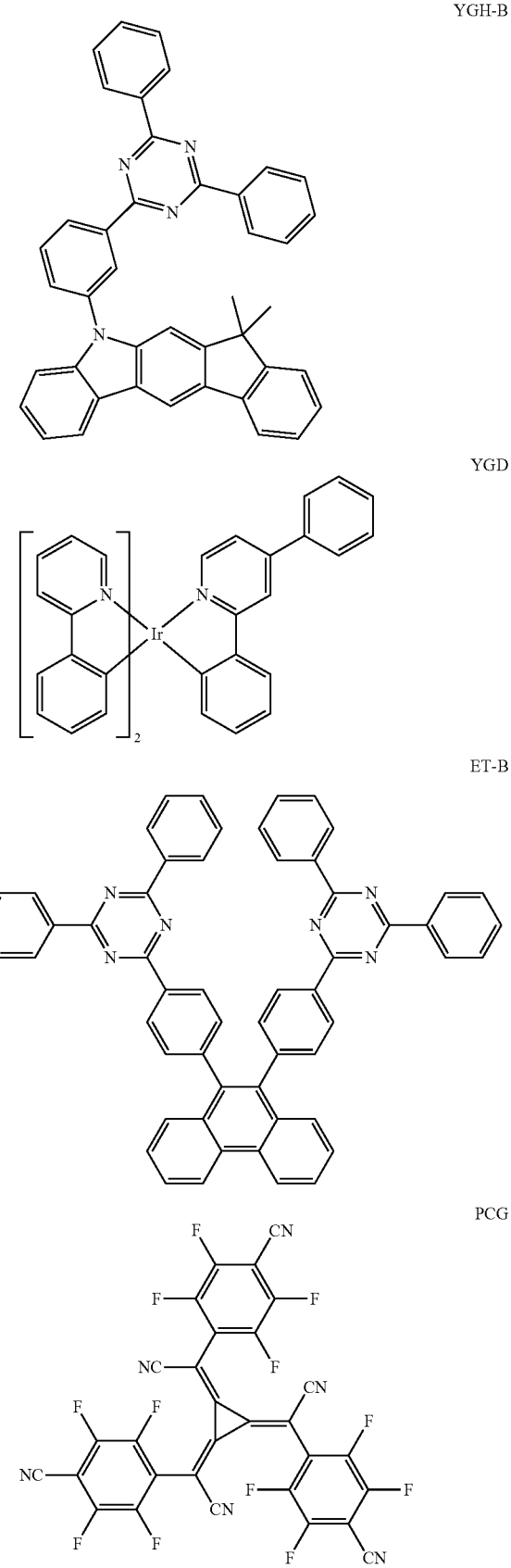

NCG

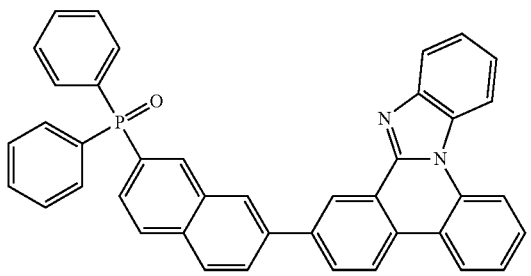

BH3

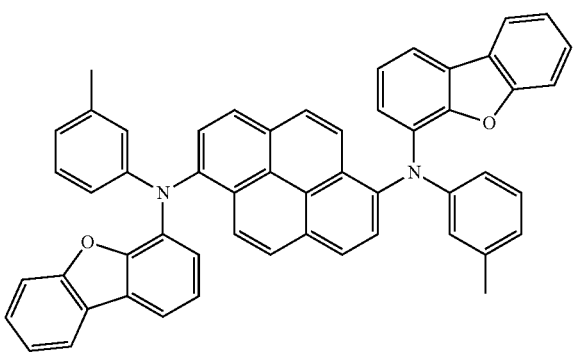

BD3

Additional Example and Comparative Example

Organic light emitting devices were manufactured in the same manner as in Example 3-1 except that compounds described in the following Table 4 were each used instead of using Compound 12 of the electron injection and transfer layer.

For each of the organic light emitting devices manufactured in the experimental examples, driving voltage and light emission efficiency were measured at current density of 10 mA/cm², and time taken for luminance decreasing to 98% compared to initial luminance (LT98) was measured at current density of 20 mA/cm². The results are shown in the following Table 4.

TABLE 4

| Experimental Example 10 mA/cm2 | Compound | Voltage (V) | Current Efficiency (cd/A) | Color Coordinate (x, y) | Lifetime 98 at 20 mA/cm² |
|---|---|---|---|---|---|
| Example 3-1 | Compound 12 | 7.78 | 67.44 | (0.334, 0.386) | 122 |
| Example 3-2 | Compound 13 | 7.71 | 65.15 | (0.334, 0.386) | 120 |
| Example 3-3 | Compound 14 | 7.69 | 68.23 | (0.329, 0.388) | 110 |
| Comparative Example 3-1 | Comparative Compound 6 | 7.91 | 51.56 | (0.332, 0.380) | 77 |
| Example 3-4 | Compound 24 | 7.81 | 69.55 | (0.334, 0.386) | 120 |
| Example 3-5 | Compound 25 | 7.79 | 68.10 | (0.334, 0.386) | 128 |
| Example 3-6 | Compound 26 | 7.85 | 71.03 | (0.334, 0.384) | 119 |
| Example 3-7 | Compound 27 | 7.89 | 68.12 | (0.334, 0.385) | 134 |
| Example 3-8 | Compound 28 | 7.85 | 66.31 | (0.334, 0.386) | 142 |
| Example 3-9 | Compound 29 | 7.77 | 72.55 | (0.331, 0.386) | 115 |
| Comparative Example 3-2 | Comparative Compound 13 | 8.01 | 55.10 | (0.332, 0.384) | 71 |
| Comparative Example 3-3 | ET1 | 8.12 | 52.10 | (0.334, 0.384) | 58 |
| Comparative Example 3-4 | ET2 | 8.05 | 53.01 | (0.334, 0.386) | 59 |
| Comparative Example 3-5 | ET3 | 8.31 | 53.13 | (0.334, 0.380) | 62 |
| Comparative Example 3-6 | ET4 | 8.06 | 52.91 | (0.334, 0.381) | 55 |
| Comparative Example 3-7 | ET5 | 9.12 | 38.42 | (0.331, 0.395) | 37 |
| Comparative Example 3-8 | ET6 | 8.20 | 53.88 | (0.334, 0.380) | 68 |
| Comparative Example 3-9 | ET7 | 8.29 | 53.51 | (0.334, 0.380) | 64 |
| Comparative Example 3-10 | ET8 | 8.04 | 53.75 | (0.334, 0.386) | 51 |
| Comparative Example 3-11 | ET9 | 8.09 | 53.63 | (0.333, 0.385) | 54 |
| Comparative Example 3-12 | ET10 | 8.08 | 53.54 | (0.333, 0.382) | 49 |
| Comparative Example 3-13 | ET11 | 8.18 | 54.01 | (0.333, 0.385) | 60 |
| Comparative Example 3-14 | ET12 | 8.79 | 47.92 | (0.331, 0.380) | 52 |

Example 4-1

A glass substrate (corning 7059 glass) on which indium tin oxide (ITO) was coated as a thin film to a thickness of 1,000 Å was placed in distilled water containing dissolved detergent and ultrasonically cleaned. A product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonically cleaned with solvents of isopropyl alcohol, acetone and methanol in this order, and then dried.

On the transparent ITO electrode prepared as above, a hole injection layer was formed by thermal vacuum depositing hexanitrile hexaazatriphenylene (HAT) to a thickness of 50 Å, and then NPB was vacuum deposited to a thickness of 100 Å to form a first hole transfer layer. Subsequently, Compound HT3 was vacuum deposited on the first hole transfer layer to a film thickness of 100 Å to foam a first electron blocking layer.

As a light emitting layer, host compound BH3 and dopant compound BD3 were vacuum deposited in a weight ratio of 96:4 to a thickness of 125 Å. On the light emitting layer, Compound 24 prepared in Synthesis Example 24 was deposited to a thickness of 200 Å as a first electron transfer layer, and then, on the first electron transfer layer the following Compound NCG and lithium (Li) were vacuum deposited in a weight ratio of 50:1 to a thickness of 100 Å to foam an N-type charge generating layer. Subsequently, a P-type charge generating layer was formed by forming HT-A to a thickness of 100 Å and doping Compound PCG in a doping concentration of 30% by weight, and only HT-A was further vacuum deposited to a thickness of 800 Å to form a second hole transfer layer.

Subsequently, a second light emitting layer was formed thereon by vacuum depositing the following compounds YGH-A, YGH-B and YGD in a weight ratio of 2:2:1 to a film thickness of 400 Å. Then, Compound ET-B was vacuum deposited on the second light emitting layer to a thickness of 250 Å to form a second electron transfer layer. Then, on the second electron transfer layer, the following Compound NCG and lithium (Li) were vacuum deposited in a weight ratio of 50:1 to a thickness of 100 Å to form a second N-type charge generating layer.

Then, a P-type charge generating layer was formed by forming HT-B to a thickness of 100 Å and doping Compound PCG in a doping concentration of 30% by weight, and only HT-B was further vacuum deposited to a thickness of 800 Å to form a third hole transfer layer. Subsequently, as a third light emitting layer, the following compounds BH3 and BD3 were vacuum deposited in a weight ratio of 96:4 to a thickness of 250 Å.

On the light emitting layer, Compound 12 prepared in Synthesis Example 12 was vacuum deposited to a thickness of 300 Å, and lithium fluoride (LiF) and aluminum were consecutively deposited to a thickness of 10 Å and to a thickness of 800 Å, respectively, to form a cathode. As a result, an organic light emitting device was manufactured.

In the above-mentioned process, the deposition rates of the organic materials were maintained at 0.4 Å/sec to 0.7 Å/sec, the deposition rates of the lithium fluoride and the aluminum of the cathode were maintained at 0.3 Å/sec and 2 Å/sec, respectively, and the degree of vacuum during the deposition was maintained at $2 \times 10^{-7}$ torr to $5 \times 10^{-6}$ torr to manufacture the organic light emitting device.

HT-B

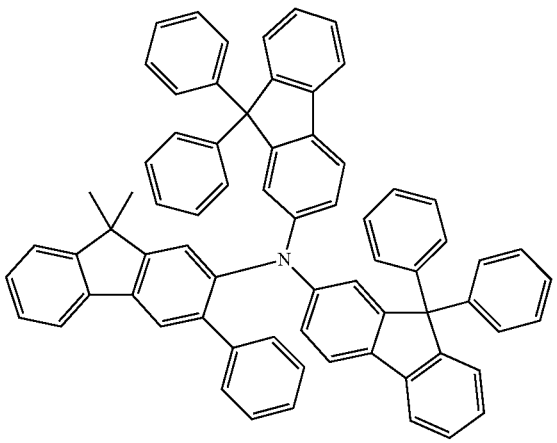

YGH-A

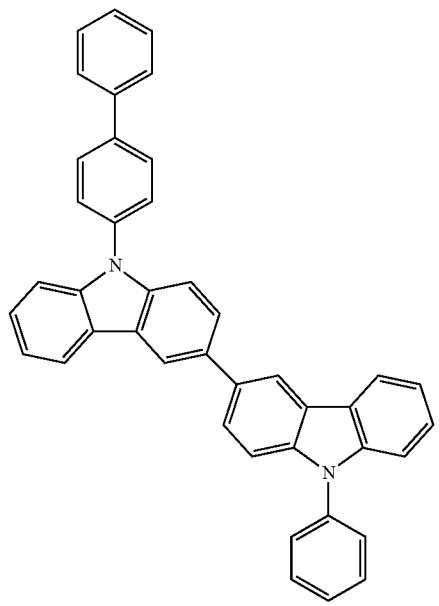

HT-A

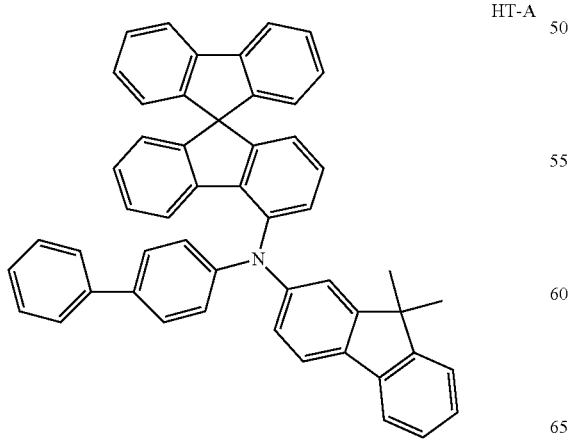

YGH-B

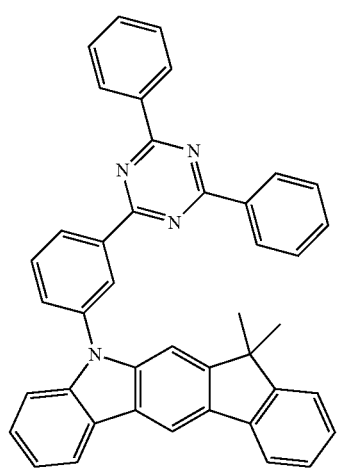

YGD

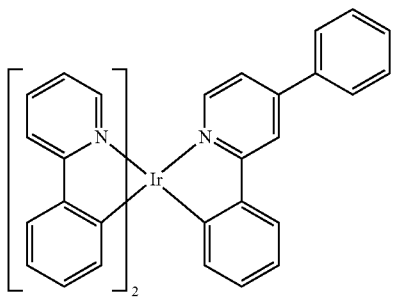

ET-B

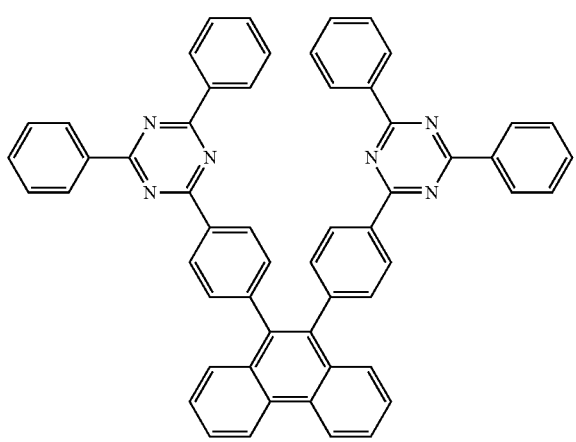

PCG

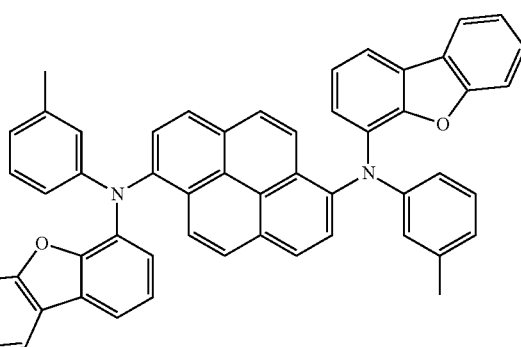

NCG

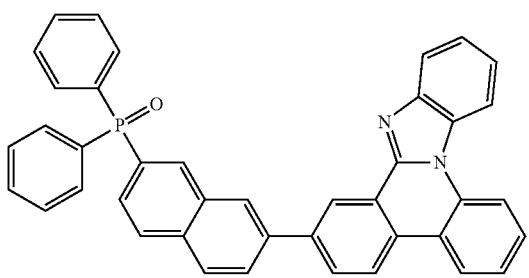

BH3

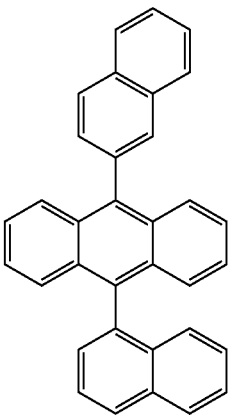

BD3

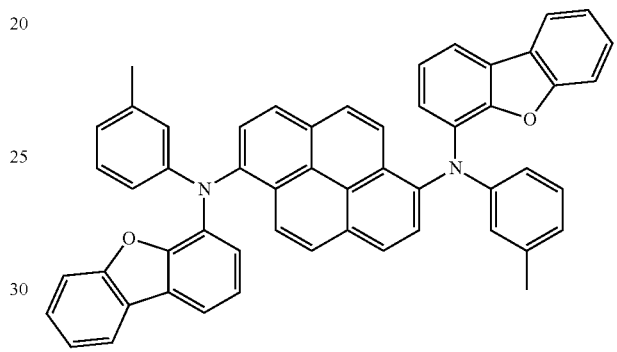

Additional Comparative Example (Comparative Example 4-1)

An organic light emitting device was manufactured in the same manner as in Example 4-1 except that Comparative Compound 6 was used instead of using Compound 12 and Comparative Compound 13 was used instead of Compound 24.

For each of the organic light emitting devices manufactured in the examples, driving voltage and light emission efficiency were measured at current density of 10 mA/cm$^2$, and time taken for luminance decreasing to 98% compared to initial luminance (LT98) was measured at current density of 20 mA/cm$^2$. The results are shown in the following Table 5.

TABLE 5

| Experimental Example 10 mA/cm2 | Compound | Voltage (V) | Current Efficiency (cd/A) | Color Coordinate (x, y) | Lifetime 98 at 20 mA/cm$^2$ |
|---|---|---|---|---|---|
| Example 4-1 | Compound 12, 24 | 11.13 | 77.92 | (0.246, 0.245) | 131 |
| Comparative Example 4-1 | Comparative Compound 6, 13 | 14.02 | 58.16 | (0.247, 0.245) | 95 |

From the experimental results of Table 2 to Table 5, it was identified that the examples including the compound of the present application had superior driving voltage, current efficiency and lifetime properties compared to the comparative examples using the compound in which one or more of Ar1 and Ar2 of Chemical Formula 1 of the present application do not include a dicyclic or higher condensed aryl group, Chemical Formula 2 of the present application bonds to one of R1 to R8, or one or more of L1 to L3 include a heteroarylene group.

The invention claimed is:
1. An organic light emitting device, comprising:
a first electrode;
a second electrode; and
one or more organic material layers provided between the first electrode and the second electrode,
wherein at least one of the one or more organic material layers includes a hole injection layer, a hole transfer layer, or a layer carrying out hole transfer and hole injection at the same time, and the hole injection layer, the hole transfer layer, or the layer carrying out hole transfer and hole injection at the same time includes a compound of Chemical Formula 1:

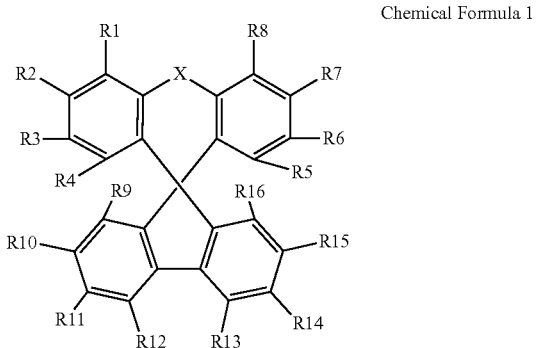

Chemical Formula 1 wherein, in Chemical Formula 1:
X is O or S;
one or more of R9 to R16 are linked to * of the following Chemical Formula 2; and
R1 to R8, and the rest of R9 to R16 not linked to Chemical Formula 2, are the same as or different from each other, and each independently is hydrogen, deuterium, a cyano group, a nitro group, a carbonyl group, a substituted or unsubstituted silyl group, a substituted or unsubstituted boron group, a substituted or unsubstituted alkyl group, a substituted or unsubstituted alkoxy group, substituted or unsubstituted aryloxy group, a substituted or unsubstituted cycloalkyl group, a substituted or unsubstituted aryl group, or a substituted or unsubstituted heterocyclic group;

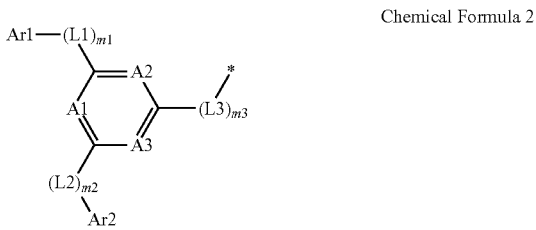

Chemical Formula 2 wherein in Chemical Formula 2:
A1 to A3 are the same as or different from each other and each independently is N or CR, and one or more of A1 to A3 are N;

L1 and L2 are the same as or different from each other, and each independently is a direct bond, a substituted or unsubstituted cycloalkylene group, or a substituted or unsubstituted arylene group;
L3 is a direct bond, a substituted or unsubstituted cycloalkylene group, a substituted or unsubstituted fluorenylene group, or a substituted or unsubstituted naphthylene group;
one or more of Ar1 and Ar2 are a substituted or unsubstituted dicyclic or higher condensed aryl group, and the rest are the same as or different from each other, and each independently is a substituted or unsubstituted aryl group or a substituted or unsubstituted heterocyclic group;
Rs are the same as or different from each other, and each independently is hydrogen, deuterium, a cyano group, a nitro group, a carbonyl group, a substituted or unsubstituted silyl group, a substituted or unsubstituted boron group, a substituted or unsubstituted alkyl group, a substituted or unsubstituted alkoxy group, a substituted or unsubstituted aryloxy group, a substituted or unsubstituted cycloalkyl group, a substituted or unsubstituted aryl group, or a substituted or unsubstituted heterocyclic group; and
m1 to m3 are each an integer of 0 to 3, and when m1 to m3 are each 2 or greater, two or more substituents in the parentheses are the same as or different from each other.

2. An organic light emitting device, comprising:
a first electrode;
a second electrode; and
one or more organic material layers provided between the first electrode and the second electrode,
wherein the one or more organic material layers include one or more light emitting layers, at least one of the one or more light emitting layers includes a host and a dopant, and the dopant is a blue fluorescent dopant having a maximum light emission wavelength of 400 nm to 520 nm, and
wherein one or more layers of the organic material layers includes a compound of Chemical Formula 1:

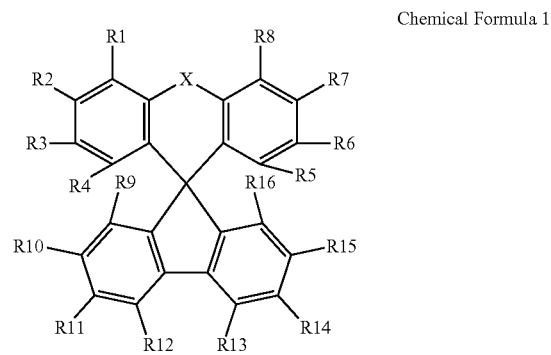

Chemical Formula 1 wherein, in Chemical Formula 1:
X is O or S;
one or more of R9 to R16 are linked to * of the following Chemical Formula 2; and
R1 to R8, and the rest of R9 to R16 not linked to Chemical Formula 2, are the same as or different from each other, and each independently is hydrogen, deuterium, a cyano group, a nitro group, a carbonyl group, a substituted or unsubstituted silyl group, a substituted or unsubstituted boron group, a substituted or unsubstituted alkyl group, a substituted or unsubstituted alkoxy group, substituted or unsubstituted aryloxy group, a substituted or unsubstituted cycloalkyl group, a substituted or unsubstituted aryl group, or a substituted or unsubstituted heterocyclic group;

Chemical Formula 2

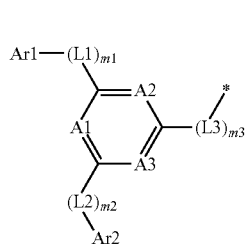

wherein in Chemical Formula 2:
A1 to A3 are the same as or different from each other and each independently is N or CR, and one or more of A1 to A3 are N;
L1 and L2 are the same as or different from each other, and each independently is a direct bond, a substituted or unsubstituted cycloalkylene group, or a substituted or unsubstituted arylene group;
L3 is a direct bond, a substituted or unsubstituted cycloalkylene group, a substituted or unsubstituted fluorenylene group, or a substituted or unsubstituted naphthylene group;
one or more of Ar1 and Ar2 are a substituted or unsubstituted dicyclic or higher condensed aryl group, and the rest are the same as or different from each other, and each independently is a substituted or unsubstituted aryl group or a substituted or unsubstituted heterocyclic group;
Rs are the same as or different from each other, and each independently is hydrogen, deuterium, a cyano group, a nitro group, a carbonyl group, a substituted or unsubstituted silyl group, a substituted or unsubstituted boron group, a substituted or unsubstituted alkyl group, a substituted or unsubstituted alkoxy group, a substituted or unsubstituted aryloxy group, a substituted or unsubstituted cycloalkyl group, a substituted or unsubstituted aryl group, or a substituted or unsubstituted heterocyclic group; and
m1 to m3 are each an integer of 0 to 3, and when m1 to m3 are each 2 or greater, two or more substituents in the parentheses are the same as or different from each other.

3. The organic light emitting device of claim 2, wherein the one or more organic material layers include two or more light emitting layers.

4. The organic light emitting device of claim 2, wherein the one or more organic material layers include:
a first stack including one or more light emitting layers; and
a second stack including one or more light emitting layers; and
one or more charge generating layers between the first stack and the second stack,
wherein at least one of the first stack or the second stack includes the light emitting layer including the host and the blue fluorescent dopant having a maximum light emission wavelength of 400 nm to 520 nm.

5. The organic light emitting device of claim 2, wherein the one or more organic material layers include:
a first stack including one or more light emitting layers;
a second stack including one or more light emitting layers;
a third stack including one or more light emitting layers; and
one or more charge generating layers between each of the first stack and the second stack, and the second stack and the third stack,
wherein at least one of the first stack, the second stack, or the third stack includes the light emitting layer including the host and the blue fluorescent dopant having a maximum light emission wavelength of 400 nm to 520 nm.

6. The organic light emitting device of claim 2, wherein two or more of A1 to A3 are N, and the rest is CR, and R has the same definition as in Chemical Formula 2.

7. The organic light emitting device of claim 2, wherein one or more of Ar1 and Ar2 are a substituted or unsubstituted spirofluorenexanthene group, a substituted or unsubstituted spirofluorenethioxanthene group, a substituted or unsubstituted dibenzofuran group, or any one of the following structures, and the rest are the same as or different from each other, and each independently is a substituted or unsubstituted aryl group or a substituted or unsubstituted heterocyclic group:

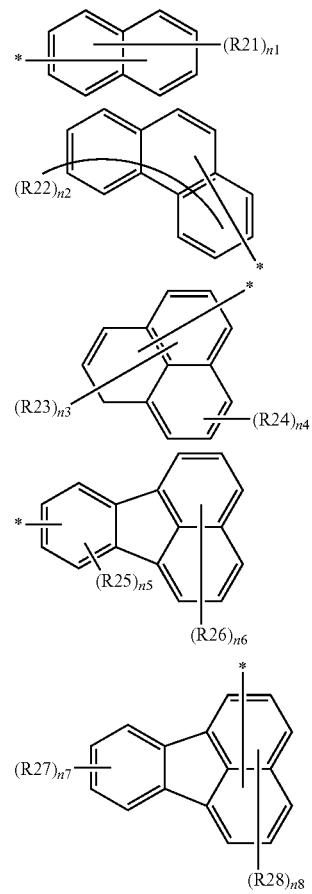

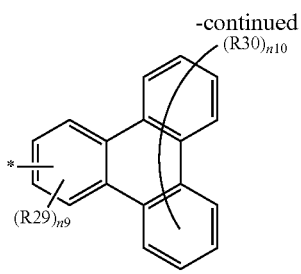

wherein in the structures:

R21 to R30 are the same as or different from each other, and each independently is hydrogen, deuterium, a cyano group, a nitro group, a carbonyl group, a substituted or unsubstituted silyl group, a substituted or unsubstituted boron group, a substituted or unsubstituted alkyl group, a substituted or unsubstituted alkoxy group, a substituted or unsubstituted aryloxy group, a substituted or unsubstituted cycloalkyl group, a substituted or unsubstituted aryl group, or a substituted or unsubstituted heterocyclic group;

n1 is an integer of 0 to 7, n2 is an integer of 0 to 9, n3 and n6 are each an integer of 0 to 6, n4, n5 and n9 are each an integer of 0 to 3, n7 is an integer of 0 to 4, n8 is an integer of 0 to 5, n10 is an integer of 0 to 8, and when n1 to n10 are each 2 or greater, two or more substituents in the parentheses are the same as or different from each other; and \* means a linked site.

8. The organic light emitting device of claim 2, wherein Chemical Formula 1 is any one of the following Chemical Formulae 3 to 8:

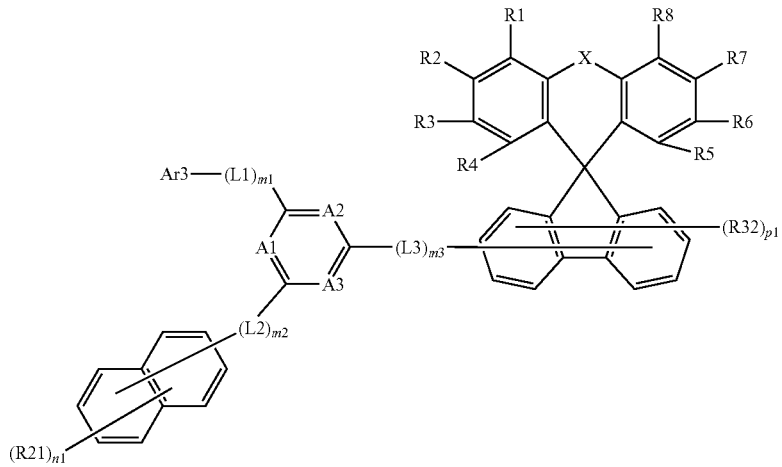

Chemical Formula 3

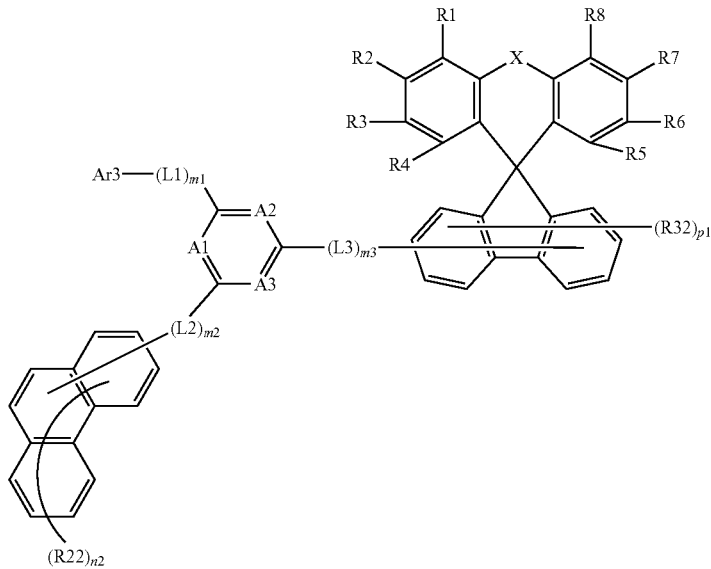

Chemical Formula 4

-continued
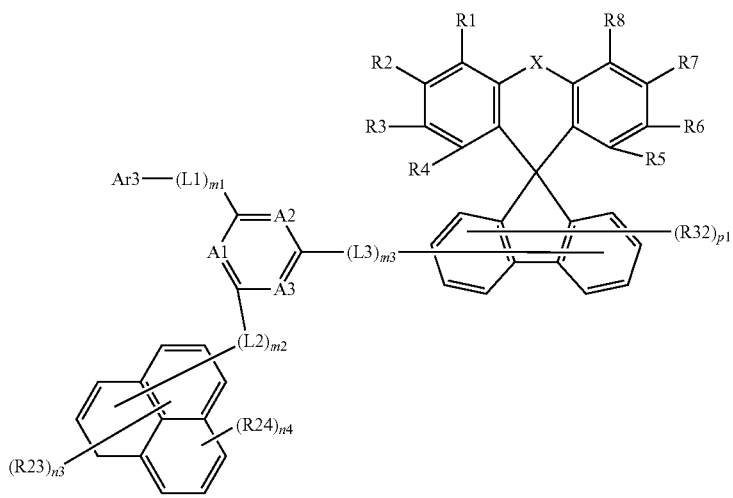
Chemical Formula 5
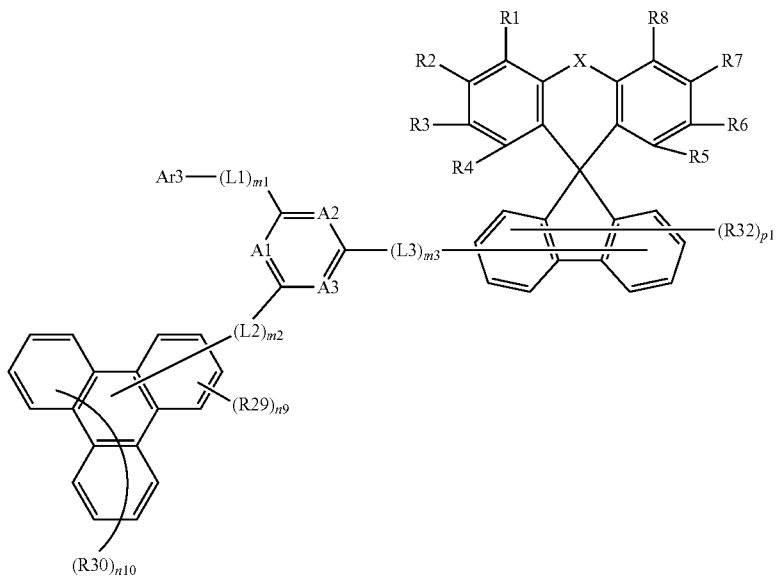
Chemical Formula 6
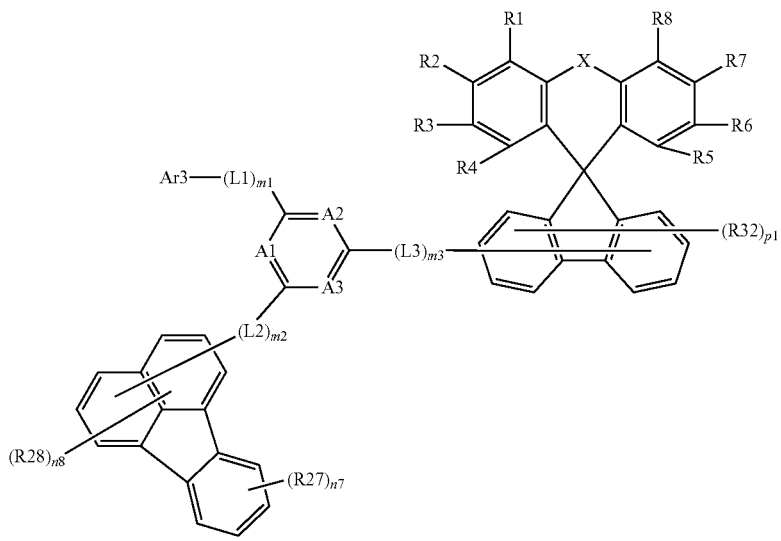
Chemical Formula 7

Chemical Formula 8

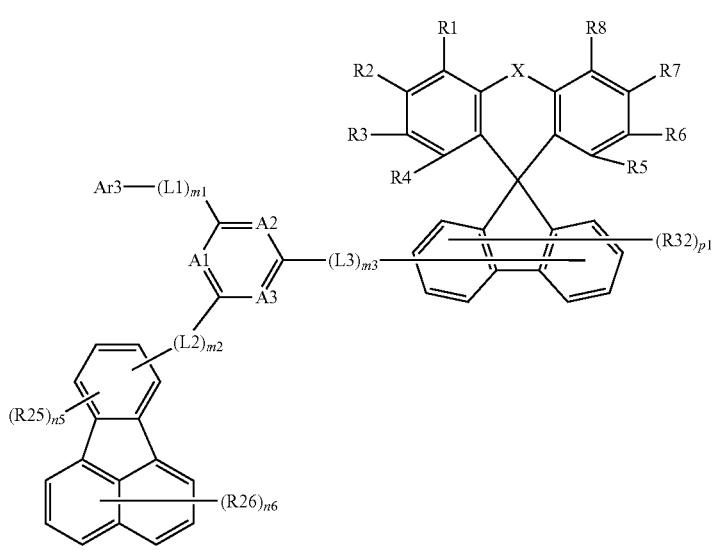

wherein in Chemical Formulae 3 to 8:

X, R1 to R8, A1 to A3, L1 to L3 and m1 to m3 have the same definitions as in Chemical Formula 1;

Ar3 is a substituted or unsubstituted dicyclic or higher condensed aryl group, a substituted or unsubstituted monocyclic aryl group, or a substituted or unsubstituted heterocyclic group;

R21 to R30 are the same as or different from each other, and each independently is hydrogen, deuterium, a cyano group, a nitro group, a carbonyl group, a substituted or unsubstituted silyl group, a substituted or unsubstituted boron group, a substituted or unsubstituted alkyl group, a substituted or unsubstituted alkoxy group, a substituted or unsubstituted aryloxy group, a substituted or unsubstituted cycloalkyl group, a substituted or unsubstituted aryl group, or a substituted or unsubstituted heterocyclic group;

R32 is hydrogen, deuterium, a cyano group, a nitro group, a carbonyl group, a substituted or unsubstituted silyl group, a substituted or unsubstituted boron group, a substituted or unsubstituted alkyl group, a substituted or unsubstituted alkoxy group, a substituted or unsubstituted aryloxy group, a substituted or unsubstituted cycloalkyl group, a substituted or unsubstituted aryl group, or a substituted or unsubstituted heterocyclic group;

n1 is an integer of 0 to 7, n2 is an integer of 0 to 9, n3 and n6 are each an integer of 0 to 6, n4, n5 and n9 are each an integer of 0 to 3, n7 is an integer of 0 to 4, n8 is an integer of 0 to 5, n10 is an integer of 0 to 8, and when n1 to n10 are each 2 or greater, two or more substituents in the parentheses are the same as or different from each other; and p1 is an integer of 0 to 7, and when p1 is 2 or greater, two or more R32s are the same as or different from each other.

9. The organic light emitting device of claim 2, wherein the compound of Chemical Formula 1 is any one compound selected from among the following compounds:

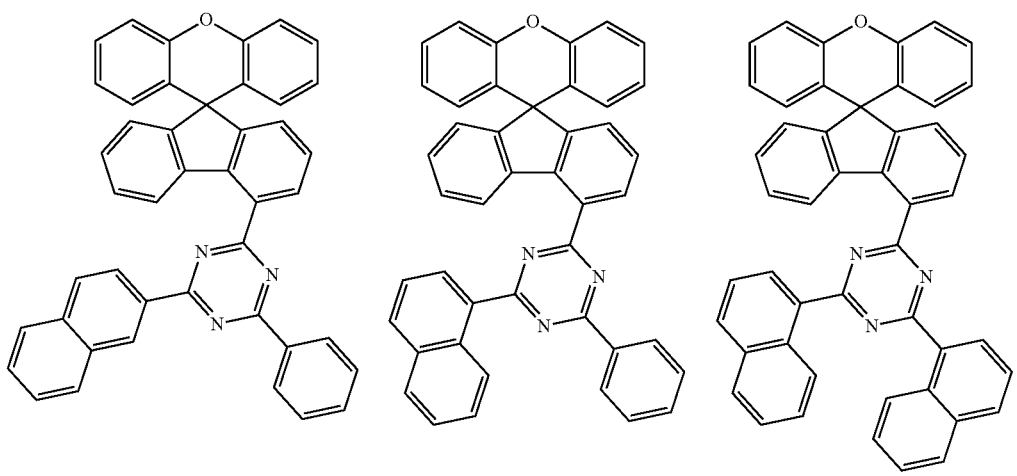

193
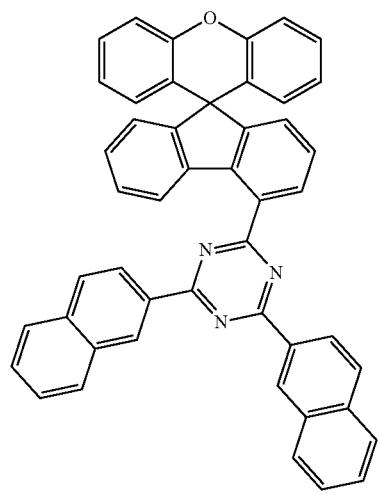
-continued
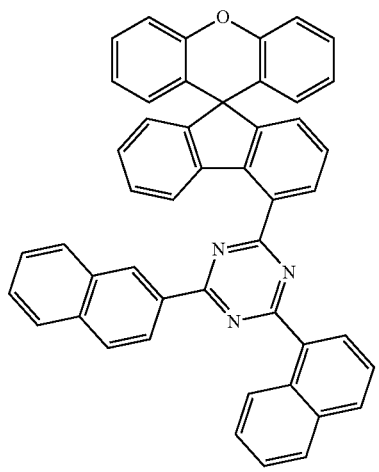
194
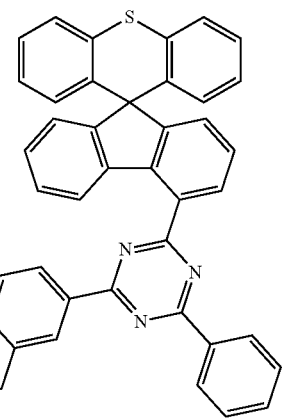
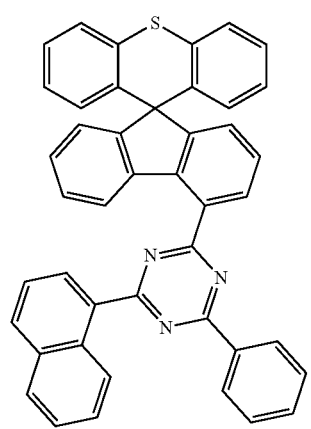
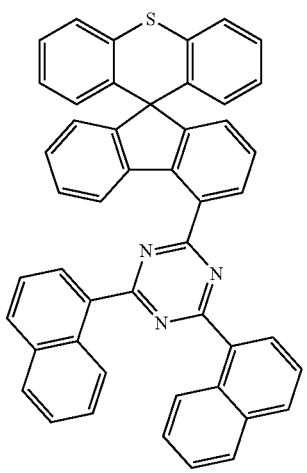
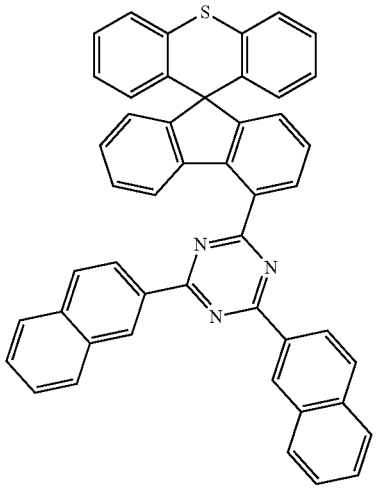
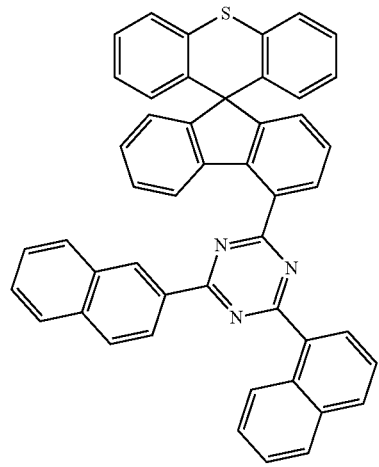
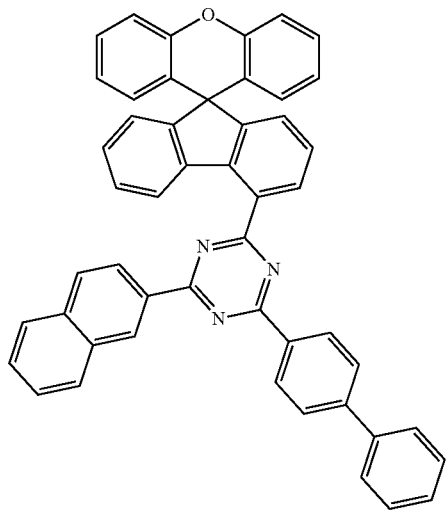
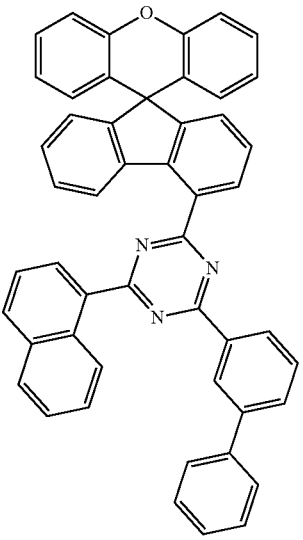 [SMILES: c1ccc(-c2cccc(-c3nc(-c4cccc5c4-c4ccccc4C54c5ccccc5Oc5ccccc54)nc(-c4cccc5ccccc45)n3)c2)cc1]

-continued
195
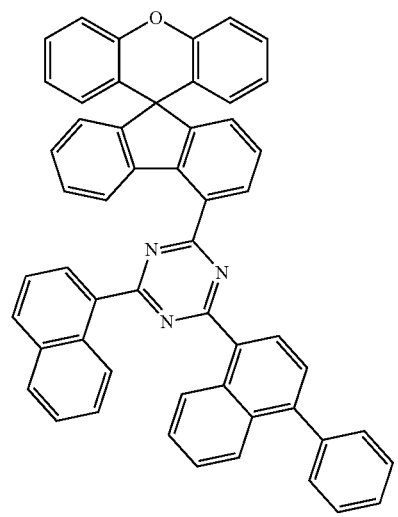
196
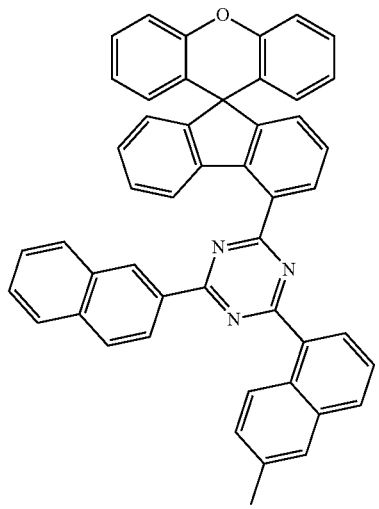
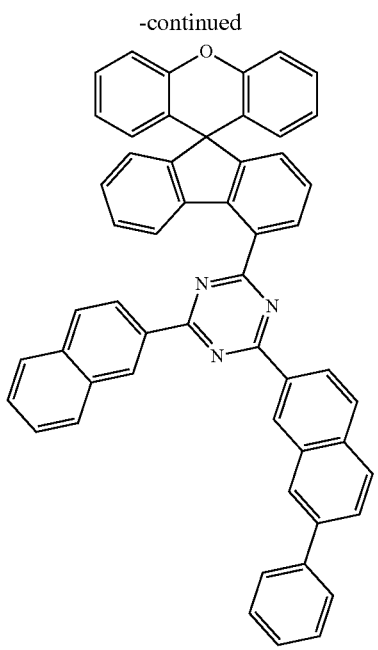
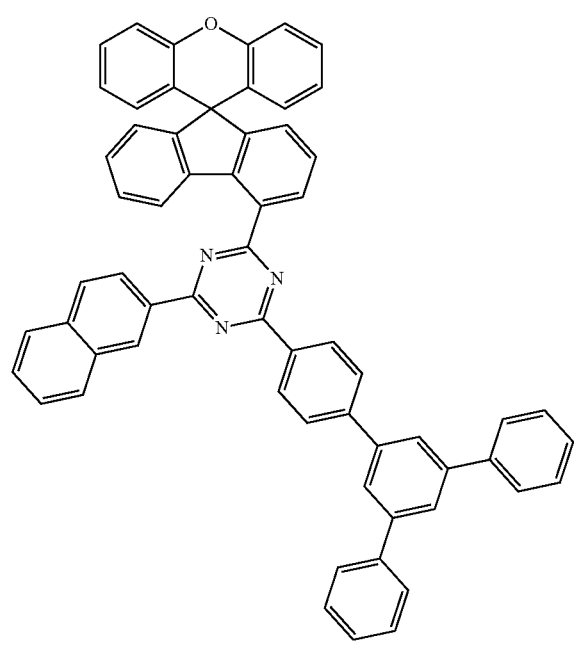
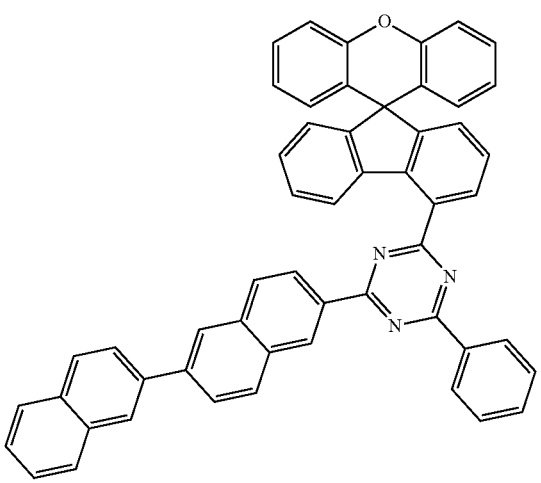

-continued
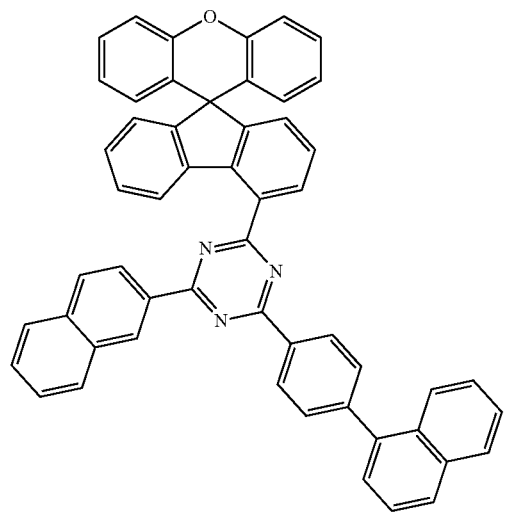
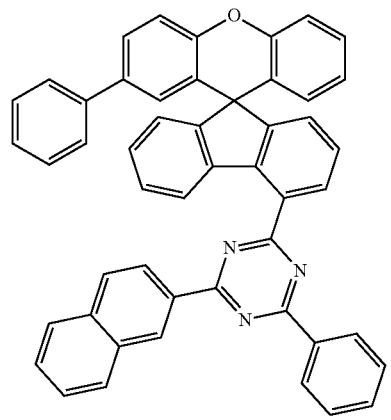
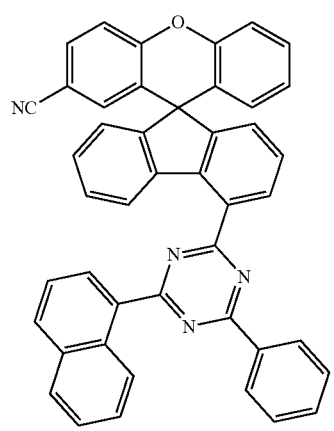
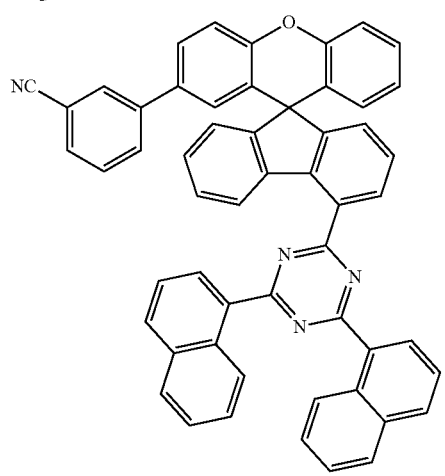
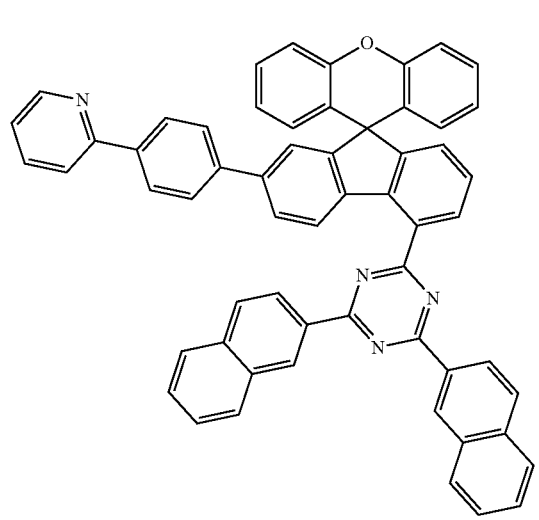
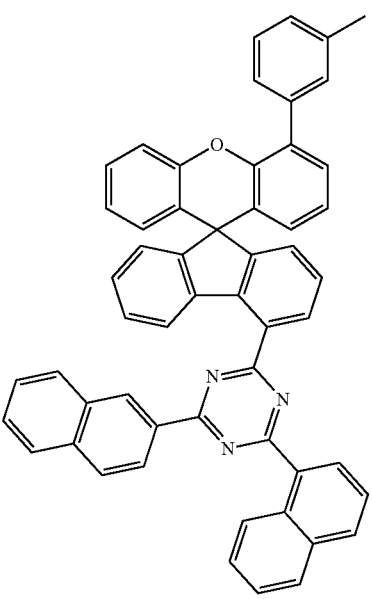

199
200
-continued
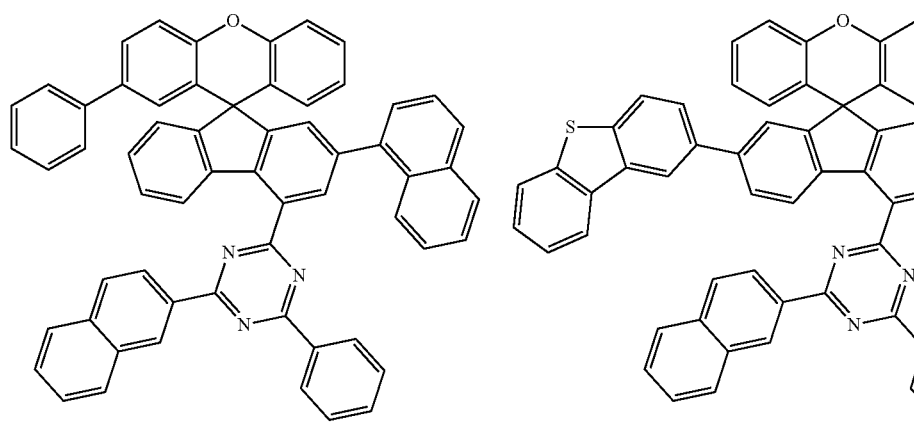

-continued
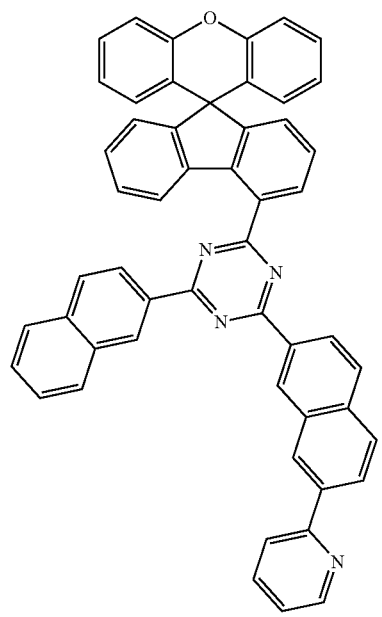
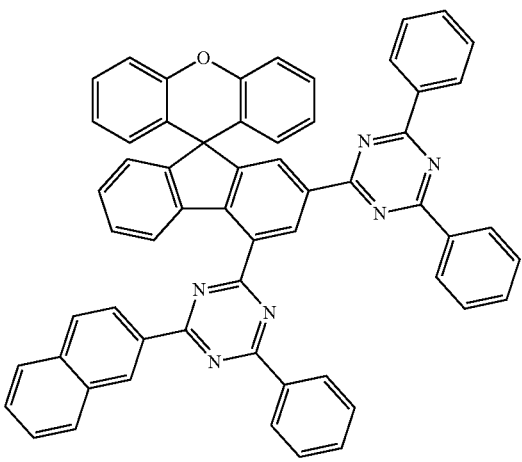
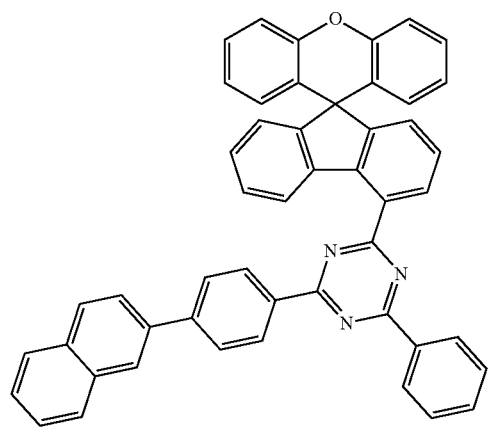
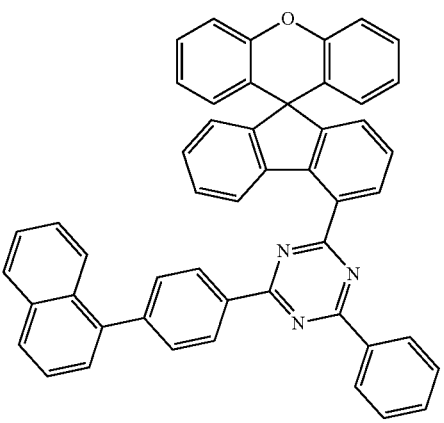
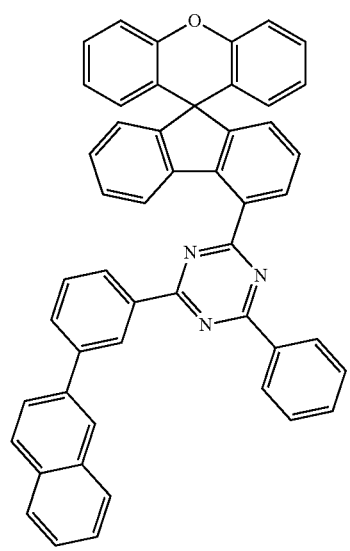
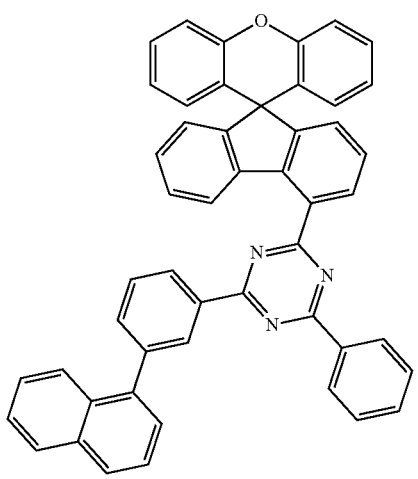

-continued
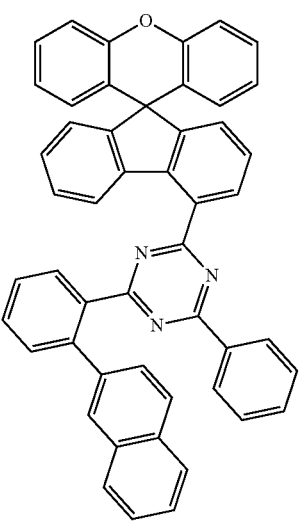
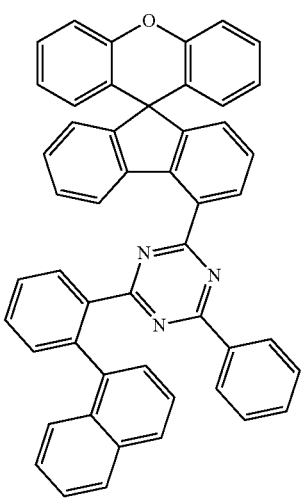
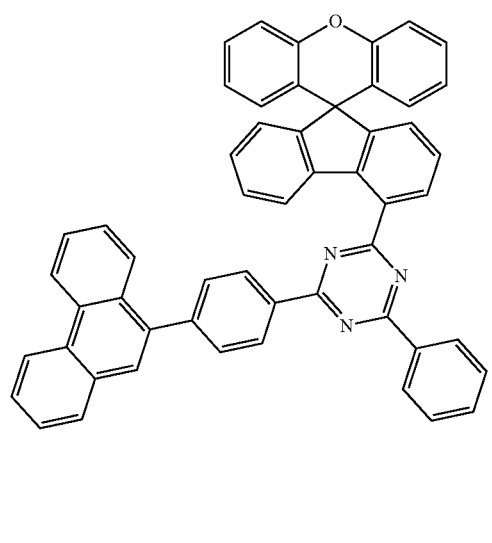
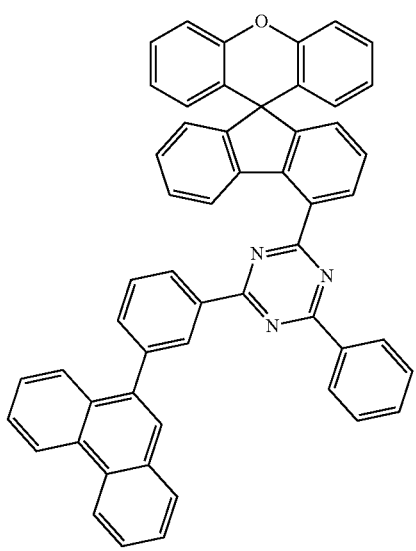
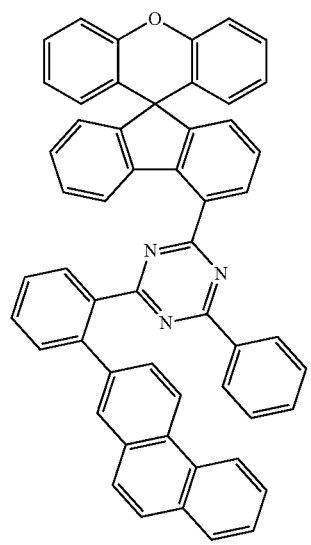
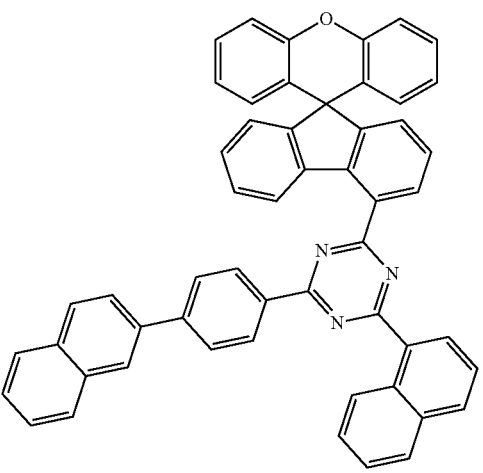

205
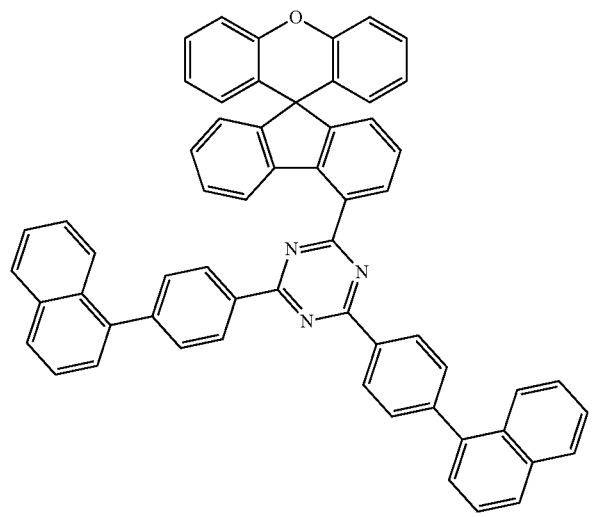
206
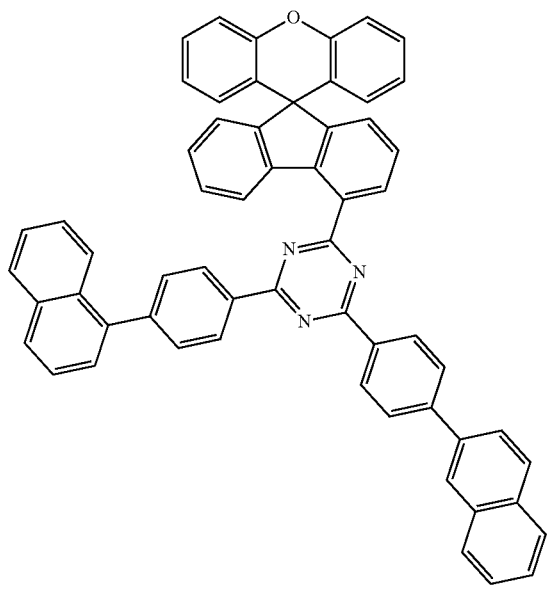
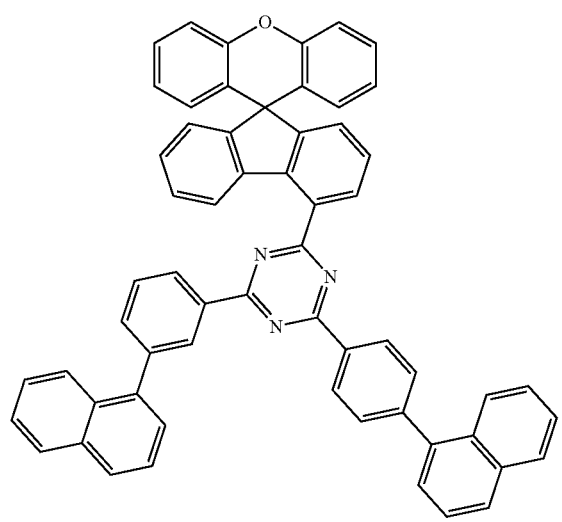
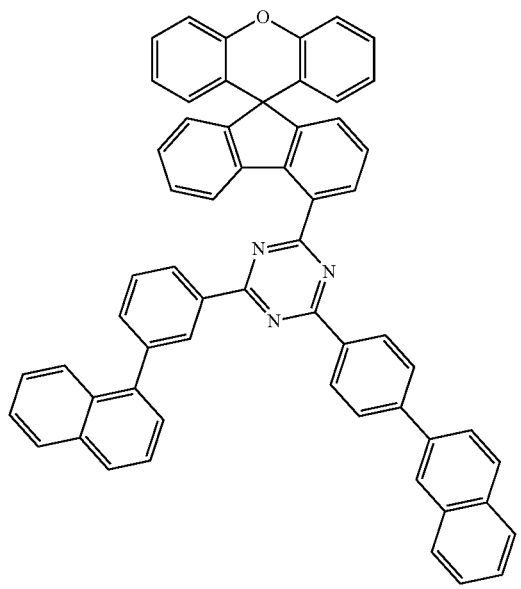
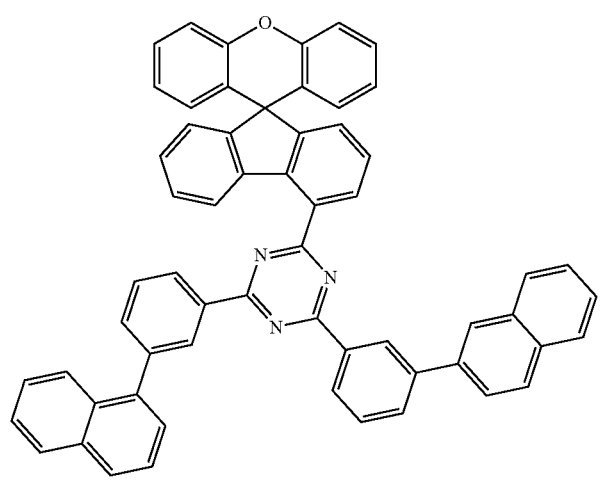

-continued
207 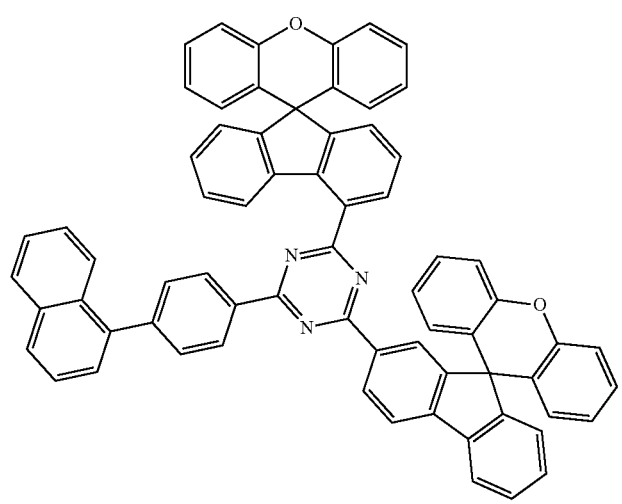
208 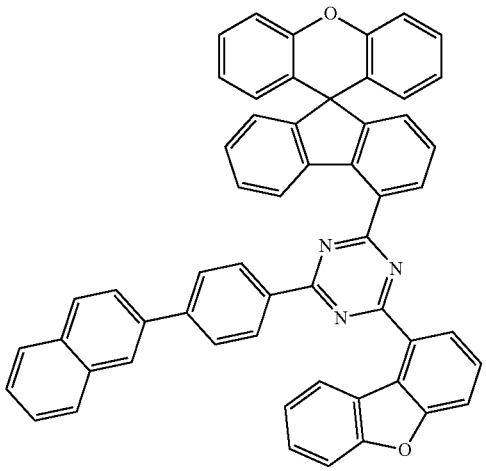
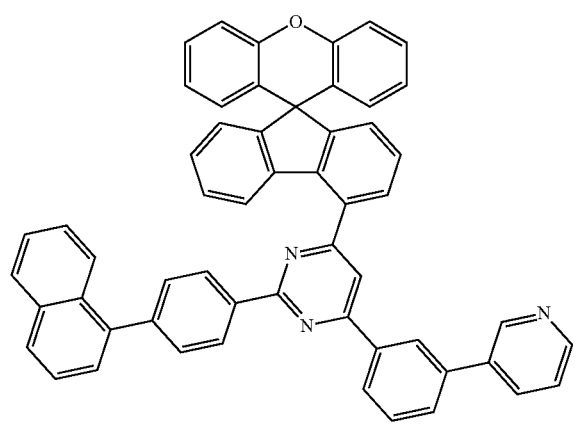
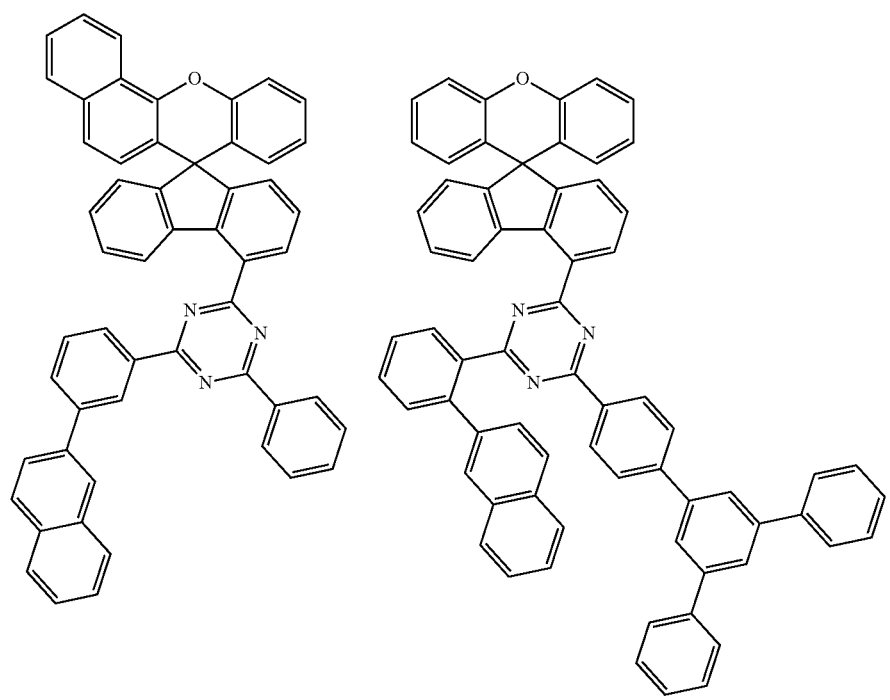

-continued
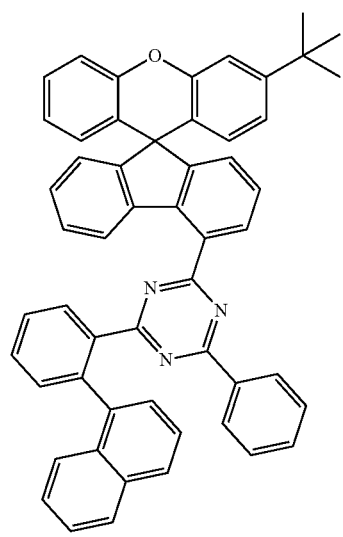
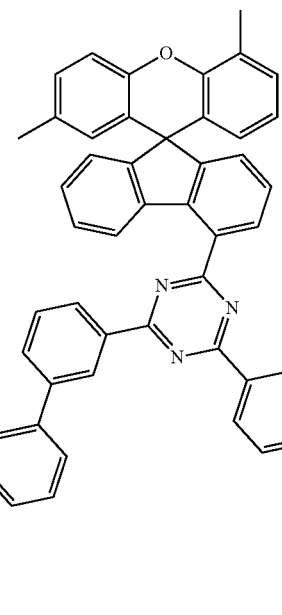
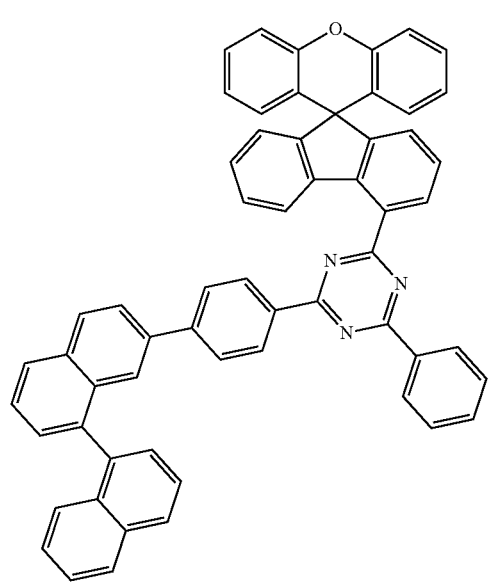
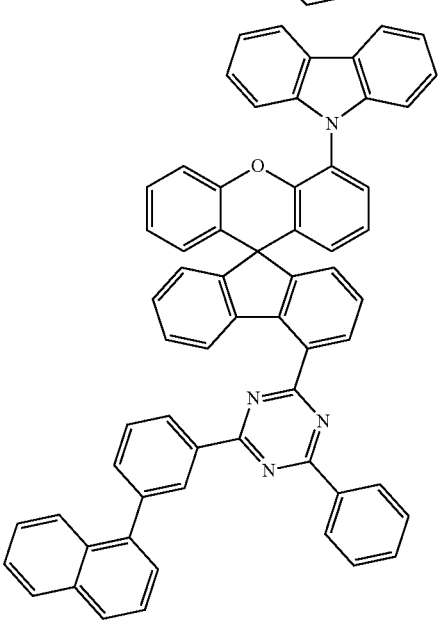
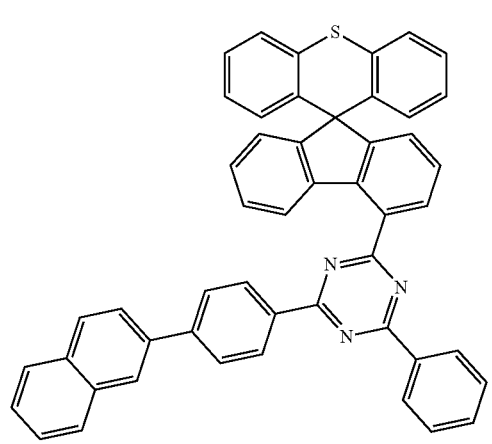
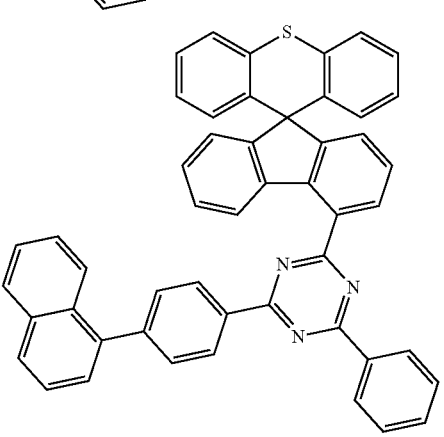

-continued
211
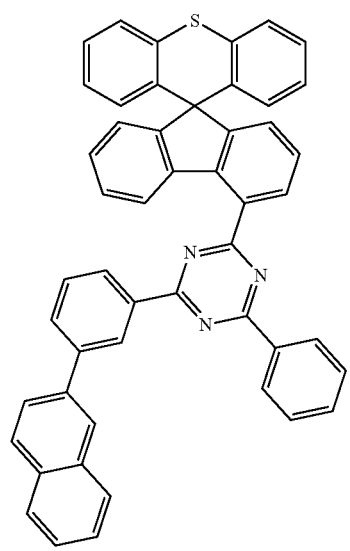
212
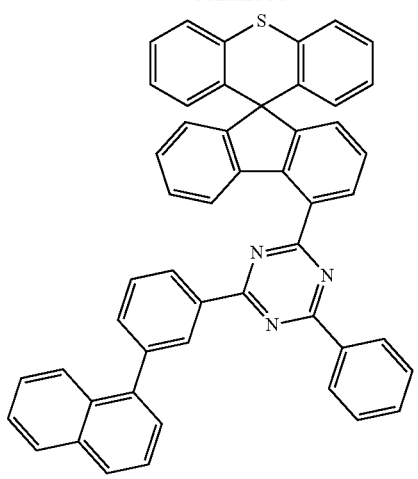
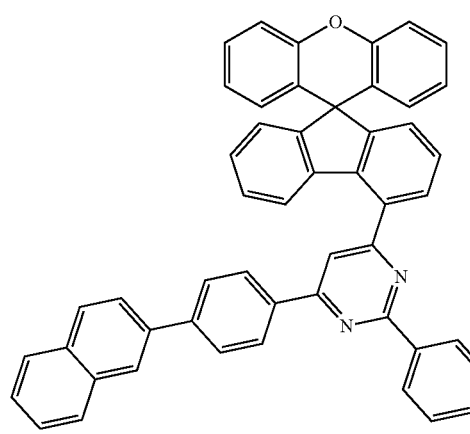
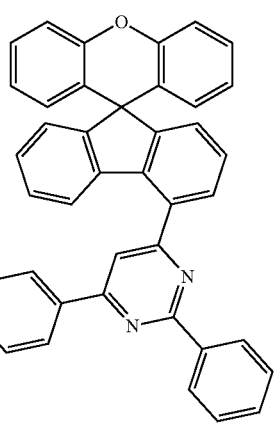
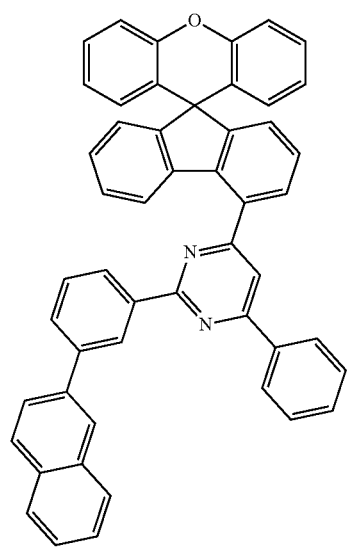
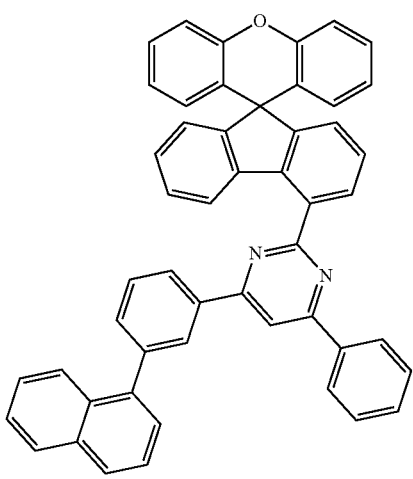

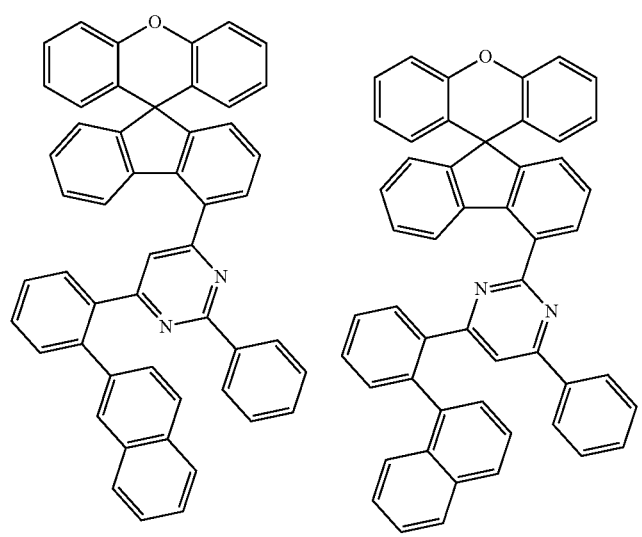
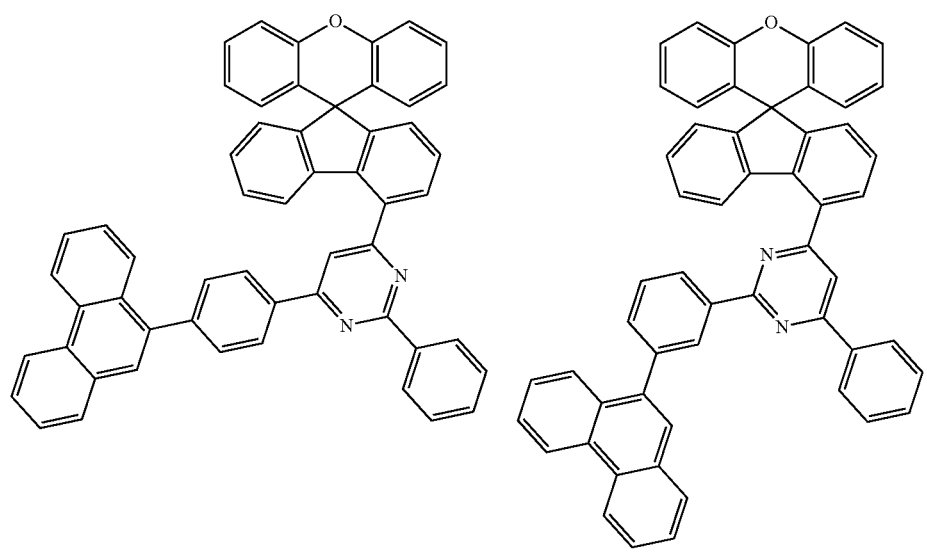
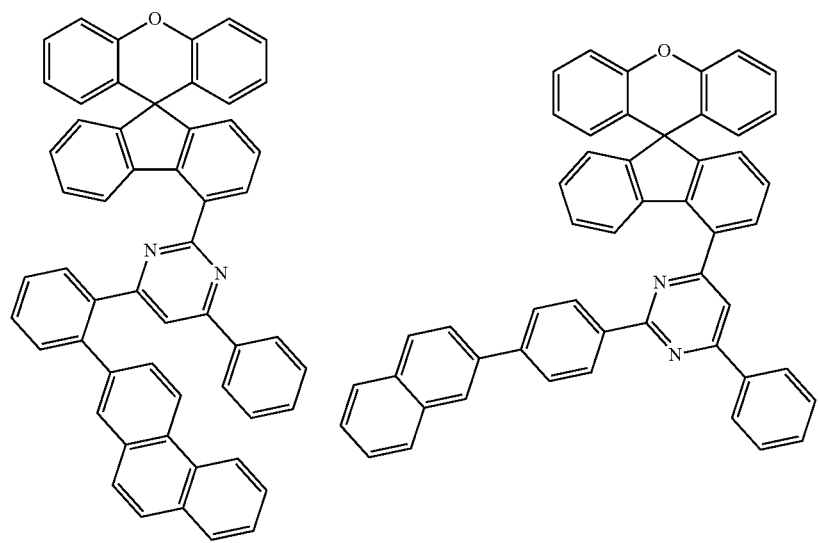

215 216
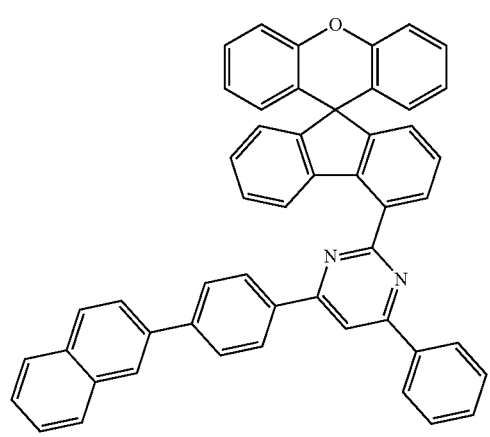
-continued

217
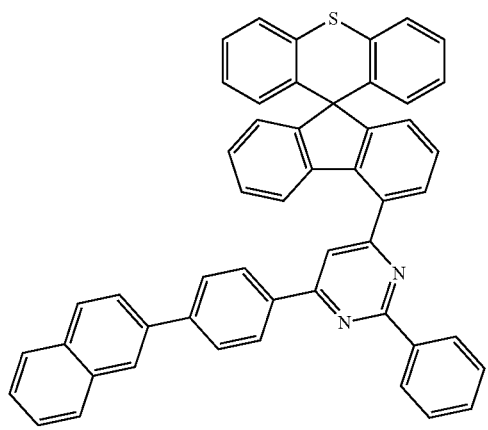
218
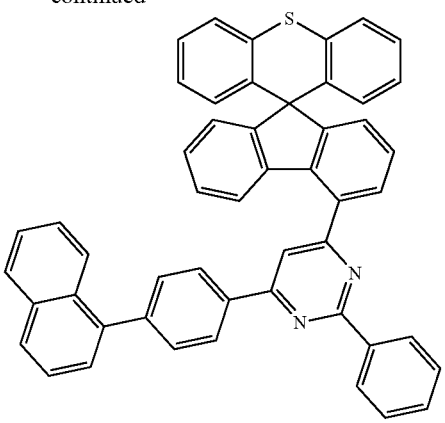
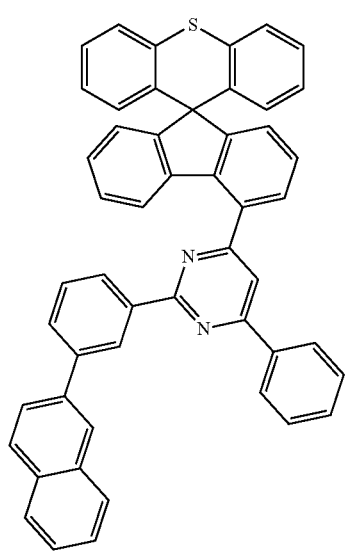
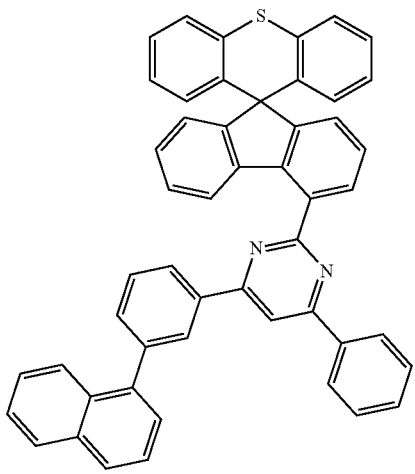
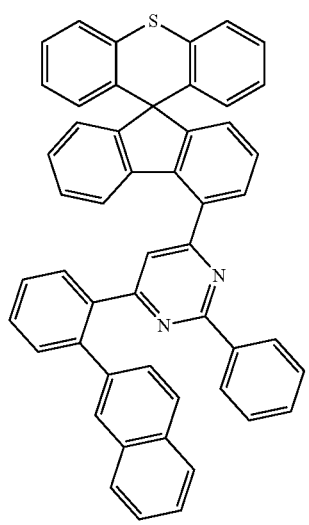
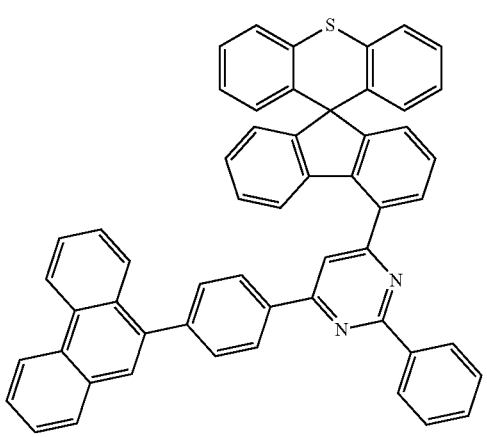

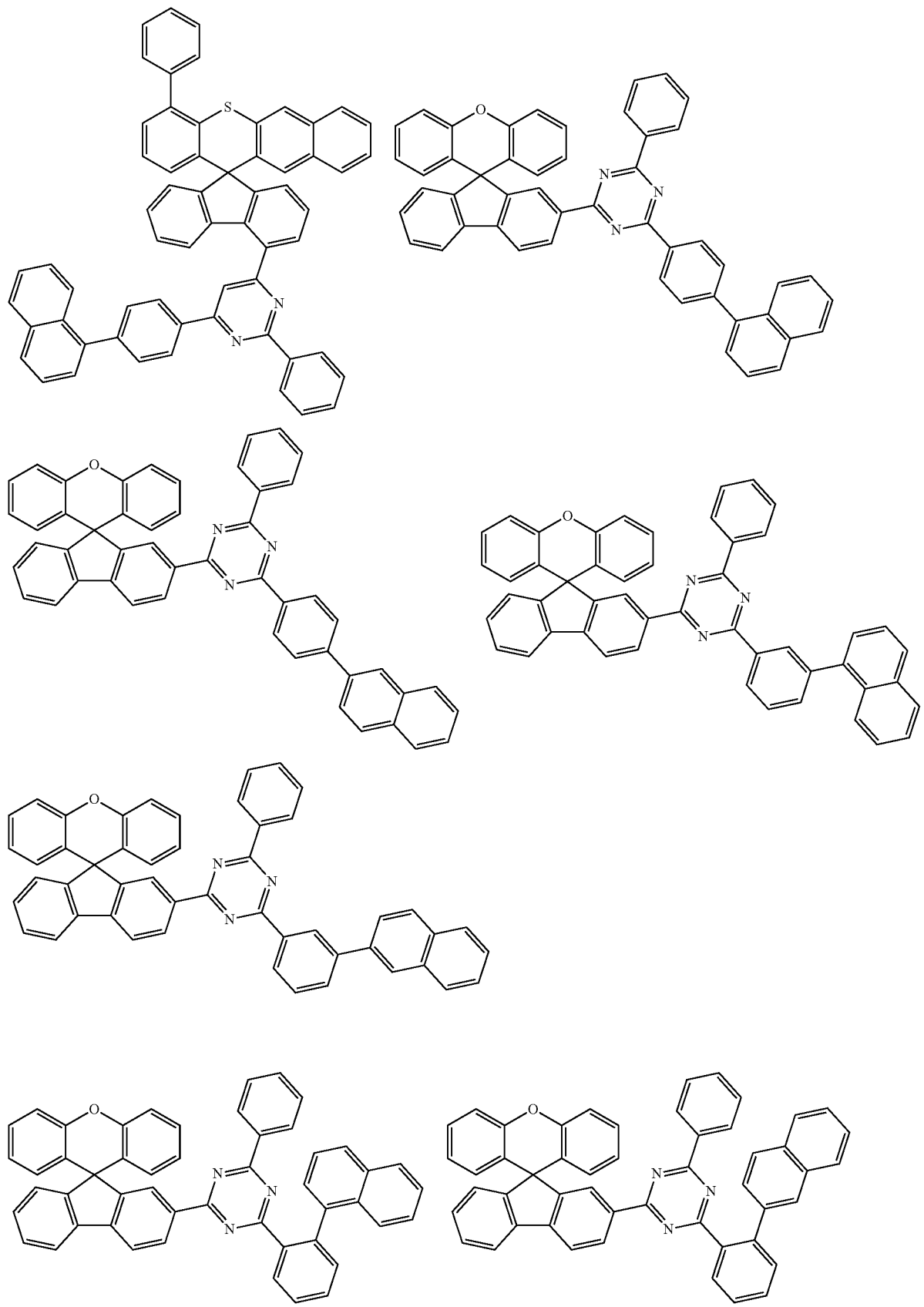

-continued
221
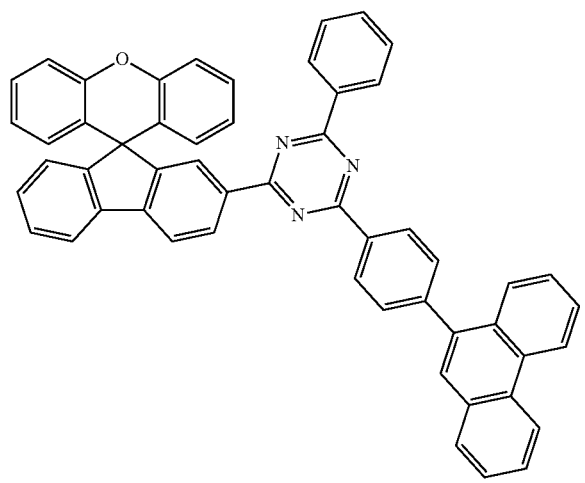
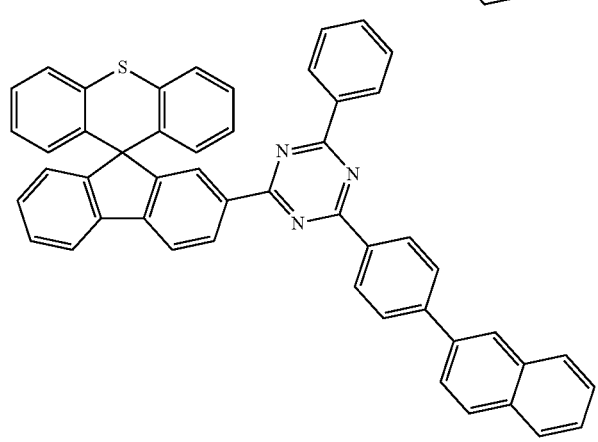
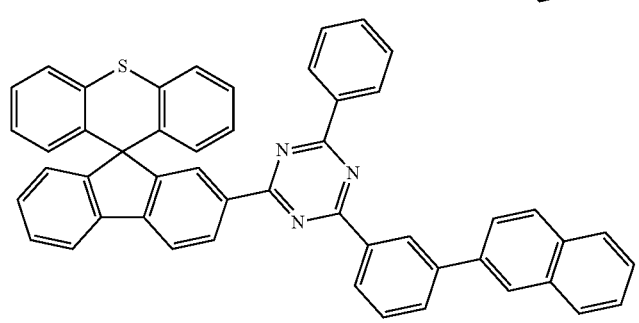
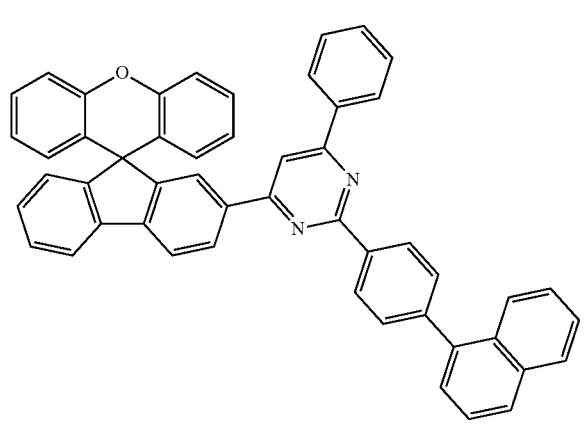
222
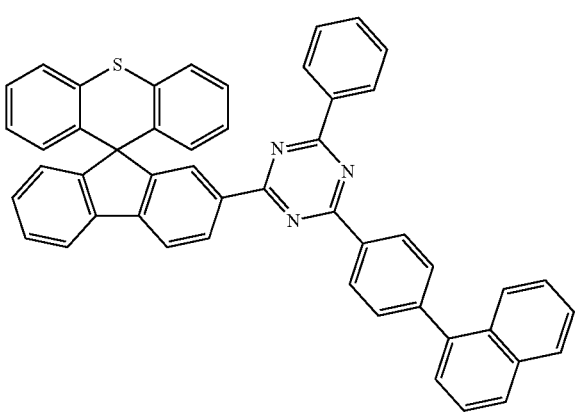
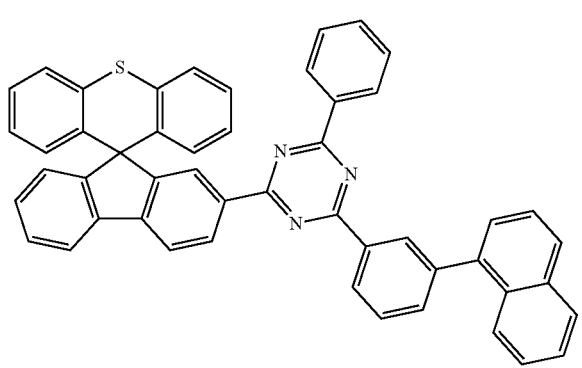
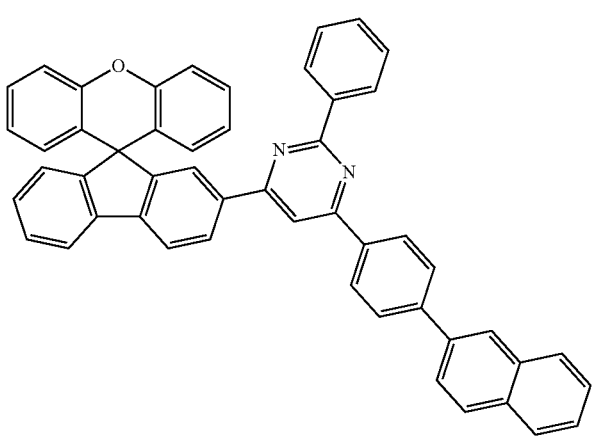

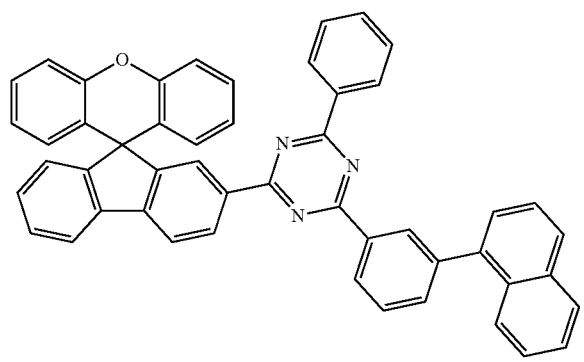
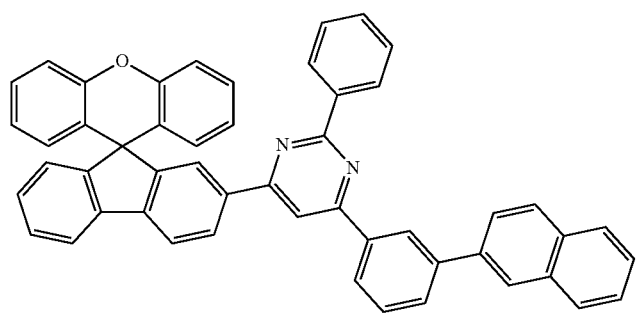
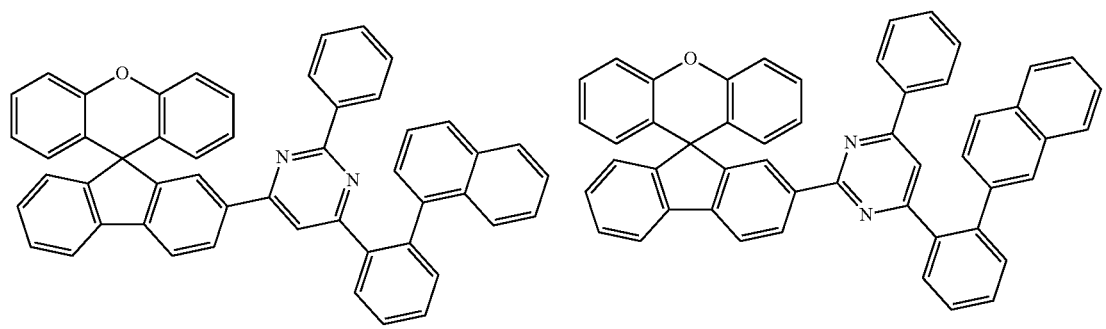
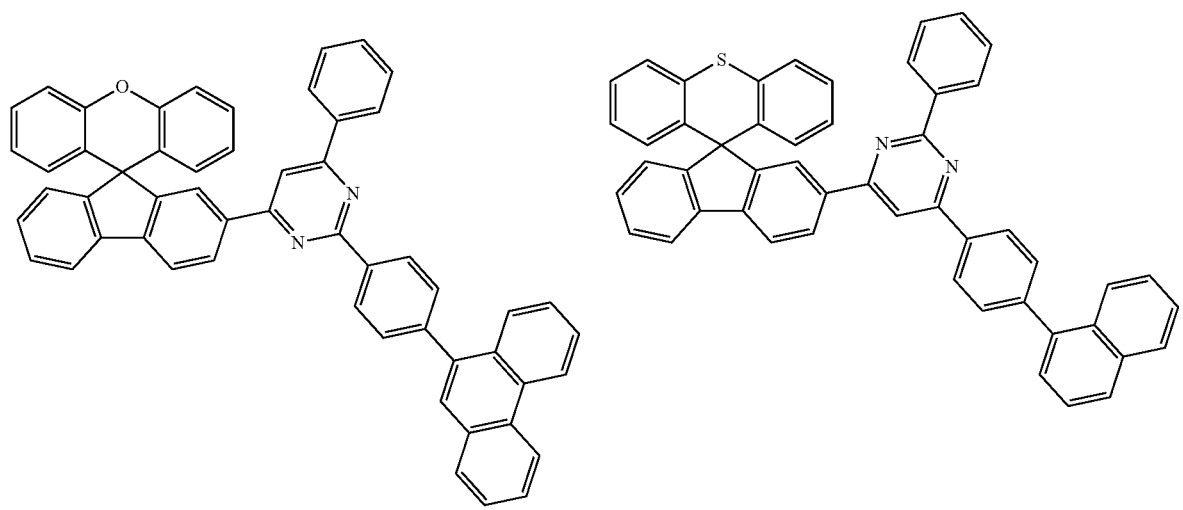

-continued
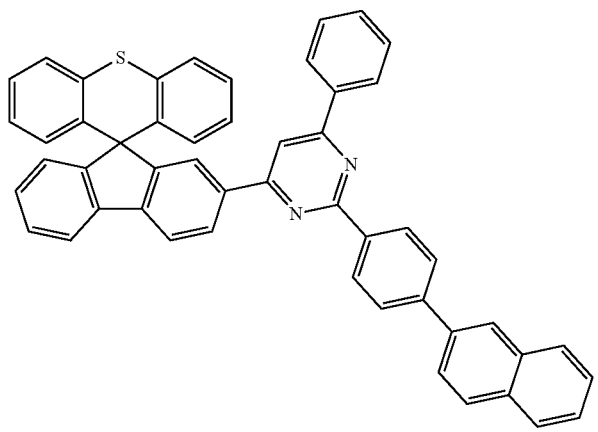
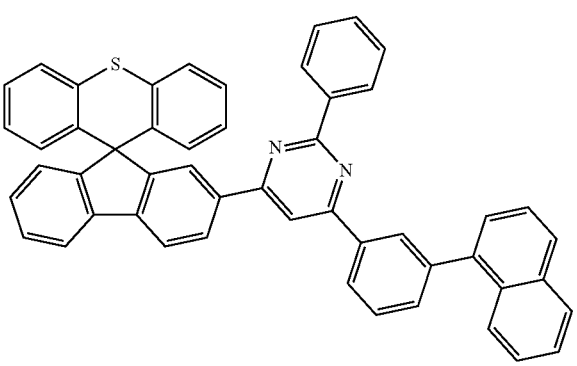
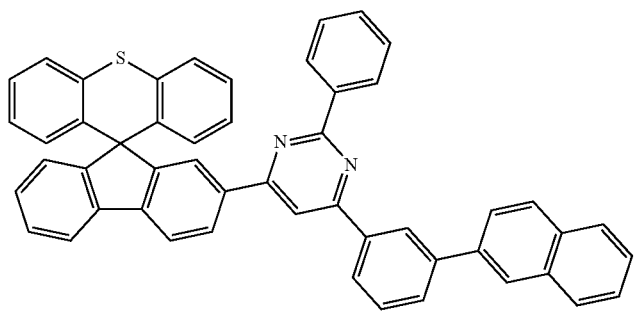
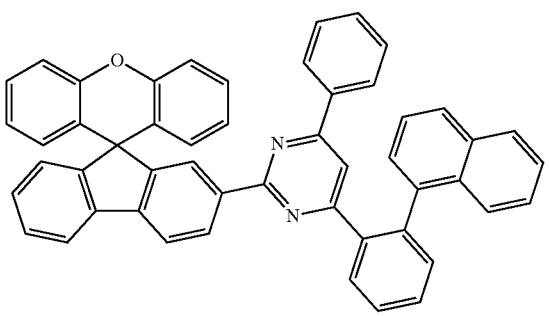
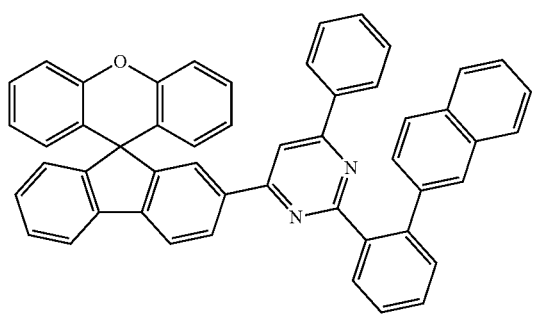
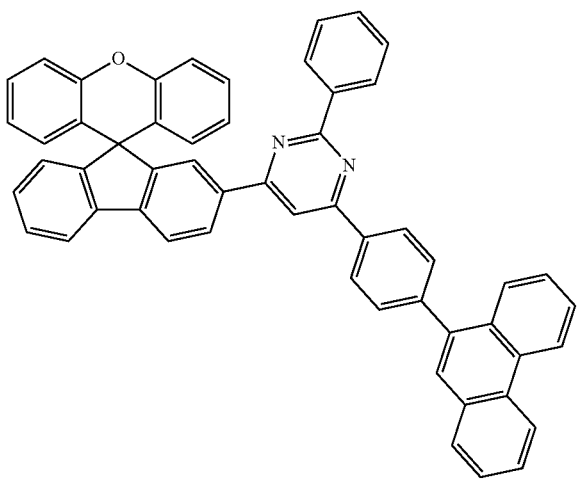
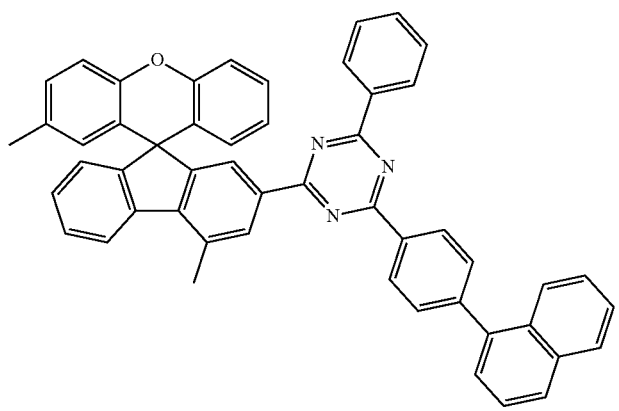

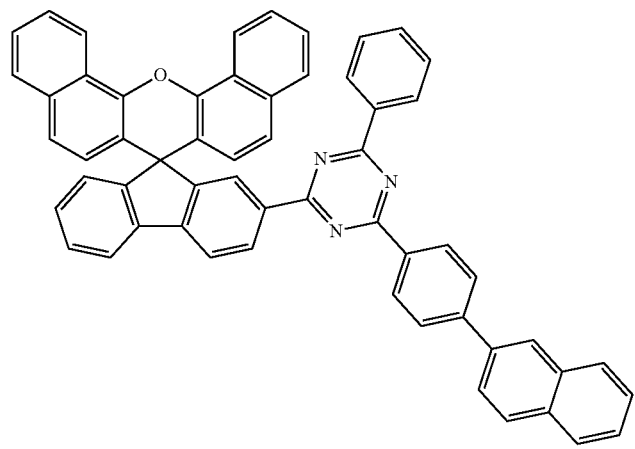
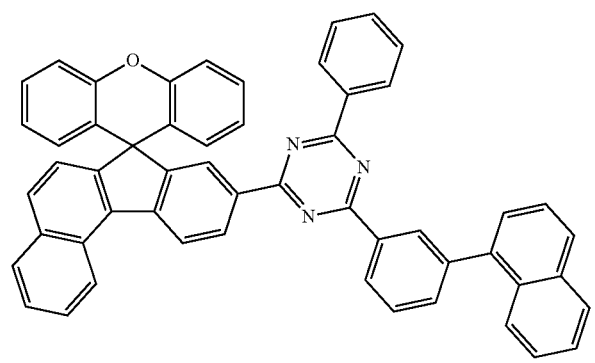
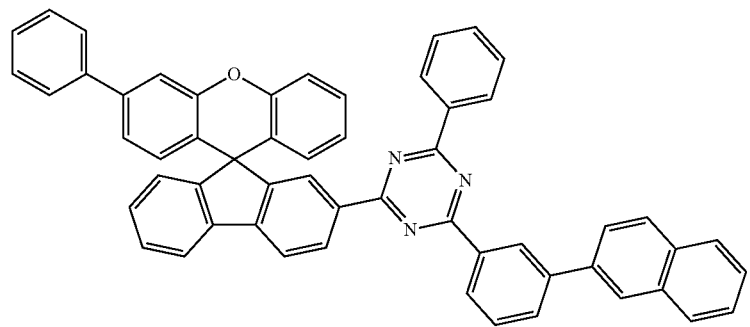

-continued
229
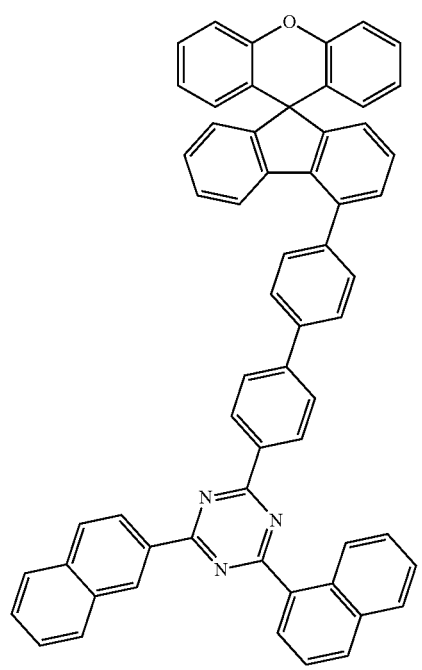
230
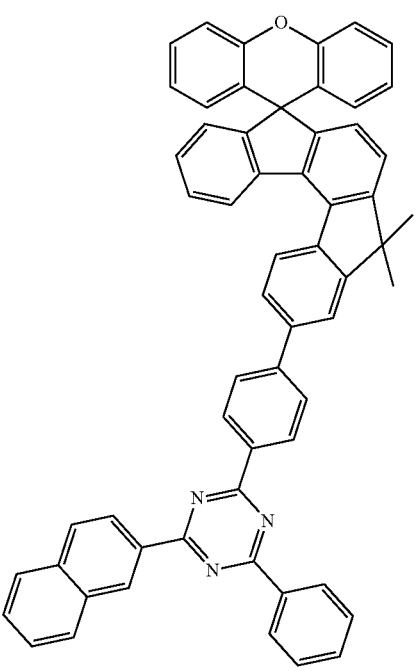
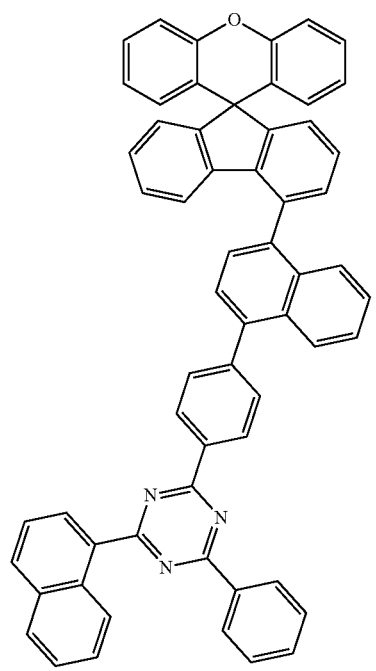
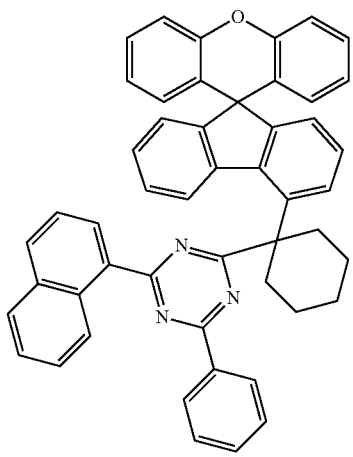

-continued
231
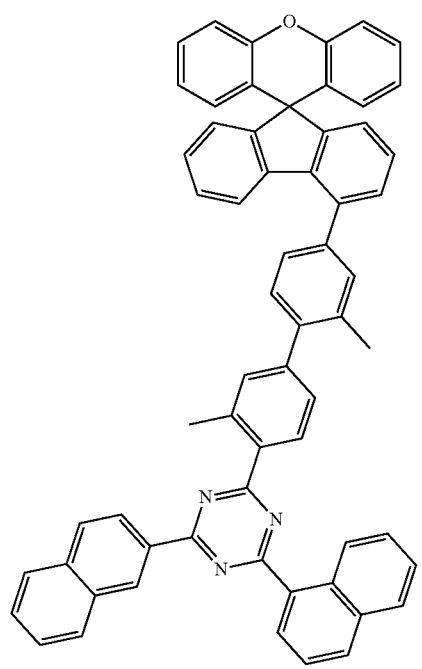
232
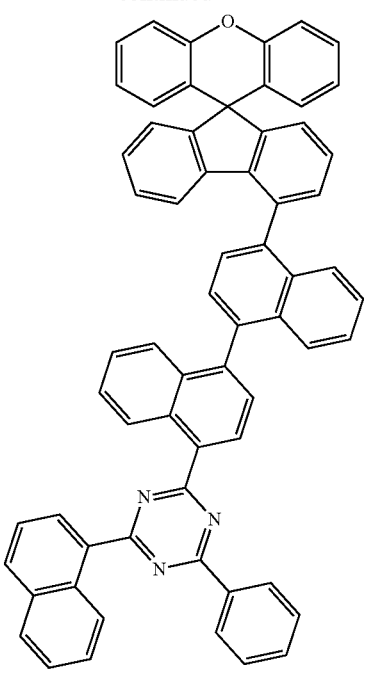
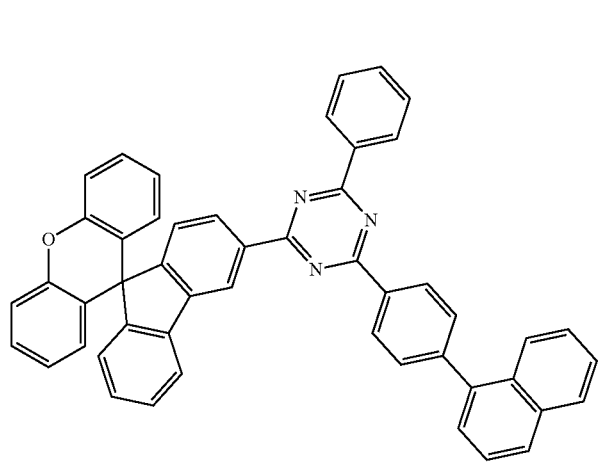
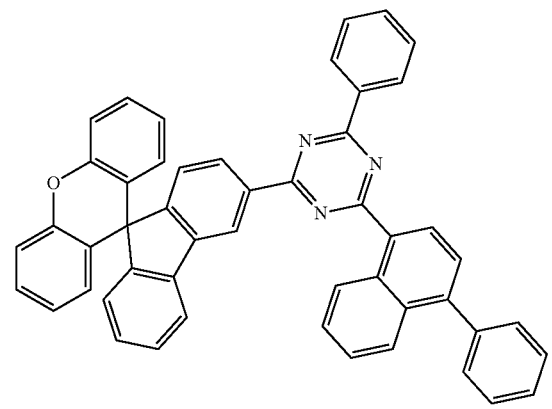
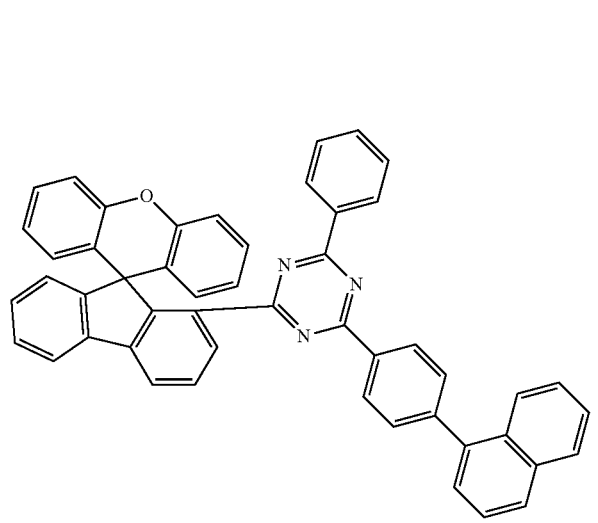
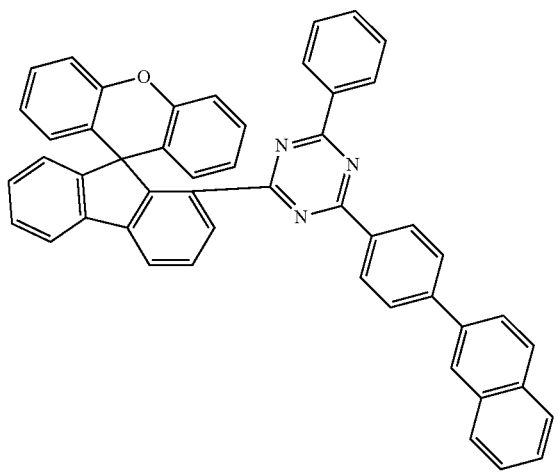

233 234
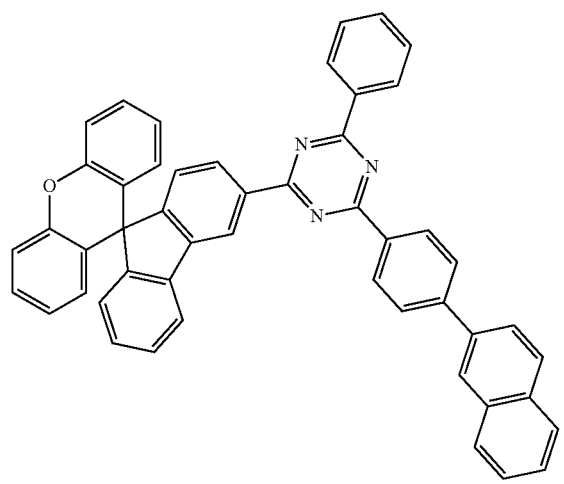 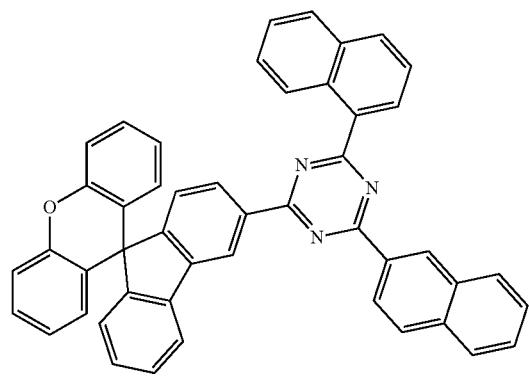
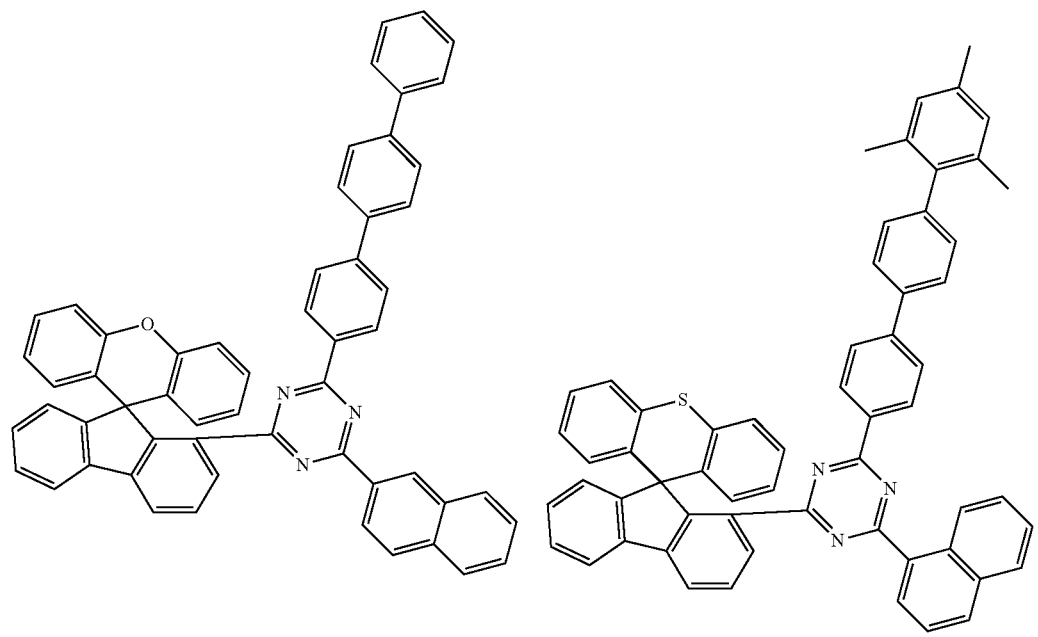
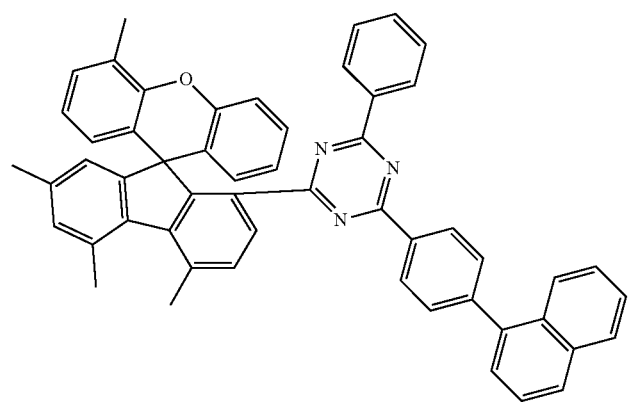

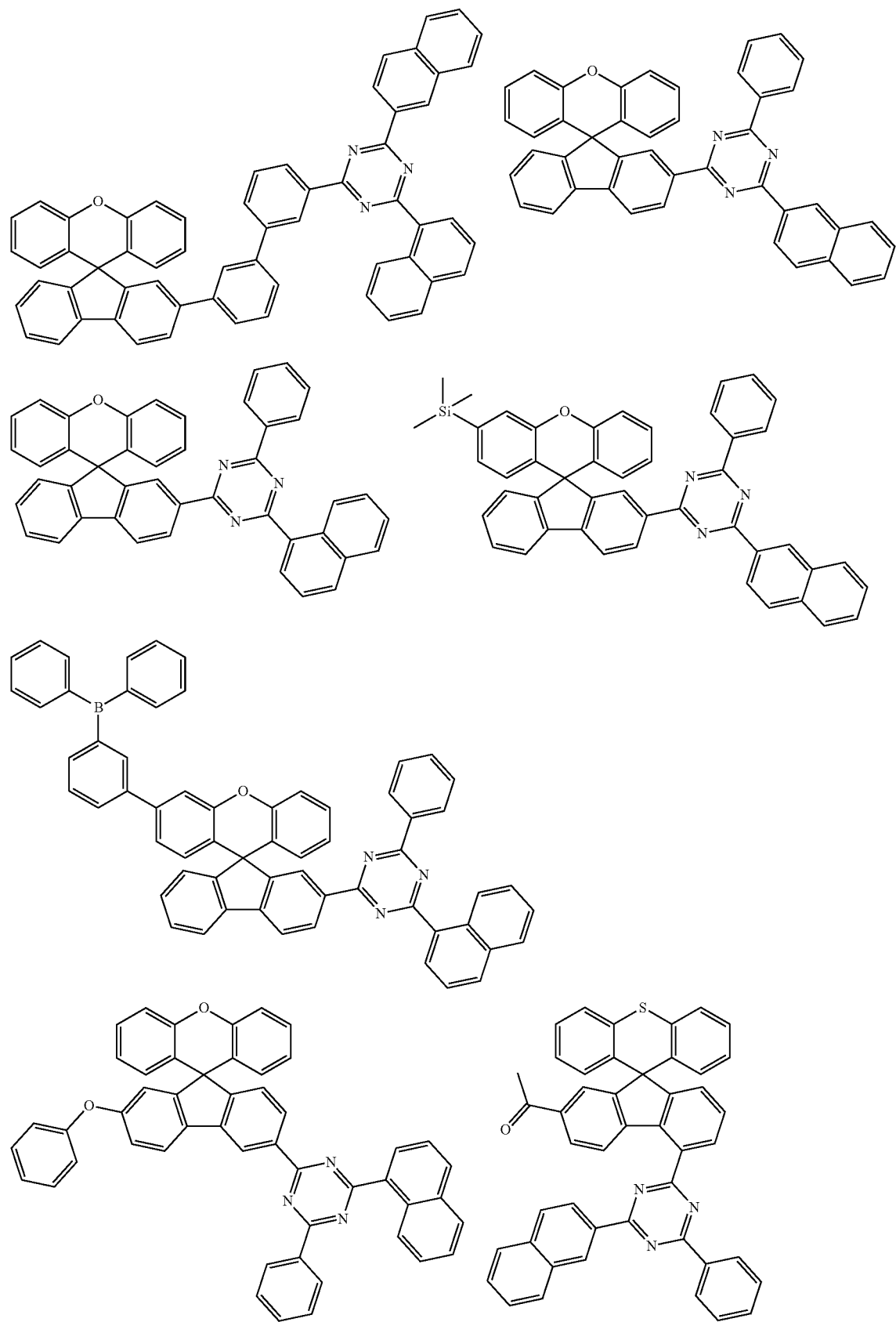

-continued
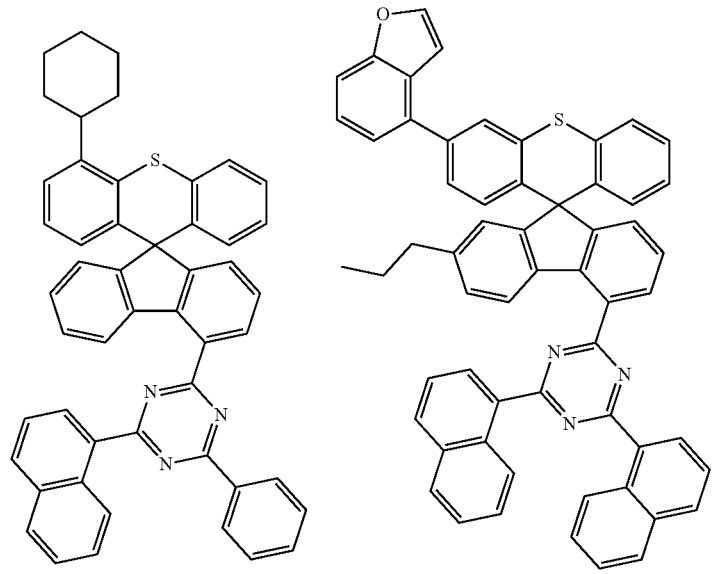
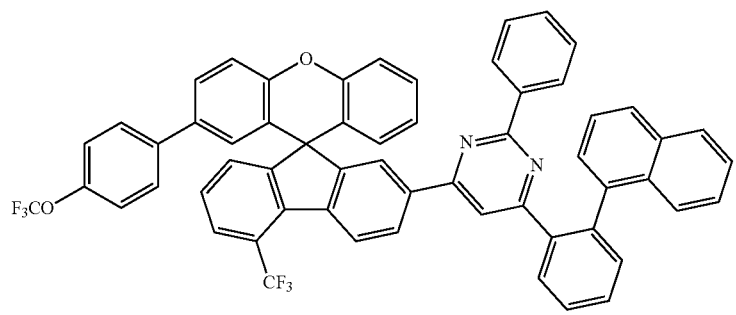
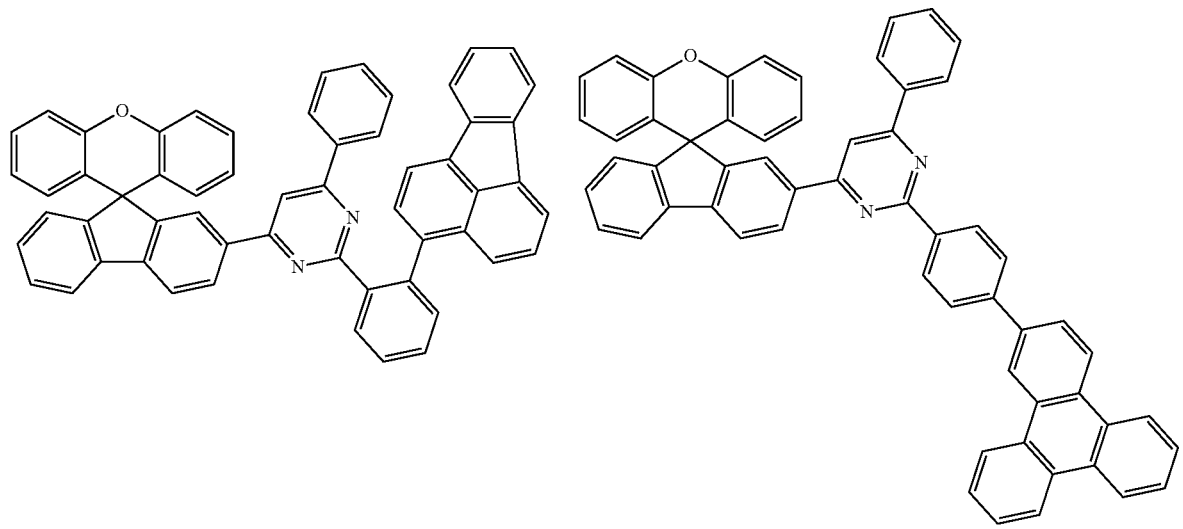

-continued
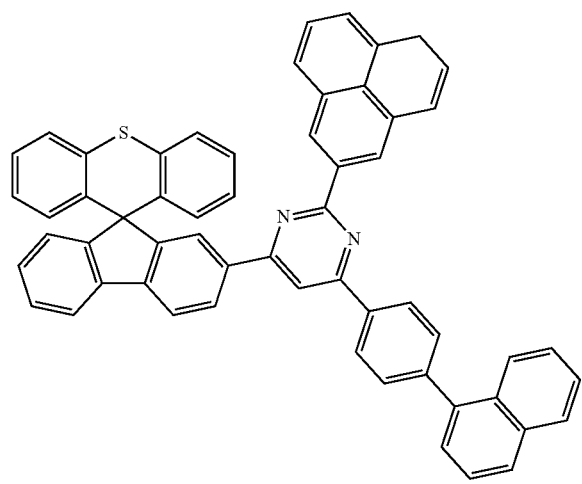
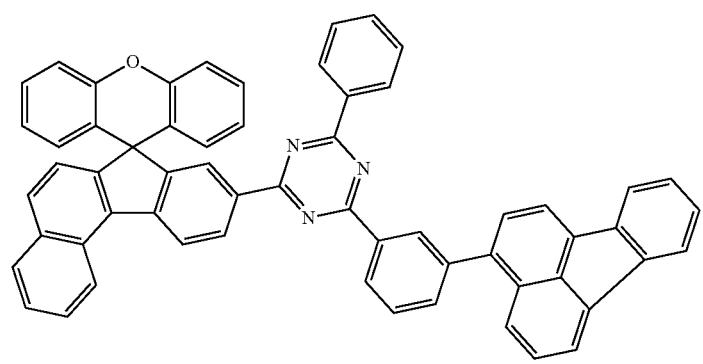
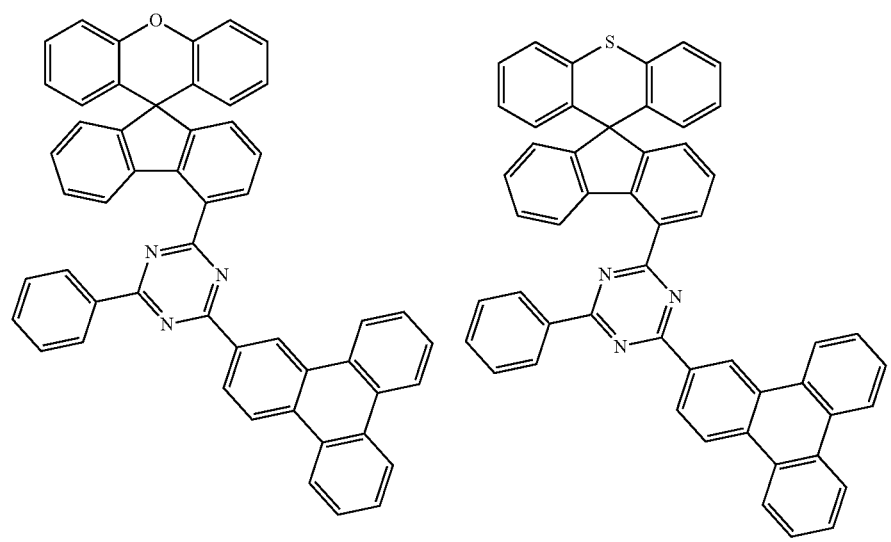

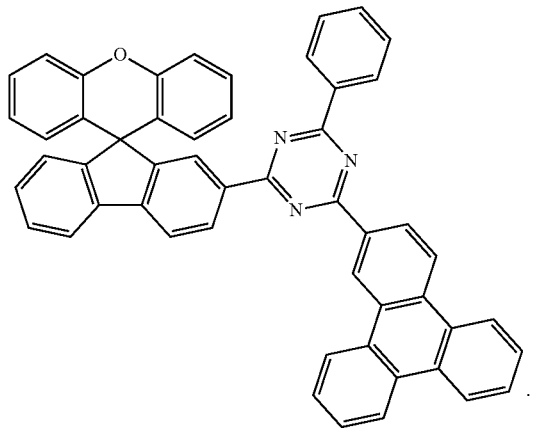

10. The organic light emitting device of claim 2, wherein the compound of Chemical Formula 1 satisfies the following Equation 1:

$$\Delta EST^C_{El} > \Delta EST_{El} \qquad \text{<Equation 1>}$$

wherein in Equation 1:
$\Delta EST^C_{El}$ is a difference between a singlet energy (S1) value and a triplet energy (T1) value of the compound of Chemical Formula 1; and
$\Delta EST_{El}$ is a difference between a singlet energy (S1) value and a triplet energy (T1) value of a compound having the same core structure as the compound of Chemical Formula 1 in which the dicyclic or higher condensed aryl group of Ar1 and/or Ar2 in the compound of Chemical Formula 1 is replaced with a phenyl group.

11. The organic light emitting device of claim 2, wherein the compound of Chemical Formula 1 satisfies the following Equation 2:

$$0.30 \text{ eV} < \Delta EST^C_{El} < 1.5 \text{ eV} \qquad \text{<Equation 2>}$$

wherein in Equation 2:
$\Delta EST^C_{El}$ is a difference between a singlet energy (S1) value and a triplet energy (T1) value of the compound of Chemical Formula 1.

12. The organic light emitting device of claim 2, wherein the compound of Chemical Formula 1 satisfies the following Equation 3:

$$\Delta EST^C_{El} - \Delta EST_{El} > 0.05 \text{ eV} \qquad \text{<Equation 3>}$$

wherein in Equation 3:
$\Delta EST^C_{El}$ is a difference between a singlet energy (S1) value and a triplet energy (T1) value of the compound of Chemical Formula 1; and
$\Delta EST_{El}$ is a difference between a singlet energy (S1) value and a triplet energy (T1) value of a compound having the same core structure as the compound of Chemical Formula 1 in which the dicyclic or higher condensed aryl group of Ar1 and/or Ar2 in the compound of Chemical Formula 1 is replaced with a phenyl group.

* * * * *

UNITED STATES PATENT AND TRADEMARK OFFICE
CERTIFICATE OF CORRECTION

PATENT NO. : 12,016,243 B2
APPLICATION NO. : 17/271762
DATED : June 18, 2024
INVENTOR(S) : Huh et al.

Page 1 of 2

It is certified that error appears in the above-identified patent and that said Letters Patent is hereby corrected as shown below:

In the Claims

In Claim 9, Column 223, the structure of the first compound should be:

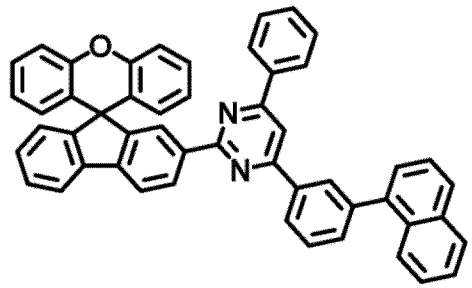

In Claim 9, Column 227, the structure of the third compound should be:

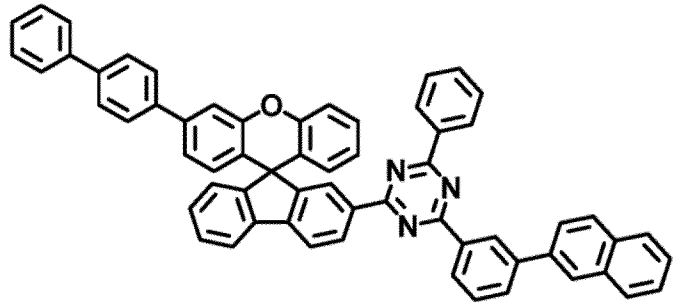

Signed and Sealed this
Sixth Day of August, 2024

Katherine Kelly Vidal
*Director of the United States Patent and Trademark Office*

In Claim 9, Column 230, the structure of the first compound should be:
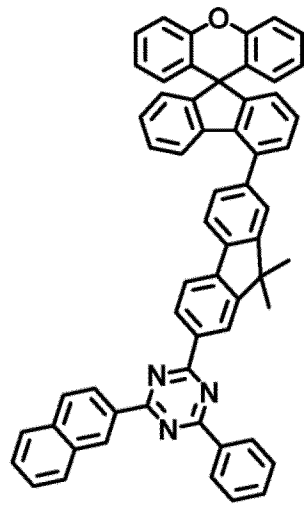
In Claim 10, Column 241, Line 24, the text of < Equation 1 > should be replaced with the following:
− $\Delta EST^C_{El} > \Delta EST_{El}$ −